(12) United States Patent
Shelton, IV et al.

(10) Patent No.: US 11,723,642 B2
(45) Date of Patent: Aug. 15, 2023

(54) COOPERATIVE ACCESS HYBRID PROCEDURES

(71) Applicant: Cilag GmbH International, Zug (CH)

(72) Inventors: Frederick E. Shelton, IV, Hillsboro, OH (US); Charles J. Scheib, Loveland, OH (US); Jason L. Harris, Lebanon, OH (US); Alexander Tarek Hassan, Ann Arbor, MI (US); Travis Michael Schuh, Los Altos, CA (US)

(73) Assignee: Cilag GmbH International, Zuf (CH)

( * ) Notice: Subject to any disclaimer, the term of this patent is extended or adjusted under 35 U.S.C. 154(b) by 0 days.

(21) Appl. No.: 17/449,765

(22) Filed: Oct. 1, 2021

(65) Prior Publication Data
US 2023/0098538 A1 Mar. 30, 2023

Related U.S. Application Data

(60) Provisional application No. 63/249,980, filed on Sep. 29, 2021.

(51) Int. Cl.
| | | |
|---|---|---|
| *A61B 17/02* | (2006.01) | |
| *A61B 5/00* | (2006.01) | |
| *A61B 17/00* | (2006.01) | |

(52) U.S. Cl.
CPC ........ *A61B 17/0218* (2013.01); *A61B 5/0075* (2013.01); *A61B 2017/00199* (2013.01);
(Continued)

(58) Field of Classification Search
CPC ................................................. A61B 17/0218
(Continued)

(56) References Cited

U.S. PATENT DOCUMENTS

| | | |
|---|---|---|
| 4,445,892 A | 5/1984 | Hussein et al. |
| 4,470,407 A | 9/1984 | Hussein |

(Continued)

FOREIGN PATENT DOCUMENTS

| | | |
|---|---|---|
| WO | 2007081800 A2 | 7/2007 |
| WO | 2014151621 A1 | 9/2014 |
| WO | 2020018566 A1 | 1/2020 |

OTHER PUBLICATIONS

Kurata et al. (2013) "Time-of-flight Near-infrared Spectroscopy for Nondestructive Measurement of Internal Quality in Grapefruit", Journal of the American Society for Horticultural Science, 138(3):225-228.

(Continued)

*Primary Examiner* — Eduardo C Robert
*Assistant Examiner* — Tara E Carter
(74) *Attorney, Agent, or Firm* — Mintz Levin Cohn Ferris GLovsky and Popeo, P.C.

(57) ABSTRACT

A method of operating a surgical anchoring system can include inserting an outer sleeve of a surgical instrument at least partially into a first natural body lumen, the outer sleeve having a working channel. The method can include inserting a channel arm of the surgical instrument through the working channel of the outer sleeve and into a second natural body lumen. The channel arm has at least one first anchor member coupled thereto and a control actuator operatively coupled to the at least one first anchor member. The method can include expanding the at least one first anchor member from an unexpanded state to an expanded state to form an anchor point at a portion of the second natural body lumen. The method can include controlling, by the control actuator, a motion of the channel arm to selectively manipulate an organ associated with the first and second natural body lumens.

14 Claims, 72 Drawing Sheets

(52) U.S. Cl.
CPC .............. *A61B 2017/00809* (2013.01); *A61B 2017/00818* (2013.01)

(58) Field of Classification Search
USPC .................................................. 600/201–245
See application file for complete search history.

(56) References Cited

U.S. PATENT DOCUMENTS

| | | | |
|---|---|---|---|
| 8,068,649 | B2 | 11/2011 | Green |
| 8,517,933 | B2 | 8/2013 | Mohr |
| 8,545,515 | B2 | 10/2013 | Prisco et al. |
| 8,551,115 | B2 | 10/2013 | Steger et al. |
| 8,623,028 | B2 | 1/2014 | Rogers et al. |
| 8,771,180 | B2 | 7/2014 | Mohr |
| 8,831,782 | B2 | 9/2014 | Itkowitz |
| 8,888,789 | B2 | 11/2014 | Prisco et al. |
| 9,254,178 | B2 | 2/2016 | Prisco et al. |
| 9,274,047 | B2 | 3/2016 | Velten et al. |
| 9,283,050 | B2 | 3/2016 | Prisco et al. |
| 9,320,416 | B2 | 4/2016 | Cooper et al. |
| 9,339,341 | B2 | 5/2016 | Cooper |
| 9,358,074 | B2 | 6/2016 | Schena et al. |
| 9,572,481 | B2 | 2/2017 | Duindam et al. |
| 9,636,186 | B2 | 5/2017 | Kumar et al. |
| 10,245,069 | B2 | 4/2019 | Rogers et al. |
| 10,492,665 | B2 | 12/2019 | Dejima |
| 10,792,034 | B2 | 10/2020 | Scheib et al. |
| 10,925,598 | B2 | 2/2021 | Scheib et al. |
| 11,051,876 | B2 | 7/2021 | Shelton, IV et al. |
| 2009/0012618 | A1 | 1/2009 | Ahrens et al. |
| 2010/0312065 | A1 | 12/2010 | Shelton, IV et al. |
| 2011/0295074 | A1 | 12/2011 | Stefanchik et al. |
| 2012/0130188 | A1 | 5/2012 | Okoniewski |
| 2013/0266029 | A1 | 10/2013 | Yi et al. |
| 2014/0066717 | A1 | 3/2014 | Rogers et al. |
| 2017/0055819 | A1 | 3/2017 | Hansen et al. |
| 2017/0086653 | A1 | 3/2017 | Yeung et al. |
| 2017/0128041 | A1 | 5/2017 | Hasser et al. |
| 2017/0128144 | A1 | 5/2017 | Hasser et al. |
| 2017/0128145 | A1 | 5/2017 | Hasser et al. |
| 2017/0251900 | A1 | 9/2017 | Hansen et al. |
| 2018/0070800 | A1* | 3/2018 | Yeung ................ A61B 1/00087 |
| 2018/0177556 | A1 | 6/2018 | Noonan |
| 2019/0117209 | A1 | 4/2019 | Augelli et al. |
| 2019/0200844 | A1 | 7/2019 | Shelton, IV et al. |
| 2019/0200981 | A1 | 7/2019 | Harris et al. |
| 2019/0201046 | A1 | 7/2019 | Shelton, IV et al. |
| 2019/0201088 | A1 | 7/2019 | Shelton, IV et al. |
| 2019/0201114 | A1 | 7/2019 | Shelton, IV et al. |
| 2019/0201136 | A1 | 7/2019 | Shelton, IV et al. |
| 2019/0201140 | A1 | 7/2019 | Yates et al. |
| 2019/0204201 | A1 | 7/2019 | Shelton, IV et al. |
| 2019/0206004 | A1 | 7/2019 | Shelton, IV et al. |
| 2019/0206555 | A1 | 7/2019 | Morgan et al. |
| 2019/0207857 | A1 | 7/2019 | Shelton, IV et al. |
| 2020/0000530 | A1 | 1/2020 | Defonzo et al. |
| 2020/0015668 | A1 | 1/2020 | Scheib |
| 2020/0015897 | A1 | 1/2020 | Scheib et al. |
| 2020/0015898 | A1 | 1/2020 | Scheib et al. |
| 2020/0015899 | A1 | 1/2020 | Scheib et al. |
| 2020/0015900 | A1 | 1/2020 | Scheib et al. |
| 2020/0015901 | A1 | 1/2020 | Scheib et al. |
| 2020/0015902 | A1 | 1/2020 | Scheib et al. |
| 2020/0015903 | A1 | 1/2020 | Scheib et al. |
| 2020/0015906 | A1 | 1/2020 | Scheib et al. |
| 2020/0015907 | A1 | 1/2020 | Scheib |
| 2020/0015914 | A1 | 1/2020 | Scheib et al. |
| 2020/0015923 | A1 | 1/2020 | Scheib et al. |
| 2020/0015924 | A1 | 1/2020 | Scheib et al. |
| 2020/0015925 | A1 | 1/2020 | Scheib |
| 2020/0037863 | A1* | 2/2020 | Harris ................ A61B 1/00087 |
| 2020/0060524 | A1 | 2/2020 | Weitzner |
| 2020/0085516 | A1 | 3/2020 | Defonzo et al. |
| 2020/0170720 | A1 | 6/2020 | Ummalaneni |
| 2020/0178948 | A1* | 6/2020 | Piskun ................ A61B 1/0058 |
| 2020/0188043 | A1 | 6/2020 | Yu et al. |
| 2021/0196108 | A1 | 7/2021 | Shelton, IV et al. |
| 2021/0196109 | A1 | 7/2021 | Shelton, IV et al. |
| 2021/0196381 | A1 | 7/2021 | Eckert et al. |
| 2021/0196383 | A1 | 7/2021 | Shelton, IV et al. |
| 2021/0196384 | A1 | 7/2021 | Shelton, IV et al. |
| 2021/0196385 | A1 | 7/2021 | Shelton, IV et al. |
| 2021/0196386 | A1 | 7/2021 | Shelton, IV et al. |
| 2021/0196423 | A1 | 7/2021 | Shelton, IV et al. |
| 2021/0196424 | A1 | 7/2021 | Shelton, IV et al. |
| 2021/0196425 | A1 | 7/2021 | Shelton, IV et al. |
| 2021/0199557 | A1 | 7/2021 | Shelton, IV et al. |
| 2021/0345952 | A1 | 11/2021 | Harris et al. |
| 2021/0345953 | A1 | 11/2021 | Shelton, IV et al. |
| 2021/0346015 | A1 | 11/2021 | Krulevitch et al. |
| 2021/0350895 | A1 | 11/2021 | Bakos et al. |
| 2021/0350896 | A1 | 11/2021 | Shelton, IV et al. |
| 2021/0350897 | A1 | 11/2021 | Shelton, IV et al. |

OTHER PUBLICATIONS

Lee et al. (Nov. 11-15, 2007) "Design of a Magnetic Field-Based Multi Degree-of-Freedom Orientation Sensor Using the Distributed-Multiple-Pole Model", IMECE2007-42106—Proceedings of IMECE2007, 2007 ASME International Mechanical Engineering Congress and Exposition, Seattle, Washington, USA, 6 pages.
U.S. Appl. No. 17/449,767, filed Oct. 1, 2021, Surgical Anchoring Systems for Endoluminal Access.
U.S. Appl. No. 17/449,769, filed Oct. 1, 2021, Instrument Control Surgical Imaging Systems.
U.S. Appl. No. 17/449,770, filed Oct. 1, 2021, Instrument Control Imaging Systems for Visualization of Upcoming Surgical Procedure Steps.
U.S. Appl. No. 17/449,771, filed Oct. 1, 2021, Coordinated Instrument Control Systems.
U.S. Appl. No. 17/449,772, filed Oct. 1, 2021, Surgical Systems and Methods for Selectively Pressurizing a Natural Body Lumen.
U.S. Appl. No. 17/491,383, filed Sep. 30, 2021, Surgical Systems With Port Devices for Instrument Control.
U.S. Appl. No. 17/491,437, filed Sep. 30, 2021, Surgical Sealing Systems for Instrument Stabilization.
U.S. Appl. No. 17/493,526, filed Oct. 4, 2021, Surgical Systems With Devices for Both Intraluminal and Extraluminal Access.
U.S. Appl. No. 17/493,535, filed Oct. 4, 2021, Surgical Systems With Intraluminal and Extraluminal Cooperative Instruments.
U.S. Appl. No. 17/493,545, filed Oct. 4, 2021, Surgical Systems for Independently Insufflating Two Separate Anatomic Spaces.
U.S. Appl. No. 17/491,375, filed Sep. 30, 2021, Surgical Sealing Devices for a Natural Body Orifice.
International Search Report and Written Opinion for International Application No. PCT/IB2022/059103, dated Jan. 2, 2023, 16 pages.
Invitation to Pay Additional Fees for International Application No. PCT/IB2022/059079 dated Jan. 12, 2023, 12 pages.
Invitation to Pay Additional Fees for International Application No. PCT/IB2022/059080 dated Dec. 9, 2022, 16 pages.

* cited by examiner

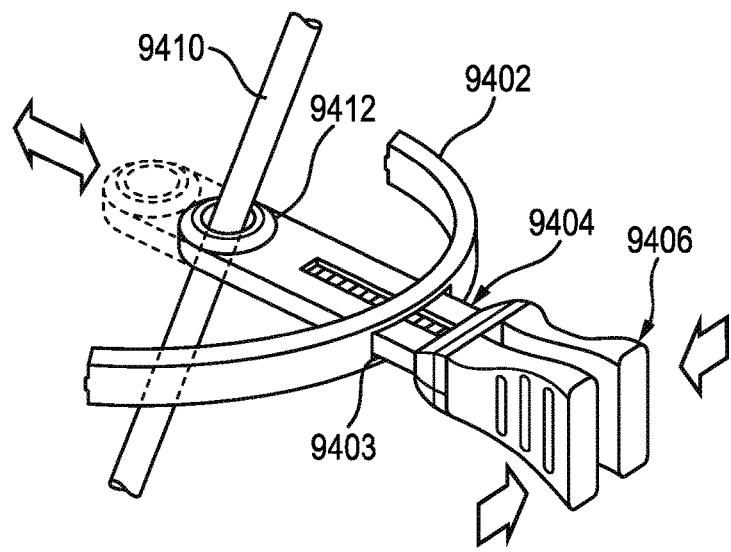
FIG. 70
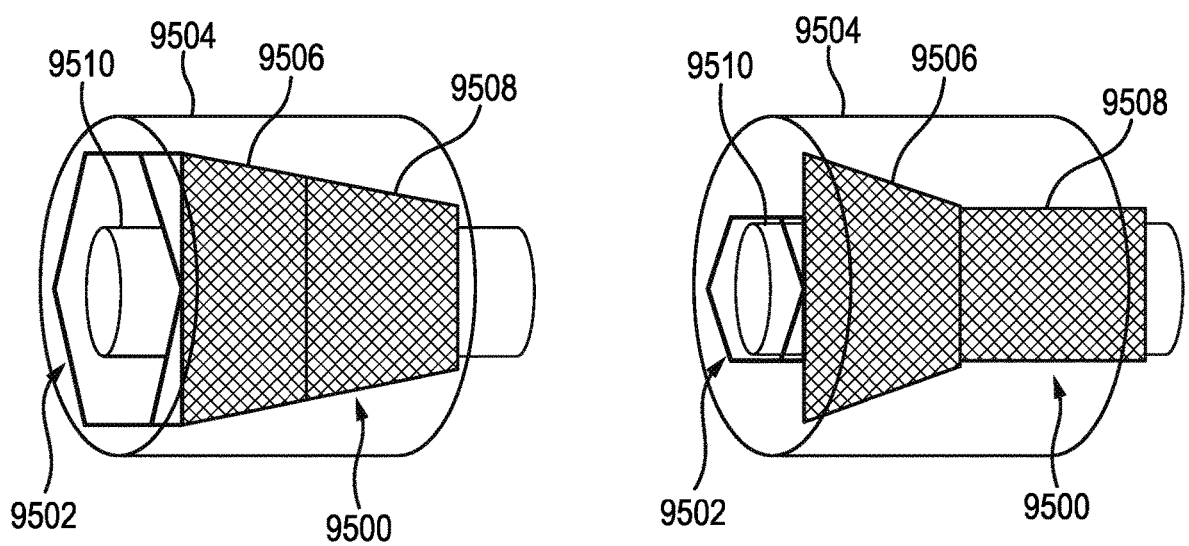
FIG. 71  FIG. 72

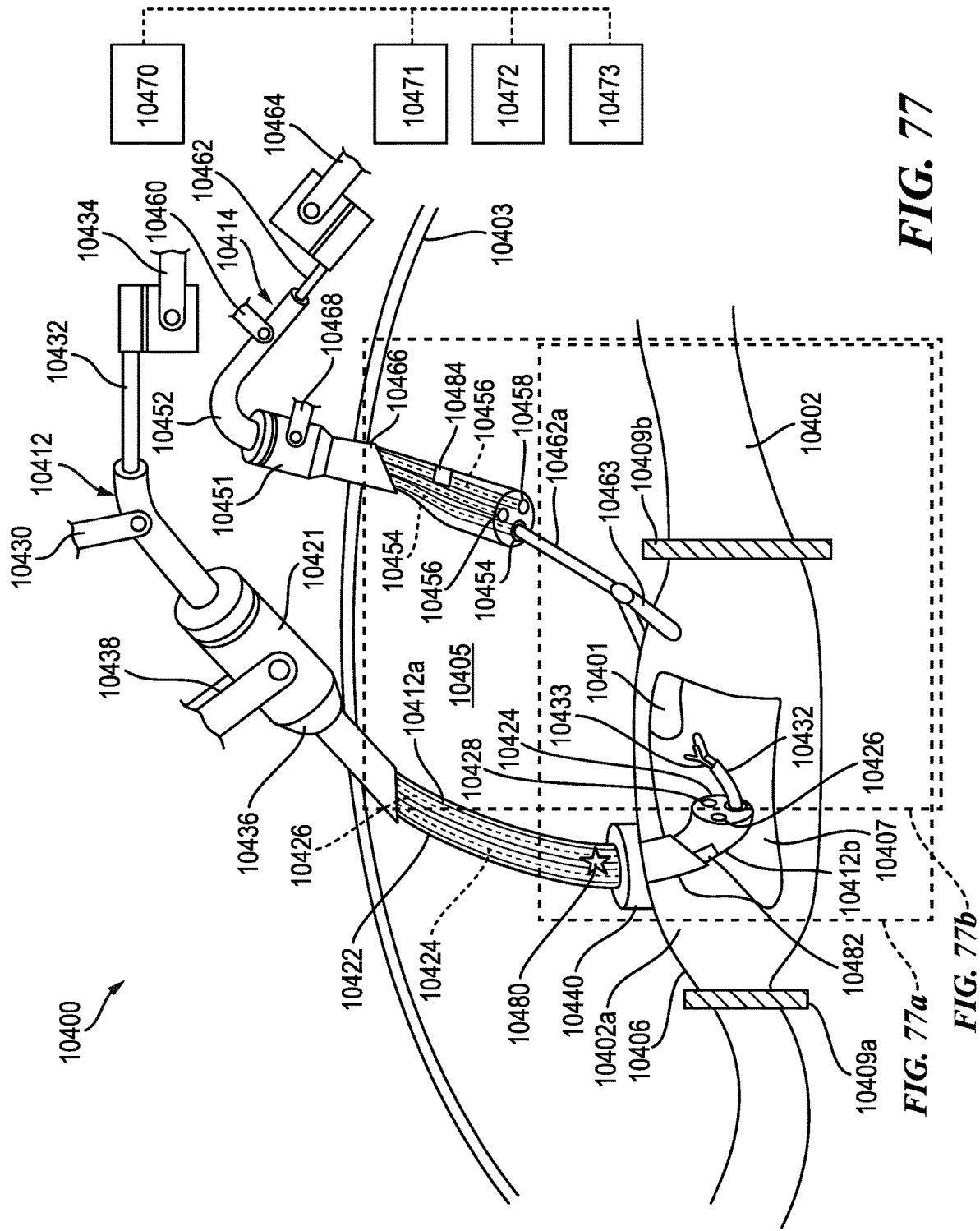

COOPERATIVE ACCESS HYBRID PROCEDURES

CROSS-REFERENCE TO RELATED APPLICATIONS

This application claims priority to U.S. Provisional Patent Application No. 63/249,980 filed on Sep. 29, 2021, and entitled "Cooperative Access," the disclosure of which is incorporated herein by reference in its entirety.

FIELD

The present invention relates generally to surgical systems and methods of using the same for anchoring, cooperative endoscopic and laparoscopic access and tissue manipulation, etc.

BACKGROUND

Surgical systems often incorporate an imaging system, which can allow medical practitioners to view a surgical site and/or one or more portions thereof on one or more displays, (e.g., a monitor, a computer tablet screen, etc.). The display(s) can be local and/or remote to a surgical theater. The imaging system can include a scope with a camera that views the surgical site and transmits the view to the one or more displays viewable by medical practitioner(s).

Imaging systems can be limited by the information that they are able to recognize and/or convey to the medical practitioner(s). For example, certain concealed structures, physical contours, and/or dimensions within a three-dimensional space may be unrecognizable intraoperatively by certain imaging systems. For another example, certain imaging systems may be incapable of communicating and/or conveying certain information to the medical practitioner(s) intraoperatively.

Accordingly, there remains a need for improved surgical imaging.

SUMMARY

Methods of operating a surgical anchoring system are provided. In one exemplary embodiment, a method includes inserting an outer sleeve of a surgical instrument at least partially into a first natural body lumen, the outer sleeve having a working channel extending therethrough, and inserting at least one channel arm of the surgical instrument through the working channel of the outer sleeve and at least partially into a second natural body lumen that is in communication with the first natural body lumen. The at least one channel arm has at least one first anchor member coupled thereto and at least one control actuator operatively coupled to the at least one first anchor member. The method further includes expanding the at least one first anchor member from an unexpanded state to an expanded state to form an anchor point at a portion of the second natural body lumen, and controlling, by the control actuator, a motion of the at least one channel arm to selectively manipulate an organ associated with the first and second natural body lumens.

In some embodiments, the surgical instrument can include at least one second anchor member that can be operatively coupled to the outer sleeve. The method can include expanding the at least one second anchor member from an unexpanded state to an expanded state to form an anchor point at a portion of the first natural body lumen. In certain embodiments, the at least one second anchor member, when in the expanded state, can at least partially contact the internal surface of the first natural body lumen.

In some embodiments, the at least one anchor member, when in the expanded state, can at least partially contact the internal surface of the second natural body lumen.

In some embodiments, the method can include applying a force to the second natural body lumen through the at least one first anchor member to manipulate the second natural body lumen relative to the first natural body lumen.

In some embodiments, the method can include coordinating, with a controller, a motion of the at least one channel arm within the second natural body lumen with a motion of at least one instrument arranged outside of the second natural body lumen to prevent tearing of the second natural body lumen.

In some embodiments, the method can include moving, by the control actuator, the at least one first anchor member axially along a length of the at least one channel arm.

In some embodiments, the method can include selectively locking, by a releasable locking mechanism, the at least one first anchor member at an axial position along a length of the at least one channel arm.

In another exemplary embodiment, a method includes inserting an instrument at least partially into a natural body lumen, in which the instrument has an anchor assembly coupled to a tubular member, and the anchor assembly has a first anchor and a second anchor that is distal to the first anchor. The method includes expanding the first anchor member from an unexpanded state to an expanded state to anchor the first anchor member to a first anatomical location within the natural body lumen, expanding the second anchor member from an unexpanded state to an expanded state to anchor the second anchor member to a second anatomical location within the natural body lumen, and moving the second anchor member relative to the first anchor member to selectively reposition the second anatomical location relative to the first anatomical location.

In some embodiments, the method can include positioning an endoscope within a central lumen of the tubular member.

The first and second anchor members can have a variety of configurations. In some embodiments, expanding the first anchor member can include deforming a plurality of expandable anchoring elements of the first anchor member such that the first anchor member can contact an inner surface of the natural body lumen at the first anatomical location. In certain embodiments, expanding the second anchor member can include deforming a plurality of expandable anchoring elements of the second anchor member such that the second anchor member can contact an inner surface of the natural body lumen at the second anatomical location.

The anchor assembly can have a variety of configurations. In some embodiments, the anchor assembly can include a plurality of actuators that can pass through the first plurality of working channels of the first anchor member, the second plurality of working channels of the second anchor member, and the third plurality of working channels of the tubular member. In such embodiments, expanding the second anchor member can include rotating the plurality of actuators to expand a plurality of expandable anchoring elements of the second anchor member. In other embodiments, the anchor assembly can include a plurality of actuators that pass through the first plurality of working channels of the first anchor member and the third plurality of working channels of the tubular member. In such embodiment, the method can include rotating the plurality of actuators to axially displace the second anchor member relative to the first anchor member. In yet other embodiments, the anchor assembly can include a plurality of actuators that pass through the first plurality of working channels of the first anchor member and the third plurality of working channels of the tubular member, and terminate at a proximal surface of the second anchor member. In such embodiments, expanding the first anchor member can include rotating the plurality of actuators to expand a plurality of expandable anchoring elements of the first anchor member.

In other embodiments, surgical anchoring systems are provided. In one exemplary embodiment, a surgical anchoring system anchoring system includes a surgical instrument having an outer sleeve defining a working channel therethrough and configured to be at least partially disposed within a first natural body lumen, and at least one channel arm configured to extend through the working channel and configured to move independently relative to each other. The at least one channel arm has at least one anchor member coupled to the at least one channel arm and at least one control actuator that extends along the at least one channel arm and is operatively coupled to the at least one anchor member. The at least one anchor member is configured to move between expanded and unexpanded states, and when in the expanded state, the at least one anchor member is configured to be at least partially disposed within a second natural body lumen, the second natural body lumen being in communication with the first natural body lumen. The at least one control actuator is operatively coupled to a drive system that is configured to control motion of the at least one channel arm to selectively manipulate an organ associated with the first and second natural body lumens.

The surgical instrument can have a variety of configurations. In some embodiments, the surgical instrument can include an anchoring balloon arranged proximal to a distal end of the outer sleeve. In certain embodiments, the anchoring balloon can be configured to expand and at least partially contact an internal surface of the first natural body lumen.

The anchor member can have a variety of configurations. In some embodiments, the at least one anchor member can be configured to expand and at least partially contact the internal surface of the second natural body lumen. In certain embodiments, the at least one anchor member can be configured to move axially along a length of the channel arm. In such embodiments, the at least one anchor member can be configured to be selectively locked at an axial position along the length of the at least one channel arm by a releasable locking mechanism.

The at least one channel arm can have a variety of configurations. In some embodiments, the at least one channel arm can be configured to apply a force to the second natural body lumen through at least one anchor member so as to manipulate the second natural body lumen relative to the first natural body lumen. In certain embodiments, the at least one channel arm can include an optical sensor arranged at a distal end of the at least one channel arm.

In some embodiments, the surgical anchoring system can include a controller that can be configured to coordinate a motion of the at least one channel arm within the second natural body lumen and a motion of at least one instrument outside of the second natural body lumen to prevent tearing of the second natural body lumen.

In another exemplary embodiment, a surgical anchoring system includes a tubular member and an anchoring assembly coupled to a distal portion of the tubular member and extending distally therefrom. The tubular member is configured for endoluminal access and has a central lumen therein configured to allow an endoscope to pass therethrough. The anchoring assembly includes a first anchor member coupled to the tubular member and a second anchor member that is moveable relative to the first anchor member and positioned distal to the first anchor member. The first anchor member is configured to engage a first anatomical location and secure the first anatomical location relative to the tubular member, and the second anchor member is configured to engage a second anatomical location that is moveable relative to the first anatomical location, in which movement of the second anchor member relative to the first anchor member is effective to selectively reposition the second anatomical location relative to the first anatomical location.

The first and second anchor members can have a variety of configurations. In some embodiments, the first anchor member can include a first plurality of working channels extending therethrough and a first plurality of expandable anchoring elements. In such embodiments, the second anchor member can include a second plurality of working channels extending therethrough and a second plurality of expandable anchoring elements. In such embodiments, the tubular member can include a third plurality of working channels extending therethrough.

In some embodiments, the surgical anchoring system can include a plurality of first actuators that pass through first working channels of the first plurality of working channels of the first anchor member and first working channels of the third plurality of working channels of the tubular member. In such embodiments, the plurality of first actuators can be configured to rotate to expand the first plurality of expandable anchoring elements.

In other embodiments, the surgical anchoring system can include a plurality of second actuators that pass through second working channels of the first plurality of working channels of the first anchor member, first working channels of the second plurality of working channels of the second anchor member, and second working channels of the third plurality of working channels of the tubular member. In such embodiments, the plurality of second actuators can be configured to rotate to expand the second plurality of expandable anchoring elements.

In yet other embodiments, the surgical anchoring system can include a plurality of third actuators that pass through third working channels of the first plurality of working channels of the first anchor member and third working channels of the third plurality of working channels of the tubular member, and can terminate at a proximal surface of the second anchor member. In certain embodiments, the plurality of third actuators can be configured to rotate to axially displace the second anchor relative to the first anchor. In some embodiments, the plurality of third actuators can be configured to be extended, retracted, or bent to selectively reposition the second anatomical location relative to the first anatomical location.

In other embodiments, surgical systems for endoscopic and laparoscopic surgical procedures are provided. In one exemplary embodiment, a surgical system includes a first scope device, a second scope device, a tracking device, and a controller. The first scope device is configured to be at least partially disposed within at least one of a natural body lumen and an organ and configured to transmit image data of a first scene within a field of view of the first scope device. The second scope device is configured to be at least partially disposed outside of the at least one of the natural body lumen and the organ and to transmit image data of a second scene within a field of view of the second scope device, the second scene being different than the first scene. The tracking device is associated with one of the first scope device or the second scope device and configured to transmit a signal indicative of a location of the one of the first scope device or the second scope device relative to the other one of the first scope device or the second scope device. The controller is configured to receive (i) the transmitted image data of the first and second scenes and (ii) the transmitted signal, to determine, based on the transmitted signal, a relative distance between the first scope device and the second scope device, and to provide, based on the transmitted image data and relative distance between the first and second scopes, a merged image of at least a portion of at least the first scope device and the second scope device in a single scene. At least one of the first scope device and the second scope device in the merged image is a representative depiction thereof.

The first and second scope devices can have a variety of configurations. In some embodiments, the first scope device and the second scope device can each be illustrated as a representative depiction thereof in the merged image. In certain embodiments, the first scope device can be an endoscope and the second scope device can be a laparoscope.

In some embodiments, the first scene cannot include the second scope device, and the second scene cannot include the first scope device.

In some embodiments, the surgical system can include a first display that can be configured to display the first scene and a second display that can be configured to display the second scene. In such embodiments, at least one of the first display and the second display can be further configured to display the single scene. In such embodiments, the surgical system can include a third display that can be configured to display the single scene.

The tracking device can have a variety of configurations. In some embodiments, the tracking device can be associated with the first scope device. In other embodiments, the tracking device can be associated with the second scope device.

In some embodiments, the signal can be further indicative of an orientation of the first scope device within one of the natural body lumen and the organ relative to the second scope device, and the controller can be further configured to determine, based on the transmitted signal, a relative orientation of the first scope device. In certain embodiments, the signal can be further indicative of an orientation of the second scope device positioned outside of the at least one of the natural body lumen and the organ relative to the first scope device, and the controller can be further configured to determine, based on the transmitted signal, a relative orientation of the second scope device.

The controller can have a variety of configurations. In some embodiments, the controller can be further configured to determine, based on at least the transmitted image data, at least one of a location and an orientation of at least one instrument positioned outside of the at least one natural body lumen and the organ relative to the first scope device, in which at least a portion of the at least one instrument can be illustrated as an actual depiction or representative depiction thereof in the merged image. In certain embodiments, the controller can be further configured to (i) receive an additional signal that is indicative of at least one of a location and an orientation of at least one instrument positioned outside of the at least one natural body lumen and the organ relative to the second scope device, (ii) to determine, based on the transmitted additional signal, at least one of a relative location and a relative orientation of the at least one instrument, in which at least a portion of the at least one instrument can be illustrated as an actual depiction or representative depiction thereof in the merged image.

Methods of operating a surgical system are also provided. In one exemplary embodiment, a method includes transmitting, by a first scope device, image data of a first scene within a field of view of the first scope device while at least a portion of the first device is positioned within at least one of a natural body lumen and an organ, transmitting, by a second scope device, image data of a second scene within a field of view of the second scope device while the second scope device is positioned outside of the at least one of the natural body lumen and the organ, the second scene being different than the first scene, and transmitting, by a tracking device, a signal indicative of a location of one of the positioned first scope device or second scope device relative to the other positioned first scope device or second scope device. The method further includes receiving, by a controller, the transmitted image data of the first and second scenes and the transmitted signals of the location of the first and second scope devices, and determining, by the controller and based on the transmitted signal, a relative distance between the first scope device and the second scope device. The method further includes generating, by the controller and based on the transmitted image data and the relative distance between the first and second scope devices, a merged image of at least a portion of at least the first scope device and the second scope device in a single scene, in which at least one of the first scope device and the second scope device in the single scene is a representative depiction thereof.

In some embodiments, the method can include illustrating a representative depiction of the first scope device in the merged image, and illustrating a representative depiction of the second scope device in the merged image.

In some embodiments, the method can include displaying the first scene on a first display, and displaying the second scene on a second display.

In some embodiments, the method can include displaying the single scene on at least one of the first display and the second display.

In some embodiments, the method can include transmitting, by the tracking device, a signal indicative of an orientation of the one of the first scope device or the second scope device relative to the other one of the first scope device or the second scope device.

In some embodiments, the method can include determining, by the controller and based on the transmitted image data, at least one of a position and an orientation of at least one or more instruments positioned outside of the at least one natural body lumen and the organ relative to the first scope device.

In other embodiments, surgical systems for endoscopic and laparoscopic surgical procedures are provided. In one exemplary embodiment, a surgical system includes an energy applying surgical instrument, a first scope device, a second scope device, and a controller. The energy applying surgical instrument is configured to be at least partially disposed within at least one of a natural body lumen and an organ and configured to apply energy to at least one of the natural body lumen and the organ. The first scope device is configured to be at least partially disposed within at least one of the natural body lumen and the organ and configured to transmit image data of a first scene within a field of view of the first scope device. The second scope device is configured to be at least partially disposed outside of at least one of the natural body lumen and the organ and configured to transmit image data of a second scene within a field of view of the second scope device. The controller is configured to receive the transmitted image data of the first and second scenes and to provide a merged image of first and second scenes. The merged image facilitates coordination of a location of energy to be applied by the energy applying surgical instrument to an inner surface of a tissue wall at a surgical site relative to an intended interaction location of a second instrument on an outer surface of the tissue wall in a subsequent procedure step at the surgical site.

In some embodiments, the surgical system can include a first display that is configured to display the first scene and a second display that is configured to display the second scene. In such embodiments, at least one of the first display and the second display can be further configured to display the merged image.

The controller can have a variety of configurations. In some embodiments, the controller can be configured to provide a representation of an intended interaction location of the second instrument in the merged image. In such embodiments, the first scene cannot include the second scope device, and the second scene does not include the first scope device. In such embodiments, the controller can be configured to determine the second interaction location based on one or more remaining steps in a procedure plan.

In some embodiments, the controller can be configured to determine, based on the transmitted image data, at least one of a location and an orientation of a second instrument positioned outside of the at least one natural body lumen and the organ relative to the first scope device, in which at least a portion of the at least one instrument can be illustrated as an actual depiction or representative depiction thereof in the merged image. In certain embodiments, the controller can be configured to calculate an insertion depth of the energy applying surgical instrument within tissue of the at least one of the natural body lumen and the organ based on the transmitted image data.

The energy applying surgical instrument can have a variety of configurations. In some embodiments, the energy applying surgical instrument can include a force sensor that can be configured to sense a force applied to at least one of the natural body lumen and the organ by the energy applying surgical instrument. In such embodiments, the controller can be configured to determine an insertion depth of the energy applying surgical instrument based on the sensed applied force.

Methods of operating a surgical system are also provided. In one exemplary embodiment, a method includes transmitting, by a first scope device, image data of a first scene within a field of view of the first scope device while at least a portion of the first device is positioned within at least one of a natural body lumen and an organ, and transmitting, by a second scope device, image data of a second scene within a field of view of the second scope device while the second scope device is positioned outside of the at least one of the natural body lumen and the organ, the second scene being different than the first scene. The method further includes inserting at least a portion of a surgical instrument into at least one of a natural body lumen and an organ. The method further includes receiving, by a controller, the transmitted image data of the first and second scenes of the first and second scope devices. The method further includes determining, by the controller and based on the transmitted image data, i) a first interaction location configured to be created inside of at least one of the natural body lumen and the organ by the surgical instrument, and ii) a second interaction location configured to be created outside of at least one of the natural body lumen and the organ. The method further includes generating, by the controller and based on the transmitted image data, the first interaction location, and the second interaction location, a merged image of at least a portion of at least the first scope device and the second scope device, and at least one of the first interaction location and the second interaction location in a single scene. At least one of the first interaction location and the second interaction location in the single scene is a representative depiction thereof.

In some embodiments, the method can include displaying the first scene on a first display and displaying the second scene on a second display. In such embodiments, the method can include displaying the merged image on at least one of the first display and the second display.

In some embodiments, the method can include determining, by the controller and based on the transmitted image data, at least one of a position and an orientation of second instrument positioned outside of the at least one natural body lumen and the organ relative to the first scope device.

In some embodiments, the method can include determining, by the controller, the first interaction location and the second interaction location based on a plurality of remaining steps in a procedure plan.

In some embodiments, the method can include positioning a second surgical instrument at least partially outside of at least one of the natural body lumen and the organ.

In some embodiments, the method can include determining, by the controller, an insertion depth of the surgical instrument within tissue of the at least one of the natural body lumen and the organ based on the transmitted image data.

In some embodiments, the method can include creating a first incision from inside of the at least one of the natural body lumen and organ using the surgical instrument along the first interaction location. In such embodiments, the method can include creating a second incision from outside of the at least one of the natural body lumen and organ using a second surgical instrument positioned at least partially outside of at least one of the natural body lumen and the organ along the second interaction location.

In some embodiments, the first interaction location can abut the second interaction location.

In other embodiments, surgical systems for endoscopic and laparoscopic surgical procedures are provided. In one exemplary embodiment, a surgical system includes a first scope device, a second scope device, a first surgical instrument, a second surgical instrument, a tracking device, and a controller. The first scope device is configured to be at least partially disposed within at least one of a natural body lumen and an organ and configured to transmit image data of a first scene within a field of view of the first scope device. The second scope device is configured to be at least partially disposed outside of the at least one of the natural body lumen and the organ and configured to transmit image data of a second scene within a field of view of the second scope device, in which the second scene is different than the first scene. The tracking device is associated with one of the first scope device or the second scope device and configured to transmit a signal indicative of a location of the one of the first scope device or the second scope device relative to the other one of the first scope device or the second scope device. The first surgical instrument is configured to be at least partially disposed within at least one of the natural body lumen and the organ and configured to interact with an internal side of a target tissue structure at a surgical site. The second surgical instrument is configured to be at least partially disposed outside of the at least one of the natural body lumen and the organ and configured to interact an external side of the target tissue structure. The controller is configured to receive (i) the transmitted image data of the first and second scenes and (ii) the transmitted signal, to determine, based on the transmitted image data and transmitted signal, a first relative distance from the first scope device to the second scope device, a second relative distance from the first scope device to the first surgical instrument positioned within at least one natural body lumen and organ, and a third relative distance from the second scope device to the second surgical instrument positioned outside of at least one natural body lumen and the organ. The relative movements of the first and second instruments at the surgical site are coordinated based on the determined relative distances.

The first and second scope devices can have a variety of configurations. In some embodiments, the first scope device can be an endoscope and the second scope device can be a laparoscope.

In some embodiments, the first scene cannot include the second scope device, and the second scene cannot include the first scope device. In other embodiments, the first scene cannot include the second instrument, and the second scene cannot include the first instrument.

The first tracking device and the second tracking device can have a variety of configurations. In some embodiments, the tracking device can be further configured to transmit a signal indicative of an orientation of the first scope device within one of the natural body lumen and the organ. In such embodiments, the tracking device can be further configured to transmit a signal indicative of an orientation of the second scope device positioned outside of the at least one of the natural body lumen and the organ.

The controller can have a variety of configurations. In some embodiments, the controller can be configured to simultaneously move the first instrument and the second instrument relative to each other based on the determined relative distances. In certain embodiments, the controller can be configured to restrict movement of the first instrument and the second instrument relative to each other at the target tissue structure based on the transmitted image data of the first and second scenes and the transmitted signal. In other embodiments, the controller can be further configured to determine an amount of strain that is applied to the target tissue structure by at least one of the first and second instruments with the use of visual markers associated with the target tissue structure. In such embodiments, the visual markers can be at least one of one or more local tissue markings on the target tissue structure, one or more projected light markings on the target tissue structure, and one or more anatomical aspects of at least one of the natural body lumen and organ.

The first and second instruments can have a variety of configurations. In some embodiments, the first instrument can include a first force sensor configured to sense an applied force to the target tissue structure by the first instrument, and the second instrument can include a second force sensor configured to sense an applied force to the target tissue structure by the second instrument.

Methods of operating a surgical system are also provided. In one exemplary embodiment, a method includes transmitting, by a first scope device, image data of a first scene within a field of view of the first device while at least a portion of the first device is positioned within at least one of a natural body lumen and an organ, and transmitting, by a second scope device, image data of a second scene within a field of view of the second scope device while the second scope device is positioned outside of the at least one of the natural body lumen and the organ, the second scene being different than the first scene. The method further includes transmitting, by a tracking device, a signal indicative of a location of the one of the first scope device or the second scope device relative to the other one of the first scope device or the second scope device. The method further includes receiving, by a controller, the transmitted image data of the first and second scenes and the transmitted signal of the location of the first and second scope devices, and determining, by the controller, a first relative distance from the first scope device to the second scope device, a second relative distance from the first scope device to the first instrument positioned within at least one natural body lumen and organ, and a third relative distance from the second scope device to the second instrument positioned outside of at least one natural body lumen and the organ. The method further includes moving, by the controller, the first instrument and the second instrument at the target tissue structure relative to each other based on the determined relative distances.

In some embodiments, the method can include transmitting, by the tracking device, a signal indicative of an orientation of the first scope device within one of the natural body lumen and the organ.

In some embodiments, the method can include transmitting, by the tracking device, a signal indicative of an orientation of the second scope device positioned outside of the at least one of the natural body lumen and the organ.

In some embodiments, the method can include simultaneously moving, by the controller, the first instrument and the second instrument relative to each other based on the determined relative distances.

In some embodiments, the method can include restricting, by the controller, movement of at least one of the first instrument and the second instrument relative to each other at the target tissue structure based on the transmitted image data of the first and second scenes and the transmitted signal.

In some embodiments, the method can include determining, by the controller, an amount of strain applied to the target tissue structure by at least one of the first and second instruments based on visual markers associated with the target tissue site.

The first instrument can have a variety of configurations. In some embodiments, the first instrument can include a force sensor. In such embodiments, the method can include sensing, via the force sensor, a force applied to the target tissue structure by the first instrument.

The second instrument can have a variety of configurations. In some embodiments, the second instrument can include a force sensor. In such embodiments, the method can include sensing, via the force sensor, a force applied to the target tissue structure by the second instrument.

In other embodiments, surgical systems for use with a surgical instrument for endoluminal access are provided. In one exemplary embodiment, the surgical instrument includes at least one deployable sealing element and fluid channel. The at least one deployable sealing element is operatively coupled to the surgical instrument and configured to move between unexpanded and expanded states. When the sealing element is in the expanded state, the deployable sealing element is configured to form a first seal at a portion of a natural body lumen or an organ. The fluid channel extends through the surgical instrument and has an opening distal to the first seal. The fluid channel is configured to allow fluid ingress and egress distal to the portion of the natural body lumen or the organ while the at least one deployable sealing member is in the expanded state, thereby selectively pressurizing the natural body lumen or the organ distal to the portion.

The at least one deployable sealing element can have a variety of configurations. In some embodiments, the at least one deployable sealing element can be configured to expand to contact an internal surface of the natural body lumen or the organ. In certain embodiments, at least one deployable sealing element can be an inflatable balloon configured to be filled with a fluid to move from the unexpanded state to the expanded state.

In some embodiments, the surgical instrument can include an optical sensor arranged at a distal end thereof.

The surgical instrument can have a variety of configurations. In some embodiments, the surgical instrument can include a second deployable sealing element coupled to the surgical instrument and distal to the opening of the fluid channel. The second deployable sealing element can be configured to move between unexpanded and expanded states. In certain embodiments, when in the expanded state, the second deployable sealing element can be configured to form a second seal at a second portion of the natural body lumen or the organ. In some embodiments, the at least one deployable sealing element and the second deployable sealing element can be expanded separately. In other embodiments, the at least one deployable sealing element and the second deployable sealing element can be expanded simultaneously.

In some embodiments, when pressurized, the portion of the natural body lumen or organ distal to the at least one deployable sealing element has a first pressure, and a portion outside of the natural body lumen or organ has a second pressure, different than the first pressure.

Methods of operating the surgical systems are also provided. In one exemplary embodiment, a method of operating a surgical system can include inserting a surgical instrument into a natural body lumen or an organ. The surgical instrument has a fluid channel extending therethrough and at least one deployable sealing element operatively coupled to the surgical instrument. The method can include expanding a first deployable sealing element of the at least one deployable sealing element from an unexpanded state to an expanded state to form a first seal within the natural body lumen or the organ. The method can further include injecting fluid through the fluid channel and into a portion of the natural body lumen or the organ distal to the first seal to thereby inflate the portion of the natural body lumen or the organ. The method can further include pressurizing the portion of the natural body lumen or the organ.

The at least one deployable sealing element can have a variety of configurations. In some embodiments, the at least one deployable sealing element can be configured to expand to contact an internal surface of the natural body lumen or the organ. In some embodiments, at least one deployable sealing element can be configured to be filled with a fluid to move from the unexpanded state to the expanded state.

The surgical instrument can have a variety of configurations. In some embodiments, the surgical instrument can further include a second deployable sealing element coupled to the surgical instrument and distal to the opening of the fluid channel. The second deployable sealing element can be configured to transition between unexpanded and expanded states. In other embodiments, when in the expanded state, the second deployable sealing element can be configured to form a second seal within the natural body lumen or the organ, wherein the portion of the natural body lumen or the organ is located between the first and second deployable sealing elements. In some embodiments, a pressure differential can be created within the portion of the natural body lumen or the organ relative to an area outside of the natural body lumen or the organ. In other embodiments, the at least one deployable sealing element and the second deployable sealing element can be expanded separately. In certain embodiments, the at least one deployable sealing element and the second deployable sealing element can be expanded simultaneously.

In other embodiments, surgical sealing devices are provided. In one exemplary embodiment, a surgical sealing device includes a seal housing and at least one retention element. The seal housing is configured to be at least partially disposed within a natural body orifice and defining a plurality of ports. The plurality of ports includes at least one first port configured to control the ingress and egress of fluid between an interior volume of the natural body orifice and an ambient environment, and at least one second port that is configured to form a seal around an instrument inserted therethrough. The at least one retention element is arranged on an exterior surface of the housing and configured to affix the housing to the natural body orifice.

In some embodiments, the at least one first port can be operatively connected to a valve arranged outside of the seal housing.

In some embodiments, the valve can have at least one monitored parameter that can be used to control a fluid transfer rate through the at least one first port. In some embodiments, the at least one monitored parameter can be a fluid transfer pressure and/or volume and a direction of the fluid transfer.

The at least one retention element can have a variety of configurations. In some embodiments, the at least one retention element can be deployable inside of the natural body lumen. In other embodiments, the at least one retention element can be deployable outside of the natural body lumen. In some embodiments, the at least one retention element can be a barb extending from the exterior surface of the housing. In other embodiments, the at least one retention element can be a balloon that can be configured to be selectively inflated to contact an internal or an external surface of the natural body orifice and secure the housing thereto.

In some embodiments, the fluid can include at least one gas or at least one liquid. In other embodiments, the fluid can include at least one gas and at least one liquid.

In some embodiments, a control system can be configured to control the ingress and egress of fluid to create a pressure differential between the interior volume of the natural body orifice and the ambient environment.

In some embodiments, the ports of the surgical sealing device can be bi-directional.

Methods of accessing a natural body lumen are also provided. In one exemplary embodiment, a method includes positioning a surgical sealing device at least partially within the natural body orifice, in which the surgical sealing device has a seal housing defining a plurality of ports, releasably positioning at least one retention element configured to affix the seal housing to the natural body orifice, controlling the ingress and egress of a fluid between an interior volume of the natural body orifice and an ambient environment through at least one first port, and passing at least one surgical instrument through at least one second port such that the at least one second port forms a seal around the at least one surgical instrument. The surgical sealing device defines at least one passageway through the natural body orifice.

In some embodiments, the method can include removing the at least one surgical instrument from the at least one second port without removing the seal housing from the natural body lumen.

In some embodiments, the at least one first port can be operatively connected to a valve arranged outside of the seal housing. In such embodiments, the valve can have at least one monitored parameter which can be used to control a fluid transfer rate through the at least one first port. In such embodiments, the at least one monitored parameter can be a fluid transfer pressure and/or volume and a direction of the fluid transfer.

The at least one retention element can have a variety of configurations. For example, in some embodiments, the at least one retention element can be deployable inside of the natural body lumen. In other embodiments, the at least one retention element can be deployable outside of the natural body lumen.

In some embodiments, the fluid can include a dye. In certain embodiments, the fluid can include at least one gas or at least one liquid. In other embodiments, the fluid can include at least one gas and at least one liquid.

In other embodiments, surgical systems are also provided. In one exemplary embodiment, a surgical system includes a first port device configured to be at least partially disposed within a body, and a second port device configured to be at least partially disposed within the body. The first port device includes a first housing defining a first plurality of ports that are each configured to allow a respective instrument of a first set of instruments to be inserted therethrough. The first port device is further configured to interact with at least one respective instrument that is inserted through its respective port of the first plurality of ports so as to apply resistive forces to the at least one respective instrument to thereby limit one or more motions of the at least one respective instrument based on at least one of a location, orientation, and a motion of at least one other instrument of the first set of instruments that is inserted through its respective port. The second port device includes a second housing defining a second plurality of ports that are each configured to allow a respective instrument of a second set of instruments to be inserted therethrough. The second port device is further configured to interact with at least one respective instrument that is inserted through its respective port of the second plurality of ports so as to apply resistive forces to the at least one respective instrument to thereby limit one or more motions of the at least one respective instrument based on at least one of a location, orientation, and a motion of the other instruments of the second set of instruments. The first port device and the second port device are each configured to allow at least a portion of the first set of instruments and at least a portion of the second set of instruments to work cooperatively together.

The first set of instruments can have a variety of configurations. In some embodiments, the first set of instruments can include a first instrument and a second instrument. When the first and second instruments are inserted into respective ports of the first plurality of ports, the first port device can be configured to allow the first instrument to move within a first range of motion relative to the first port device and to allow the second instrument to move within a second range of motion relative to the first port device that at least partially overlaps with the first range of motion.

The second set of instruments can have a variety of configurations. In some embodiments, the second set of instruments can include a first instrument and a second instrument. When the first and second instruments are inserted into respective ports of the second plurality of ports, the second port device can be configured to allow the first instrument to move within a first range of motion relative to the second port device and to allow the second instrument to move within a second range of motion relative to the second port device that at least partially overlaps with the first range of motion.

The surgical systems can have a variety of configurations. In some embodiments, the surgical system can include a tracking device that can be configured to transmit a signal indicative of a location of the first port device relative to the second port device. In certain embodiments, the surgical system can include a tracking device that can be configured to transmit a signal indicative of at least one of a location, an orientation, and a motion of at least one inserted instrument of the first set of instruments relative to the second port device. In some embodiments, the surgical system can include a tracking device that can be configured to transmit a signal indicative of at least one of a location, an orientation, and a motion of at least one inserted instrument of the second set of instruments relative to the first port device.

The first and second plurality of ports can have a variety of configurations. In some embodiments, at least one port of the first plurality of ports can be configured to form a seal around a respective instrument of the first set of instruments when the respective instrument is inserted therethrough. In other embodiments, at least one port of the second plurality of ports can be configured to seal around a respective instrument of the second set of instruments when the respective instrument is inserted therethrough.

Methods of operating a surgical system are also provided. In one exemplary embodiment, a method includes inserting at least one instrument of a first set of instruments through a respective port of a first plurality of ports of a first port device that is at least partially positioned within the body, the first port device includes a first housing that defines the first plurality of ports, and inserting at least one instrument of a second set of instruments through a respective port of a second plurality of ports of a second port device that is at least partially positioned within the body, the second port device includes a second housing that defines the second plurality of ports. The method also includes transmitting, by a tracking device associated with one of the first port device or the second port device, a signal indicative of a location of one of the first port device or the second port device relative to the other one of the first port device or the second port device, a signal indicative of at least one of a location, an orientation, and a motion of at least one inserted instrument of the first set of instruments relative to the second port device, a signal indicative of at least one of a location, an orientation, and a motion of at least one inserted instrument of the second set of instruments relative to the first port device, or any combination. The method also includes moving at least one inserted instrument of the first set of instruments relative to the first housing to allow the first housing to interact with the at least one inserted instrument to thereby limit one or more motions of the at least one inserted instrument based on one or more of the transmitted signals, and moving at least one inserted instrument of the second set of instruments relative to the second housing to allow the second housing to interact with the at least one inserted instrument to thereby limit one or more motions of the at least one inserted instrument based on one or more of the transmitted signals.

In some embodiments, the method can include determining, by a controller, a relative location of the first port device and the second port device based on the respective transmitted signal. In certain embodiments, the method can include determining, by a controller, at least one of a location, an orientation, and a motion of the at least one inserted instrument of the first set of instruments relative to the second port device based on the respective transmitted signal. In other embodiments, the method can include determining, by a controller, at least one of a location, an orientation, and a motion of the at least one inserted instrument of the second set of instruments relative to the first port device based on the respective transmitted signal.

In some embodiments, the method can include creating a seal around a portion of the at least one inserted instrument of the first set of instruments. In certain embodiments, the method can include creating a seal around a portion the at least one inserted instrument of the second set of instruments.

In some embodiments, the method can include moving another inserted instrument of the first set of instruments to allow the first housing to interact with the another inserted instrument to thereby limit one or more motions of the another inserted instrument based on at least one of a location, an orientation, and a motion of the at least one inserted instrument of the first set of instruments. In certain embodiments, the method can include moving another inserted instrument of the second set of instruments to allow the second housing to interact with the another inserted instrument to thereby limit one or more motions of the another inserted instrument based on at least one of a location, an orientation, and a motion of the at least one inserted instrument of the second set of instruments.

In some embodiments, the method can include moving the at least one inserted instrument of the first set of instruments and the at least one inserted instrument of the second set of instruments in a coordinated direction relative to each other to cause the at least one inserted instrument of the first set of instruments and the at least one inserted instrument of the second set of instruments to work cooperatively together.

In other embodiments, surgical sealing systems are also provided. In one exemplary embodiment, the sealing system includes a sealing device having a seal housing with a predetermined size and shape. The seal housing is configured to be at least partially disposed within a body cavity and has a plurality of ports. Each of the plurality of ports has a nominal size and shape and each is configured to assume a selected size and/or shape that is different from the nominal size and/or shape. The selected size and/or shape of each port being constrained by the size and shape of each of the other plurality of ports, Each of the plurality of ports is configured to form a seal around an instrument inserted therethrough. The position of an instrument that is positioned within one port of the plurality of ports and a force applied thereto is effective to change the size and/or shape of the ports based on the movement, direction, and force of the instrument, and the ability to alter the nominal shape of any one port is constrained or limited by the size and/or shape of the other ports, thereby enabling a force applied to one instrument positioned within one of the plurality of ports to stabilize at least one other instrument positioned within others of the plurality of ports.

In some embodiments, the surgical sealing system can include at least one electromechanical arm, in which at least one instrument that is inserted into a respective port of the plurality of ports can be connected to the at least one electromechanical arm.

The surgical sealing device can have a variety of configurations. In some embodiments, the sealing device can include a retractor that can be coupled to the seal housing and can be configured to be positioned in a natural body orifice or an opening formed in tissue. In other embodiments, the sealing device can include at least one retention element that can be configured to affix the seal housing to tissue.

The plurality of ports can have a variety of configurations. In some embodiments, a first port of the plurality of ports can be configured to apply a first force to a first instrument that is inserted therethrough to thereby limit movement thereof within a first plane, and a second port of the plurality of ports can be configured to apply a second force to a second instrument that is inserted therethrough to thereby limit movement thereof within a second plane, the second plane being non-parallel to the first plane. In certain embodiments, one or more ports of the plurality of ports can be rigid relative to one or more other ports of the plurality of ports.

In some embodiments, at least one port of the plurality of ports can include a threaded restraint configured to fixate an instrument inserted therethrough. In other embodiments, at least one port of the plurality of ports can be configured to change shape and size in response to external energy being applied thereto.

In some embodiments, at least one port of the plurality of ports can be formed of a ferromagnetic material that can be configured to be structurally altered in response to exposure to an electromagnet. In other embodiments, at least one port of the plurality of ports can include a locking arm arranged within a slot of the seal housing, the locking arm can be configured to lock a position of the at least one port relative to the seal housing.

In some embodiments, at least one port of the plurality of ports can include a locking structure that can be configured to interact and collapse around an instrument passing therethrough to fixate the inserted instrument within the at least one port. In one embodiment, the locking structure can have a honeycomb configuration.

In some embodiments, a first instrument and a second instrument that can be inserted into respective ports of the plurality of ports can be stabilized simultaneously by a central anchoring tool that can be configured to be inserted through a port of the plurality of ports.

The surgical housing can have a variety of configurations. In some embodiments, the sealing housing can include a flexible inner body member and a rigid outer body member, wherein each port of the plurality of ports can be arranged within the inner body member. In one embodiment, at least one port of the plurality of ports can include a rigid ring encapsulated by the flexible inner body member.

In other embodiments, surgical systems are provided. In one exemplary embodiment, a surgical system includes a first scope device having a first portion configured to be inserted into and positioned within an extraluminal anatomical space and a second portion distal to the first portion and configured to be positioned within an intraluminal anatomical space, and a second instrument configured to be inserted into the extraluminal anatomical space and configured to couple to and move the first portion of the first scope device within the extraluminal anatomical space to facilitate movement of the second portion of the first scope device while the second portion is positioned within the intraluminal anatomical space. The first scope device includes a flexible body with a working channel extending therethrough and a first imaging system at a distal end thereof, the working channel being configured to enable a distal end of a first instrument to be inserted into and through the extraluminal anatomical space and into the intraluminal anatomical space such that the first instrument is present in both the extraluminal and intraluminal spaces.

The second instrument can have a variety of configurations. In some embodiments, the second instrument can be configured to couple to the first portion of the first scope device at a predefined location within the extraluminal anatomical space and directly adjacent a tissue wall defining at least a portion of the intraluminal anatomical space. In certain embodiments, the second instrument can include a rigid shaft with an end effector at a distal end thereof. The end effector can be configured to couple to the first portion of the first scope device.

In some embodiments, the system can include a cannula having a lumen extending therethrough. The cannula can be configured to be disposed within a tissue wall defining at least a portion of the intraluminal anatomical space and can be configured to allow a distal end of the flexible body to be inserted from the extraluminal anatomical space, through the lumen, and into the intraluminal anatomical space. In certain embodiments, the second instrument can be further configured to couple to and move the cannula to facilitate the movement of the second portion of the first scope device while the distal end of the flexible body is within the intraluminal anatomical space. In such embodiments, the second instrument can include a rigid shaft with an end effector at a distal end thereof. The end effector can be configured to couple to the cannula.

In some embodiments, the system can include a fluid port that can be configured to insufflate the extraluminal anatomical space.

In another exemplary embodiment, a surgical system can include an anchor member configured to be positioned within an extraluminal anatomical space and in contact with a tissue wall that at least partially defines an intraluminal anatomical space, a cannula having a first portion configured to be inserted into and positioned within the extraluminal anatomical space and a second portion distal to the first portion that is configured to be positioned within an intraluminal anatomical space, and a selectively deployable stabilizing member arranged on the first portion of the cannula in the extraluminal anatomical space. The cannula is configured to allow a distal end of a first instrument to be inserted into and through the extraluminal anatomical space and into the intraluminal anatomical space such that the first instrument is present in both the extraluminal and intraluminal anatomical spaces. The selectively deployable stabilizing member is configured to couple to the anchor member when in a deployed state to provide an anchor point for the first instrument to facilitate pivotal movement of the first instrument within the intraluminal anatomical space.

The anchor member can have a variety of configurations. In some embodiments, the anchor member can be further configured to seal a portion of the intraluminal anatomical space.

In some embodiments, the system can further include a magnet arranged within the anchor member. The magnet can be configured to couple the selectively deployable stabilizing member to the anchor member when the selectively deployable stabilizing member is in a deployed state.

In some embodiments, the system can include a first scope device that can be configured to be inserted into and through a lumen of the cannula such that a first portion of the scope device is present in the extraluminal anatomical space, and a second portion distal to the first portion is positioned in the intraluminal anatomical space.

Methods are also provided. In one exemplary embodiment, a method includes inserting a first portion of a first scope device into an extraluminal anatomical space, in which the first scope device has a flexible body with a working channel extending therethrough, inserting a second portion of the first scope device, distal to the first portion, into an intraluminal anatomical space, inserting a first instrument through the working channel to position the first instrument within both the extraluminal and intraluminal spaces, inserting a second instrument into the extraluminal anatomical space, and moving the second instrument to cause the inserted second portion of the first scope device to move within the intraluminal anatomical space.

In some embodiments, the method can includes coupling the second instrument to the first portion of the first scope device at a predefined location within the extraluminal anatomical space and directly adjacent a tissue wall defining at least a portion of the intraluminal anatomical space.

In some embodiments, the method can include inserting a cannula through a tissue wall defining at least a portion of the intraluminal anatomical space, in which the cannula includes a lumen extending therethrough, and inserting a distal end of the flexible body through the lumen and into the intraluminal anatomical space. In such embodiments, the method can include coupling the second instrument to the cannula and moving the cannula to cause the second portion of the first scope to move within the intraluminal anatomical space.

In some embodiments, the method can include insufflating the extraluminal anatomical space via a fluid port operatively coupled to the first portion of the first scope device.

In other embodiments, surgical systems are provided. In one exemplary embodiment, a surgical system includes a first scope device, a second scope device, and a controller. The first scope device has a first portion configured to be partially inserted into and positioned within an extraluminal anatomical space and a second portion distal to the first portion configured to be positioned within an intraluminal anatomical space. The first scope device is configured to transmit image data of a first scene within a field of view of the first scope device. The second scope device is configured to be at least partially inserted into and disposed within the extraluminal anatomical space and to transmit image data of a second scene within a field of view of the second scope device, the second scene being different than the first scene, in which at least a portion the first portion of the first instrument is present within the field of view of the second scope device to thereby track the first scope device relative to the second scope device. The controller is configured to receive the transmitted image data of the first and second scenes, to determine a relative distance from the second portion of the first scope device within the intraluminal anatomical space to the second scope device within the extraluminal space, and to provide a merged image of at least a portion of the first scope device and the second scope device in a single scene, in which at least one of a portion of the first scope device and the second scope device in the merged image is a representative depiction thereof.

In some embodiments, a portion of the first scope device and the second scope can be each shown as a representative depiction thereof in the merged image. In other embodiments, at least a portion of at least one of the first scope device and the second scope device can be shown as an actual depiction thereof in the merged image.

In some embodiments, the system can include a first display that can be configured to display the first scene and a second display that is configured to display the second scene. In certain embodiments, at least one of the first display and the second display can be configured to display the single scene. In certain embodiments, the system can include a third display that can be configured to display the single scene.

In some embodiments, the first scene cannot include the second scope device, and the second scene cannot include the second segment of the first scope device.

In some embodiments, the first scope device can include a flexible body with a working channel extending therethrough. The working channel can be configured to allow a distal end of an instrument to be inserted into and through the extraluminal space and into the intraluminal space such that the instrument is present in both the extraluminal and intraluminal spaces. In such embodiments, the second scene cannot include the distal end of the instrument.

In some embodiments, the first scope device can include a fiducial marker disposed on the first portion of the first scope device. In such embodiments, the controller can be configured to track the second portion of the first scope device based on the fiducial marker.

Methods are also provided. In one exemplary embodiments, a method includes transmitting, by a first scope device, image data of a first scene within a field of view of the first scope device while a first segment of a first scope device is positioned within an extraluminal anatomical space and a second segment of the first scope device, distal to the first segment, is positioned within an intraluminal anatomical space, transmitting, by a second scope device, image data of a second scene within a field of view of the second scope device while the second scope device is positioned within the extraluminal space, the second scene being different than the first scene, receiving, by a controller, the transmitted image data of the first and second scenes; determining, by the controller, a relative distance from the second segment of the first scope device within the intraluminal anatomical space to the second scope device within the extraluminal space, and generating a merged image of at least a portion of the first scope device and the second scope device in a single scene, wherein at least one of a portion of the first scope device and the second scope device shown in the single scene is a representative depiction thereof.

In some embodiments, the method can include displaying a representative depiction of a portion of the first scope device in the merged image, and displaying a representative depiction of the second scope device in the merged image.

In some embodiments, the method can include displaying the first scene on the first display, and displaying the second scene on the second display.

In some embodiments, the method can include displaying the single scene on at least one of the first display and the second display.

In some embodiments, the method can include displaying the single scene on a third display.

In some embodiments, the method can include inserting an instrument through a working channel of a flexible body of the first scope device to pass a distal end of an instrument into and through the extraluminal space and into the intraluminal space such that the instrument is present in both the extraluminal and intraluminal spaces. In such embodiments, the second scene cannot include the distal end of the instrument.

In some embodiments, the method includes tracking, by the controller, the second segment of the first scope device arranged within the intraluminal space based on a fiducial marker arranged on the first segment of the first scope device.

In some embodiments, the first scene cannot include the second scope device, and the second scene cannot include the first segment of the first scope device.

In other embodiments, surgical systems are provided. In one exemplary embodiment, a surgical system includes a first scope device, a first instrument, a second scope device, and a second instrument. The first scope device has a first portion configured to be inserted into and positioned within an extraluminal anatomical space and a second portion distal to the first portion and configured to be positioned within an intraluminal anatomical space. The first scope device includes a first insufflation port operatively coupled to the second portion of the first scope device and configured to insufflate the intraluminal anatomical space into a first insufflated space. The first instrument is configured to be inserted into and through the extraluminal anatomical space and into the intraluminal anatomical space such that the first instrument is present in both the extraluminal and intraluminal anatomical spaces. The second scope device is configured to be inserted into the extraluminal anatomical space. The second scope device has a second insufflation port operatively coupled to the second scope device and configured to insufflate the extraluminal anatomical space into a second insufflated space. The second instrument is configured to be inserted into the extraluminal anatomical space.

In some embodiments, a sealing port can be arranged in a tissue wall separating the extraluminal anatomical space from the intraluminal anatomical space. The sealing port can be configured to allow the second portion of the first scope to pass into the intraluminal anatomical space.

The first and second instruments can have a variety of configurations. In some embodiments, the first scope device can be configured to create a seal in the intraluminal anatomical space. In certain embodiments, the second instrument can be configured to create a seal in the intraluminal anatomical space while within the extraluminal anatomical space.

In some embodiments, an imaging system can be arranged on the second portion of the first scope device and can be configured to transmit image data of a scene within a field of view of the first scope device. In certain embodiments, an imaging system can be arranged on the second scope device and can be configured to transmit image data of a scene within a field of view of the second scope device.

In some embodiments, the first insufflated space can be pressurized to a first pressure and the second insufflated space can be pressurized to a second pressure, in which the first pressure is different than the second pressure.

The first scope device can have a variety of configurations. In some embodiments, the first scope device can include a flexible body with a working channel extending therethrough and can be configured to allow a distal end of the first instrument to be inserted into and through the extraluminal anatomical space and into the anatomical intraluminal space such that the first instrument is present in both the extraluminal and intraluminal anatomical spaces.

Methods are also provided. In one exemplary embodiment, a method includes inserting a first portion of a first scope device into an extraluminal anatomical space, inserting a second portion of the first scope device, distal to the first portion, into an intraluminal anatomical space, the first scope device having a first insufflation port, inserting a first instrument through the extraluminal anatomical space and into the intraluminal anatomical space such that the first instrument is present in both the extraluminal and intraluminal anatomical spaces, inserting a second scope device into the extraluminal anatomical space, the second scope device having a second insufflation port, inserting a second instrument into the extraluminal anatomical space, insufflating the extraluminal anatomical space to a first pressure through the second insufflation port of the second scope device, and insufflating the intraluminal space to a second pressure through the first insufflation port of the first scope device.

In some embodiments, the method includes passing the second portion of the first scope device to into the intraluminal anatomical space through a sealing port placed within a tissue wall separating the extraluminal anatomical space from the intraluminal space. In such embodiments, the method can include inserting the second portion of the first scope device through the sealing port and into the intraluminal anatomical space.

In some embodiments, the first pressure amount can be different than the second pressure amount.

In some embodiments, the method can include transmitting image data of a scene within a field of view of the first scope device via an imaging system arranged on the second portion of the first scope device. In certain embodiments, the method can include transmitting image data of a scene within a field of view of the second scope device via an imaging system arranged on the second scope device.

In some embodiments, the method can include inserting a distal end of the first instrument into and through a working channel of a flexible body of the first scope device such that the first instrument is present in both the extraluminal and intraluminal anatomical spaces. In such embodiments, the method can include removing the first instrument from the working channel while the second portion of the first scope device is positioned within the intraluminal anatomical space. In such embodiments, the method can include arranging a third instrument within the working channel while the second portion of the first scope device is positioned within the intraluminal anatomical space.

In some embodiments, the method can include manipulating a tissue wall at least partially defining the intraluminal anatomical space via the second instrument.

In some embodiments, the method can include enlarging a working volume within the extraluminal anatomical space by depressurizing the intraluminal anatomical space through the second insufflation port.

BRIEF DESCRIPTION OF DRAWINGS

The present invention is described by way of reference to the accompanying figures which are as follows:

FIG. 70 is schematic view of an embodiment of a locking arm; and

FIG. 71 is a schematic view of one embodiment of a locking structure prior to exposure to external energy; and FIG. 72 is the locking structure of FIG. 71 after exposure to external energy.

FIG. 77 is a schematic view of an exemplary embodiment of a surgical system having a laparoscopic instrument and an endoluminal instrument, showing the endoluminal instrument being inserted into a colon through a laparoscopic approach.

DETAILED DESCRIPTION

Figure 1:
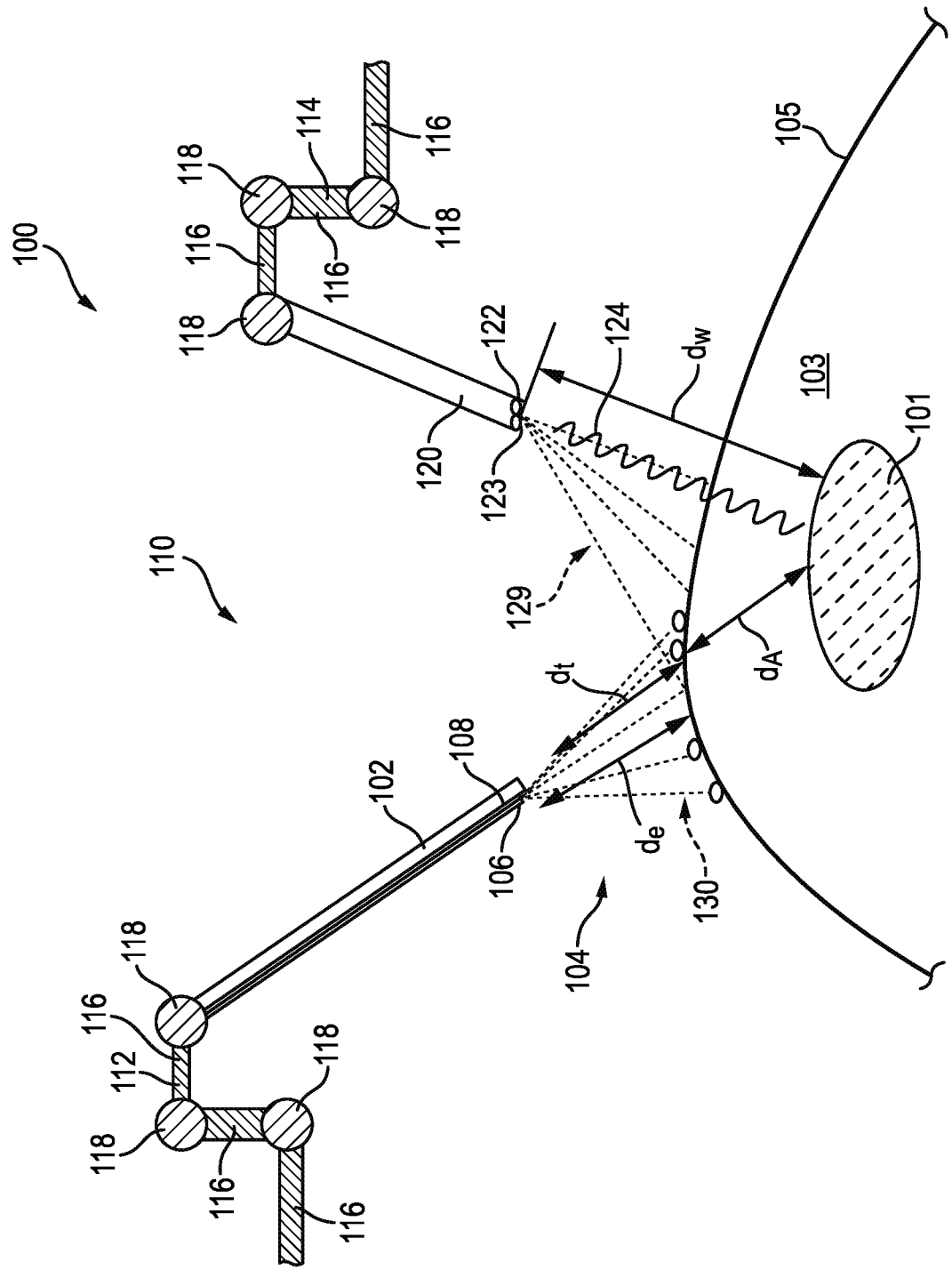
FIG. 1 is a schematic view of one embodiment of a surgical visualization system.

Certain exemplary embodiments will now be described to provide an overall understanding of the principles of the structure, function, manufacture, and use of the devices, systems, and methods disclosed herein. One or more examples of these embodiments are illustrated in the accompanying drawings. A person skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. A person skilled in the art will appreciate that a dimension may not be a precise value but nevertheless be considered to be at about that value due to any number of factors such as manufacturing tolerances and sensitivity of measurement equipment. Sizes and shapes of the systems and devices, and the components thereof, can depend at least on the size and shape of components with which the systems and devices will be used.

Surgical Visualization

In general, a surgical visualization system is configured to leverage "digital surgery" to obtain additional information about a patient's anatomy and/or a surgical procedure. The surgical visualization system is further configured to convey data to one or more medical practitioners in a helpful manner. Various aspects of the present disclosure provide improved visualization of the patient's anatomy and/or the surgical procedure, and/or use visualization to provide improved control of a surgical tool (also referred to herein as a "surgical device" or a "surgical instrument").

"Digital surgery" can embrace robotic systems, advanced imaging, advanced instrumentation, artificial intelligence, machine learning, data analytics for performance tracking and benchmarking, connectivity both inside and outside of the operating room (OR), and more. Although various surgical visualization systems described herein can be used in combination with a robotic surgical system, surgical visualization systems are not limited to use with a robotic surgical system. In certain instances, surgical visualization using a surgical visualization system can occur without robotics and/or with limited and/or optional robotic assistance. Similarly, digital surgery can occur without robotics and/or with limited and/or optional robotic assistance.

In certain instances, a surgical system that incorporates a surgical visualization system may enable smart dissection in order to identify and avoid critical structures. Critical structures include anatomical structures such as a ureter, an artery such as a superior mesenteric artery, a vein such as a portal vein, a nerve such as a phrenic nerve, and/or a tumor, among other anatomical structures. In other instances, a critical structure can be a foreign structure in the anatomical field, such as a surgical device, a surgical fastener, a clip, a tack, a bougie, a band, a plate, and other foreign structures. Critical structures can be determined on a patient-by-patient and/or a procedure-by-procedure basis. Smart dissection technology may provide, for example, improved intraoperative guidance for dissection and/or may enable smarter decisions with critical anatomy detection and avoidance technology.

A surgical system incorporating a surgical visualization system may enable smart anastomosis technologies that provide more consistent anastomoses at optimal location(s) with improved workflow. Cancer localization technologies may be improved with a surgical visualization platform. For example, cancer localization technologies can identify and track a cancer location, orientation, and its margins. In certain instances, the cancer localization technologies may compensate for movement of a surgical instrument, a patient, and/or the patient's anatomy during a surgical procedure in order to provide guidance back to the point of interest for medical practitioner(s).

A surgical visualization system may provide improved tissue characterization and/or lymph node diagnostics and mapping. For example, tissue characterization technologies may characterize tissue type and health without the need for physical haptics, especially when dissecting and/or placing stapling devices within the tissue. Certain tissue characterization technologies may be utilized without ionizing radiation and/or contrast agents. With respect to lymph node diagnostics and mapping, a surgical visualization platform may, for example, preoperatively locate, map, and ideally diagnose the lymph system and/or lymph nodes involved in cancerous diagnosis and staging.

During a surgical procedure, information available to a medical practitioner via the "naked eye" and/or an imaging system may provide an incomplete view of the surgical site. For example, certain structures, such as structures embedded or buried within an organ, can be at least partially concealed or hidden from view. Additionally, certain dimensions and/or relative distances can be difficult to ascertain with existing sensor systems and/or difficult for the "naked eye" to perceive. Moreover, certain structures can move pre-operatively (e.g., before a surgical procedure but after a preoperative scan) and/or intraoperatively. In such instances, the medical practitioner can be unable to accurately determine the location of a critical structure intraoperatively.

When the position of a critical structure is uncertain and/or when the proximity between the critical structure and a surgical tool is unknown, a medical practitioner's decision-making process can be inhibited. For example, a medical practitioner may avoid certain areas in order to avoid inadvertent dissection of a critical structure; however, the avoided area may be unnecessarily large and/or at least partially misplaced. Due to uncertainty and/or overly/excessive exercises in caution, the medical practitioner may not access certain desired regions. For example, excess caution may cause a medical practitioner to leave a portion of a tumor and/or other undesirable tissue in an effort to avoid a critical structure even if the critical structure is not in the particular area and/or would not be negatively impacted by the medical practitioner working in that particular area. In certain instances, surgical results can be improved with increased knowledge and/or certainty, which can allow a surgeon to be more accurate and, in certain instances, less conservative/more aggressive with respect to particular anatomical areas.

A surgical visualization system can allow for intraoperative identification and avoidance of critical structures. The surgical visualization system may thus enable enhanced intraoperative decision making and improved surgical outcomes. The surgical visualization system can provide advanced visualization capabilities beyond what a medical practitioner sees with the "naked eye" and/or beyond what an imaging system can recognize and/or convey to the medical practitioner. The surgical visualization system can augment and enhance what a medical practitioner is able to know prior to tissue treatment (e.g., dissection, etc.) and, thus, may improve outcomes in various instances. As a result, the medical practitioner can confidently maintain momentum throughout the surgical procedure knowing that the surgical visualization system is tracking a critical structure, which may be approached during dissection, for example. The surgical visualization system can provide an indication to the medical practitioner in sufficient time for the medical practitioner to pause and/or slow down the surgical procedure and evaluate the proximity to the critical structure to prevent inadvertent damage thereto. The surgical visualization system can provide an ideal, optimized, and/or customizable amount of information to the medical practitioner to allow the medical practitioner to move confidently and/or quickly through tissue while avoiding inadvertent damage to healthy tissue and/or critical structure(s) and, thus, to minimize the risk of harm resulting from the surgical procedure.

Surgical visualization systems are described in detail below. In general, a surgical visualization system can include a first light emitter configured to emit a plurality of spectral waves, a second light emitter configured to emit a light pattern, and a receiver, or sensor, configured to detect visible light, molecular responses to the spectral waves (spectral imaging), and/or the light pattern. The surgical visualization system can also include an imaging system and a control circuit in signal communication with the receiver and the imaging system. Based on output from the receiver, the control circuit can determine a geometric surface map, e.g., three-dimensional surface topography, of the visible surfaces at the surgical site and a distance with respect to the surgical site, such as a distance to an at least partially concealed structure. The imaging system can convey the geometric surface map and the distance to a medical practitioner. In such instances, an augmented view of the surgical site provided to the medical practitioner can provide a representation of the concealed structure within the relevant context of the surgical site. For example, the imaging system can virtually augment the concealed structure on the geometric surface map of the concealing and/or obstructing tissue similar to a line drawn on the ground to indicate a utility line below the surface. Additionally or alternatively, the imaging system can convey the proximity of a surgical tool to the visible and obstructing tissue and/or to the at least partially concealed structure and/or a depth of the concealed structure below the visible surface of the obstructing tissue. For example, the visualization system can determine a distance with respect to the augmented line on the surface of the visible tissue and convey the distance to the imaging system.

Throughout the present disclosure, any reference to "light," unless specifically in reference to visible light, can include electromagnetic radiation (EMR) or photons in the visible and/or non-visible portions of the EMR wavelength spectrum. The visible spectrum, sometimes referred to as the optical spectrum or luminous spectrum, is that portion of the electromagnetic spectrum that is visible to (e.g., can be detected by) the human eye and may be referred to as "visible light" or simply "light." A typical human eye will respond to wavelengths in air that are from about 380 nm to about 750 nm. The invisible spectrum (e.g., the non-luminous spectrum) is that portion of the electromagnetic spectrum that lies below and above the visible spectrum. The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

FIG. 1 illustrates one embodiment of a surgical visualization system 100. The surgical visualization system 100 is configured to create a visual representation of a critical structure 101 within an anatomical field. The critical structure 101 can include a single critical structure or a plurality of critical structures. As discussed herein, the critical structure 101 can be any of a variety of structures, such as an anatomical structure, e.g., a ureter, an artery such as a superior mesenteric artery, a vein such as a portal vein, a nerve such as a phrenic nerve, a vessel, a tumor, or other anatomical structure, or a foreign structure, e.g., a surgical device, a surgical fastener, a surgical clip, a surgical tack, a bougie, a surgical band, a surgical plate, or other foreign structure. As discussed herein, the critical structure 101 can be identified on a patient-by-patient and/or a procedure-by-procedure basis. Embodiments of critical structures and of identifying critical structures using a visualization system are further described in U.S. Pat. No. 10,792,034 entitled "Visualization Of Surgical Devices" issued Oct. 6, 2020, which is hereby incorporated by reference in its entirety.

In some instances, the critical structure 101 can be embedded in tissue 103. The tissue 103 can be any of a variety of tissues, such as fat, connective tissue, adhesions, and/or organs. Stated differently, the critical structure 101 may be positioned below a surface 105 of the tissue 103. In such instances, the tissue 103 conceals the critical structure 101 from the medical practitioner's "naked eye" view. The tissue 103 also obscures the critical structure 101 from the view of an imaging device 120 of the surgical visualization system 100. Instead of being fully obscured, the critical structure 101 can be partially obscured from the view of the medical practitioner and/or the imaging device 120.

The surgical visualization system 100 can be used for clinical analysis and/or medical intervention. In certain instances, the surgical visualization system 100 can be used intraoperatively to provide real-time information to the medical practitioner during a surgical procedure, such as real-time information regarding proximity data, dimensions, and/or distances. A person skilled in the art will appreciate that information may not be precisely real time but nevertheless be considered to be real time for any of a variety of reasons, such as time delay induced by data transmission, time delay induced by data processing, and/or sensitivity of measurement equipment. The surgical visualization system 100 is configured for intraoperative identification of critical structure(s) and/or to facilitate the avoidance of the critical structure(s) 101 by a surgical device. For example, by identifying the critical structure 101, a medical practitioner can avoid maneuvering a surgical device around the critical structure 101 and/or a region in a predefined proximity of the critical structure 101 during a surgical procedure. For another example, by identifying the critical structure 101, a medical practitioner can avoid dissection of and/or near the critical structure 101, thereby helping to prevent damage to the critical structure 101 and/or helping to prevent a surgical device being used by the medical practitioner from being damaged by the critical structure 101.

The surgical visualization system 100 is configured to incorporate tissue identification and geometric surface mapping in combination with the surgical visualization system's distance sensor system 104. In combination, these features of the surgical visualization system 100 can determine a position of a critical structure 101 within the anatomical field and/or the proximity of a surgical device 102 to the surface 105 of visible tissue 103 and/or to the critical structure 101. Moreover, the surgical visualization system 100 includes an imaging system that includes the imaging device 120 configured to provide real-time views of the surgical site. The imaging device 120 can include, for example, a spectral camera (e.g., a hyperspectral camera, multispectral camera, or selective spectral camera), which is configured to detect reflected spectral waveforms and generate a spectral cube of images based on the molecular response to the different wavelengths. Views from the imaging device 120 can be provided in real time to a medical practitioner, such as on a display (e.g., a monitor, a computer tablet screen, etc.). The displayed views can be augmented with additional information based on the tissue identification, landscape mapping, and the distance sensor system 104. In such instances, the surgical visualization system 100 includes a plurality of subsystems—an imaging subsystem, a surface mapping subsystem, a tissue identification subsystem, and/or a distance determining subsystem. These subsystems can cooperate to intra-operatively provide advanced data synthesis and integrated information to the medical practitioner.

The imaging device 120 can be configured to detect visible light, spectral light waves (visible or invisible), and a structured light pattern (visible or invisible). Examples of the imaging device 120 includes scopes, e.g., an endoscope, an arthroscope, an angioscope, a bronchoscope, a choledochoscope, a colonoscope, a cytoscope, a duodenoscope, an enteroscope, an esophagogastro-duodenoscope (gastroscope), a laryngoscope, a nasopharyngo-neproscope, a sigmoidoscope, a thoracoscope, an ureteroscope, or an exoscope. Scopes can be particularly useful in minimally invasive surgical procedures. In open surgery applications, the imaging device 120 may not include a scope.

The tissue identification subsystem can be achieved with a spectral imaging system. The spectral imaging system can rely on imaging such as hyperspectral imaging, multispectral imaging, or selective spectral imaging. Embodiments of hyperspectral imaging of tissue are further described in U.S. Pat. No. 9,274,047 entitled "System And Method For Gross Anatomic Pathology Using Hyperspectral Imaging" issued Mar. 1, 2016, which is hereby incorporated by reference in its entirety.

The surface mapping subsystem can be achieved with a light pattern system. Various surface mapping techniques using a light pattern (or structured light) for surface mapping can be utilized in the surgical visualization systems described herein. Structured light is the process of projecting a known pattern (often a grid or horizontal bars) on to a surface. In certain instances, invisible (or imperceptible) structured light can be utilized, in which the structured light is used without interfering with other computer vision tasks for which the projected pattern may be confusing. For example, infrared light or extremely fast frame rates of visible light that alternate between two exact opposite patterns can be utilized to prevent interference. Embodiments of surface mapping and a surgical system including a light source and a projector for projecting a light pattern are further described in U.S. Pat. Pub. No. 2017/0055819 entitled "Set Comprising A Surgical Instrument" published Mar. 2, 2017, U.S. Pat. Pub. No. 2017/0251900 entitled "Depiction System" published Sep. 7, 2017, and U.S. patent application Ser. No. 16/729,751 entitled "Surgical Systems For Generating Three Dimensional Constructs Of Anatomical Organs And Coupling Identified Anatomical Structures Thereto" filed Dec. 30, 2019, which are hereby incorporated by reference in their entireties.

The distance determining system can be incorporated into the surface mapping system. For example, structured light can be utilized to generate a three-dimensional (3D) virtual model of the visible surface 105 and determine various distances with respect to the visible surface 105. Additionally or alternatively, the distance determining system can rely on time-of-flight measurements to determine one or more distances to the identified tissue (or other structures) at the surgical site.

The surgical visualization system 100 also includes a surgical device 102. The surgical device 102 can be any suitable surgical device. Examples of the surgical device 102 includes a surgical dissector, a surgical stapler, a surgical grasper, a clip applier, a smoke evacuator, a surgical energy device (e.g., mono-polar probes, bi-polar probes, ablation probes, an ultrasound device, an ultrasonic end effector, etc.), etc. In some embodiments, the surgical device 102 includes an end effector having opposing jaws that extend from a distal end of a shaft of the surgical device 102 and that are configured to engage tissue therebetween.

The surgical visualization system 100 can be configured to identify the critical structure 101 and a proximity of the surgical device 102 to the critical structure 101. The imaging device 120 of the surgical visualization system 100 is configured to detect light at various wavelengths, such as visible light, spectral light waves (visible or invisible), and a structured light pattern (visible or invisible). The imaging device 120 can include a plurality of lenses, sensors, and/or receivers for detecting the different signals. For example, the imaging device 120 can be a hyperspectral, multispectral, or selective spectral camera, as described herein. The imaging device 120 can include a waveform sensor 122 (such as a spectral image sensor, detector, and/or three-dimensional camera lens). For example, the imaging device 120 can include a right-side lens and a left-side lens used together to record two two-dimensional images at the same time and, thus, generate a three-dimensional (3D) image of the surgical site, render a three-dimensional image of the surgical site, and/or determine one or more distances at the surgical site. Additionally or alternatively, the imaging device 120 can be configured to receive images indicative of the topography of the visible tissue and the identification and position of hidden critical structures, as further described herein. For example, a field of view of the imaging device 120 can overlap with a pattern of light (structured light) on the surface 105 of the tissue 103, as shown in FIG. 1.

As in this illustrated embodiment, the surgical visualization system 100 can be incorporated into a robotic surgical system 110. The robotic surgical system 110 can have a variety of configurations, as discussed herein. In this illustrated embodiment, the robotic surgical system 110 includes a first robotic arm 112 and a second robotic arm 114. The robotic arms 112, 114 each include rigid structural members 116 and joints 118, which can include servomotor controls. The first robotic arm 112 is configured to maneuver the surgical device 102, and the second robotic arm 114 is configured to maneuver the imaging device 120. A robotic control unit of the robotic surgical system 110 is configured to issue control motions to the first and second robotic arms 112, 114, which can affect the surgical device 102 and the imaging device 120, respectively.

In some embodiments, one or more of the robotic arms 112, 114 can be separate from the main robotic system 110 used in the surgical procedure. For example, at least one of the robotic arms 112, 114 can be positioned and registered to a particular coordinate system without a servomotor control. For example, a closed-loop control system and/or a plurality of sensors for the robotic arms 112, 114 can control and/or register the position of the robotic arm(s) 112, 114 relative to the particular coordinate system. Similarly, the position of the surgical device 102 and the imaging device 120 can be registered relative to a particular coordinate system.

Examples of robotic surgical systems include the Ottava™ robotic-assisted surgery system (Johnson & Johnson of New Brunswick, N.J.), da Vinci® surgical systems (Intuitive Surgical, Inc. of Sunnyvale, Calif.), the Hugo™ robotic-assisted surgery system (Medtronic PLC of Minneapolis, Minn.), the Versius® surgical robotic system (CMR Surgical Ltd of Cambridge, UK), and the Monarch® platform (Auris Health, Inc. of Redwood City, Calif.). Embodiments of various robotic surgical systems and using robotic surgical systems are further described in U.S. Pat. Pub. No. 2018/0177556 entitled "Flexible Instrument Insertion Using An Adaptive Force Threshold" filed Dec. 28, 2016, U.S. Pat. Pub. No. 2020/0000530 entitled "Systems And Techniques For Providing Multiple Perspectives During Medical Procedures" filed Apr. 16, 2019, U.S. Pat. Pub. No. 2020/0170720 entitled "Image-Based Branch Detection And Mapping For Navigation" filed Feb. 7, 2020, U.S. Pat. Pub. No. 2020/0188043 entitled "Surgical Robotics System" filed Dec. 9, 2019, U.S. Pat. Pub. No. 2020/0085516 entitled "Systems And Methods For Concomitant Medical Procedures" filed Sep. 3, 2019, U.S. Pat. No. 8,831,782 entitled "Patient-Side Surgeon Interface For A Teleoperated Surgical Instrument" filed Jul. 15, 2013, and Intl. Pat. Pub. No. WO 2014151621 entitled "Hyperdexterous Surgical System" filed Mar. 13, 2014, which are hereby incorporated by reference in their entireties.

The surgical visualization system 100 also includes an emitter 106. The emitter 106 is configured to emit a pattern of light, such as stripes, grid lines, and/or dots, to enable the determination of the topography or landscape of the surface 105. For example, projected light arrays 130 can be used for three-dimensional scanning and registration on the surface 105. The projected light arrays 130 can be emitted from the emitter 106 located on the surgical device 102 and/or one of the robotic arms 112, 114 and/or the imaging device 120. In one aspect, the projected light array 130 is employed by the surgical visualization system 100 to determine the shape defined by the surface 105 of the tissue 103 and/or motion of the surface 105 intraoperatively. The imaging device 120 is configured to detect the projected light arrays 130 reflected from the surface 105 to determine the topography of the surface 105 and various distances with respect to the surface 105.

As in this illustrated embodiment, the imaging device 120 can include an optical waveform emitter 123, such as by being mounted on or otherwise attached on the imaging device 120. The optical waveform emitter 123 is configured to emit electromagnetic radiation 124 (near-infrared (NIR) photons) that can penetrate the surface 105 of the tissue 103 and reach the critical structure 101. The imaging device 120 and the optical waveform emitter 123 can be positionable by the robotic arm 114. The optical waveform emitter 123 is mounted on or otherwise on the imaging device 122 but in other embodiments can be positioned on a separate surgical device from the imaging device 120. A corresponding waveform sensor 122 (e.g., an image sensor, spectrometer, or vibrational sensor) of the imaging device 120 is configured to detect the effect of the electromagnetic radiation received by the waveform sensor 122. The wavelengths of the electromagnetic radiation 124 emitted by the optical waveform emitter 123 are configured to enable the identification of the type of anatomical and/or physical structure, such as the critical structure 101. The identification of the critical structure 101 can be accomplished through spectral analysis, photo-acoustics, and/or ultrasound, for example. In one aspect, the wavelengths of the electromagnetic radiation 124 can be variable. The waveform sensor 122 and optical waveform emitter 123 can be inclusive of a multispectral imaging system and/or a selective spectral imaging system, for example. In other instances, the waveform sensor 122 and optical waveform emitter 123 can be inclusive of a photoacoustic imaging system, for example.

The distance sensor system 104 of the surgical visualization system 100 is configured to determine one or more distances at the surgical site. The distance sensor system 104 can be a time-of-flight distance sensor system that includes an emitter, such as the emitter 106 as in this illustrated embodiment, and that includes a receiver 108. In other instances, the time-of-flight emitter can be separate from the structured light emitter. The emitter 106 can include a very tiny laser source, and the receiver 108 can include a matching sensor. The distance sensor system 104 is configured to detect the "time of flight," or how long the laser light emitted by the emitter 106 has taken to bounce back to the sensor portion of the receiver 108. Use of a very narrow light source in the emitter 106 enables the distance sensor system 104 to determining the distance to the surface 105 of the tissue 103 directly in front of the distance sensor system 104.

The receiver 108 of the distance sensor system 104 is positioned on the surgical device 102 in this illustrated embodiment, but in other embodiments the receiver 108 can be mounted on a separate surgical device instead of the surgical device 102. For example, the receiver 108 can be mounted on a cannula or trocar through which the surgical device 102 extends to reach the surgical site. In still other embodiments, the receiver 108 for the distance sensor system 104 can be mounted on a separate robotically-controlled arm of the robotic system 110 (e.g., on the second robotic arm 114) than the first robotic arm 112 to which the surgical device 102 is coupled, can be mounted on a movable arm that is operated by another robot, or be mounted to an operating room (OR) table or fixture. In some embodiments, the imaging device 120 includes the receiver 108 to allow for determining the distance from the emitter 106 to the surface 105 of the tissue 103 using a line between the emitter 106 on the surgical device 102 and the imaging device 120. For example, the distance $d_e$ can be triangulated based on known positions of the emitter 106 (on the surgical device 102) and the receiver 108 (on the imaging device 120) of the distance sensor system 104. The three-dimensional position of the receiver 108 can be known and/or registered to the robot coordinate plane intraoperatively.

As in this illustrated embodiment, the position of the emitter 106 of the distance sensor system 104 can be controlled by the first robotic arm 112, and the position of the receiver 108 of the distance sensor system 104 can be controlled by the second robotic arm 114. In other embodiments, the surgical visualization system 100 can be utilized apart from a robotic system. In such instances, the distance sensor system 104 can be independent of the robotic system.

In FIG. 1, $d_e$ is emitter-to-tissue distance from the emitter 106 to the surface 105 of the tissue 103, and $d_t$ is device-to-tissue distance from a distal end of the surgical device 102 to the surface 105 of the tissue 103. The distance sensor system 104 is configured to determine the emitter-to-tissue distance $d_e$. The device-to-tissue distance $d_t$ is obtainable from the known position of the emitter 106 on the surgical device 102, e.g., on a shaft thereof proximal to the surgical device's distal end, relative to the distal end of the surgical device 102. In other words, when the distance between the emitter 106 and the distal end of the surgical device 102 is known, the device-to-tissue distance $d_t$ can be determined from the emitter-to-tissue distance $d_e$. In some embodiments, the shaft of the surgical device 102 can include one or more articulation joints and can be articulatable with respect to the emitter 106 and jaws at the distal end of the surgical device 102. The articulation configuration can include a multi-joint vertebrae-like structure, for example. In some embodiments, a three-dimensional camera can be utilized to triangulate one or more distances to the surface 105.

In FIG. 1, $d_w$ is camera-to-critical structure distance from the optical waveform emitter 123 located on the imaging device 120 to the surface of the critical structure 101, and $d_A$ is a depth of the critical structure 101 below the surface 105 of the tissue 103 (e.g., the distance between the portion of the surface 105 closest to the surgical device 102 and the critical structure 101). The time-of-flight of the optical waveforms emitted from the optical waveform emitter 123 located on the imaging device 120 are configured to determine the camera-to-critical structure distance $d_w$.

Figure 2:
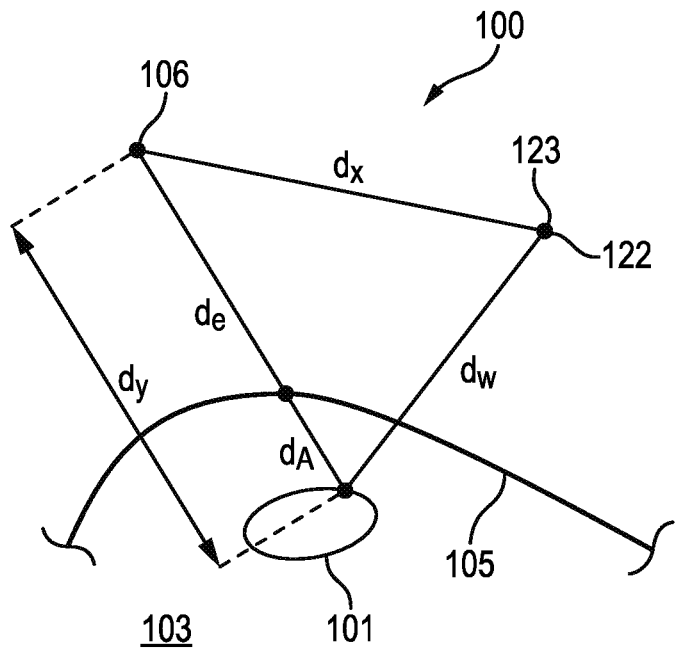
FIG. 2 is a schematic view of triangularization between a surgical device, an imaging device, and a critical structure of FIG. 1.

As shown in FIG. 2, the depth $d_A$ of the critical structure 101 relative to the surface 105 of the tissue 103 can be determined by triangulating from the distance $d_w$ and known positions of the emitter 106 on the surgical device 102 and the optical waveform emitter 123 on the imaging device 120 (and, thus, the known distance $d_x$ therebetween) to determine the distance $d_y$, which is the sum of the distances $d_e$ and $d_A$. Additionally or alternatively, time-of-flight from the optical waveform emitter 123 can be configured to determine the distance from the optical waveform emitter 123 to the surface 105 of the tissue 103. For example, a first waveform (or range of waveforms) can be utilized to determine the camera-to-critical structure distance $d_w$ and a second waveform (or range of waveforms) can be utilized to determine the distance to the surface 105 of the tissue 103. In such instances, the different waveforms can be utilized to determine the depth of the critical structure 101 below the surface 105 of the tissue 103.

Additionally or alternatively, the distance $d_A$ can be determined from an ultrasound, a registered magnetic resonance imaging (MRI), or computerized tomography (CT) scan. In still other instances, the distance $d_A$ can be determined with spectral imaging because the detection signal received by the imaging device 120 can vary based on the type of material, e.g., type of the tissue 103. For example, fat can decrease the detection signal in a first way, or a first amount, and collagen can decrease the detection signal in a different, second way, or a second amount.

Figure 3:
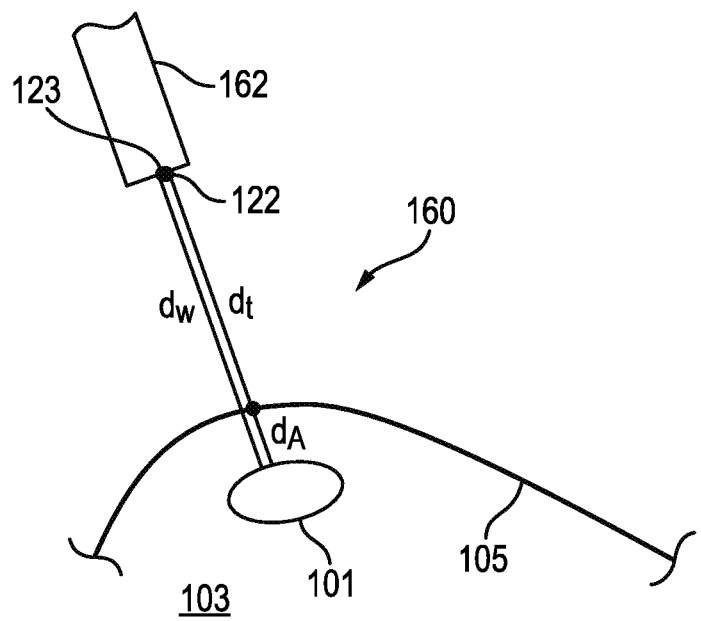
FIG. 3 is a schematic view of another embodiment of a surgical visualization system.

In another embodiment of a surgical visualization system 160 illustrated in FIG. 3, a surgical device 162, and not the imaging device 120, includes the optical waveform emitter 123 and the waveform sensor 122 that is configured to detect the reflected waveforms. The optical waveform emitter 123 is configured to emit waveforms for determining the distances $d_t$ and $d_w$ from a common device, such as the surgical device 162, as described herein. In such instances, the distance $d_A$ from the surface 105 of the tissue 103 to the surface of the critical structure 101 can be determined as follows:

$$d_A = d_w - d_t$$

Figure 4:
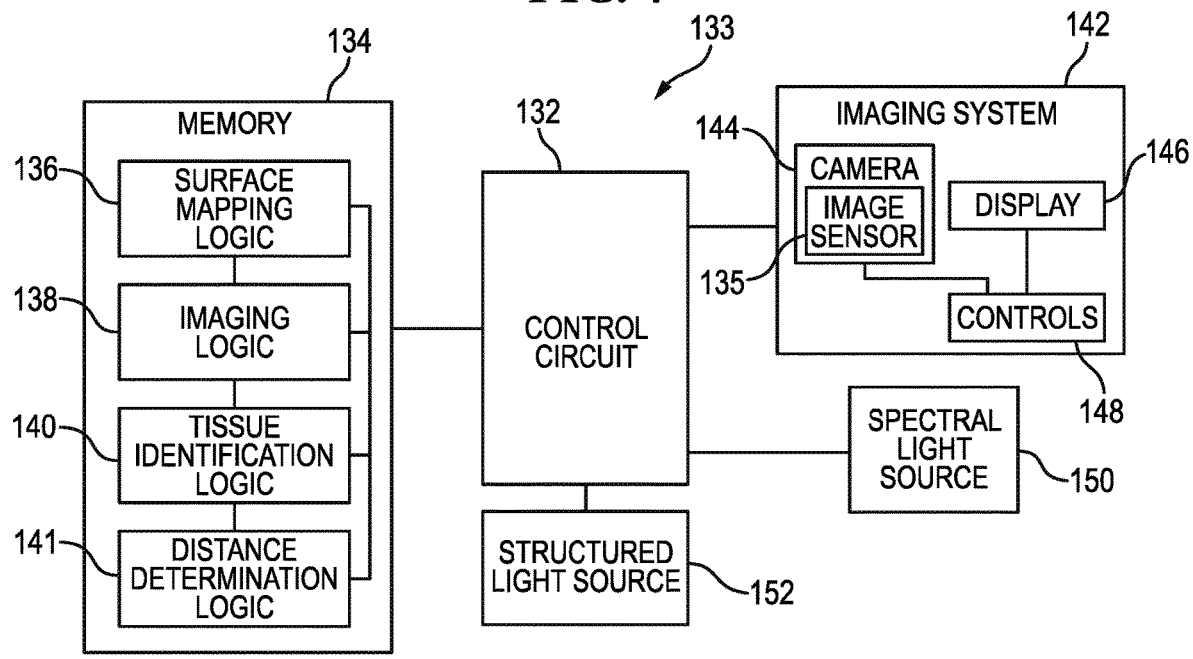
FIG. 4 is a schematic view of one embodiment of a control system for a surgical visualization system.

The surgical visualization system 100 includes a control system configured to control various aspects of the surgical visualization system 100. FIG. 4 illustrates one embodiment of a control system 133 that can be utilized as the control system of the surgical visualization system 100 (or other surgical visualization system described herein). The control system 133 includes a control circuit 132 configured to be in signal communication with a memory 134. The memory 134 is configured to store instructions executable by the control circuit 132, such as instructions to determine and/or recognize critical structures (e.g., the critical structure 101 of FIG. 1), instructions to determine and/or compute one or more distances and/or three-dimensional digital representations, and instructions to communicate information to a medical practitioner. As in this illustrated embodiment, the memory 134 can store surface mapping logic 136, imaging logic 138, tissue identification logic 140, and distance determining logic 141, although the memory 134 can store any combinations of the logics 136, 138, 140, 141 and/or can combine various logics together. The control system 133 also includes an imaging system 142 including a camera 144 (e.g., the imaging system including the imaging device 120 of FIG. 1), a display 146 (e.g., a monitor, a computer tablet screen, etc.), and controls 148 of the camera 144 and the display 146. The camera 144 includes an image sensor 135 (e.g., the waveform sensor 122) configured to receive signals from various light sources emitting light at various visible and invisible spectra (e.g., visible light, spectral imagers, three-dimensional lens, etc.). The display 146 is configured to depict real, virtual, and/or virtually-augmented images and/or information to a medical practitioner.

In an exemplary embodiment, the image sensor 135 is a solid-state electronic device containing up to millions of discrete photodetector sites called pixels. The image sensor 135 technology falls into one of two categories: Charge-Coupled Device (CCD) and Complementary Metal Oxide Semiconductor (CMOS) imagers and more recently, short-wave infrared (SWIR) is an emerging technology in imaging. Another type of the image sensor 135 employs a hybrid CCD/CMOS architecture (sold under the name "sCMOS") and consists of CMOS readout integrated circuits (ROICs) that are bump bonded to a CCD imaging substrate. CCD and CMOS image sensors 135 are sensitive to wavelengths in a range of about 350 nm to about 1050 nm, such as in a range of about 400 nm to about 1000 nm. A person skilled in the art will appreciate that a value may not be precisely at a value but nevertheless considered to be about that value for any of a variety of reasons, such as sensitivity of measurement equipment and manufacturing tolerances. CMOS sensors are, in general, more sensitive to IR wavelengths than CCD sensors. Solid state image sensors 135 are based on the photoelectric effect and, as a result, cannot distinguish between colors. Accordingly, there are two types of color CCD cameras: single chip and three-chip. Single chip color CCD cameras offer a common, low-cost imaging solution and use a mosaic (e.g., Bayer) optical filter to separate incoming light into a series of colors and employ an interpolation algorithm to resolve full color images. Each color is, then, directed to a different set of pixels. Three-chip color CCD cameras provide higher resolution by employing a prism to direct each section of the incident spectrum to a different chip. More accurate color reproduction is possible, as each point in space of the object has separate RGB intensity values, rather than using an algorithm to determine the color. Three-chip cameras offer extremely high resolutions.

The control system 133 also includes an emitter (e.g., the emitter 106) including a spectral light source 150 and a structured light source 152 each operably coupled to the control circuit 133. A single source can be pulsed to emit wavelengths of light in the spectral light source 150 range and wavelengths of light in the structured light source 152 range. Alternatively, a single light source can be pulsed to provide light in the invisible spectrum (e.g., infrared spectral light) and wavelengths of light on the visible spectrum. The spectral light source 150 can be, for example, a hyperspectral light source, a multispectral light source, and/or a selective spectral light source. The tissue identification logic 140 is configured to identify critical structure(s) (e.g., the critical structure 101 of FIG. 1) via data from the spectral light source 150 received by the image sensor 135 of the camera 144. The surface mapping logic 136 is configured to determine the surface contours of the visible tissue (e.g., the tissue 103) based on reflected structured light. With time-of-flight measurements, the distance determining logic 141 is configured to determine one or more distance(s) to the visible tissue and/or the critical structure. Output from each of the surface mapping logic 136, the tissue identification logic 140, and the distance determining logic 141 is configured to be provided to the imaging logic 138, and combined, blended, and/or overlaid by the imaging logic 138 to be conveyed to a medical practitioner via the display 146 of the imaging system 142.

Figure 5:
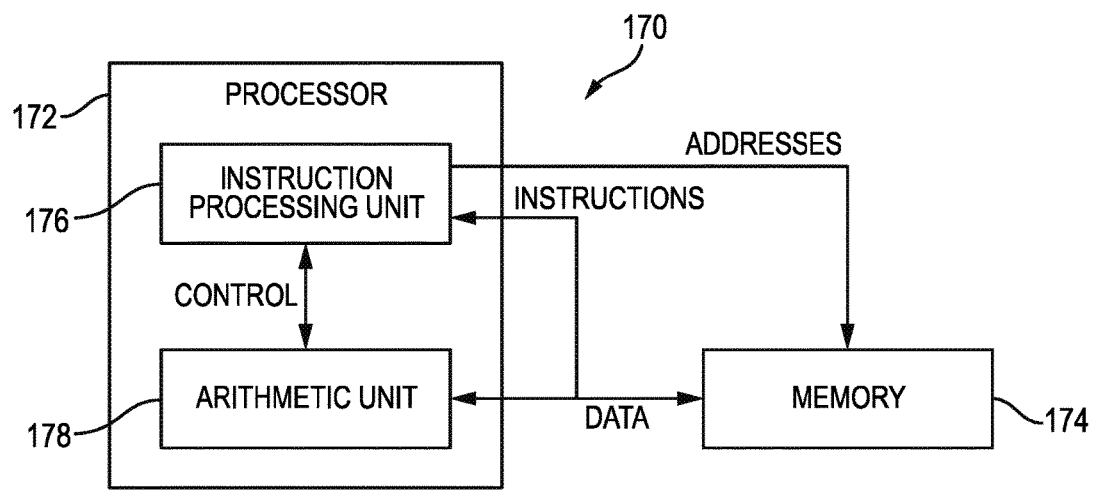
FIG. 5 is a schematic view of one embodiment of a control circuit of a control system for a surgical visualization system.

The control circuit 132 can have a variety of configurations. FIG. 5 illustrates one embodiment of a control circuit 170 that can be used as the control circuit 132 configured to control aspects of the surgical visualization system 100. The control circuit 170 is configured to implement various processes described herein. The control circuit 170 includes a microcontroller that includes a processor 172 (e.g., a microprocessor or microcontroller) operably coupled to a memory 174. The memory 174 is configured to store machine-executable instructions that, when executed by the processor 172, cause the processor 172 to execute machine instructions to implement various processes described herein. The processor 172 can be any one of a number of single-core or multicore processors known in the art. The memory 174 can include volatile and non-volatile storage media. The processor 172 includes an instruction processing unit 176 and an arithmetic unit 178. The instruction processing unit 176 is configured to receive instructions from the memory 174.

Figure 6:
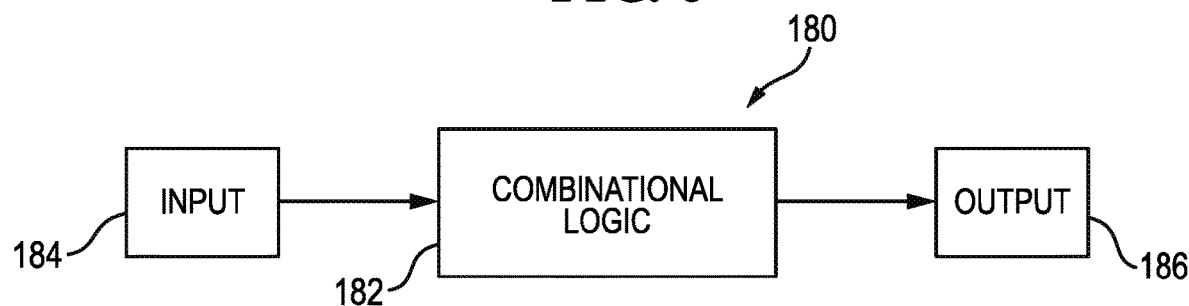
FIG. 6 is a schematic view of one embodiment of a combinational logic circuit of a surgical visualization system.

The surface mapping logic 136, the imaging logic 138, the tissue identification logic 140, and the distance determining logic 141 can have a variety of configurations. FIG. 6 illustrates one embodiment of a combinational logic circuit 180 configured to control aspects of the surgical visualization system 100 using logic such as one or more of the surface mapping logic 136, the imaging logic 138, the tissue identification logic 140, and the distance determining logic 141. The combinational logic circuit 180 includes a finite state machine that includes a combinational logic 182 configured to receive data associated with a surgical device (e.g. the surgical device 102 and/or the imaging device 120) at an input 184, process the data by the combinational logic 182, and provide an output 184 to a control circuit (e.g., the control circuit 132).

Figure 7:
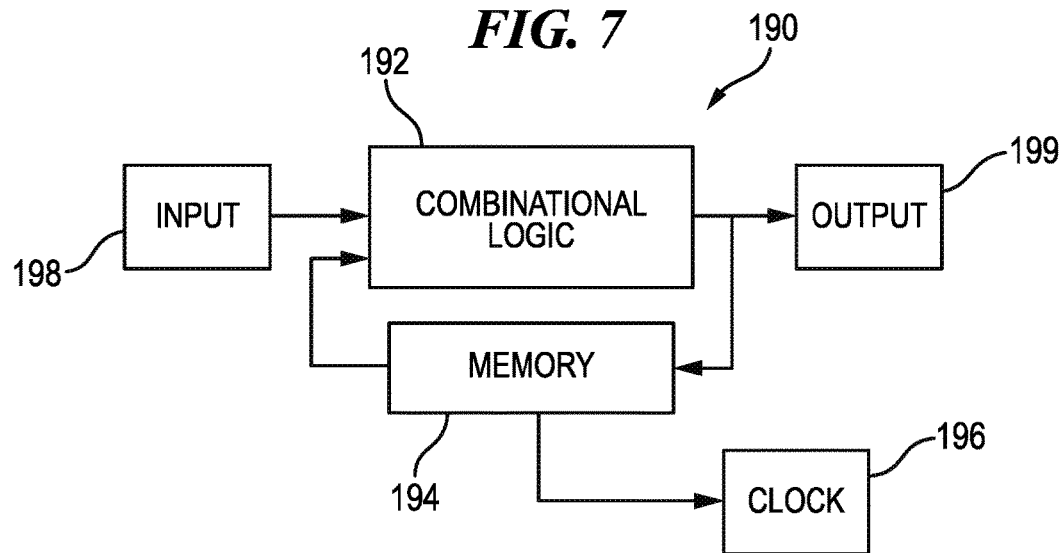
FIG. 7 is a schematic view of one embodiment of a sequential logic circuit of a surgical visualization system.

FIG. 7 illustrates one embodiment of a sequential logic circuit 190 configured to control aspects of the surgical visualization system 100 using logic such as one or more of the surface mapping logic 136, the imaging logic 138, the tissue identification logic 140, and the distance determining logic 141. The sequential logic circuit 190 includes a finite state machine that includes a combinational logic 192, a memory 194, and a clock 196. The memory 194 is configured to store a current state of the finite state machine. The sequential logic circuit 190 can be synchronous or asynchronous. The combinational logic 192 is configured to receive data associated with a surgical device (e.g. the surgical device 102 and/or the imaging device 120) at an input 426, process the data by the combinational logic 192, and provide an output 499 to a control circuit (e.g., the control circuit 132). In some embodiments, the sequential logic circuit 190 can include a combination of a processor (e.g., processor 172 of FIG. 5) and a finite state machine to implement various processes herein. In some embodiments, the finite state machine can include a combination of a combinational logic circuit (e.g., the combinational logic circuit 192 of FIG. 7) and the sequential logic circuit 190.

Figure 8:
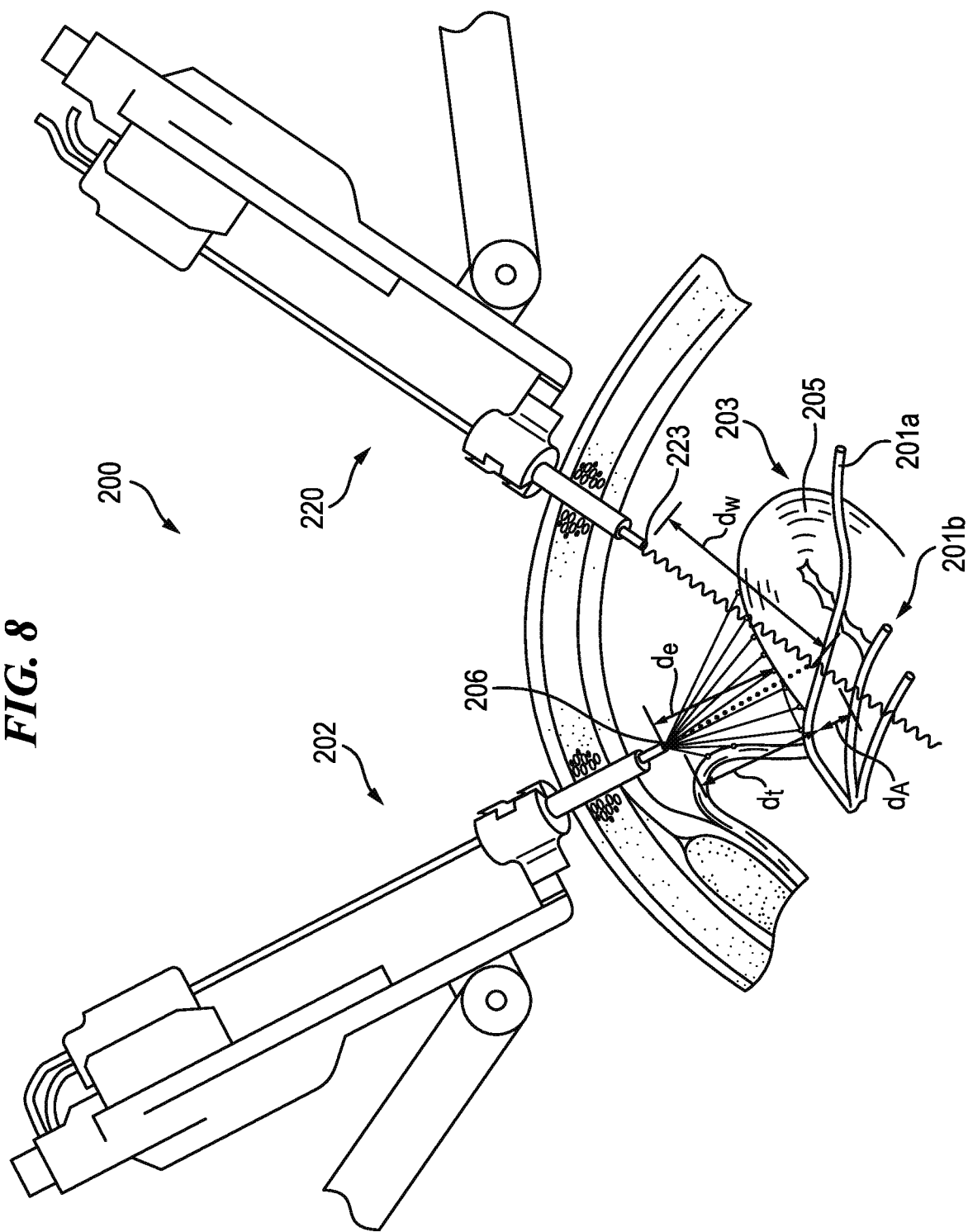
FIG. 8 is a schematic view of yet another embodiment of a surgical visualization system.

FIG. 8 illustrates another embodiment of a surgical visualization system 200. The surgical visualization system 200 is generally configured and used similar to the surgical visualization system 100 of FIG. 1, e.g., includes a surgical device 202 and an imaging device 220. The imaging device 220 includes a spectral light emitter 223 configured to emit spectral light in a plurality of wavelengths to obtain a spectral image of hidden structures, for example. The imaging device 220 can also include a three-dimensional camera and associated electronic processing circuits. The surgical visualization system 200 is shown being utilized intraoperatively to identify and facilitate avoidance of certain critical structures, such as a ureter 201a and vessels 201b, in an organ 203 (a uterus in this embodiment) that are not visible on a surface 205 of the organ 203.

The surgical visualization system 200 is configured to determine an emitter-to-tissue distance $d_e$ from an emitter 206 on the surgical device 202 to the surface 205 of the uterus 203 via structured light. The surgical visualization system 200 is configured to extrapolate a device-to-tissue distance $d_t$ from the surgical device 202 to the surface 205 of the uterus 203 based on the emitter-to-tissue distance $d_e$. The surgical visualization system 200 is also configured to determine a tissue-to-ureter distance $d_A$ from the ureter 201a to the surface 205 and a camera-to-ureter distance $d_w$ from the imaging device 220 to the ureter 201a. As described herein, e.g., with respect to the surgical visualization system 100 of FIG. 1, the surgical visualization system 200 is configured to determine the distance $d_w$ with spectral imaging and time-of-flight sensors, for example. In various embodiments, the surgical visualization system 200 can determine (e.g., triangulate) the tissue-to-ureter distance $d_A$ (or depth) based on other distances and/or the surface mapping logic described herein.

Figure 9:
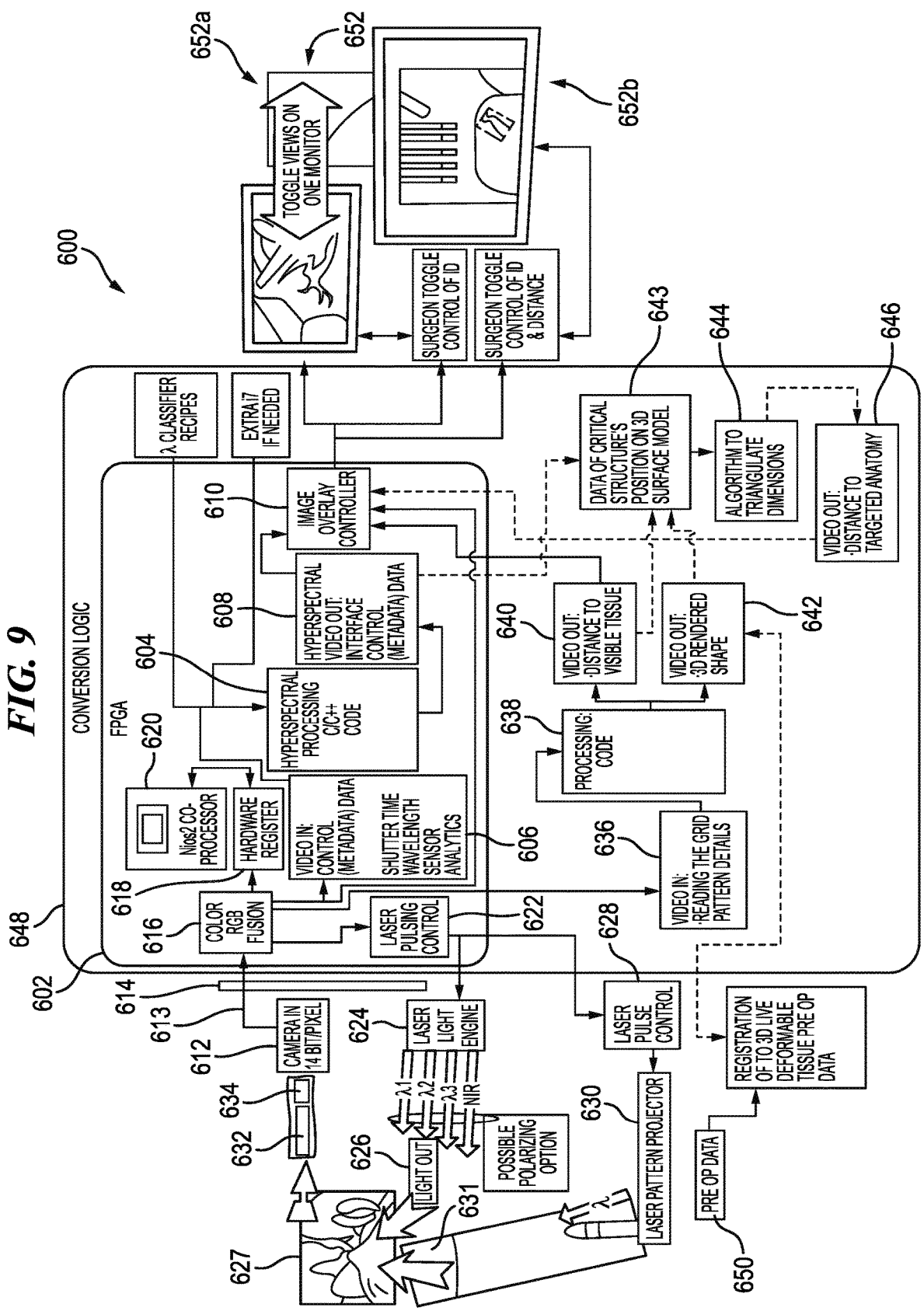
FIG. 9 is a schematic view of another embodiment of a control system for a surgical visualization system.

As mentioned above, a surgical visualization system includes a control system configured to control various aspects of the surgical visualization system. The control system can have a variety of configurations. FIG. 9 illustrates one embodiment of a control system 600 for a surgical visualization system, such as the surgical visualization system 100 of FIG. 1, the surgical visualization system 200 of FIG. 8, or other surgical visualization system described herein. The control system 600 is a conversion system that integrates spectral signature tissue identification and structured light tissue positioning to identify a critical structure, especially when those structure(s) are obscured by tissue, e.g., by fat, connective tissue, blood tissue, and/or organ(s), and/or by blood, and/or to detect tissue variability, such as differentiating tumors and/or non-healthy tissue from healthy tissue within an organ.

The control system 600 is configured for implementing a hyperspectral imaging and visualization system in which a molecular response is utilized to detect and identify anatomy in a surgical field of view. The control system 600 includes a conversion logic circuit 648 configured to convert tissue data to usable information for surgeons and/or other medical practitioners. For example, variable reflectance based on wavelengths with respect to obscuring material can be utilized to identify the critical structure in the anatomy. Moreover, the control system 600 is configured to combine the identified spectral signature and the structural light data in an image. For example, the control system 600 can be employed to create of three-dimensional data set for surgical use in a system with augmentation image overlays. Techniques can be employed both intraoperatively and preoperatively using additional visual information. In various embodiments, the control system 600 is configured to provide warnings to a medical practitioner when in the proximity of one or more critical structures. Various algorithms can be employed to guide robotic automation and semi-automated approaches based on the surgical procedure and proximity to the critical structure(s).

A projected array of lights is employed by the control system 600 to determine tissue shape and motion intraoperatively. Alternatively, flash Lidar may be utilized for surface mapping of the tissue.

The control system 600 is configured to detect the critical structure, which as mentioned above can include one or more critical structures, and provide an image overlay of the critical structure and measure the distance to the surface of the visible tissue and the distance to the embedded/buried critical structure(s). The control system 600 can measure the distance to the surface of the visible tissue or detect the critical structure and provide an image overlay of the critical structure.

The control system 600 includes a spectral control circuit 602. The spectral control circuit 602 can be a field programmable gate array (FPGA) or another suitable circuit configuration, such as the configurations described with respect to FIG. 6, FIG. 7, and FIG. 8. The spectral control circuit 602 includes a processor 604 configured to receive video input signals from a video input processor 606. The processor 604 can be configured for hyperspectral processing and can utilize C/C++ code, for example. The video input processor 606 is configured to receive video-in of control (metadata) data such as shutter time, wave length, and sensor analytics, for example. The processor 604 is configured to process the video input signal from the video input processor 606 and provide a video output signal to a video output processor 608, which includes a hyperspectral video-out of interface control (metadata) data, for example. The video output processor 608 is configured to provides the video output signal to an image overlay controller 610.

The video input processor 606 is operatively coupled to a camera 612 at the patient side via a patient isolation circuit 614. The camera 612 includes a solid state image sensor 634. The patient isolation circuit 614 can include a plurality of transformers so that the patient is isolated from other circuits in the system. The camera 612 is configured to receive intraoperative images through optics 632 and the image sensor 634. The image sensor 634 can include a CMOS image sensor, for example, or can include another image sensor technology, such as those discussed herein in connection with FIG. 4. The camera 612 is configured to output 613 images in 14 bit/pixel signals. A person skilled in the art will appreciate that higher or lower pixel resolutions can be employed. The isolated camera output signal 613 is provided to a color RGB fusion circuit 616, which in this illustrated embodiment employs a hardware register 618 and a Nios2 co-processor 620 configured to process the camera output signal 613. A color RGB fusion output signal is provided to the video input processor 606 and a laser pulsing control circuit 622.

The laser pulsing control circuit 622 is configured to control a laser light engine 624. The laser light engine 624 is configured to output light in a plurality of wavelengths (λ1, λ2, λ3 . . . λn) including near infrared (NIR). The laser light engine 624 can operate in a plurality of modes. For example, the laser light engine 624 can operate in two modes. In a first mode, e.g., a normal operating mode, the laser light engine 624 is configured to output an illuminating signal. In a second mode, e.g., an identification mode, the laser light engine 624 is configured to output RGBG and NIR light. In various embodiments, the laser light engine 624 can operate in a polarizing mode.

Light output 626 from the laser light engine 624 is configured to illuminate targeted anatomy in an intraoperative surgical site 627. The laser pulsing control circuit 622 is also configured to control a laser pulse controller 628 for a laser pattern projector 630 configured to project a laser light pattern 631, such as a grid or pattern of lines and/or dots, at a predetermined wavelength (λ2) on an operative tissue or organ at the surgical site 627. The camera 612 is configured to receive the patterned light as well as the reflected light output through the camera optics 632. The image sensor 634 is configured to convert the received light into a digital signal.

The color RGB fusion circuit 616 is also configured to output signals to the image overlay controller 610 and a video input module 636 for reading the laser light pattern 631 projected onto the targeted anatomy at the surgical site 627 by the laser pattern projector 630. A processing module 638 is configured to process the laser light pattern 631 and output a first video output signal 640 representative of the distance to the visible tissue at the surgical site 627. The data is provided to the image overlay controller 610. The processing module 638 is also configured to output a second video signal 642 representative of a three-dimensional rendered shape of the tissue or organ of the targeted anatomy at the surgical site.

The first and second video output signals 640, 642 include data representative of the position of the critical structure on a three-dimensional surface model, which is provided to an integration module 643. In combination with data from the video out processor 608 of the spectral control circuit 602, the integration module 643 is configured to determine the distance (e.g., distance $d_4$ of FIG. 1) to a buried critical structure (e.g., via triangularization algorithms 644), and the distance to the buried critical structure can be provided to the image overlay controller 610 via a video out processor 646. The foregoing conversion logic can encompass the conversion logic circuit 648 intermediate video monitors 652 and the camera 624/laser pattern projector 630 positioned at the surgical site 627.

Preoperative data 650, such as from a CT or MRI scan, can be employed to register or align certain three-dimensional deformable tissue in various instances. Such preoperative data 650 can be provided to the integration module 643 and ultimately to the image overlay controller 610 so that such information can be overlaid with the views from the camera 612 and provided to the video monitors 652. Embodiments of registration of preoperative data are further described in U.S. Pat. Pub. No. 2020/0015907 entitled "Integration Of Imaging Data" filed Sep. 11, 2018, which is hereby incorporated by reference herein in its entirety.

The video monitors 652 are configured to output the integrated/augmented views from the image overlay controller 610. A medical practitioner can select and/or toggle between different views on one or more displays. On a first display 652a, which is a monitor in this illustrated embodiment, the medical practitioner can toggle between (A) a view in which a three-dimensional rendering of the visible tissue is depicted and (B) an augmented view in which one or more hidden critical structures are depicted over the three-dimensional rendering of the visible tissue. On a second display 652b, which is a monitor in this illustrated embodiment, the medical practitioner can toggle on distance measurements to one or more hidden critical structures and/or the surface of visible tissue, for example.

The various surgical visualization systems described herein can be utilized to visualize various different types of tissues and/or anatomical structures, including tissues and/or anatomical structures that may be obscured from being visualized by EMR in the visible portion of the spectrum. The surgical visualization system can utilize a spectral imaging system, as mentioned above, which can be configured to visualize different types of tissues based upon their varying combinations of constituent materials. In particular, a spectral imaging system can be configured to detect the presence of various constituent materials within a tissue being visualized based on the absorption coefficient of the tissue across various EMR wavelengths. The spectral imaging system can be configured to characterize the tissue type of the tissue being visualized based upon the particular combination of constituent materials.

Figure 10:
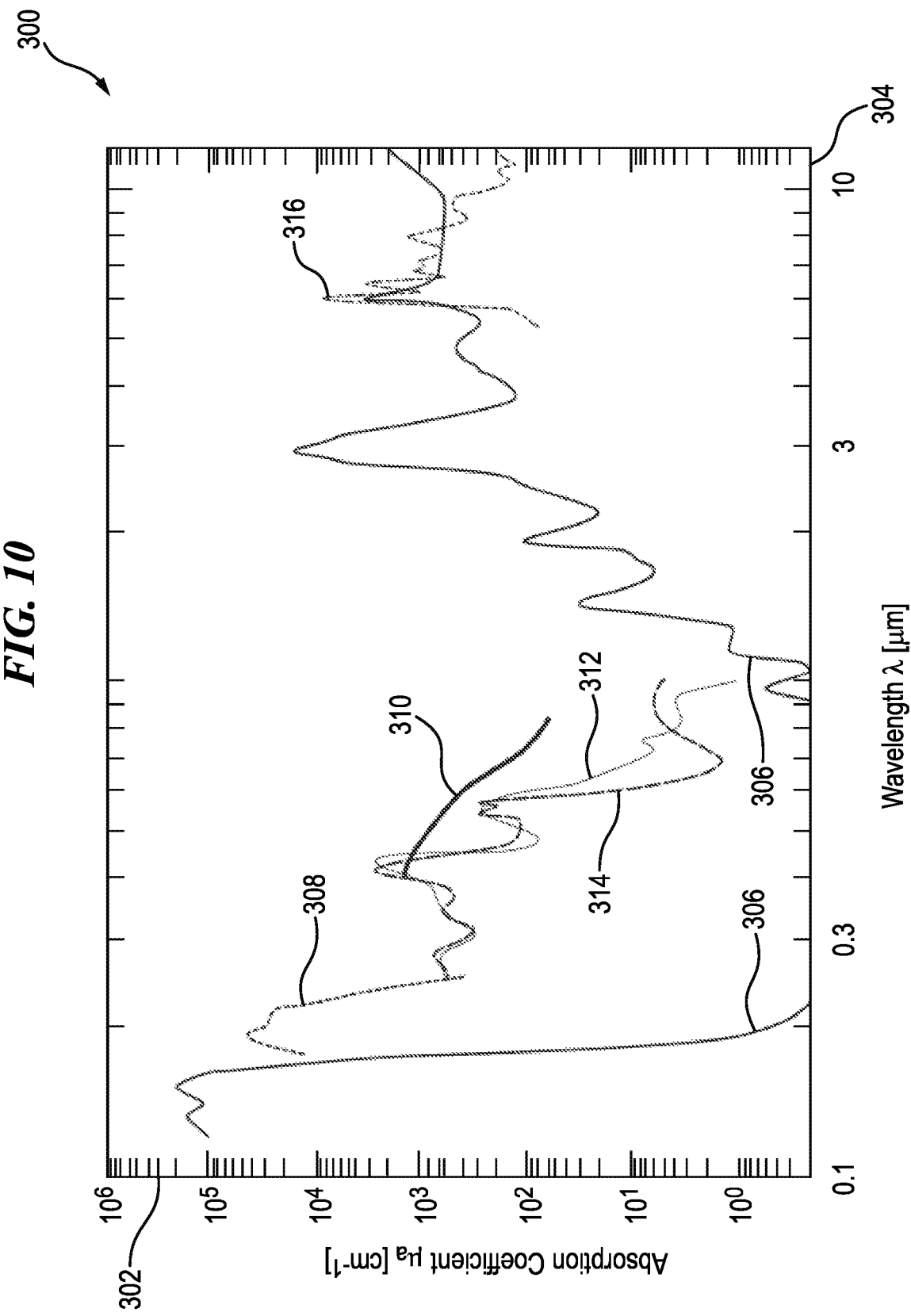
FIG. 10 is a graph showing wavelength versus absorption coefficient for various biological materials.

FIG. 10 shows a graph 300 depicting how the absorption coefficient of various biological materials varies across the EMR wavelength spectrum. In the graph 300, the vertical axis 302 represents absorption coefficient of the biological material in $cm^{-1}$, and the horizontal axis 304 represents EMR wavelength in μm. A first line 306 in the graph 300 represents the absorption coefficient of water at various EMR wavelengths, a second line 308 represents the absorption coefficient of protein at various EMR wavelengths, a third line 310 represents the absorption coefficient of melanin at various EMR wavelengths, a fourth line 312 represents the absorption coefficient of deoxygenated hemoglobin at various EMR wavelengths, a fifth line 314 represents the absorption coefficient of oxygenated hemoglobin at various EMR wavelengths, and a sixth line 316 represents the absorption coefficient of collagen at various EMR wavelengths. Different tissue types have different combinations of constituent materials and, therefore, the tissue type(s) being visualized by a surgical visualization system can be identified and differentiated between according to the particular combination of detected constituent materials. Accordingly, a spectral imaging system of a surgical visualization system can be configured to emit EMR at a number of different wavelengths, determine the constituent materials of the tissue based on the detected absorption EMR absorption response at the different wavelengths, and then characterize the tissue type based on the particular detected combination of constituent materials.

Figure 11:
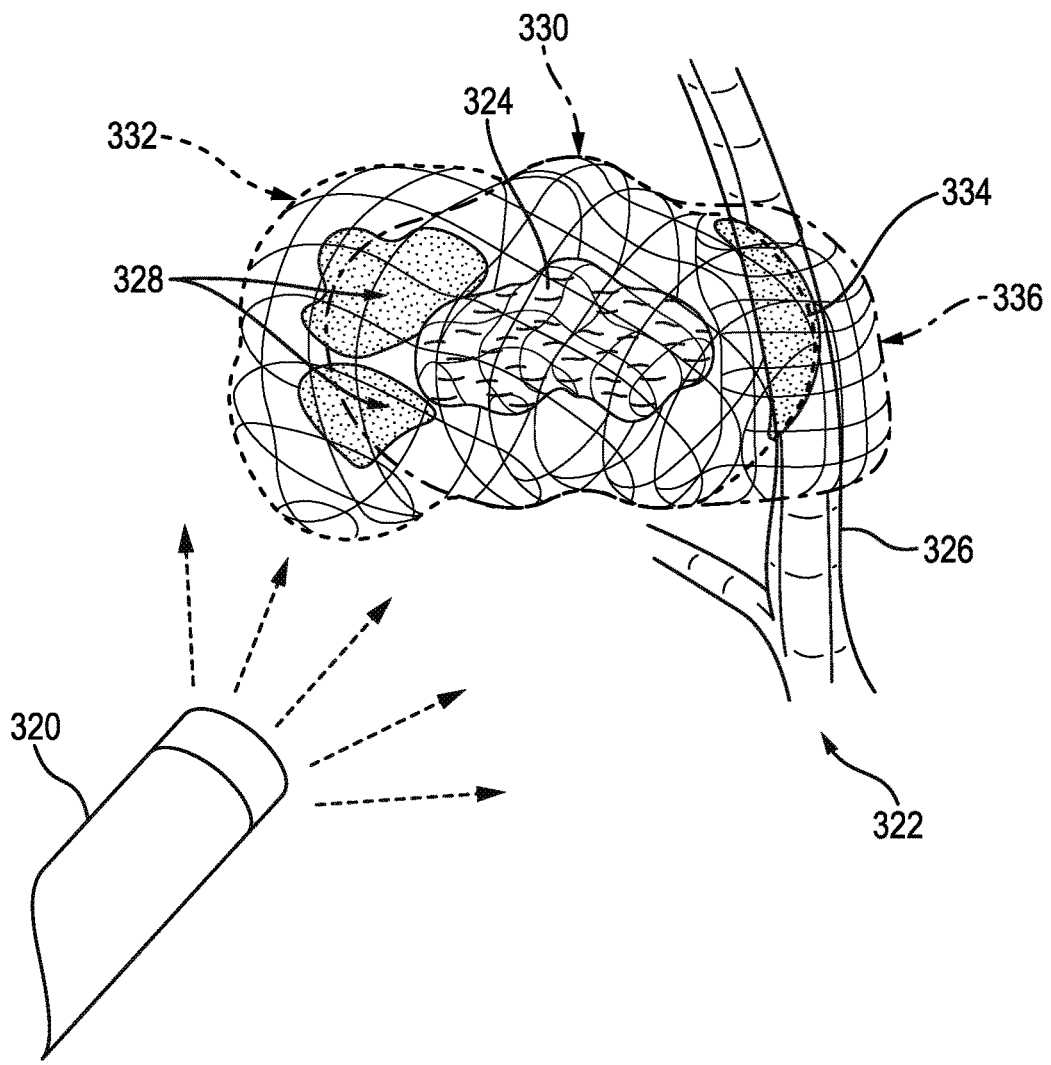
FIG. 11 is a schematic view of one embodiment of a spectral emitter visualizing a surgical site.

FIG. 11 shows an embodiment of the utilization of spectral imaging techniques to visualize different tissue types and/or anatomical structures. In FIG. 11, a spectral emitter 320 (e.g., the spectral light source 150 of FIG. 4) is being utilized by an imaging system to visualize a surgical site 322. The EMR emitted by the spectral emitter 320 and reflected from the tissues and/or structures at the surgical site 322 is received by an image sensor (e.g., the image sensor 135 of FIG. 4) to visualize the tissues and/or structures, which can be either visible (e.g., be located at a surface of the surgical site 322) or obscured (e.g., underlay other tissue and/or structures at the surgical site 322). In this embodiment, an imaging system (e.g., the imaging system 142 of FIG. 4) visualizes a tumor 324, an artery 326, and various abnormalities 328 (e.g., tissues not confirming to known or expected spectral signatures) based upon the spectral signatures characterized by the differing absorptive characteristics (e.g., absorption coefficient) of the constituent materials for each of the different tissue/structure types. The visualized tissues and structures can be displayed on a display screen associated with or coupled to the imaging system (e.g., the display 146 of the imaging system 142 of FIG. 4), on a primary display (e.g., the primary display 819 of FIG. 19), on a non-sterile display (e.g., the non-sterile displays 807, 809 of FIG. 19), on a display of a surgical hub (e.g., the display of the surgical hub 806 of FIG. 19), on a device/instrument display, and/or on another display.

The imaging system can be configured to tailor or update the displayed surgical site visualization according to the identified tissue and/or structure types. For example, as shown in FIG. 11, the imaging system can display a margin 330 associated with the tumor 324 being visualized on a display screen associated with or coupled to the imaging system, on a primary display, on a non-sterile display, on a display of a surgical hub, on a device/instrument display, and/or on another display. The margin 330 can indicate the area or amount of tissue that should be excised to ensure complete removal of the tumor 324. The surgical visualization system's control system (e.g., the control system 133 of FIG. 4) can be configured to control or update the dimensions of the margin 330 based on the tissues and/or structures identified by the imaging system. In this illustrated embodiment, the imaging system has identified multiple abnormalities 328 within the field of view (FOV). Accordingly, the control system can adjust the displayed margin 330 to a first updated margin 332 having sufficient dimensions to encompass the abnormalities 328. Further, the imaging system has also identified the artery 326 partially overlapping with the initially displayed margin 330 (as indicated by a highlighted region 334 of the artery 326). Accordingly, the control system can adjust the displayed margin to a second updated margin 336 having sufficient dimensions to encompass the relevant portion of the artery 326.

Figure 12:
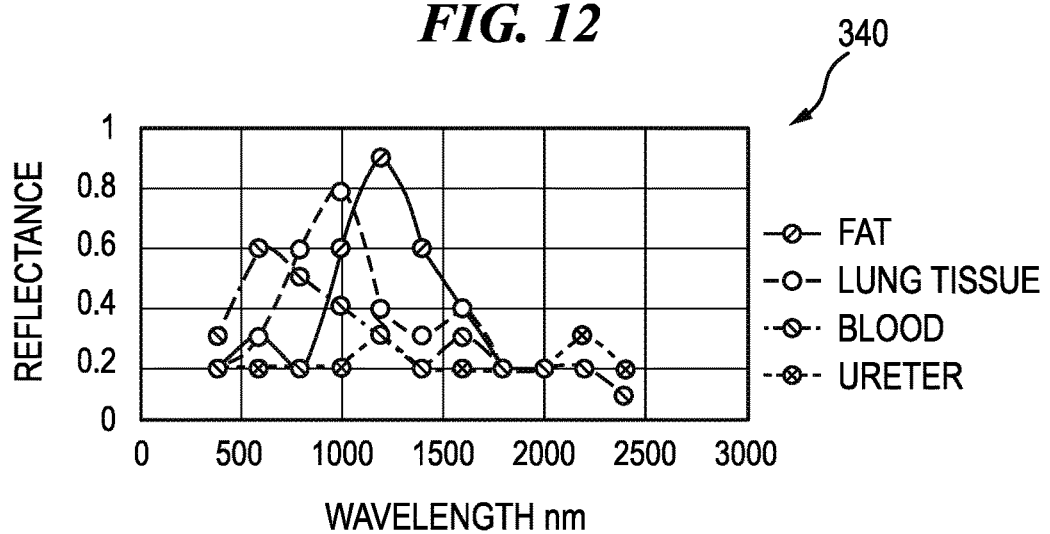
FIG. 12 is a graph depicting illustrative hyperspectral identifying signatures to differentiate a ureter from obscurants.
Figure 13:
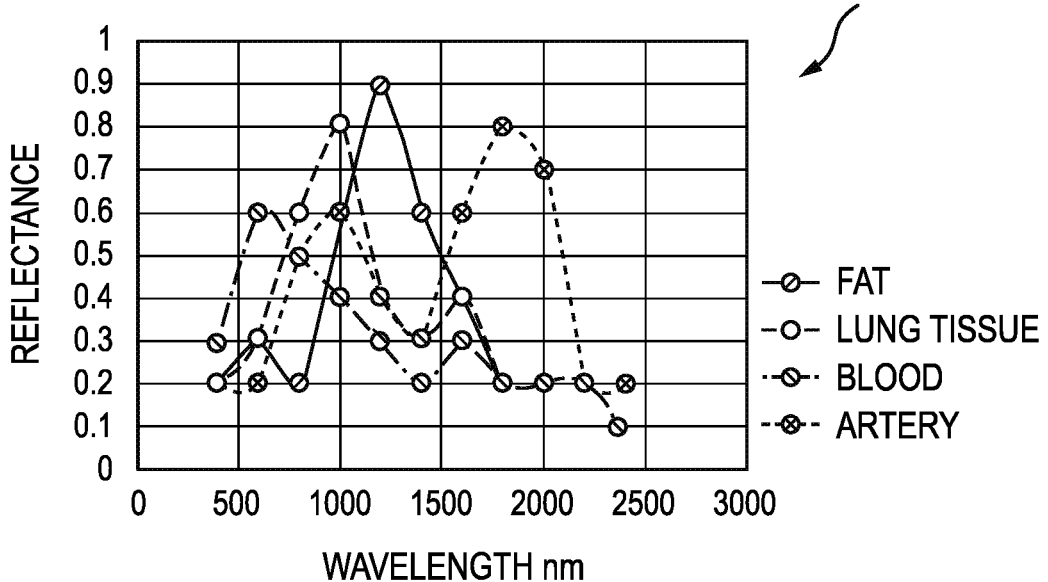
FIG. 13 is a graph depicting illustrative hyperspectral identifying signatures to differentiate an artery from obscurants.
Figure 14:
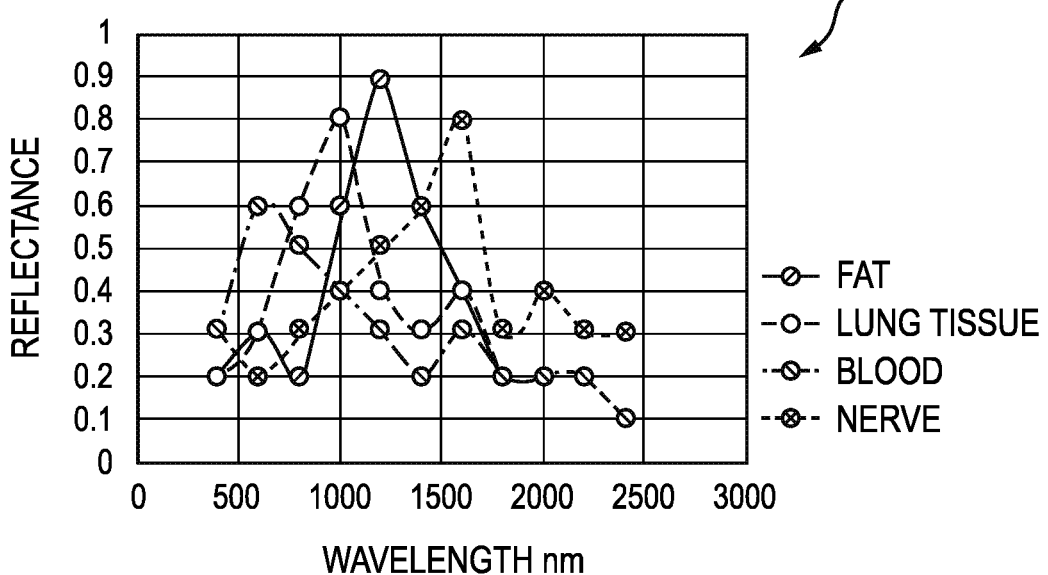
FIG. 14 is a graph depicting illustrative hyperspectral identifying signatures to differentiate a nerve from obscurants.

Tissues and/or structures can also be imaged or characterized according to their reflective characteristics, in addition to or in lieu of their absorptive characteristics described above with respect to FIG. 10 and FIG. 11, across the EMR wavelength spectrum. For example, FIG. 12, FIG. 13, and FIG. 14 illustrate various graphs of reflectance of different types of tissues or structures across different EMR wavelengths. FIG. 12 is a graphical representation 340 of an illustrative ureter signature versus obscurants. FIG. 13 is a graphical representation 342 of an illustrative artery signature versus obscurants. FIG. 14 is a graphical representation 344 of an illustrative nerve signature versus obscurants. The plots in FIG. 12, FIG. 13, and FIG. 14 represent reflectance as a function of wavelength (nm) for the particular structures (ureter, artery, and nerve) relative to the corresponding reflectances of fat, lung tissue, and blood at the corresponding wavelengths. These graphs are simply for illustrative purposes and it should be understood that other tissues and/or structures could have corresponding detectable reflectance signatures that would allow the tissues and/or structures to be identified and visualized.

Select wavelengths for spectral imaging can be identified and utilized based on the anticipated critical structures and/or obscurants at a surgical site (e.g., "selective spectral" imaging). By utilizing selective spectral imaging, the amount of time required to obtain the spectral image can be minimized such that the information can be obtained in real-time and utilized intraoperatively. The wavelengths can be selected by a medical practitioner or by a control circuit based on input by a user, e.g., a medical practitioner. In certain instances, the wavelengths can be selected based on machine learning and/or big data accessible to the control circuit via, e.g., a cloud or surgical hub.

Figure 15:
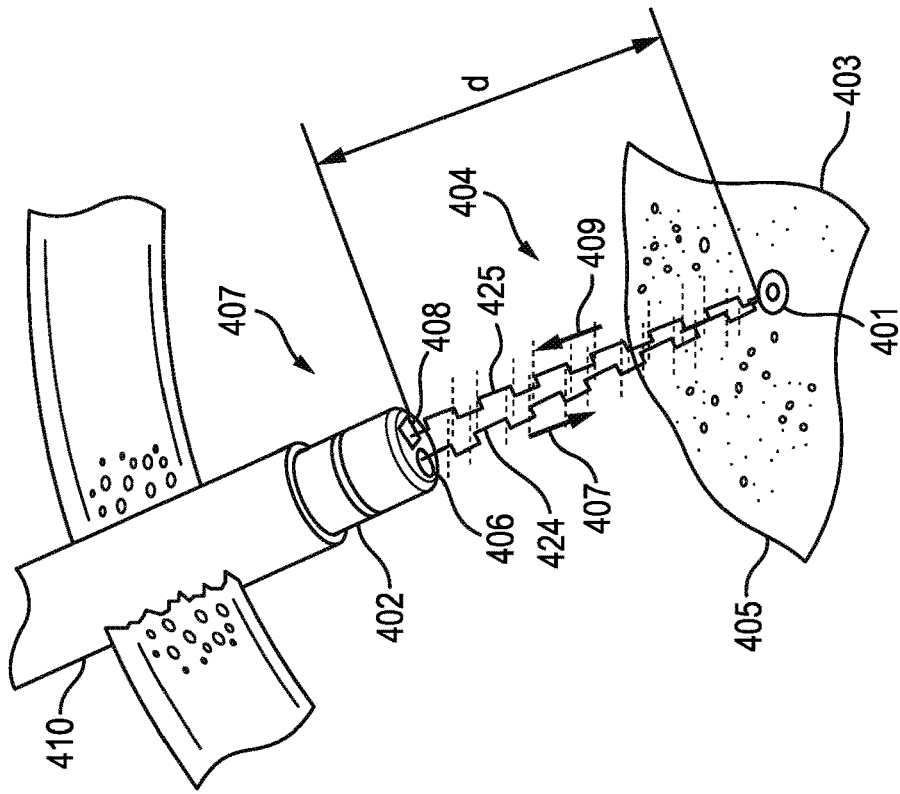
FIG. 15 is a schematic view of one embodiment of a near infrared (NIR) time-of-flight measurement system being utilized intraoperatively.

FIG. 15 illustrates one embodiment of spectral imaging to tissue being utilized intraoperatively to measure a distance between a waveform emitter and a critical structure that is obscured by tissue. FIG. 15 shows an embodiment of a time-of-flight sensor system 404 utilizing waveforms 424, 425. The time-of-flight sensor system 404 can be incorporated into a surgical visualization system, e.g., as the sensor system 104 of the surgical visualization system 100 of FIG. 1. The time-of-flight sensor system 404 includes a waveform emitter 406 and a waveform receiver 408 on the same surgical device 402 (e.g., the emitter 106 and the receiver 108 on the same surgical device 102 of FIG. 1). The emitted wave 400 extends to a critical structure 401 (e.g., the critical structure 101 of FIG. 1) from the emitter 406, and the received wave 425 is reflected back to by the receiver 408 from the critical structure 401. The surgical device 402 in this illustrated embodiment is positioned through a trocar 410 that extends into a cavity 407 in a patient. Although the trocar 410 is used in this in this illustrated embodiment, other trocars or other access devices can be used, or no access device may be used.

Figure 16:
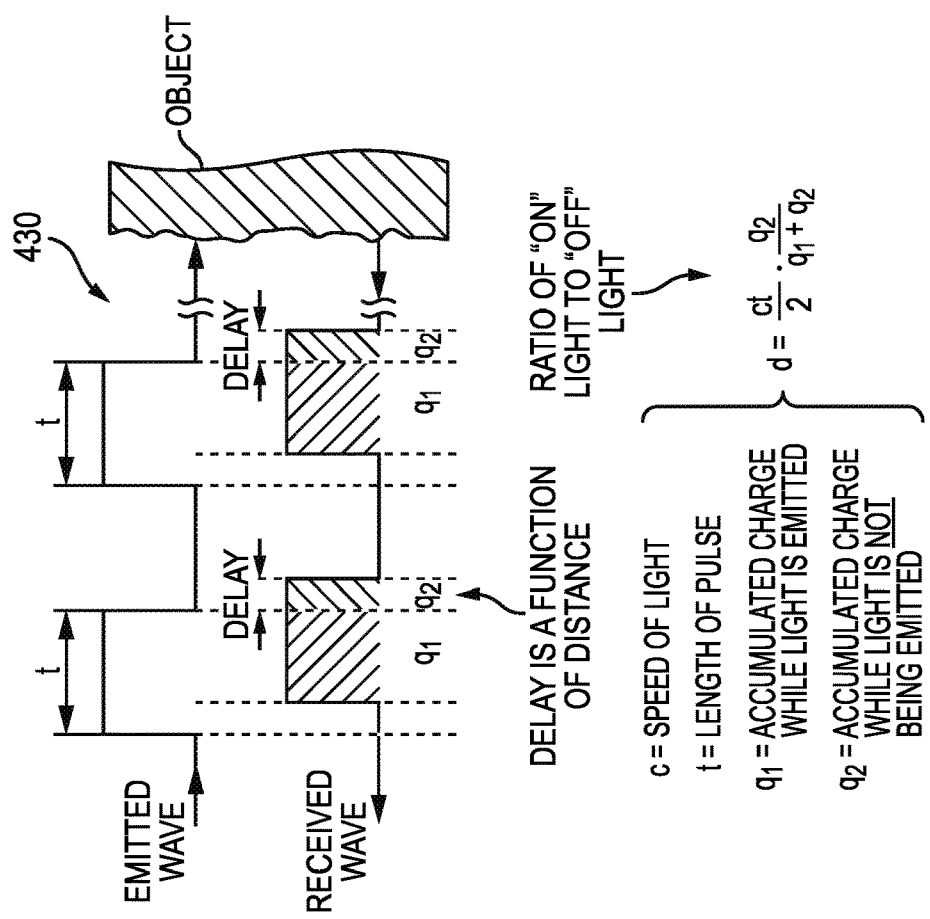
FIG. 16 shows a time-of-flight timing diagram for the system of FIG. 15.

The waveforms 424, 425 are configured to penetrate obscuring tissue 403, such as by having wavelengths in the NIR or SWIR spectrum of wavelengths. A spectral signal (e.g., hyperspectral, multispectral, or selective spectral) or a photoacoustic signal is emitted from the emitter 406, as shown by a first arrow 407 pointing distally, and can penetrate the tissue 403 in which the critical structure 401 is concealed. The emitted waveform 424 is reflected by the critical structure 401, as shown by a second arrow 409 pointing proximally. The received waveform 425 can be delayed due to a distance d between a distal end of the surgical device 402 and the critical structure 401. The waveforms 424, 425 can be selected to target the critical structure 401 within the tissue 403 based on the spectral signature of the critical structure 401, as described herein. The emitter 406 is configured to provide a binary signal on and off, as shown in FIG. 16, for example, which can be measured by the receiver 408.

Based on the delay between the emitted wave 424 and the received wave 425, the time-of-flight sensor system 404 is configured to determine the distance d. A time-of-flight timing diagram 430 for the emitter 406 and the receiver 408 of FIG. 15 is shown in FIG. 16. The delay is a function of the distance d and the distance d is given by:

$$d = \frac{ct}{2} \cdot \frac{q_2}{q_1 + q_2}$$

where c=the speed of light; t=length of pulse; q1=accumulated charge while light is emitted; and q2=accumulated charge while light is not being emitted.

The time-of-flight of the waveforms 424, 425 corresponds to the distance d in FIG. 15. In various instances, additional emitters/receivers and/or pulsing signals from the emitter 406 can be configured to emit a non-penetrating signal. The non-penetrating signal can be configured to determine the distance from the emitter 406 to the surface 405 of the obscuring tissue 403. In various instances, a depth of the critical structure 401 can be determined by:

$$d_A = d_w - d_t$$

where $d_A$=the depth of the critical structure 401; $d_w$=the distance from the emitter 406 to the critical structure 401 (d in FIG. 15); and $d_t$=the distance from the emitter 406 (on the distal end of the surgical device 402) to the surface 405 of the obscuring tissue 403.

Figure 17:
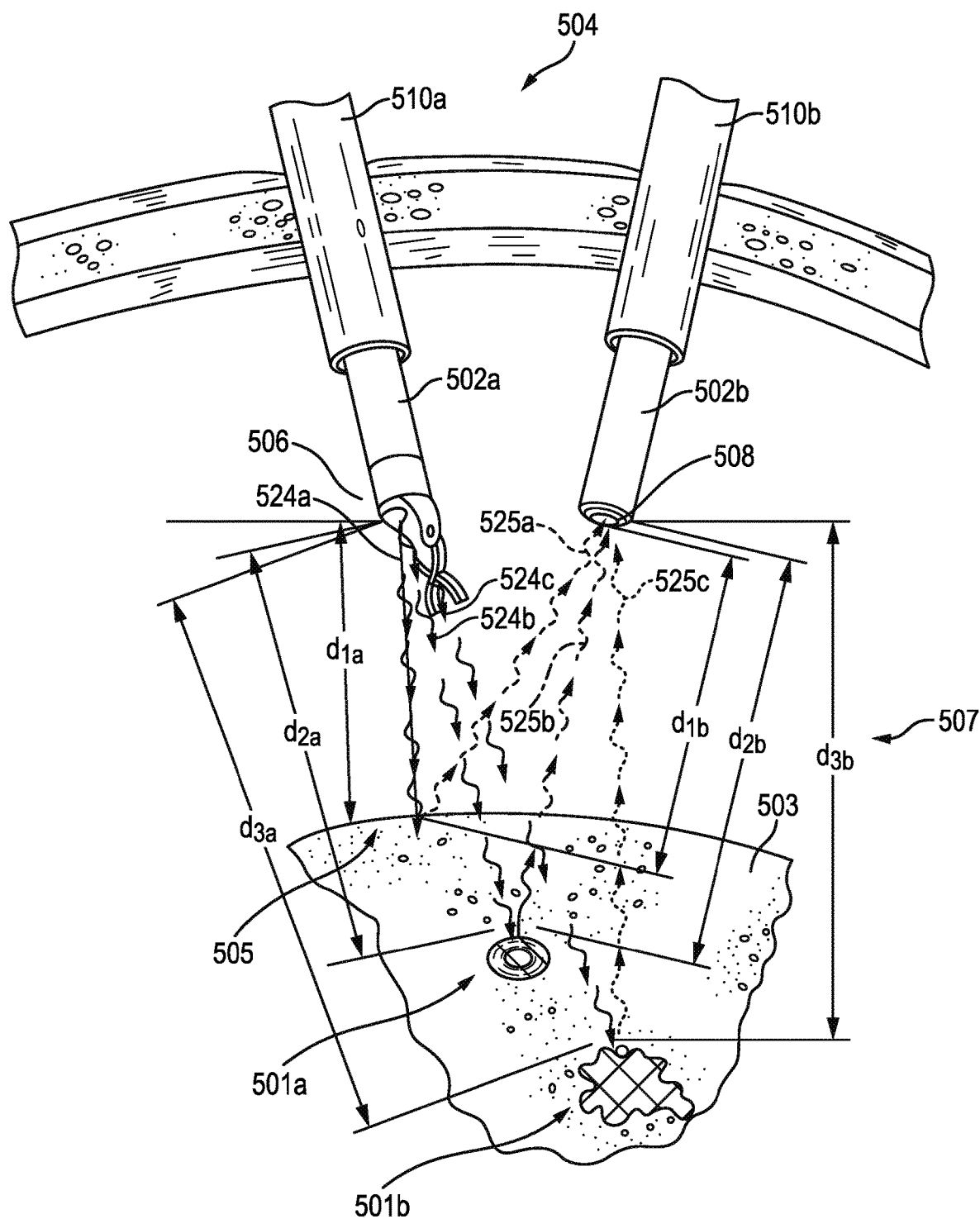
FIG. 17 is a schematic view of another embodiment of a near infrared (NIR) time-of-flight measurement system being utilized intraoperatively.

FIG. 17 illustrates another embodiment of a time-of-flight sensor system 504 utilizing waves 524a, 524b, 524c, 525a, 525b, 525c is shown. The time-of-flight sensor system 504 can be incorporated into a surgical visualization system, e.g., as the sensor system 104 of the surgical visualization system 100 of FIG. 1. The time-of-flight sensor system 504 includes a waveform emitter 506 and a waveform receiver 508 (e.g., the emitter 106 and the receiver 108 of FIG. 1). The waveform emitter 506 is positioned on a first surgical device 502a (e.g., the surgical device 102 of FIG. 1), and the waveform receiver 508 is positioned on a second surgical device 502b. The surgical devices 502a, 502b are positioned through first and second trocars 510a, 510b, respectively, which extend into a cavity 507 in a patient. Although the trocars 510a, 510b are used in this in this illustrated embodiment, other trocars or other access devices can be used, or no access device may be used. The emitted waves 524a, 524b, 524c extend toward a surgical site from the emitter 506, and the received waves 525a, 525b, 525c are reflected back to the receiver 508 from various structures and/or surfaces at the surgical site.

The different emitted waves 524a, 524b, 524c are configured to target different types of material at the surgical site. For example, the wave 524a targets obscuring tissue 503, the wave 524b targets a first critical structure 501a (e.g., the critical structure 101 of FIG. 1), which is a vessel in this illustrated embodiment, and the wave 524c targets a second critical structure 501b (e.g., the critical structure 101 of FIG. 1), which is a cancerous tumor in this illustrated embodiment. The wavelengths of the waves 524a, 524b, 524c can be in the visible light, NIR, or SWIR spectrum of wavelengths. For example, visible light can be reflected off a surface 505 of the tissue 503, and NIR and/or SWIR waveforms can penetrate the surface 505 of the tissue 503. In various aspects, as described herein, a spectral signal (e.g., hyperspectral, multispectral, or selective spectral) or a photoacoustic signal can be emitted from the emitter 506. The waves 524b, 524c can be selected to target the critical structures 501a, 501b within the tissue 503 based on the spectral signature of the critical structure 501a, 501b, as described herein. Photoacoustic imaging is further described in various U.S. patent applications, which are incorporated by reference herein in the present disclosure.

The emitted waves 524a, 524b, 524c are reflected off the targeted material, namely the surface 505, the first critical structure 501a, and the second structure 501b, respectively. The received waveforms 525a, 525b, 525c can be delayed due to distances $d_{1a}$, $d_{2a}$, $d_{3a}$, $d_{1b}$, $d_{2b}$, $d_{2c}$.

In the time-of-flight sensor system 504, in which the emitter 506 and the receiver 508 are independently positionable (e.g., on separate surgical devices 502a, 502b and/or controlled by separate robotic arms), the various distances $d_{1a}$, $d_{2a}$, $d_{3a}$, $d_{1b}$, $d_{2b}$, $d_{2c}$ can be calculated from the known position of the emitter 506 and the receiver 508. For example, the positions can be known when the surgical devices 502a, 502b are robotically-controlled. Knowledge of the positions of the emitter 506 and the receiver 508, as well as the time of the photon stream to target a certain tissue and the information received by the receiver 508 of that particular response can allow a determination of the distances $d_{1a}$, $d_{2a}$, $d_{3a}$, $d_{1b}$, $d_{2b}$, $d_{2c}$. In one aspect, the distance to the obscured critical structures 501a, 501b can be triangulated using penetrating wavelengths. Because the speed of light is constant for any wavelength of visible or invisible light, the time-of-flight sensor system 504 can determine the various distances.

In a view provided to the medical practitioner, such as on a display, the receiver 508 can be rotated such that a center of mass of the target structure in the resulting images remains constant, e.g., in a plane perpendicular to an axis of a select target structure 503, 501a, or 501b. Such an orientation can quickly communicate one or more relevant distances and/or perspectives with respect to the target structure. For example, as shown in FIG. 17, the surgical site is displayed from a viewpoint in which the critical structure 501a is perpendicular to the viewing plane (e.g., the vessel is oriented in/out of the page). Such an orientation can be default setting; however, the view can be rotated or otherwise adjusted by a medical practitioner. In certain instances, the medical practitioner can toggle between different surfaces and/or target structures that define the viewpoint of the surgical site provided by the imaging system.

As in this illustrated embodiment, the receiver 508 can be mounted on the trocar 510b (or other access device) through which the surgical device 502b is positioned. In other embodiments, the receiver 508 can be mounted on a separate robotic arm for which the three-dimensional position is known. In various instances, the receiver 508 can be mounted on a movable arm that is separate from a robotic surgical system that controls the surgical device 502a or can be mounted to an operating room (OR) table or fixture that is intraoperatively registerable to the robot coordinate plane. In such instances, the position of the emitter 506 and the receiver 508 can be registerable to the same coordinate plane such that the distances can be triangulated from outputs from the time-of-flight sensor system 504.

Combining time-of-flight sensor systems and near-infrared spectroscopy (NIRS), termed TOF-NIRS, which is capable of measuring the time-resolved profiles of NIR light with nanosecond resolution can be found in "Time-Of-Flight Near-Infrared Spectroscopy For Nondestructive Measurement Of Internal Quality In Grapefruit," Journal of the American Society for Horticultural Science, May 2013 vol. 138 no. 3 225-228, which is hereby incorporated by reference in its entirety.

Embodiments of visualization systems and aspects and uses thereof are described further in U.S. Pat. Pub. No. 2020/0015923 entitled "Surgical Visualization Platform" filed Sep. 11, 2018, U.S. Pat. Pub. No. 2020/0015900 entitled "Controlling An Emitter Assembly Pulse Sequence" filed Sep. 11, 2018, U.S. Pat. Pub. No. 2020/0015668 entitled "Singular EMR Source Emitter Assembly" filed Sep. 11, 2018, U.S. Pat. Pub. No. 2020/0015925 entitled "Combination Emitter And Camera Assembly" filed Sep. 11, 2018, U.S. Pat. Pub. No. 2020/00015899 entitled "Surgical Visualization With Proximity Tracking Features" filed Sep. 11, 2018, U.S. Pat. Pub. No. 2020/00015903 entitled "Surgical Visualization Of Multiple Targets" filed Sep. 11, 2018, U.S. Pat. No. 10,792,034 entitled "Visualization Of Surgical Devices" filed Sep. 11, 2018, U.S. Pat. Pub. No. 2020/0015897 entitled "Operative Communication Of Light" filed Sep. 11, 2018, U.S. Pat. Pub. No. 2020/0015924 entitled "Robotic Light Projection Tools" filed Sep. 11, 2018, U.S. Pat. Pub. No. 2020/0015898 entitled "Surgical Visualization Feedback System" filed Sep. 11, 2018, U.S. Pat. Pub. No. 2020/0015906 entitled "Surgical Visualization And Monitoring" filed Sep. 11, 2018, U.S. Pat. Pub. No. 2020/0015907 entitled "Integration Of Imaging Data" filed Sep. 11, 2018, U.S. Pat. No. 10,925,598 entitled "Robotically-Assisted Surgical Suturing Systems" filed Sep. 11, 2018, U.S. Pat. Pub. No. 2020/0015901 entitled "Safety Logic For Surgical Suturing Systems" filed Sep. 11, 2018, U.S. Pat. Pub. No. 2020/0015914 entitled "Robotic Systems With Separate Photoacoustic Receivers" filed Sep. 11, 2018, U.S. Pat. Pub. No. 2020/0015902 entitled "Force Sensor Through Structured Light Deflection" filed Sep. 11, 2018, U.S. Pat. Pub. No. 2019/0201136 entitled "Method Of Hub Communication" filed Dec. 4, 2018, U.S. patent application Ser. No. 16/729,772 entitled "Analyzing Surgical Trends By A Surgical System" filed Dec. 30, 2019, U.S. patent application Ser. No. 16/729,747 entitled "Dynamic Surgical Visualization Systems" filed Dec. 30, 2019, U.S. patent application Ser. No. 16/729,744 entitled "Visualization Systems Using Structured Light" filed Dec. 30, 2019, U.S. patent application Ser. No. 16/729,778 entitled "System And Method For Determining, Adjusting, And Managing Resection Margin About A Subject Tissue" filed Dec. 30, 2019, U.S. patent application Ser. No. 16/729,729 entitled "Surgical Systems For Proposing And Corroborating Organ Portion Removals" filed Dec. 30, 2019, U.S. patent application Ser. No. 16/729,778 entitled "Surgical System For Overlaying Surgical Instrument Data Onto A Virtual Three Dimensional Construct Of An Organ" filed Dec. 30, 2019, U.S. patent application Ser. No. 16/729,751 entitled "Surgical Systems For Generating Three Dimensional Constructs Of Anatomical Organs And Coupling Identified Anatomical Structures Thereto" filed Dec. 30, 2019, U.S. patent application Ser. No. 16/729,740 entitled "Surgical Systems Correlating Visualization Data And Powered Surgical Instrument Data" filed Dec. 30, 2019, U.S. patent application Ser. No. 16/729,737 entitled "Adaptive Surgical System Control According To Surgical Smoke Cloud Characteristics" filed Dec. 30, 2019, U.S. patent application Ser. No. 16/729,796 entitled "Adaptive Surgical System Control According To Surgical Smoke Particulate Characteristics" filed Dec. 30, 2019, U.S. patent application Ser. No. 16/729,803 entitled "Adaptive Visualization By A Surgical System" filed Dec. 30, 2019, U.S. patent application Ser. No. 16/729,807 entitled "Method Of Using Imaging Devices In Surgery" filed Dec. 30, 2019, U.S. Prov. Pat. App. No. 63/249,652 entitled "Surgical Devices, Systems, and Methods Using Fiducial Identification and Tracking" filed on Sep. 29, 2021, U.S. Prov. Pat. App. No. 63/249,658 entitled "Surgical Devices, Systems, and Methods for Control of One Visualization with Another" filed on Sep. 29, 2021, U.S. Prov. Pat. App. No. 63/249,870 entitled "Methods and Systems for Controlling Cooperative Surgical Instruments" filed on Sep. 29, 2021, U.S. Prov. Pat. App. No. 63/249,881 entitled "Methods and Systems for Controlling Cooperative Surgical Instruments with Variable Surgical Site Access Trajectories" filed on Sep. 29, 2021, U.S. Prov. Pat. App. No. 63/249,877 entitled "Methods and Systems for Controlling Cooperative Surgical Instruments" filed on Sep. 29, 2021, and U.S. Prov. Pat. App. No. 63/249,980 entitled "Cooperative Access" filed on Sep. 29, 2021, which are hereby incorporated by reference in their entireties.

Surgical Hubs

The various visualization or imaging systems described herein can be incorporated into a system that includes a surgical hub. In general, a surgical hub can be a component of a comprehensive digital medical system capable of spanning multiple medical facilities and configured to provide integrated and comprehensive improved medical care to a vast number of patients. The comprehensive digital medical system includes a cloud-based medical analytics system that is configured to interconnect to multiple surgical hubs located across many different medical facilities. The surgical hubs are configured to interconnect with one or more elements, such as one or more surgical instruments that are used to conduct medical procedures on patients and/or one or more visualization systems that are used during performance of medical procedures. The surgical hubs provide a wide array of functionality to improve the outcomes of medical procedures. The data generated by the various surgical devices, visualization systems, and surgical hubs about the patient and the medical procedure may be transmitted to the cloud-based medical analytics system. This data may then be aggregated with similar data gathered from many other surgical hubs, visualization systems, and surgical instruments located at other medical facilities. Various patterns and correlations may be found through the cloud-based analytics system analyzing the collected data. Improvements in the techniques used to generate the data may be generated as a result, and these improvements may then be disseminated to the various surgical hubs, visualization systems, and surgical instruments. Due to the interconnectedness of all of the aforementioned components, improvements in medical procedures and practices may be found that otherwise may not be found if the many components were not so interconnected.

Examples of surgical hubs configured to receive, analyze, and output data, and methods of using such surgical hubs, are further described in U.S. Pat. Pub. No. 2019/0200844 entitled "Method Of Hub Communication, Processing, Storage And Display" filed Dec. 4, 2018, U.S. Pat. Pub. No. 2019/0200981 entitled "Method Of Compressing Tissue Within A Stapling Device And Simultaneously Displaying The Location Of The Tissue Within The Jaws" filed Dec. 4, 2018, U.S. Pat. Pub. No. 2019/0201046 entitled "Method For Controlling Smart Energy Devices" filed Dec. 4, 2018, U.S. Pat. Pub. No. 2019/0201114 entitled "Adaptive Control Program Updates For Surgical Hubs" filed Mar. 29, 2018, U.S. Pat. Pub. No. 2019/0201140 entitled "Surgical Hub Situational Awareness" filed Mar. 29, 2018, U.S. Pat. Pub. No. 2019/0206004 entitled "Interactive Surgical Systems With Condition Handling Of Devices And Data Capabilities" filed Mar. 29, 2018, U.S. Pat. Pub. No. 2019/0206555 entitled "Cloud-based Medical Analytics For Customization And Recommendations To A User" filed Mar. 29, 2018, and U.S. Pat. Pub. No. 2019/0207857 entitled "Surgical Network Determination Of Prioritization Of Communication, Interaction, Or Processing Based On System Or Device Needs" filed Nov. 6, 2018, which are hereby incorporated by reference in their entireties.

Figure 18:
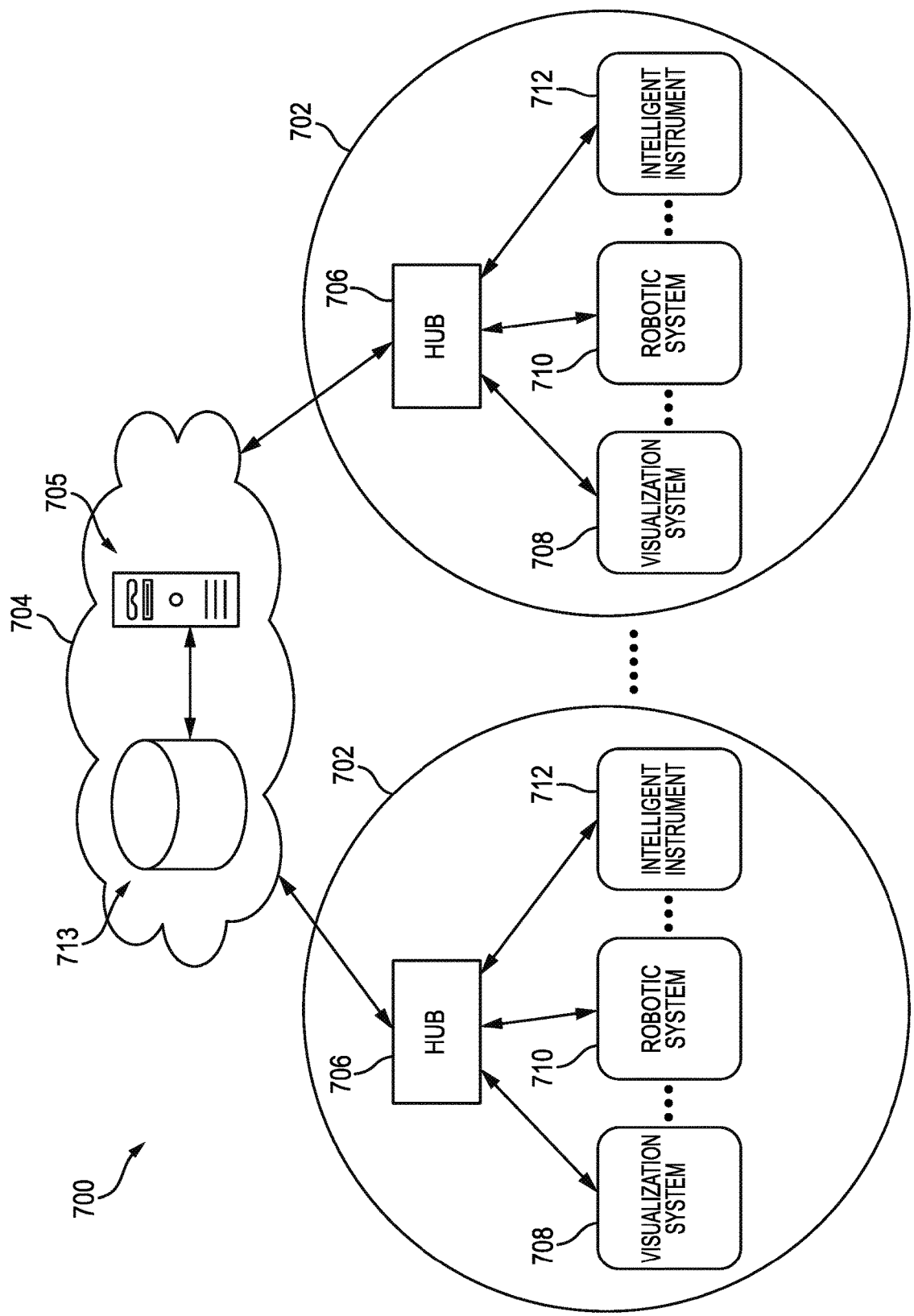
FIG. 18 is a schematic view of one embodiment of a computer-implemented interactive surgical system.

FIG. 18 illustrates one embodiment of a computer-implemented interactive surgical system 700 that includes one or more surgical systems 702 and a cloud-based system (e.g., a cloud 704 that can include a remote server 713 coupled to a storage device 705). Each surgical system 702 includes at least one surgical hub 706 in communication with the cloud 704. In one example, as illustrated in FIG. 18, the surgical system 702 includes a visualization system 708, a robotic system 710, and an intelligent (or "smart") surgical instrument 712, which are configured to communicate with one another and/or the hub 706. The intelligent surgical instrument 712 can include imaging device(s). The surgical system 702 can include an M number of hubs 706, an N number of visualization systems 708, an O number of robotic systems 710, and a P number of intelligent surgical instruments 712, where M, N, O, and P are integers greater than or equal to one that may or may not be equal to any one or more of each other. Various exemplary intelligent surgical instruments and robotic systems are described herein.

Data received by a surgical hub from a surgical visualization system can be used in any of a variety of ways. In an exemplary embodiment, the surgical hub can receive data from a surgical visualization system in use with a patient in a surgical setting, e.g., in use in an operating room during performance of a surgical procedure. The surgical hub can use the received data in any of one or more ways, as discussed herein.

The surgical hub can be configured to analyze received data in real time with use of the surgical visualization system and adjust control one or more of the surgical visualization system and/or one or more intelligent surgical instruments in use with the patient based on the analysis of the received data. Such adjustment can include, for example, adjusting one or operational control parameters of intelligent surgical instrument(s), causing one or more sensors of one or more intelligent surgical instruments to take a measurement to help gain an understanding of the patient's current physiological condition, and/or current operational status of an intelligent surgical instrument, and other adjustments. Controlling and adjusting operation of intelligent surgical instruments is discussed further below. Examples of operational control parameters of an intelligent surgical instrument include motor speed, cutting element speed, time, duration, level of energy application, and light emission. Examples of surgical hubs and of controlling and adjusting intelligent surgical instrument operation are described further in previously mentioned U.S. patent application Ser. No. 16/729,772 entitled "Analyzing Surgical Trends By A Surgical System" filed Dec. 30, 2019, U.S. patent application Ser. No. 16/729,747 entitled "Dynamic Surgical Visualization Systems" filed Dec. 30, 2019, U.S. patent application Ser. No. 16/729,744 entitled "Visualization Systems Using Structured Light" filed Dec. 30, 2019, U.S. patent application Ser. No. 16/729,778 entitled "System And Method For Determining, Adjusting, And Managing Resection Margin About A Subject Tissue" filed Dec. 30, 2019, U.S. patent application Ser. No. 16/729,729 entitled "Surgical Systems For Proposing And Corroborating Organ Portion Removals" filed Dec. 30, 2019, U.S. patent application Ser. No. 16/729,778 entitled "Surgical System For Overlaying Surgical Instrument Data Onto A Virtual Three Dimensional Construct Of An Organ" filed Dec. 30, 2019, U.S. patent application Ser. No. 16/729,751 entitled "Surgical Systems For Generating Three Dimensional Constructs Of Anatomical Organs And Coupling Identified Anatomical Structures Thereto" filed Dec. 30, 2019, U.S. patent application Ser. No. 16/729,740 entitled "Surgical Systems Correlating Visualization Data And Powered Surgical Instrument Data" filed Dec. 30, 2019, U.S. patent application Ser. No. 16/729,737 entitled "Adaptive Surgical System Control According To Surgical Smoke Cloud Characteristics" filed Dec. 30, 2019, U.S. patent application Ser. No. 16/729,796 entitled "Adaptive Surgical System Control According To Surgical Smoke Particulate Characteristics" filed Dec. 30, 2019, U.S. patent application Ser. No. 16/729,803 entitled "Adaptive Visualization By A Surgical System" filed Dec. 30, 2019, and U.S. patent application Ser. No. 16/729,807 entitled "Method Of Using Imaging Devices In Surgery" filed Dec. 30, 2019, and in U.S. patent application Ser. No. 17/068,857 entitled "Adaptive Responses From Smart Packaging Of Drug Delivery Absorbable Adjuncts" filed Oct. 13, 2020, U.S. patent application Ser. No. 17/068,858 entitled "Drug Administration Devices That Communicate With Surgical Hubs" filed Oct. 13, 2020, U.S. patent application Ser. No. 17/068,859 entitled "Controlling Operation Of Drug Administration Devices Using Surgical Hubs" filed Oct. 13, 2020, U.S. patent application Ser. No. 17/068,863 entitled "Patient Monitoring Using Drug Administration Devices" filed Oct. 13, 2020, U.S. patent application Ser. No. 17/068,865 entitled "Monitoring And Communicating Information Using Drug Administration Devices" filed Oct. 13, 2020, and U.S. patent application Ser. No. 17/068,867 entitled "Aggregating And Analyzing Drug Administration Data" filed Oct. 13, 2020, which are hereby incorporated by reference in their entireties.

The surgical hub can be configured to cause visualization of the received data to be provided in the surgical setting on a display so that a medical practitioner in the surgical setting can view the data and thereby receive an understanding of the operation of the imaging device(s) in use in the surgical setting. Such information provided via visualization can include text and/or images.

Figure 19:
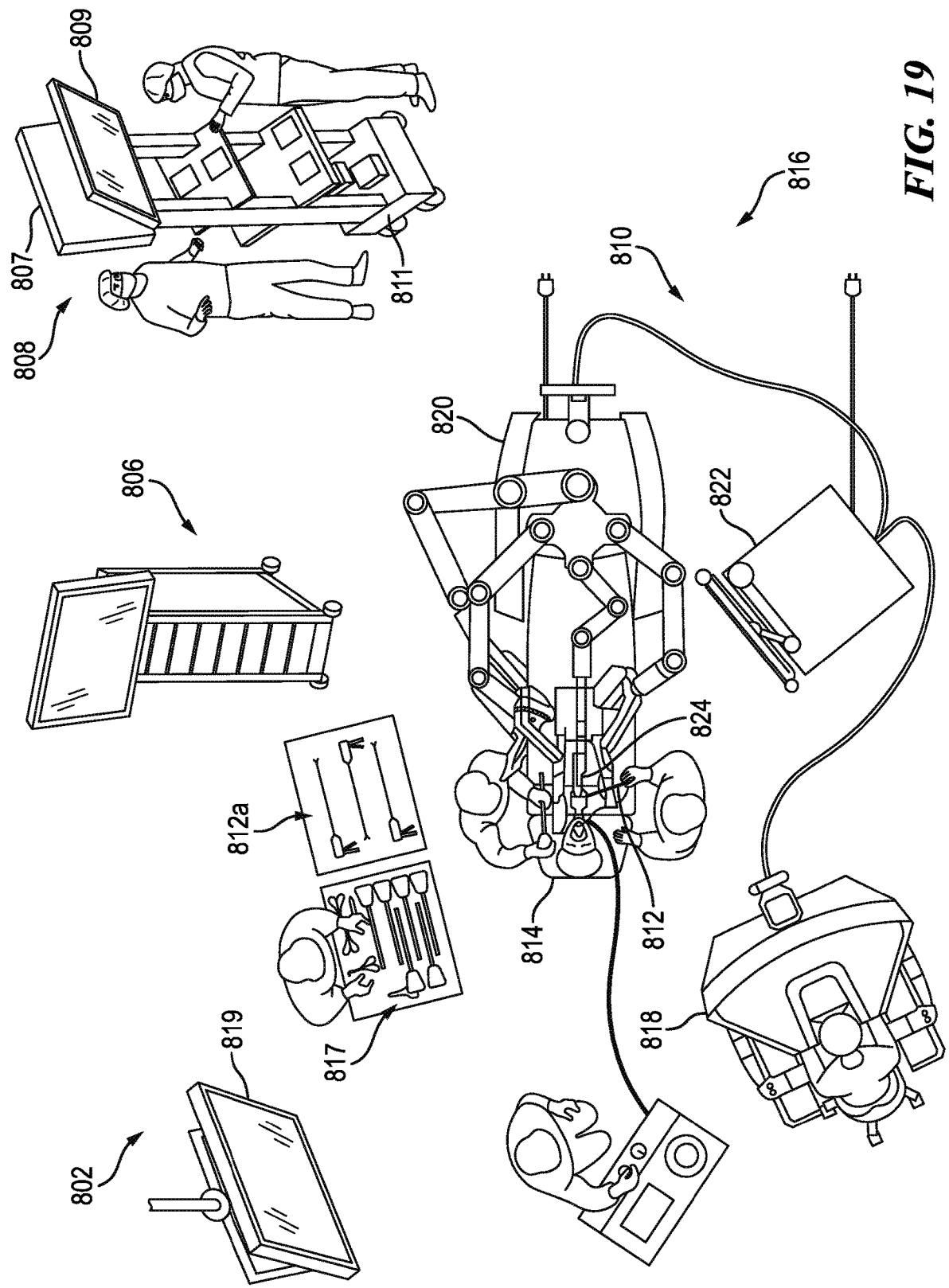
FIG. 19 is a schematic view of one embodiment a surgical system being used to perform a surgical procedure in an operating room.

FIG. 19 illustrates one embodiment of a surgical system 802 including a surgical hub 806 (e.g., the surgical hub 706 of FIG. 18 or other surgical hub described herein), a robotic surgical system 810 (e.g., the robotic surgical system 110 of FIG. 1 or other robotic surgical system herein), and a visualization system 808 (e.g., the visualization system 100 of FIG. 1 or other visualization system described herein). The surgical hub 806 can be in communication with a cloud, as discussed herein. FIG. 19 shows the surgical system 802 being used to perform a surgical procedure on a patient who is lying down on an operating table 814 in a surgical operating room 816. The robotic system 810 includes a surgeon's console 818, a patient side cart 820 (surgical robot), and a robotic system surgical hub 822. The robotic system surgical hub 822 is generally configured similar to the surgical hub 822 and can be in communication with a cloud. In some embodiments, the robotic system surgical hub 822 and the surgical hub 806 can be combined. The patient side cart 820 can manipulate an intelligent surgical tool 812 through a minimally invasive incision in the body of the patient while a medical practitioner, e.g., a surgeon, nurse, and/or other medical practitioner, views the surgical site through the surgeon's console 818. An image of the surgical site can be obtained by an imaging device 824 (e.g., the imaging device 120 of FIG. 1 or other imaging device described herein), which can be manipulated by the patient side cart 820 to orient the imaging device 824. The robotic system surgical hub 822 can be used to process the images of the surgical site for subsequent display to the surgeon through the surgeon's console 818.

A primary display 819 is positioned in the sterile field of the operating room 816 and is configured to be visible to an operator at the operating table 814. In addition, as in this illustrated embodiment, a visualization tower 818 can positioned outside the sterile field. The visualization tower 818 includes a first non-sterile display 807 and a second non-sterile display 809, which face away from each other. The visualization system 808, guided by the surgical hub 806, is configured to utilize the displays 807, 809, 819 to coordinate information flow to medical practitioners inside and outside the sterile field. For example, the surgical hub 806 can cause the visualization system 808 to display a snapshot and/or a video of a surgical site, as obtained by the imaging device 824, on one or both of the non-sterile displays 807, 809, while maintaining a live feed of the surgical site on the primary display 819. The snapshot and/or video on the non-sterile display 807 and/or 809 can permit a non-sterile medical practitioner to perform a diagnostic step relevant to the surgical procedure, for example.

The surgical hub 806 is configured to route a diagnostic input or feedback entered by a non-sterile medical practitioner at the visualization tower 818 to the primary display 819 within the sterile field, where it can be viewed by a sterile medical practitioner at the operating table 814. For example, the input can be in the form of a modification to the snapshot and/or video displayed on the non-sterile display 807 and/or 809, which can be routed to the primary display 819 by the surgical hub 806.

The surgical hub 806 is configured to coordinate information flow to a display of the intelligent surgical instrument 812, as is described in various U.S. Patent Applications that are incorporated by reference herein in the present disclosure. A diagnostic input or feedback entered by a non-sterile operator at the visualization tower 818 can be routed by the surgical hub 806 to the display 819 within the sterile field, where it can be viewed by the operator of the surgical instrument 812 and/or by other medical practitioner(s) in the sterile field.

The intelligent surgical instrument 812 and the imaging device 824, which is also an intelligent surgical tool, is being used with the patient in the surgical procedure as part of the surgical system 802. Other intelligent surgical instruments 812a that can be used in the surgical procedure, e.g., that can be removably coupled to the patient side cart 820 and be in communication with the robotic surgical system 810 and the surgical hub 806, are also shown in FIG. 19 as being available. Non-intelligent (or "dumb") surgical instruments 817, e.g., scissors, trocars, cannulas, scalpels, etc., that cannot be in communication with the robotic surgical system 810 and the surgical hub 806 are also shown in FIG. 19 as being available for use.

Operating Intelligent Surgical Instruments

An intelligent surgical device can have an algorithm stored thereon, e.g., in a memory thereof, configured to be executable on board the intelligent surgical device, e.g., by a processor thereof, to control operation of the intelligent surgical device. In some embodiments, instead of or in addition to being stored on the intelligent surgical device, the algorithm can be stored on a surgical hub, e.g., in a memory thereof, that is configured to communicate with the intelligent surgical device.

The algorithm is stored in the form of one or more sets of pluralities of data points defining and/or representing instructions, notifications, signals, etc. to control functions of the intelligent surgical device. In some embodiments, data gathered by the intelligent surgical device can be used by the intelligent surgical device, e.g., by a processor of the intelligent surgical device, to change at least one variable parameter of the algorithm. As discussed above, a surgical hub can be in communication with an intelligent surgical device, so data gathered by the intelligent surgical device can be communicated to the surgical hub and/or data gathered by another device in communication with the surgical hub can be communicated to the surgical hub, and data can be communicated from the surgical hub to the intelligent surgical device. Thus, instead of or in addition to the intelligent surgical device being configured to change a stored variable parameter, the surgical hub can be configured to communicate the changed at least one variable, alone or as part of the algorithm, to the intelligent surgical device and/or the surgical hub can communicate an instruction to the intelligent surgical device to change the at least one variable as determined by the surgical hub.

The at least one variable parameter is among the algorithm's data points, e.g., are included in instructions for operating the intelligent surgical device, and are thus each able to be changed by changing one or more of the stored pluralities of data points of the algorithm. After the at least one variable parameter has been changed, subsequent execution of the algorithm is according to the changed algorithm. As such, operation of the intelligent surgical device over time can be managed for a patient to increase the beneficial results use of the intelligent surgical device by taking into consideration actual situations of the patient and actual conditions and/or results of the surgical procedure in which the intelligent surgical device is being used. Changing the at least one variable parameter is automated to improve patient outcomes. Thus, the intelligent surgical device can be configured to provide personalized medicine based on the patient and the patient's surrounding conditions to provide a smart system. In a surgical setting in which the intelligent surgical device is being used during performance of a surgical procedure, automated changing of the at least one variable parameter may allow for the intelligent surgical device to be controlled based on data gathered during the performance of the surgical procedure, which may help ensure that the intelligent surgical device is used efficiently and correctly and/or may help reduce chances of patient harm by harming a critical anatomical structure.

The at least one variable parameter can be any of a variety of different operational parameters. Examples of variable parameters include motor speed, motor torque, energy level, energy application duration, tissue compression rate, jaw closure rate, cutting element speed, load threshold, etc.

Figure 20:
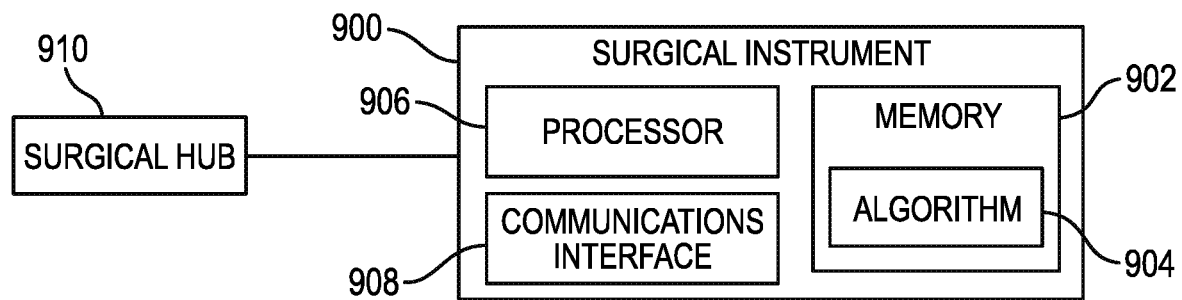
FIG. 20 is a schematic view of one embodiment of a surgical system including a smart surgical instrument and a surgical hub.

FIG. 20 illustrates one embodiment of an intelligent surgical instrument 900 including a memory 902 having an algorithm 904 stored therein that includes at least one variable parameter. The algorithm 904 can be a single algorithm or can include a plurality of algorithms, e.g., separate algorithms for different aspects of the surgical instrument's operation, where each algorithm includes at least one variable parameter. The intelligent surgical instrument 900 can be the surgical device 102 of FIG. 1, the imaging device 120 of FIG. 1, the surgical device 202 of FIG. 8, the imaging device 220 of FIG. 8, the surgical device 402 of FIG. 15, the surgical device 502a of FIG. 17, the surgical device 502b of FIG. 17, the surgical device 712 of FIG. 18, the surgical device 812 of FIG. 19, the imaging device 824 of FIG. 19, or other intelligent surgical instrument. The surgical instrument 900 also includes a processor 906 configured to execute the algorithm 904 to control operation of at least one aspect of the surgical instrument 900. To execute the algorithm 904, the processor 906 is configured to run a program stored in the memory 902 to access a plurality of data points of the algorithm 904 in the memory 902.

The surgical instrument 900 also includes a communications interface 908, e.g., a wireless transceiver or other wired or wireless communications interface, configured to communicate with another device, such as a surgical hub 910. The communications interface 908 can be configured to allow one-way communication, such as providing data to a remote server (e.g., a cloud server or other server) and/or to a local, surgical hub server, and/or receiving instructions or commands from a remote server and/or a local, surgical hub server, or two-way communication, such as providing information, messages, data, etc. regarding the surgical instrument 900 and/or data stored thereon and receiving instructions, such as from a doctor; a remote server regarding updates to software; a local, surgical hub server regarding updates to software; etc.

The surgical instrument 900 is simplified in FIG. 20 and can include additional components, e.g., a bus system, a handle, a elongate shaft having an end effector at a distal end thereof, a power source, etc. The processor 906 can also be configured to execute instructions stored in the memory 902 to control the device 900 generally, including other electrical components thereof such as the communications interface 908, an audio speaker, a user interface, etc.

The processor 906 is configured to change at least one variable parameter of the algorithm 904 such that a subsequent execution of the algorithm 904 will be in accordance with the changed at least one variable parameter. To change the at least one variable parameter of the algorithm 904, the processor 906 is configured to modify or update the data point(s) of the at least one variable parameter in the memory 902. The processor 906 can be configured to change the at least one variable parameter of the algorithm 904 in real time with use of the surgical device 900 during performance of a surgical procedure, which may accommodate real time conditions.

Additionally or alternatively to the processor 906 changing the at least one variable parameter, the processor 906 can be configured to change the algorithm 904 and/or at least one variable parameter of the algorithm 904 in response to an instruction received from the surgical hub 910. In some embodiments, the processor 906 is configured to change the at least one variable parameter only after communicating with the surgical hub 910 and receiving an instruction therefrom, which may help ensure coordinated action of the surgical instrument 900 with other aspects of the surgical procedure in which the surgical instrument 900 is being used.

In an exemplary embodiment, the processor 906 executes the algorithm 904 to control operation of the surgical instrument 900, changes the at least one variable parameter of the algorithm 904 based on real time data, and executes the algorithm 904 after changing the at least one variable parameter to control operation of the surgical instrument 900.

Figure 21:
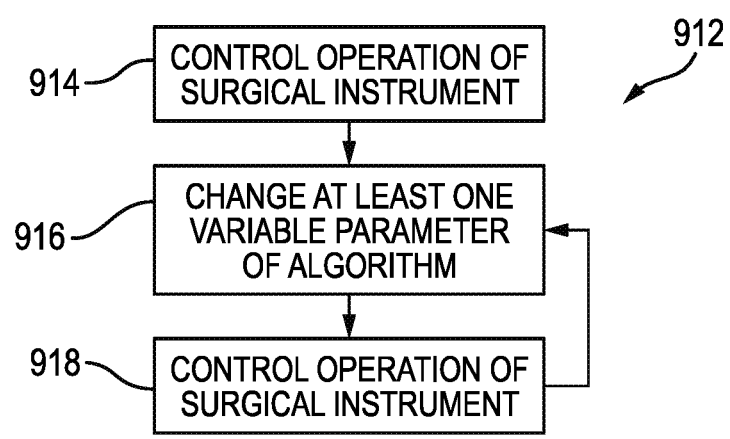
FIG. 21 is a flowchart showing a method of controlling the smart surgical instrument of FIG. 20.

FIG. 21 illustrates one embodiment of a method 912 of using of the surgical instrument 900 including a change of at least one variable parameter of the algorithm 904. The processor 906 controls 914 operation of the surgical instrument 900 by executing the algorithm 904 stored in the memory 902. Based on any of this subsequently known data and/or subsequently gathered data, the processor 904 changes 916 the at least one variable parameter of the algorithm 904 as discussed above. After changing the at least one variable parameter, the processor 906 controls 918 operation of the surgical instrument 900 by executing the algorithm 904, now with the changed at least one variable parameter. The processor 904 can change 916 the at least one variable parameter any number of times during performance of a surgical procedure, e.g., zero, one, two, three, etc. During any part of the method 912, the surgical instrument 900 can communicate with one or more computer systems, e.g., the surgical hub 910, a remote server such as a cloud server, etc., using the communications interface 908 to provide data thereto and/or receive instructions therefrom.

Situational Awareness

Operation of an intelligent surgical instrument can be altered based on situational awareness of the patient. The operation of the intelligent surgical instrument can be altered manually, such as by a user of the intelligent surgical instrument handling the instrument differently, providing a different input to the instrument, ceasing use of the instrument, etc. Additionally or alternatively, the operation of an intelligent surgical instrument can be changed automatically by an algorithm of the instrument being changed, e.g., by changing at least one variable parameter of the algorithm. As mentioned above, the algorithm can be adjusted automatically without user input requesting the change. Automating the adjustment during performance of a surgical procedure may help save time, may allow medical practitioners to focus on other aspects of the surgical procedure, and/or may ease the process of using the surgical instrument for a medical practitioner, which each may improve patient outcomes, such as by avoiding a critical structure, controlling the surgical instrument with consideration of a tissue type the instrument is being used on and/or near, etc.

The visualization systems described herein can be utilized as part of a situational awareness system that can be embodied or executed by a surgical hub, e.g., the surgical hub 706, the surgical hub 806, or other surgical hub described herein.

In particular, characterizing, identifying, and/or visualizing surgical instruments (including their positions, orientations, and actions), tissues, structures, users, and/or other things located within the surgical field or the operating theater can provide contextual data that can be utilized by a situational awareness system to infer various information, such as a type of surgical procedure or a step thereof being performed, a type of tissue(s) and/or structure(s) being manipulated by a surgeon or other medical practitioner, and other information. The contextual data can then be utilized by the situational awareness system to provide alerts to a user, suggest subsequent steps or actions for the user to undertake, prepare surgical devices in anticipation for their use (e.g., activate an electrosurgical generator in anticipation of an electrosurgical instrument being utilized in a subsequent step of the surgical procedure, etc.), control operation of intelligent surgical instruments (e.g., customize surgical instrument operational parameters of an algorithm as discussed further below), and so on.

Although an intelligent surgical device including an algorithm that responds to sensed data, e.g., by having at least one variable parameter of the algorithm changed, can be an improvement over a "dumb" device that operates without accounting for sensed data, some sensed data can be incomplete or inconclusive when considered in isolation, e.g., without the context of the type of surgical procedure being performed or the type of tissue that is being operated on. Without knowing the procedural context (e.g., knowing the type of tissue being operated on or the type of procedure being performed), the algorithm may control the surgical device incorrectly or sub-optimally given the particular context-free sensed data. For example, the optimal manner for an algorithm to control a surgical instrument in response to a particular sensed parameter can vary according to the particular tissue type being operated on. This is due to the fact that different tissue types have different properties (e.g., resistance to tearing, ease of being cut, etc.) and thus respond differently to actions taken by surgical instruments. Therefore, it may be desirable for a surgical instrument to take different actions even when the same measurement for a particular parameter is sensed. As one example, the optimal manner in which to control a surgical stapler in response to the surgical stapler sensing an unexpectedly high force to close its end effector will vary depending upon whether the tissue type is susceptible or resistant to tearing. For tissues that are susceptible to tearing, such as lung tissue, the surgical instrument's control algorithm would optimally ramp down the motor in response to an unexpectedly high force to close to avoid tearing the tissue, e.g., change a variable parameter controlling motor speed or torque so the motor is slower. For tissues that are resistant to tearing, such as stomach tissue, the instrument's algorithm would optimally ramp up the motor in response to an unexpectedly high force to close to ensure that the end effector is clamped properly on the tissue, e.g., change a variable parameter controlling motor speed or torque so the motor is faster. Without knowing whether lung or stomach tissue has been clamped, the algorithm may be sub-optimally changed or not changed at all.

A surgical hub can be configured to derive information about a surgical procedure being performed based on data received from various data sources and then control modular devices accordingly. In other words, the surgical hub can be configured to infer information about the surgical procedure from received data and then control the modular devices operably coupled to the surgical hub based upon the inferred context of the surgical procedure. Modular devices can include any surgical device that is controllable by a situational awareness system, such as visualization system devices (e.g., a camera, a display screen, etc.), smart surgical instruments (e.g., an ultrasonic surgical instrument, an electrosurgical instrument, a surgical stapler, smoke evacuators, scopes, etc.). A modular device can include sensor(s)s configured to detect parameters associated with a patient with which the device is being used and/or associated with the modular device itself.

The contextual information derived or inferred from the received data can include, for example, a type of surgical procedure being performed, a particular step of the surgical procedure that the surgeon (or other medical practitioner) is performing, a type of tissue being operated on, or a body cavity that is the subject of the surgical procedure. The situational awareness system of the surgical hub can be configured to derive the contextual information from the data received from the data sources in a variety of different ways. In an exemplary embodiment, the contextual information received by the situational awareness system of the surgical hub is associated with a particular control adjustment or set of control adjustments for one or more modular devices. The control adjustments each correspond to a variable parameter. In one example, the situational awareness system includes a pattern recognition system, or machine learning system (e.g., an artificial neural network), that has been trained on training data to correlate various inputs (e.g., data from databases, patient monitoring devices, and/or modular devices) to corresponding contextual information regarding a surgical procedure. In other words, a machine learning system can be trained to accurately derive contextual information regarding a surgical procedure from the provided inputs. In another example, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling at least one modular device. In another example, the situational awareness system includes a further machine learning system, lookup table, or other such system, which generates or retrieves one or more control adjustments for one or more modular devices when provided the contextual information as input.

A surgical hub including a situational awareness system may provide any number of benefits for a surgical system. One benefit includes improving the interpretation of sensed and collected data, which would in turn improve the processing accuracy and/or the usage of the data during the course of a surgical procedure. Another benefit is that the situational awareness system for the surgical hub may improve surgical procedure outcomes by allowing for adjustment of surgical instruments (and other modular devices) for the particular context of each surgical procedure (such as adjusting to different tissue types) and validating actions during a surgical procedure. Yet another benefit is that the situational awareness system may improve surgeon's and/or other medical practitioners' efficiency in performing surgical procedures by automatically suggesting next steps, providing data, and adjusting displays and other modular devices in the surgical theater according to the specific context of the procedure. Another benefit includes proactively and automatically controlling modular devices according to the particular step of the surgical procedure that is being performed to reduce the number of times that medical practitioners are required to interact with or control the surgical system during the course of a surgical procedure, such as by a situationally aware surgical hub proactively activating a generator to which an RF electrosurgical instrument is connected if it determines that a subsequent step of the procedure requires the use of the instrument. Proactively activating the energy source allows the instrument to be ready for use a soon as the preceding step of the procedure is completed.

For example, a situationally aware surgical hub can be configured to determine what type of tissue is being operated on. Therefore, when an unexpectedly high force to close a surgical instrument's end effector is detected, the situationally aware surgical hub can be configured to correctly ramp up or ramp down a motor of the surgical instrument for the type of tissue, e.g., by changing or causing change of at least one variable parameter of an algorithm for the surgical instrument regarding motor speed or torque.

For another example, a type of tissue being operated can affect adjustments that are made to compression rate and load thresholds of a surgical stapler for a particular tissue gap measurement. A situationally aware surgical hub can be configured to infer whether a surgical procedure being performed is a thoracic or an abdominal procedure, allowing the surgical hub to determine whether the tissue clamped by an end effector of the surgical stapler is lung tissue (for a thoracic procedure) or stomach tissue (for an abdominal procedure). The surgical hub can then be configured to cause adjustment of the compression rate and load thresholds of the surgical stapler appropriately for the type of tissue, e.g., by changing or causing change of at least one variable parameter of an algorithm for the surgical stapler regarding compression rate and load threshold.

As yet another example, a type of body cavity being operated in during an insufflation procedure can affect the function of a smoke evacuator. A situationally aware surgical hub can be configured to determine whether the surgical site is under pressure (by determining that the surgical procedure is utilizing insufflation) and determine the procedure type. As a procedure type is generally performed in a specific body cavity, the surgical hub can be configured to control a motor rate of the smoke evacuator appropriately for the body cavity being operated in, e.g., by changing or causing change of at least one variable parameter of an algorithm for the smoke evacuator regarding motor rate. Thus, a situationally aware surgical hub may provide a consistent amount of smoke evacuation for both thoracic and abdominal procedures.

As yet another example, a type of procedure being performed can affect the optimal energy level for an ultrasonic surgical instrument or radio frequency (RF) electrosurgical instrument to operate at. Arthroscopic procedures, for example, require higher energy levels because an end effector of the ultrasonic surgical instrument or RF electrosurgical instrument is immersed in fluid. A situationally aware surgical hub can be configured to determine whether the surgical procedure is an arthroscopic procedure. The surgical hub can be configured to adjust an RF power level or an ultrasonic amplitude of the generator (e.g., adjust energy level) to compensate for the fluid filled environment, e.g., by changing or causing change of at least one variable parameter of an algorithm for the instrument and/or a generator regarding energy level. Relatedly, a type of tissue being operated on can affect the optimal energy level for an ultrasonic surgical instrument or RF electrosurgical instrument to operate at. A situationally aware surgical hub can be configured to determine what type of surgical procedure is being performed and then customize the energy level for the ultrasonic surgical instrument or RF electrosurgical instrument, respectively, according to the expected tissue profile for the surgical procedure, e.g., by changing or causing change of at least one variable parameter of an algorithm for the instrument and/or a generator regarding energy level. Furthermore, a situationally aware surgical hub can be configured to adjust the energy level for the ultrasonic surgical instrument or RF electrosurgical instrument throughout the course of a surgical procedure, rather than just on a procedure-by-procedure basis. A situationally aware surgical hub can be configured to determine what step of the surgical procedure is being performed or will subsequently be performed and then update the control algorithm(s) for the generator and/or ultrasonic surgical instrument or RF electrosurgical instrument to set the energy level at a value appropriate for the expected tissue type according to the surgical procedure step.

As another example, a situationally aware surgical hub can be configured to determine whether the current or subsequent step of a surgical procedure requires a different view or degree of magnification on a display according to feature(s) at the surgical site that the surgeon and/or other medical practitioner is expected to need to view. The surgical hub can be configured to proactively change the displayed view (supplied by, e.g., an imaging device for a visualization system) accordingly so that the display automatically adjusts throughout the surgical procedure.

As yet another example, a situationally aware surgical hub can be configured to determine which step of a surgical procedure is being performed or will subsequently be performed and whether particular data or comparisons between data will be required for that step of the surgical procedure. The surgical hub can be configured to automatically call up data screens based upon the step of the surgical procedure being performed, without waiting for the surgeon or other medical practitioner to ask for the particular information.

As another example, a situationally aware surgical hub can be configured to determine whether a surgeon and/or other medical practitioner is making an error or otherwise deviating from an expected course of action during the course of a surgical procedure, e.g., as provided in a preoperative surgical plan. For example, the surgical hub can be configured to determine a type of surgical procedure being performed, retrieve a corresponding list of steps or order of equipment usage (e.g., from a memory), and then compare the steps being performed or the equipment being used during the course of the surgical procedure to the expected steps or equipment for the type of surgical procedure that the surgical hub determined is being performed. The surgical hub can be configured to provide an alert (visual, audible, and/or tactile) indicating that an unexpected action is being performed or an unexpected device is being utilized at the particular step in the surgical procedure.

In certain instances, operation of a robotic surgical system, such as any of the various robotic surgical systems described herein, can be controlled by the surgical hub based on its situational awareness and/or feedback from the components thereof and/or based on information from a cloud (e.g., the cloud 713 of FIG. 18).

Embodiments of situational awareness systems and using situational awareness systems during performance of a surgical procedure are described further in previously mentioned U.S. patent application Ser. No. 16/729,772 entitled "Analyzing Surgical Trends By A Surgical System" filed Dec. 30, 2019, U.S. patent application Ser. No. 16/729,747 entitled "Dynamic Surgical Visualization Systems" filed Dec. 30, 2019, U.S. patent application Ser. No. 16/729,744 entitled "Visualization Systems Using Structured Light" filed Dec. 30, 2019, U.S. patent application Ser. No. 16/729,778 entitled "System And Method For Determining, Adjusting, And Managing Resection Margin About A Subject Tissue" filed Dec. 30, 2019, U.S. patent application Ser. No. 16/729,729 entitled "Surgical Systems For Proposing And Corroborating Organ Portion Removals" filed Dec. 30, 2019, U.S. patent application Ser. No. 16/729,778 entitled "Surgical System For Overlaying Surgical Instrument Data Onto A Virtual Three Dimensional Construct Of An Organ" filed Dec. 30, 2019, U.S. patent application Ser. No. 16/729,751 entitled "Surgical Systems For Generating Three Dimensional Constructs Of Anatomical Organs And Coupling Identified Anatomical Structures Thereto" filed Dec. 30, 2019, U.S. patent application Ser. No. 16/729,740 entitled "Surgical Systems Correlating Visualization Data And Powered Surgical Instrument Data" filed Dec. 30, 2019, U.S. patent application Ser. No. 16/729,737 entitled "Adaptive Surgical System Control According To Surgical Smoke Cloud Characteristics" filed Dec. 30, 2019, U.S. patent application Ser. No. 16/729,796 entitled "Adaptive Surgical System Control According To Surgical Smoke Particulate Characteristics" filed Dec. 30, 2019, U.S. patent application Ser. No. 16/729,803 entitled "Adaptive Visualization By A Surgical System" filed Dec. 30, 2019, and U.S. patent application Ser. No. 16/729,807 entitled "Method Of Using Imaging Devices In Surgery" filed Dec. 30, 2019.

Integrated Anchoring Elements

In certain embodiments, surgical anchoring systems that are configured for endoluminal access and enable non-traumatic retraction or manipulation of the surgical site to improve access thereto (e.g., visual and/or operational purposes). Unlike conventional systems (e.g., systems that use laparoscopically arranged instruments, such as graspers, to grasp the fragile exterior tissue surfaces of an organ), the present surgical anchoring systems are designed to manipulate the organ using anchor members, which not only have a larger surface area than conventional graspers, but are also configured to apply a manipulation force to an inner tissue layer of an organ, which is typically tougher and less fragile than the organ's outer tissue layer(s). This inner manipulation force can increase the mobilization of an organ at a treatment site to thereby improve access and movement (e.g., for dissection and resection) without damaging the exterior tissue layer of an organ or reducing blood flow to the treatment site. The organ can include multiple natural body lumens (e.g., bronchioles of a lung), whereas in other embodiments, the organ includes a single natural body lumen (e.g., a colon).

In one exemplary embodiment, the surgical anchor systems can include a surgical instrument configured for endoluminal access (e.g., an endoscope) that includes an outer sleeve defining a working channel therethrough and at least one channel arm configured to extend through the working channel. The at least one channel arm includes at least one anchor member coupled to the at least one channel arm and configured to move between expanded and unexpanded states, and at least one control actuator extending along the at least one channel arm and operatively coupled to the at least one anchor member. The at least one control actuator is also operatively coupled to a drive system that is configured to control motion of the at least one channel arm. The at least one anchor member can be configured to be at least partially disposed within a natural body lumen such that, when in the expanded state, the at least one anchor member can contact an inner surface of the natural body lumen and therefore anchor the at least one channel arm to the natural body lumen. As a result, the motion of the channel arm can selectively manipulate the natural body lumen anchored thereto (e.g., internally manipulate) and consequently, the organ which is associated with the natural body lumen.

In another exemplary embodiment, the surgical anchoring systems can include a surgical instrument configured for endoluminal access (e.g., an endoscope) that includes dual coupled deployable fixation elements. The dual coupled deployable fixation elements are configured to interact with both a fixed anatomical location and a moveable anatomical location to manipulate and reposition an organ. The surgical instrument can include a first deployable fixation element that is deployed at a natural body orifice of the organ, which acts as a fixed anatomical location. The surgical instrument can include a second deployable fixation element that is deployed at a moveable anatomical location spaced apart from the fixed anatomical location. The surgical instrument can be configured to manipulate and reposition the organ to improve access and visibility from the opposite side of the organ wall. Due to the coupling of the first deployable fixation element to a fixed anatomical location, the forces and restraints of the fixed anatomical location can be communicated to the second first deployable fixation element to allow for induced lateral forces and movements to the organ.

The term "expanded" is intended to mean that the anchor member(s) has/have increased in size in a desired amount through mechanical means or fluid pressure. These terms are not intended to mean that the anchor member(s) is/are necessarily entirely or 100% filled with a fluid when the anchor member(s) are "expanded" (however, such embodiments are within the scope of the term "filled"). Similarly, the term "unexpanded" does not necessarily mean that the anchor member(s) is/are entirely empty or at 0 pressure. There may be some fluid and the anchor member(s) may have a non-zero pressure in an "unexpanded" state. An "uninflated" anchor member(s) is/are intended to mean that the anchor member(s) is/are mechanically collapsed to a smaller size than the expanded size, or does/do not include fluid in an amount or at a pressure that would be desired after the anchor member(s) is/are filled.

An exemplary surgical anchoring system can include a variety of features as described herein and illustrated in the drawings. However, a person skilled in the art will appreciate that the surgical anchoring systems can include only some of these features and/or it can include a variety of other features known in the art. The surgical anchoring systems described herein are merely intended to represent certain exemplary embodiments. Moreover, while the surgical anchoring systems are shown and described in connection with a lung and a colon, a person skilled in the art will appreciate that these surgical anchoring systems can be used in connection with any other suitable natural body lumens or organs.

A lung resection (e.g., a lobectomy) is a surgical procedure in which all or part (e.g., one or more lobes) of the lung is removed. The purpose of performing a lung resection is to treat a damaged or diseased lung as a result of, for example, lung cancer, emphysema, or bronchiectasis. During a lung resection, the lung or lungs are first deflated, and thereafter one or more incisions are made on the patient's side between the ribs to reach the lungs laparoscopically. Instruments, such as graspers and a laparoscope, are inserted through the incision. Once the infected or damaged area of the lung is identified, the area is dissected from the lung and removed from the one or more incisions. The dissected area and the one or more incisions can be closed, for example, with a surgical stapler or stitches.

Since the lung is deflated during surgery, the lung, or certain portions thereof, may need to be mobilized to allow the instruments to reach the surgical site. This mobilization can be carried out by grasping the outer tissue layer of the lung with graspers and applying a force to the lung through the graspers. However, the pleura and parenchyma of the lung are very fragile and therefore can be easily ripped or torn under the applied force. Additionally, during mobilization, the graspers can cut off blood supply to one or more areas of the lung.

Figure 22:
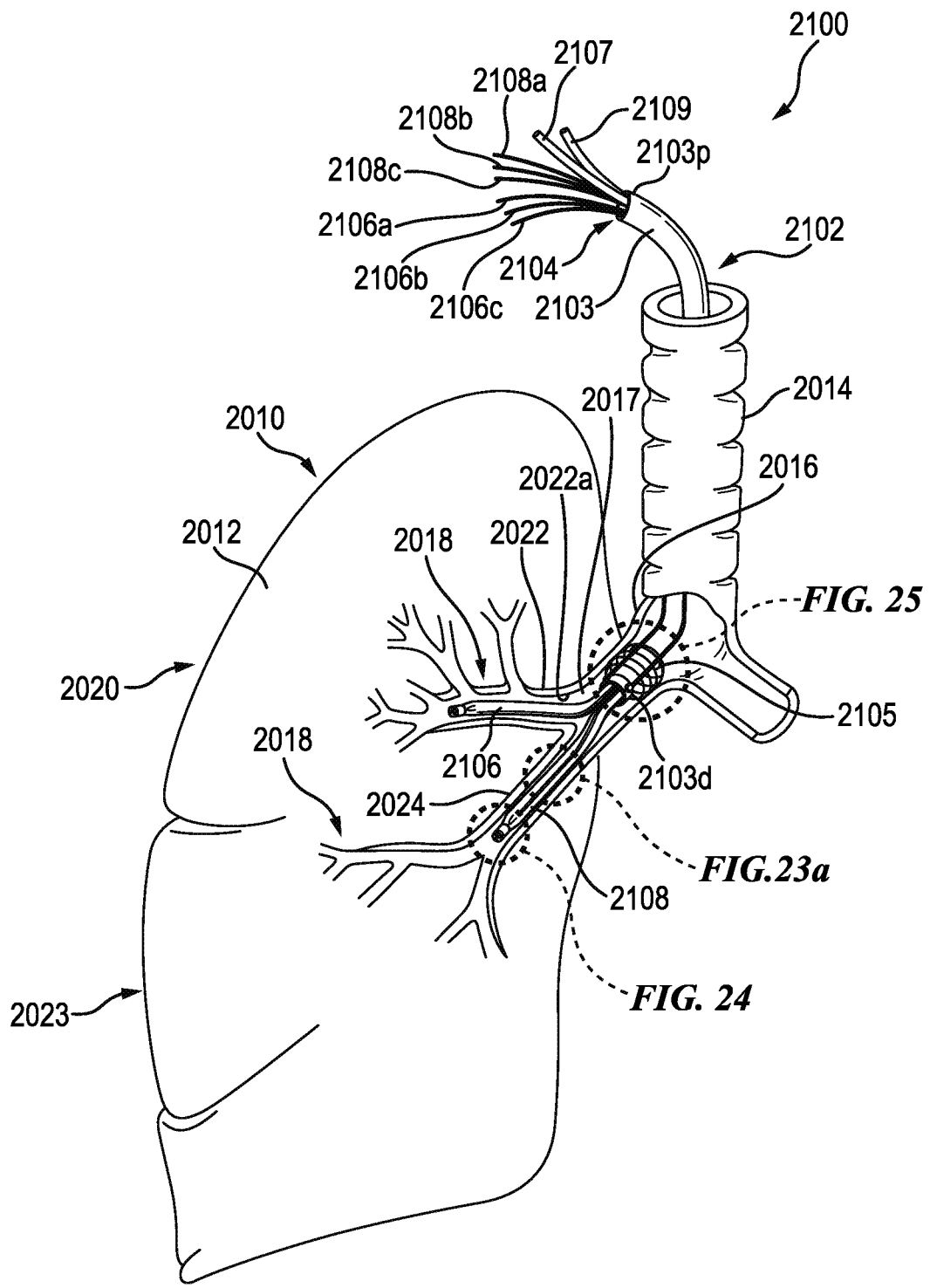
FIG. 22 is a schematic view of one embodiment of a surgical anchoring system having an outer sleeve and channel arms that extend through the outer sleeve in which the channel arms include respective anchor members, showing the surgical anchoring system inserted through a throat and into a lung with a portion the outer sleeve passing through the throat and into the lung and the channel arms extending through the outer sleeve and into respective portions of the lung with the respective anchor members in an unexpanded state.

FIG. 22 illustrates an exemplary embodiment of a surgical anchoring system 2100 that is configured for endoluminal access into a lung 2010. As will be described in more detail below, the surgical anchoring system 2100 is used to manipulate a lung 2010 through contact with a natural body lumen (e.g., first bronchiole 2022) within the lung 2010. For purposes of simplicity, certain components of the surgical anchoring system 2100 and the lung 2010 are not illustrated.

As shown, the lung 2010 includes an outer tissue surface 2012, a trachea 2014, a right bronchus 2016, and bronchioles 2018. The trachea 2014, right bronchus 2016, and the bronchioles 2018 are in fluid communication with each other. Additionally, the lung 2010 includes an upper lobe 2020, which includes first bronchiole 2022, and a middle lobe 2023, which includes second bronchiole 2024. As illustrated in FIG. 22, the lung 2010 is in an inflated state while the surgical anchoring system 2100 is initially inserted into the lung 2010. When operating in the thoracic cavity, the lung 2010 is collapsed to provide sufficient working space between the rib cage and the lungs such that laparoscopically arranged instruments can access and manipulate the lung 2010. In use, as described in more detail below, the surgical anchoring system 2100 can manipulate (e.g., mobilize) a portion of the lung 2010.

The surgical anchoring system 2100 includes a surgical instrument 2102 configured for endoluminal access through the trachea 2014 and into the lung 2010. The surgical instrument can have a variety of configurations. For example, in this illustrated embodiment, the surgical instrument 2102 includes an outer sleeve 2103 and first and second channel arms 2106, 2108. While two channel arms 2106, 2108 are illustrated, in other embodiments, the surgical instrument can include a single channel arm or more than two channel arms. The outer sleeve 2103 is configured to be inserted through a patient's mouth (not shown) and down the trachea 2014. The outer sleeve 2103 includes a working channel 2104 that is configured to allow the first and second channel arms 2106, 2108 to be inserted through the outer sleeve 2103 and access the lung 2010. As such, the first and second channel arms 2106, 2108 can be configured to move independently of the working channel 2014.

Figure 23A:
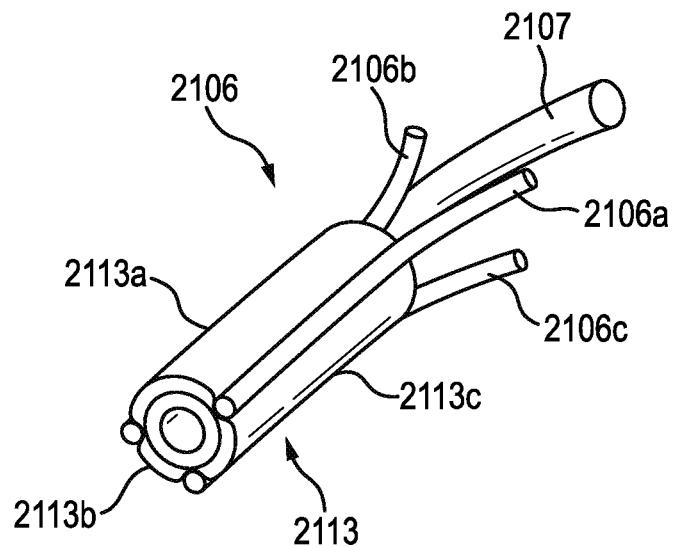
FIG. 23A is a magnified view of a portion of one of the channel arms of the surgical anchoring system of FIG. 22 with the lung removed and a portion of the respective anchor members.
Figure 23B:
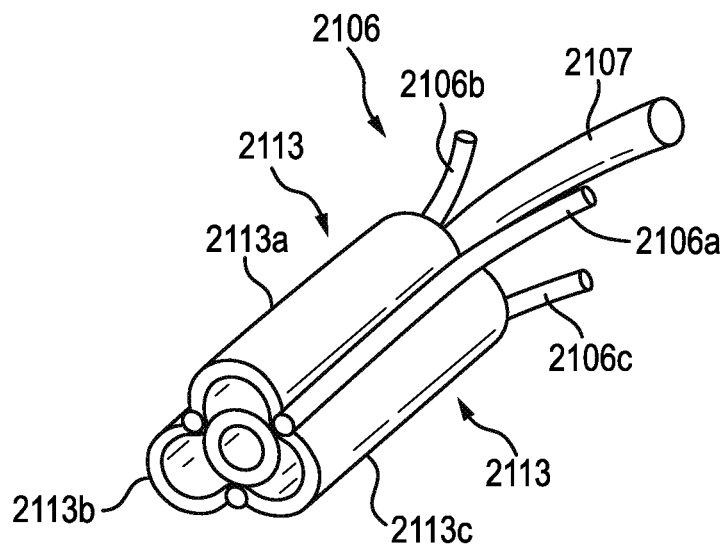
FIG. 23B is the channel arm of FIG. 23A, showing the anchor members in an expanded state.
Figure 24:
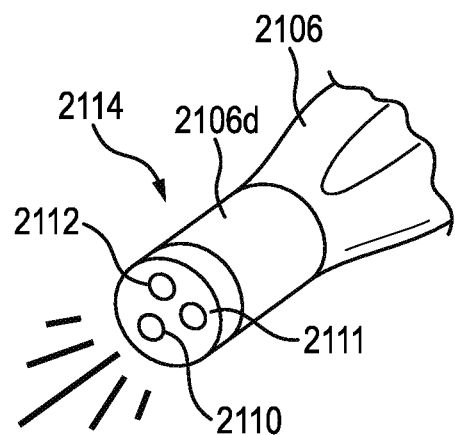
FIG. 24 is a magnified view of a distal end of a channel arm of the surgical anchoring system of FIG. 22 with the lung removed.

Each of the first and second channel arms 2106, 2108 can include at least one anchor member coupled to the at least one channel arm and configured to move between expanded and unexpanded states. When in the expanded state, the at least one anchor member is configured to be at least partially disposed within a second natural body lumen, the second natural body lumen being in communication with a first natural body lumen that the outer sleeve is partially disposed within. In this illustrated embodiment, a first anchor member 2113 (see FIG. 23A, FIG. 23B, and FIG. 24) is coupled to first channel arm 2106 and a second anchor member 2115 (see FIG. 26) is coupled to the second channel arm 2108. Further, as shown in FIG. 22 and FIG. 23, the first natural body lumen is the right bronchus 2016 and the second natural body lumen is the first bronchiole 2022.

Further, each of the first and second channel arms 2106, 2108 also include control actuators and a fluid tube which extend along the length of the channel arms and further extends from the proximal end 2103*p* of the outer sleeve 2103. As shown in FIG. 22, the first channel arm 2106 includes three control actuators 2106*a*, 2106*b*, 2106*c* and a first fluid tube 2107. The second channel arm 2108 includes three control actuators 2108*a*, 2108*b*, 2108*c* and a second fluid tube 2109. As described in more detail below, the control actuators of each control arm are configured to allow for manipulation of the lung 2010, and the fluid tubes 2107, 2109 are configured to provide a fluid to the first and second anchor members 2113, 2115 coupled to the first and second channel arms 2106, 2108.

Figure 26:
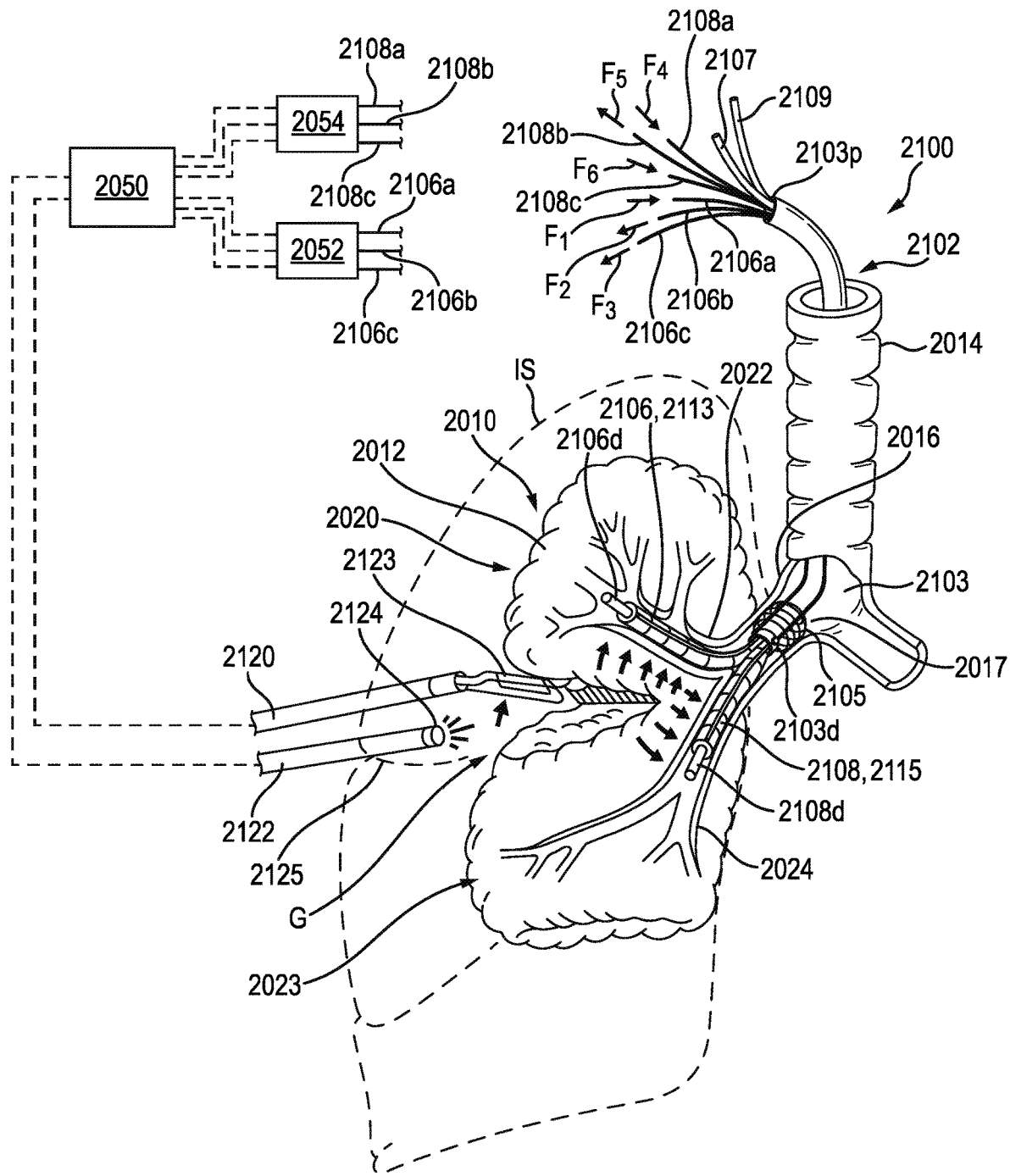
FIG. 26 is a schematic view of the surgical anchoring system of FIG. 22, showing the anchor members in an expanded state while manipulating the lung from an intraluminal space and from an extraluminal space using laparoscopically inserted instruments.

In use, as shown in FIG. 22, the outer sleeve 2103 is passed into the trachea 2014 through a patient's mouth (not shown). With the outer sleeve in position, the anchor member 2105 moves to an expanded state, where the anchor member 2105 at least partially contacts an internal surface 2017 of the right bronchus 2016. By contacting the inner surface 2017, the outer sleeve 2103 is fixated to the trachea 2014 and the right bronchus 2016. The first channel arm 2106 is passed into the lung 2010 through the right bronchus 2016 via the outer sleeve 2105, and into the first bronchiole 2022 of the upper lobe 2020, and the second channel arm 2108 is passed into the lung 2010 through the right bronchus 2016, and into the second bronchiole 2024 of the middle lobe 2023. Once the first and second channel arms 2106, 2108 are properly positioned within the first and second bronchi 2022, 2024, respectively, the first and second anchor member 2113, 2115 can be expanded to at least partially contact the inner surface of the bronchioles 2022, 2024. For sake of simplicity, the following description is with respect to the first anchor member 2113. A person skilled in the art will understand, however, that the following discussion is also appliactuator to the second anchor member 2115, which as shown in FIG. 26 is structurally similar to that of the first anchor member 2113. A detailed partial view of the first anchor member 2113 is illustrated in an unexpanded state (FIG. 23A) and in an expanded state (FIG. 23B).

As shown, the first anchor member 2113 is arranged distal to the distal end 2103*d* of the outer sleeve 2103 such that the first anchor member 2113 can be positioned within the first bronchiole 2022. The first anchor member 2113 is configured to move between an unexpanded state (FIG. 23A) and an expanded state (FIG. 23B). The first anchor member 2113 can have a variety of configurations. For example, in some embodiments, the first anchor member can be an inflatable balloon, whereas in other embodiments, the first anchor member can be a mechanically expandable stent.

As illustrated in FIG. 23A and FIG. 23B, the first anchor member 2113 includes three bladders 2113*a*, 2113*b*, 2113*c* arranged about an outer surface of the first fluid tube 2107. The bladders 2113*a*, 2113*b*, 2113*c* are separated from one another (e.g., by control actuators 2106*a*, 2106*b*, and 2106*c* arranged between the bladders 2113*a*, 2113*b*, 2113*c*). The bladders 2113*a*, 2113*b*, 2113*c* are expanded by the ingress of fluid through the first fluid tube 2107, which is in fluid communication with each bladder 2113*a*, 2113*b*, 2113*c*, and unexpanded through the egress of fluid from the bladders 2113*a*, 2113*b*, 2113*c* through the first fluid tube 2107. In some embodiments, each bladder 2113*a*, 2113*b*, 2113*c* extends along the length of the first channel arm 2106. Alternatively, in certain embodiments, the bladders 2113*a*, 2113*b*, 2113*c* are arranged along only a portion of the length of the first channel arm 2106.

Figure 25:
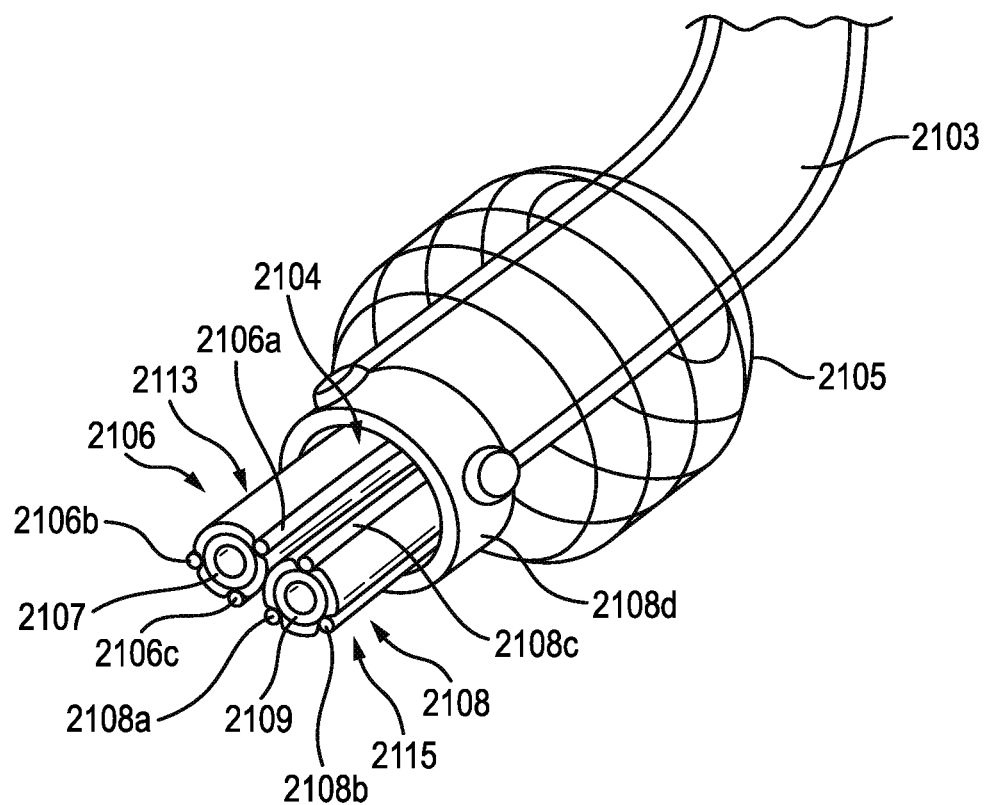
FIG. 25 is a magnified view of a portion of the surgical anchoring system of FIG. 22 with the lung removed.

Alternatively, or in addition, at least one of the first and second channel arms 2106, 2108 can include an optical sensor. By way of example, FIG. 25 illustrates a partial view of a distal end 2106*d* of the first channel arm 2106. As shown, the distal end 2106*d* of the channel arm 2106 can include a scope 2114 with an optical sensor 2110 arranged thereon. The optical sensor 2110 can be configured to allow a user to determine the location of the first channel arm 2106 within the lung 2010 and to help the user position the distal tip 2106*d* into the desired bronchiole, such as first bronchiole 2022. Views from the optical sensor 2110 can be provided in real time to a user (e.g., a surgeon), such as on a display (e.g., a monitor, a computer tablet screen, etc.). The scope 2114 can also include a light 2111 and a working channel and/or a fluid channel 2112 that is configured to allow for the insertion and extraction of a surgical instrument and/or for the ingress and egress of a surgical instrument or fluid to the treatment site within the lung 2010. A person skilled in the art will appreciate that the second channel arm can alternatively or in addition include a scope that is similar to scope 2114 in FIG. 25.

In some embodiments, the outer sleeve 2103 can include additional elements. For example, as shown in FIG. 22, and in more detail in FIG. 25, the outer sleeve 2103 includes an anchor member 2105 arranged proximate to a distal end 2103*d* of the outer sleeve 2103. In other embodiments, the anchor member 2105 can be arranged at the distal end 2103*d*.

A detailed partial view of the distal end 2130*d* of the outer sleeve 2103 and the channel arms 2106, 2108 is illustrated in FIG. 25. As shown, the channel arms 2106, 2108 extend outward from the distal end 2103*d* of the outer sleeve 2103. In some embodiments, the channel arms 2106, 2108 can move relative to each other, and the outer sleeve 2103. As stated above, an anchor member 2105 is arranged on the outer sleeve 2103. The anchor member 2105 is configured to move between expanded and unexpanded states. In an expanded state, the anchor member 2105 is configured to at least partially contact an internal surface 2017 of the right bronchus 2016. By contacting the inner surface 2017, the outer sleeve 2103 can be fixated to the trachea 2014 and the right bronchus 2016. This fixation can allow for a manipulation force (e.g., twisting force) to be applied to the lung 2010 through the channel arms 2106, 2108. As a result, the lung 2010 can be mobilized relative to the trachea 2014 and the right bronchus 2016.

Increasing of the distribution of forces applied to the lung 2010 and reducing the tissue interaction pressure can be achieved by increasing the internal surface area in which the anchor members interact with. The anchor elements are configured to expand to the internal diameter of the bronchus. By spreading to the full internal diameter, and having the channel arms extended from the distal end of the outer sleeve, the surgical anchoring system acts as a skeleton system within the lung. By moving the outer sleeve and/or channel arms, the bronchioles or bronchus are moved, thereby moving the lung. Since the outer sleeve and anchoring elements are spread out over a large area, the forces applied to the lung are not concentrated, compared to manipulating the lung with small graspers from the laparoscopic side. Additionally the cartridge rings and wall strength of the bronchus make it more ideal for instrument interaction for gross lung movement or repositioning without collateral damage to the surrounding softer and more fragile pleura and parenchyma.

In an example embodiment, bifurcating and extending a portion of the surgical anchor system down two separate distal branches from the outer sleeve 2103 can be used to better hold a larger, more triangulated area of the lung 2010. Additionally, a portion of the outer sleeve 2103 can expand in addition to the channel arms 2106, 2108 extending from the working channel. Additionally the outer sleeve 2103 can include radial expandable elements that would provide additional contact area within the trachea 2014 that would allow the surgical anchoring system 2100 to completely control both the flexion, but also twist, expansion, and/or compression of the lung 2010. This would enable the surgical anchoring system 2100 to guide the lung to the correct location and position within the thoracic cavity, but also to control the shape of the lung so that a dissection and/or transection could be done from the thoracic cavity side.

The anchor member 2105 can have a variety of configurations. For example, in some embodiments, the anchor member 2105 can be an inflatable anchoring balloon. In embodiments where the anchor member 2105 is an inflatable anchoring balloon, the anchor member 2105 is configured to expand or collapse through the ingress or egress of a fluid passing through a fluid tube (not shown) in fluid communication with the anchor member 2105. The fluid tube extends along the length of the outer sleeve 2103 and can be controlled outside of a patient's body. In other embodiments, the anchor member 2105 can be a mechanically expandable stent.

With the channel arms 2106, 2108 properly arranged within the bronchioles 2022, 2024, the lung 2010 is collapsed. This results in the lung considerably shrinking in size relative to its size in its inflated state. The lung 2010 as illustrated in FIG. 26 is in a collapsed state, with the previous inflated state being represented as a dashed-line border IS. In use, when in the expanded state as shown in FIG. 26, the first anchor member 2113 is configured to at least partially contact the internal surface 2022a of the first bronchiole 2022. This contact fixates the first anchor member 2113 to the first bronchiole 2022, and thereby the lung 2010. The first anchor member 2113 can alternate between its unexpanded and expanded states by passing fluid into or removing fluid from the bladders 2113a, 2113b, 2113c through the fluid tube 2107 that passes through the length of the channel arm 2106. The fluid passed into or out of the bladders 2113a, 2113b, 2113c can be any suitable fluid (e.g., saline, carbon dioxide gas, and the like). A proximal-most end (not shown) of the fluid tube 2107 is configured to couple to fluid system that can be used to control the ingress or egress of fluid into the bladders 2113a, 2113b, 2113c. The fluid system can include a pump and a fluid reservoir. The pump creates a pressure which pushes the fluid into the bladders 2113a, 2113b, 2113c, to expand the bladders 2113a, 2113b, 2113c, and creates a suction that draws the fluid from the bladders 2113a, 2113b, 2113c in order to collapse the bladders 2113a, 2113b, 2113c. A person skilled in the art will appreciate that the second anchor member 2115 can be moved between an expanded and unexpanded state within the second bronchiole 2024 in a similar way as discussed above with respect to the first anchor member 2113.

Further, in use other surgical instruments 2120, 2122 can be introduced laparoscopically within the thoracic cavity in order to visualize and/or operate on the lung 2010 from the extraluminal space. The surgical instruments 2120, 2122 can include a variety of surgical tools, such as graspers 2123, optical sensors 2124, and/or electrosurgical tool 2125. In an exemplary embodiment, where the surgical instrument 2122 is or includes an optical sensor 2124, a user (e.g., a surgeon) can visually inspect the collapsed lung 2010 (FIG. 26) to perform an incision on the lung 2010 using the graspers 2123 or the electrosurgical tool 2125.

Moreover, in use, with the anchor members 2113, 2115 in expanded states, manipulation forces can be applied to the lung 2010 through the control actuators 2106a, 2106b, 2106c, 2108a, 2108b, 2108c. In some embodiments, the surgical anchoring system 2100 includes a controller 2050 that is configured to coordinate a motion of the channel arms 2106, 2108 within the bronchioles 2022, 2024 and a motion of at least one instrument 2120, 2122 outside of the lung 2010 to prevent tearing of the bronchioles 2022, 2024 or the exterior tissue surface 2012 of the lung 2010. The controller 2050 can be communicatively coupled to the robotic arms (not shown) which the instruments 2120, 2122 are connected to, and to actuators 2052, 2054. The actuator 2052 is configured to apply the manipulation forces $F_1$, $F_2$, $F_3$ to control actuators 2106a, 2106b, 2106c, and the actuator 2054 is configured to apply the manipulation forces $F_4$, $F_5$, $F_6$ to control actuators 2108a, 2108b, 2108c.

In use, manipulation force $F_1$ is applied to control actuator 2106a, manipulation force $F_2$ is applied to control actuator 2106b, manipulation force $F_3$ is applied to control actuator 2106c, manipulation force $F_4$ is applied to control actuator 2108a, manipulation force $F_5$ is applied to control actuator 2108b, and manipulation force $F_6$ is applied to control actuator 2108c. With the manipulation forces applied to the lung 2010, the horizontal fissure between the upper lobe 2020 and the middle lobe 2023 can be widened to form a gap G. The gap G allows for access to the lung 2010 so the horizontal fissure can be further expanded. The manipulation forces cause the channel arms 2106, 2108 to move in opposite directions, causing the upper lobe 2020 to move away from the middle lobe 2023. The anchor member 2115, in an expanded state within the right bronchus 2016, prevents unintended twisting of the lung 2010 while the manipulation forces are applied to the lung 2010. As such, the lung 2010 can be manipulated in a single plane in order to increase the gap G in an efficient manner. With the manipulation complete, the anchor members 2113, 2115 are deflated and removed from the bronchioles 2022, 2024 and out through the outer sleeve 2103. The anchor member 2105 is also deflated, allowing the outer sleeve 2103 to also be removed from the trachea 2014, causing little to no damage to the trachea 2014 or lung 2020 when compared to conventional procedures using graspers only to mobilize the lung 2020.

If a surgeon has at least one channel arm 2106, 2108 deployed within a bronchiole, and the grasper 2123 arranged on the laparoscopic side of the lung 2010, both the channel arm and the instrument could be driven together to move in the same direction or in opposed directions. Moving both in the same direction would allow for supported movement of the section grasped between them. Moving both in opposite directions would create tissue tension which would make it easier for dissection or tissue plane separation. Moving both in the same direction could also be coordinated in a coupled motion or an antagonistic manner where either the channel arm or instrument was the driver coupling, and the other would be the follower while providing a defined sustainable force between the channel arm and instrument. In some embodiments, other forms of synchronized motion can include a maximum threshold for coupled forces, position control, and/or velocity matching.

Figure 27:
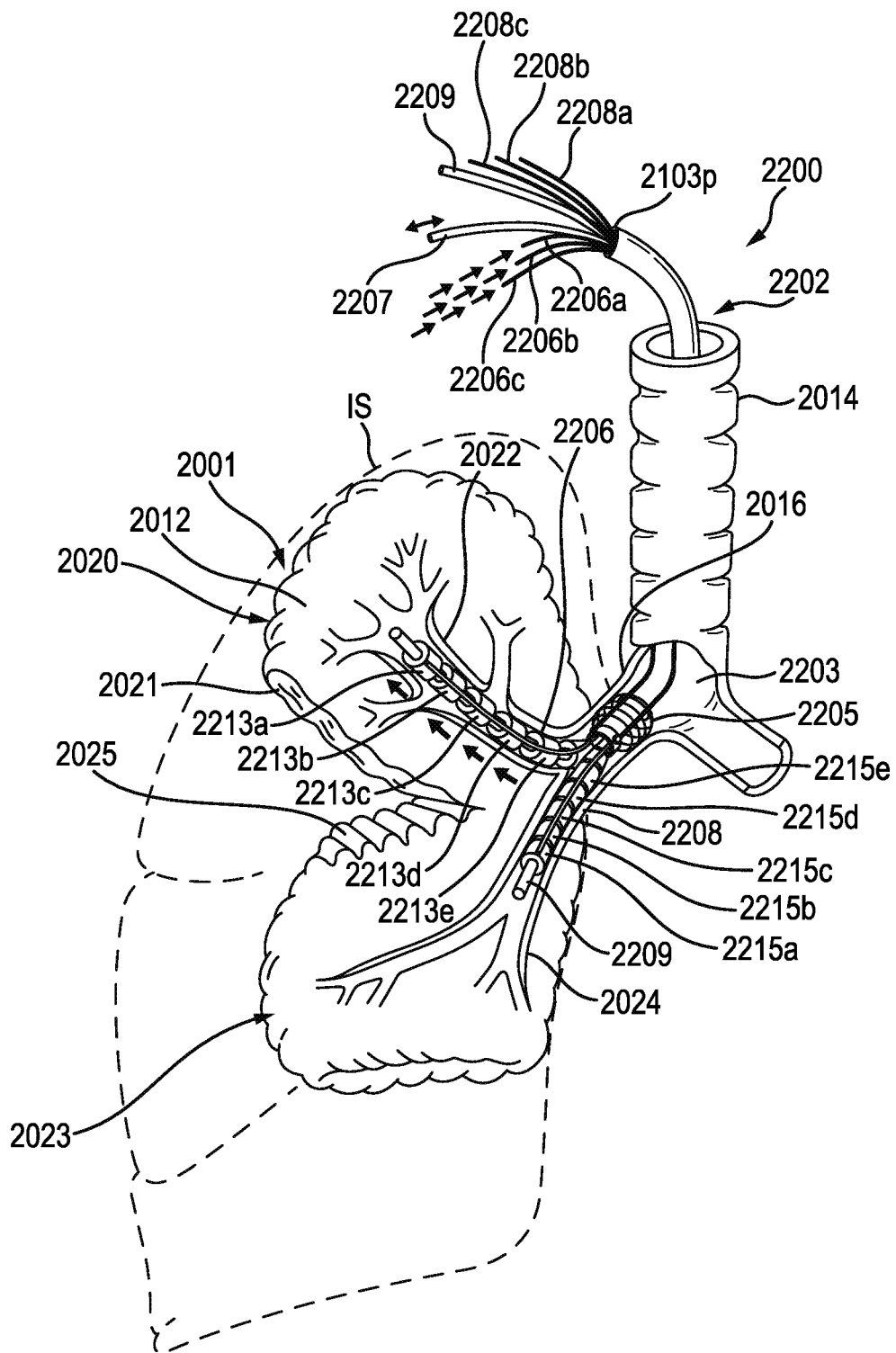
FIG. 27 is a schematic view of another embodiment of a surgical anchoring system, showing the surgical anchoring system inserted through the throat and into a lung.

FIG. 27 illustrates a schematic view of a surgical anchoring system 2200 arranged within a collapsed lung 2201. Aside from the differences described in detail below, the surgical anchoring system 2200 and the collapsed lung 2201 can be similar to the surgical anchoring system 2100 in FIG. 22 and FIG. 26 and the collapsed lung 2010 in FIG. 26 and therefore common features are not described in detail herein.

The surgical anchoring system 2200 includes a surgical instrument 2202, an outer sleeve 2203, an anchor member 2205 coupled to the outer sleeve 2203, a first channel arm 2206, and a second channel arm 2208. The first channel arm 2206 includes control actuators 2206a, 2206b, 2206c extending along the length of the channel arm 2206 and configured to provide a manipulation force to the lung 2201 (e.g., through the first bronchiole 2022). The second channel arm 2208 includes control actuators 2208a, 2208b, 2208c extending along the length of the second channel arm 2208 and configured to provide a manipulation force to the lung 2201 (e.g., through the second bronchiole 2024).

As shown in FIG. 27, the first channel arm 2206 includes anchor members 2213a, 2213b, 2213c, 2213d, 2213e that are arranged on a clutch actuator 2207 that extends through the first channel arm 2206. Each of the anchor members 2213a, 2213b, 2213c, 2213d, 2213e are configured to move axially along the length of the channel arm 2206. The clutch actuator 2207 is configured to selectively position the anchor members 2213a, 2213b, 2213c, 2213d, 2213e at an axial position along the length of the first channel arm 2206. Similar to the anchor member 2113, the anchor members 2213a, 2213b, 2213c, 2213d, 2213e each include inflatable bladders which can be mechanically expanded or filled with a fluid through a fluid channel extending through the length of the clutch actuator 2207.

Additionally, second channel arm 2208 includes anchor members 2215a, 2215b, 2215c, 2215d, 2215e arranged on a clutch actuator 2209. Each of the anchor members 2215a, 2215b, 2215c, 2215d, 2215e are configured to move axially along the length of the second channel arm 2208. The clutch actuator 2209 is configured to selectively position the anchor members 2215a, 2215b, 2215c, 2215d, 2215e at an axial position along the length of the second channel arm 2208. Similar to the anchor member 2115, the anchor members 2215a, 2215b, 2215c, 2215d, 2215e each include inflatable bladders which can be mechanically expanded or filled with a fluid through a fluid channel extending through the length of the clutch actuator 2209.

In use, the outer sleeve 2203 is inserted and the anchor member 2205 is moved to an expanded state to contact the inner tissue surface 2022a of the right bronchus 2016. The first and second channel arms 2206, 2208 are inserted into and arranged within the bronchioles 2022, 2024 prior to the lung 2010 being collapsed. After the lung 2010 is collapsed, the anchor members 2213a, 2213b, 2213c, 2213d, 2213e, 2215a, 2215b, 2215c, 2215d, 2215e are moved to an expanded state to contact an inner tissue surface 2022a of the bronchioles 2022, 2024.

With the anchor members 2213a, 2213b, 2213c, 2213d, 2213e, 2215a, 2215b, 2215c, 2215d, 2215e in an expanded state, the clutch actuators 2207, 2209 can be axially displaced relative to the outer sleeve 2103, pushing the clutch actuators 2207, 2209 further into the first and second bronchioles 2022, 2024. In some embodiments, the anchor members 2213a, 2213b, 2213c, 2213d, 2213e, 2215a, 2215b, 2215c, 2215d, 2215e can slide relatively along the clutch actuators 2207, 2209 a prescribed amount before being coupled to the clutch actuators 2207, 2209. This allows for a space to form between each of the anchor members 2213a, 2213b, 2213c, 2213d, 2213e, 2215a, 2215b, 2215c, 2215d, 2215e, which pulls the loose tissue surrounding the first and second bronchioles 2022, 2024 taut. As the clutch actuators 2207, 2209 are retracted from the lung 2201, the gap between each of the anchor members 2213a, 2213b, 2213c, 2213d, 2213e, 2215a, 2215b, 2215c, 2215d, 2215e is reduced, collapsing the tissue surrounding the first and second bronchioles 2022, 2024.

In addition to manipulating the lung 2201 using the control actuators of the first channel arms 2206, the first clutch actuator 2207 can be used to axially move the anchor members 2213a, 2213b, 2213c, 2213d, 2213e along a length of the first channel arm 2206. By axially moving the anchor members 2213a, 2213b, 2213c, 2213d, 2213e, the upper lobe 2020 and first bronchiole 2022 are partially expanded to an inflated state through the mechanical expansion of the anchor members 2213a, 2213b, 2213c, 2213d, 2213e. As illustrated, the exterior tissue surface 2021 of the upper lobe 2020 at the horizontal fissure is taut due to the axially expansion of the anchor members 2213a, 2213b, 2213c, 2213d, 2213e when compared to the exterior tissue surface 2025 of the middle lobe 2023, which is bunched up due to the collapsed state of the lung 2010. The axial expansion of the anchor members 2213a, 2213b, 2213c, 2213d, 2213e also places the upper lobe 2020 in a similar shape to when the lung 2201 is inflated, as shown by the inflated state line IS.

Similarly, in addition to manipulating the lung 2201 using the control actuators of the second channel arm 2208, the second clutch actuator 2209 can be used to axially move the anchor members 2215a, 2215b, 2215c, 2215d, 2215e along a length of the second channel arm 2208. By axially moving the anchor members 2215a, 2215b, 2215c, 2215d, 2215e, the middle lobe 2023 and second bronchiole 2024 can partially expanded, similar the upper lobe 2020. The axial expansion of the anchor members 2215a, 2215b, 2215c, 2215d, 2215e also can place the middle lobe 2023 in a similar shape to when the lung 2201 is inflated, as shown by the inflated state line IS.

In other embodiments, the amount of axial extension by the anchor members can be guided by a user, but have force limits corresponding to the amount of force capable of being exerted between two anchor members. Additionally, there can be a maximum limit on the amount of displacement between two anchor members to prevent over distention of the organ. In certain embodiments, the anchor members themselves can also have load limits by either controlling the maximum expansive force for limiting friction. The anchor members can have integrated sensors that would limit the externally applied forces between the anchor members as they are axially displaced. The force applied radially could be proportionately coupled to the longitudinal forces applied to prevent inadvertent diametric stretch damage even when applying only a small delicate stretching motion. Alternatively or in addition, the surgical anchoring system can be run in a form of load/creep control, allowing for the maintaining of a predefined force, and then automatically continuing to extend proportionate to the creep in the tissue of the organ. This would allow the viscoelastic properties of the tissue of the organ to be used to help the expansion of the organ rather than hinder the expansion.

In certain embodiments, prior to the activation of the axial movement of the anchor members, a structured light scan can be taken of the tissue, providing a 3D surface model of the pre-stretched anatomy of the organ. This image can be stored and overlaid to the stretch condition of the organ, providing visual information on the nature of the organ shape change, providing insights to the unseen branching of the organ below the exterior tissue surface.

As noted above, the present surgical anchoring systems can be configured to manipulate other natural body lumens or organs. For example, as discussed below, the present surgical anchoring systems can be configured to manipulate one or more portions of the colon endoscopically.

Figure 28:
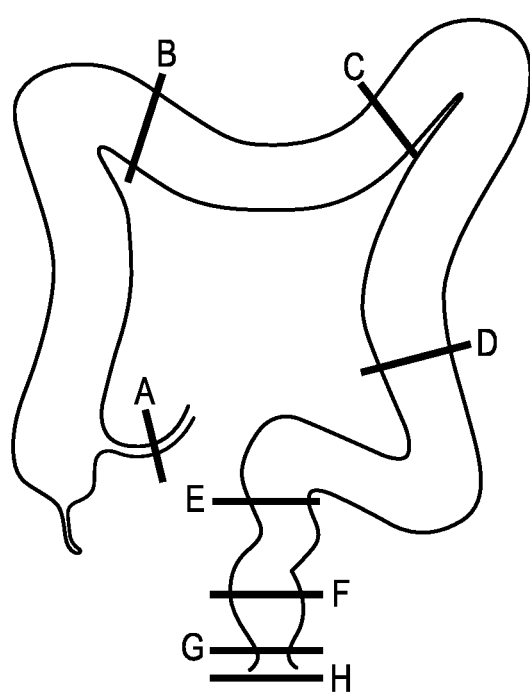
FIG. 28 is a schematic view of a colon.

Surgery is often the primary treatment for early-stage colon cancers. The type of surgery used depends on the stage (extent) of the cancer, its location in the colon, and the goal of the surgery. Some early colon cancers (stage 0 and some early stage I tumors) and most polyps can be removed during a colonoscopy. However, if the cancer has progressed, a local excision or colectomy, a surgical procedure that removes all or part of the colon, may be required. In certain instances, nearby lymph nodes are also removed. A hemicolectomy, or partial colectomy, can be performed if only part of the colon is removed. In a segmental resection of the colon the surgeon removes the diseased part of the colon along with a small segment of non-diseased colon on either side. Usually, about one-fourth to one-third of the colon is removed, depending on the size and location of the cancer. Major resections of the colon are illustrated in FIG. 28, in which (i) A-B is a right hemicolectomy, A-C is an extended right hemicolectomy, B-C is a transverse colectomy, C-E is a left hemicolectomy, D-E is a sigmoid colectomy, D-F is an anterior resection, D-G is a (ultra) low anterior resection, D-H is an abdomino-perineal resection, A-D is a subtotal colectomy, A-E is a total colectomy, and A-H is a total proctocolectomy. Once the resection is complete, the remaining intact sections of colon are then reattached.

During a laparoscopic-assisted colectomy procedure, it is often difficult to obtain an adequate operative field. Often times, dissections are made deep in the pelvis which makes it difficult to obtain adequate visualization of the area. As a result, the lower rectum must be lifted and rotated to gain access to the veins and arteries around both sides of the rectum during mobilization. During manipulation of the lower rectum, bunching of tissue and/or overstretching of tissue can occur. Additionally, a tumor within the rectum can cause adhesions in the surrounding pelvis, and as a result, this can require freeing the rectal stump and mobilizing the mesentery and blood supply before transection and removal of the tumor.

Figure 29:
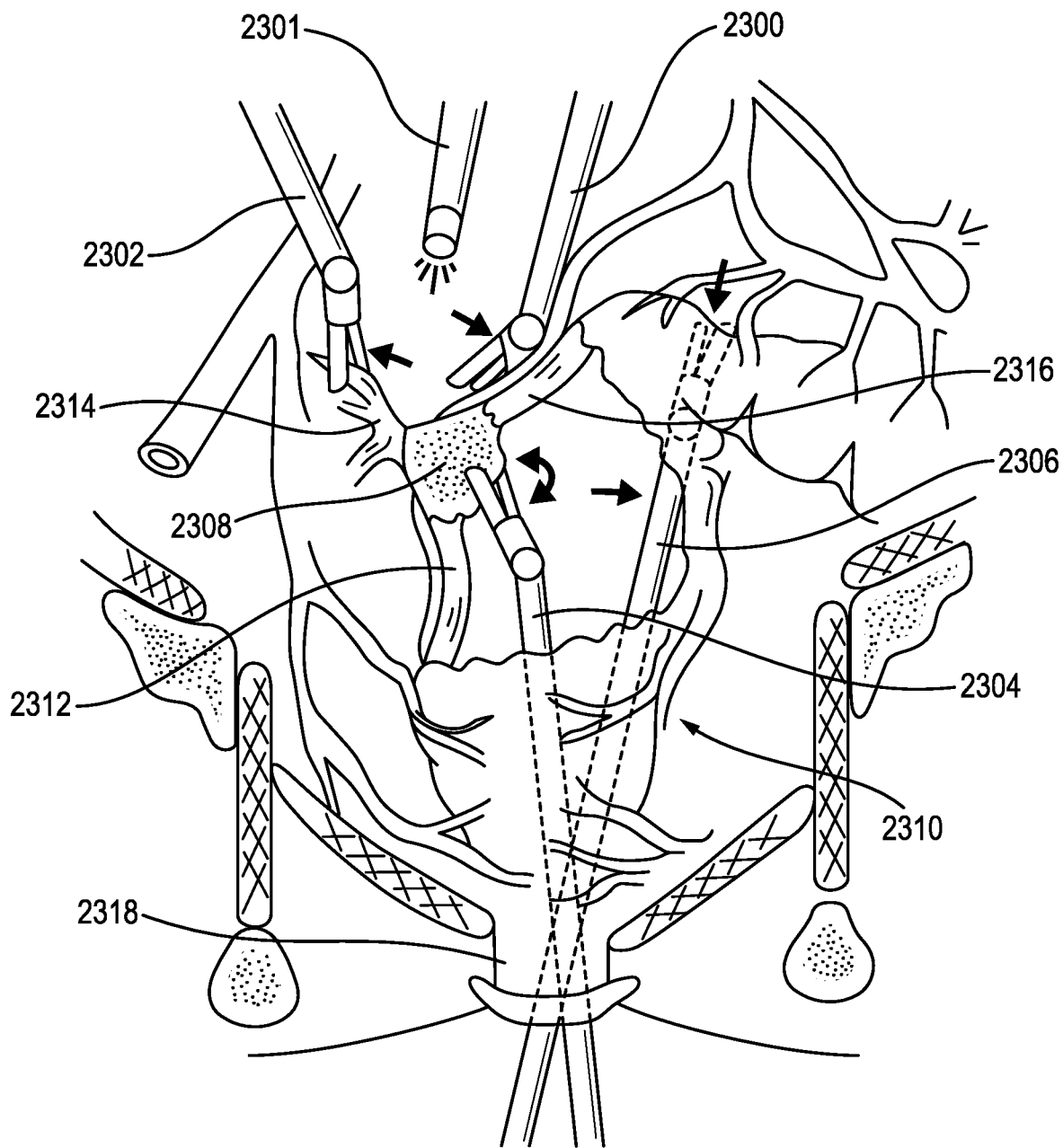
FIG. 29 is a schematic view of a conventional surgical system inserted into an organ.

Further, as illustrated in FIG. 29, multiple graspers 2300, 2302, 2304, 2306 and a laparoscope 2301 are needed to position a tumor 2308 for removal from the colon 2310. During dissection of the colon 2310, the tumor 2308 should be placed under tension, which requires grasping and stretching the surrounding healthy tissue 2312, 2314, 2316 of the colon 2310. However, the manipulating of the tissue 2312, 2314, 2316 surrounding the tumor 2308 can suffer from reduced blood flow and trauma due to the graspers 2300, 2302, 2304, 2306 placing a high grip force on the tissue 2312, 2314, 2316. Additionally, during a colectomy, the transverse colon and upper descending colon may need to be mobilized allowing the good remaining colon to be brought down to connect to the rectum 2318 after the section of the colon 2310 containing the tumor 2308 is transected and removed. A surgical tool that can be used to safely manipulate the colon to provide the surgeon with better visualization and access to the arteries and veins during mobilization would help prevent trauma and blood loss to the surrounding area during a colectomy.

Figure 30:
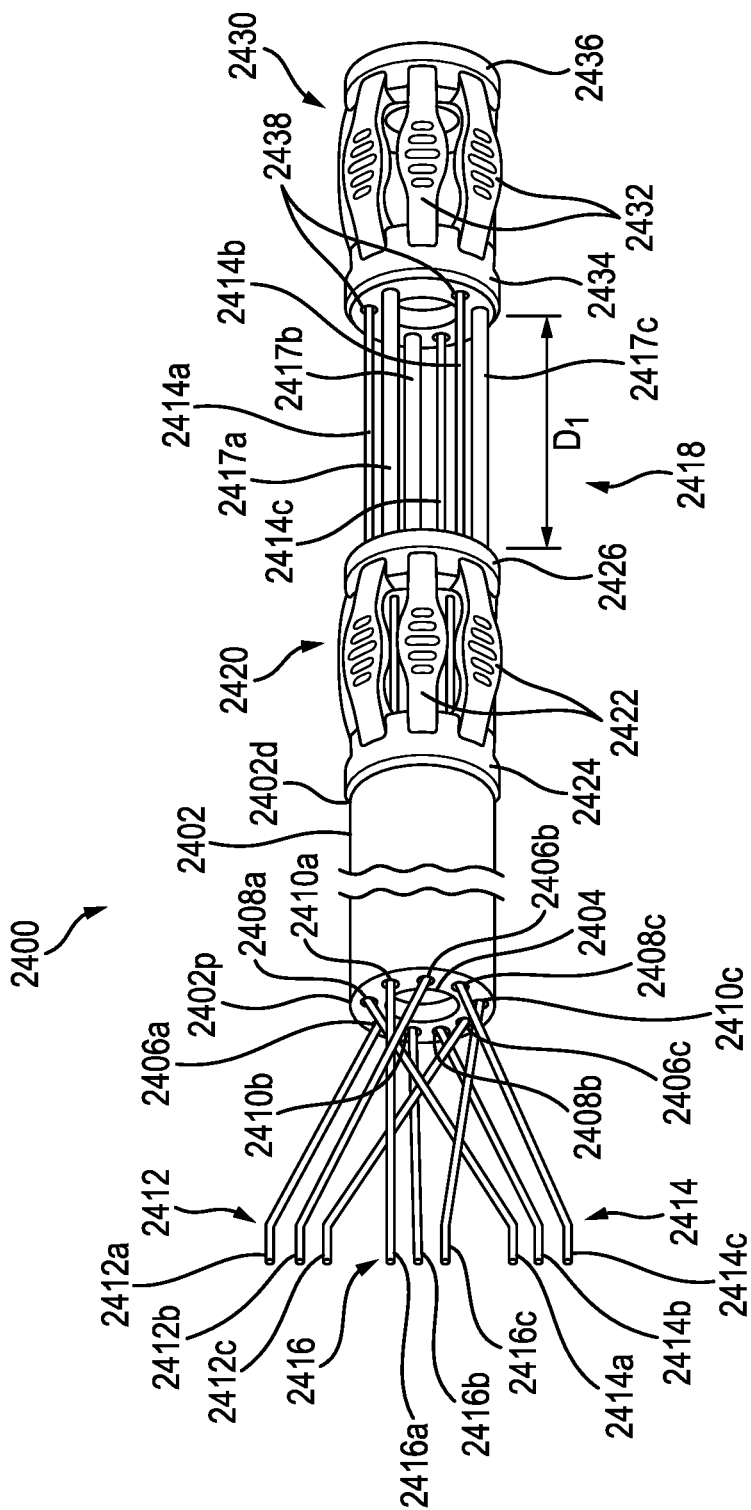
FIG. 30 is a schematic view of another embodiment of a surgical anchoring system having first and second anchor members, showing the first and second anchor members in an unexpanded state.
Figure 31:
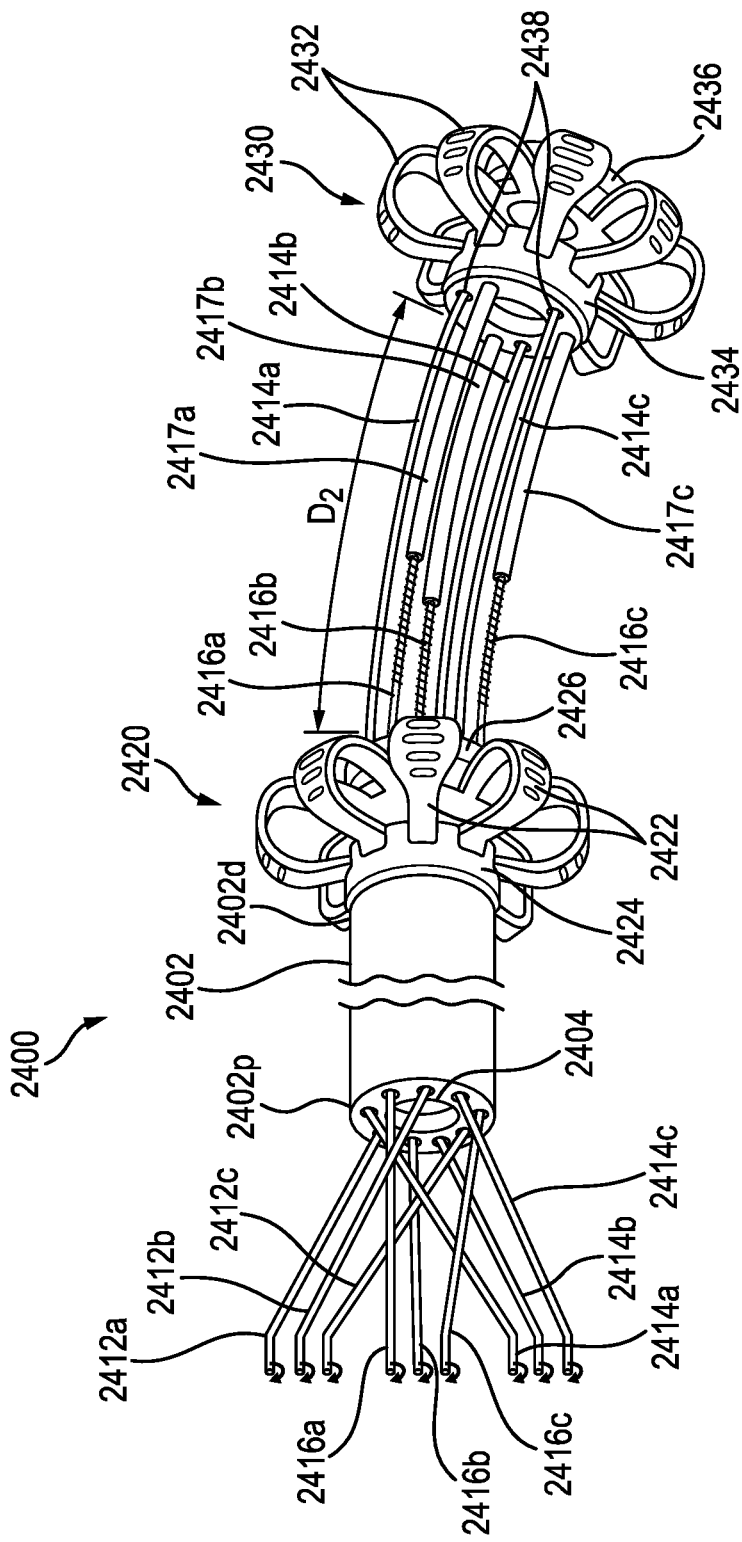
FIG. 31 is a schematic view of the surgical anchoring system of FIG. 30, showing the first and second anchor members in an expanded state.

FIG. 30 and FIG. 31 illustrate one embodiment of a surgical anchoring system 2400 that is configured for endoluminal access into and manipulation of a colon 2310. As will be described in more detail below, the surgical anchoring system 2400 is used to manipulate and tension a portion of the colon 2310 (e.g., section F). For purposes of simplicity, certain components of the surgical anchoring system 2400 and the colon 2310 are not illustrated. While this surgical anchoring system 2400 is shown and described in connection with manipulation of section F of the colon 2310, a person skilled in the art will appreciate that the surgical anchoring system 2400 can be used to additionally, or in the alternative, inflate other sections of the colon 2310.

As illustrated in FIG. 30 and FIG. 31, the surgical anchoring system 2400 can have a variety of configurations. In some embodiments, the surgical anchoring system 2400 includes a tubular member 2402 configured for endoluminal access through a natural orifice, such as the rectum 2318 and into the colon 2310. The tubular member 2402 includes a central lumen 2404 arranged therein and configured to receive an endoscope. Additionally, the tubular member 2402 includes a plurality of working channels formed from working channels 2406a, 2406b, 2406c, 2408a, 2408b, 2408c, 2410a, 2410b, 2410c extending therethrough. In other embodiments, the tubular member can have other suitable configurations and shapes.

Figure 32:
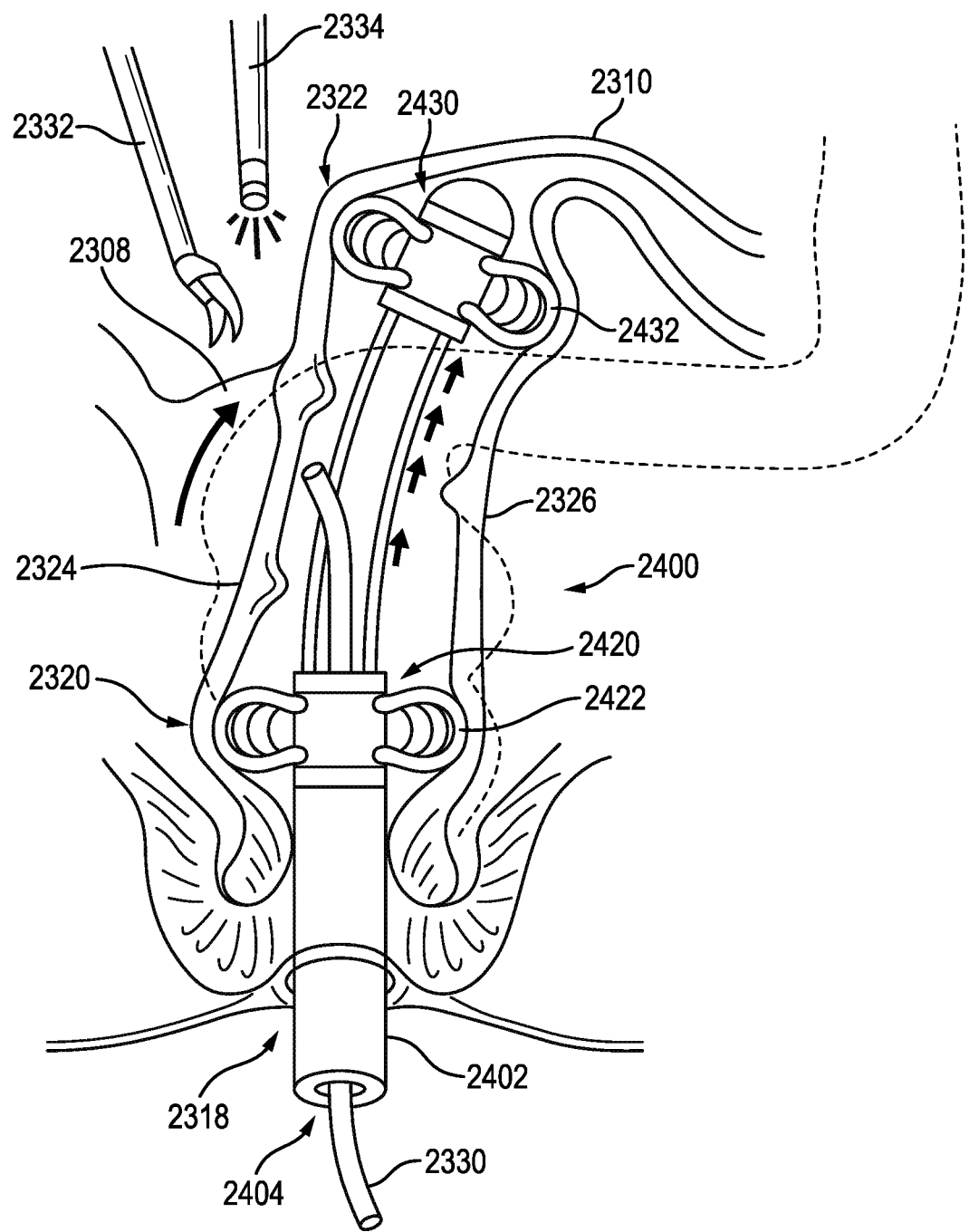
FIG. 32 is a cross-sectional view of the surgical anchoring system of FIG. 31, showing the surgical anchoring system inserted into an organ.

The surgical anchoring system 2400 also includes an anchoring assembly 2418 coupled to the tubular member 2402 and extending distally from the distal end 2402d of the tubular member 2402. The anchoring assembly 2418 includes a first anchor member 2420 and a second anchor member 2430. The first anchor member 2420 is coupled to the distal end 2402d of the tubular member 2402 and is configured to engage a first anatomical location and secure the first anatomical location relative to the tubular member 2402 (FIG. 32). The first anchor member 2420 includes a first plurality of expandable anchoring elements 2422 extending between a proximal collar 2424 and a distal collar 2426. The distal collar 2426 is configured to axially move relative to the proximal collar 2424, such that when the distal collar 2426 moves axially towards the proximal collar 2424, the expandable anchoring elements 2422 expand radially outward from the axis of axial movement by the distal collar 2426. By expanding radially outward, the expandable anchoring elements 2422 are configured to at least partially contact an inner tissue surface of a natural body lumen or organ while in an expanded state.

In order to axially displace the distal collar 2426 towards the proximal collar 2424, a first plurality of actuators 2412 is connected to the distal collar 2426. The first plurality of actuators 2412 includes actuators 2412a, 2412b, 2412c, where actuator 2412a passes through the working channel 2406a, actuator 2412b passes through the working channel 2406b, and the actuator 2412c passes through the working channel 2406c. As the actuators 2412a, 2412b, 2412c are tensioned and pulled through or rotated within the working channels, the distal collar 2426 is axially displaced towards the proximal collar 2424, expanding the expandable anchoring elements 2422. In order for the actuators 2412a, 2412b, 2412c to interact with the distal collar 2426, the actuators 2412a, 2412b, 2412c pass through a plurality of working channels (not shown) within the proximal collar 2424.

The second anchor member 2430 is moveable relative to the first anchor member 2420 and positioned distal to the first anchor member 2420 at a distance $D_1$. The second anchor member 2430 is configured to engage a second anatomical location and is moveable relative to the first anatomical location (FIG. 32). The second anchor member 2430 includes a second plurality of expandable anchoring elements 2432 extending between a proximal collar 2434 and a distal collar 2436. The distal collar 2436 is configured to axially move relative to the proximal collar 2434, such that when the distal collar 2436 moves axially towards the proximal collar 2434, the expandable anchoring elements 2432 expand radially outward from the axis of axial movement by the distal collar 2436. By expanding radially outward, the expandable anchoring elements 3432 are configured to at least partially contact an inner tissue surface of a natural body lumen or organ while in an expanded state.

In order to axially displace the distal collar 2436 towards the proximal collar 2434, a second plurality of actuators 2414 is connected to the distal collar 2436. The second plurality of actuators 2414 includes actuators 2414a, 2414b, 2414c, where actuator 2414a passes through the working channel 2408a, actuator 2414b passes through the working channel 2408b, and the actuator 2414c passes through the working channel 2408c. As the actuators 2414a, 2414b, 2414c are tensioned and pulled through or rotated within the working channels, the distal collar 2436 is axially displaced towards the proximal collar 2434, expanding the expandable anchoring elements 2432. In order for the actuators 2414a, 2414b, 2414c to interact with the distal collar 2436, the actuators 2414a, 2414b, 2414c pass through working channels 2438 within the proximal collar 2434, and a plurality of working channels (not shown) within the proximal collar 2424 and the distal collar 2426 of the first anchoring element 2420.

As illustrated in FIG. 31 and FIG. 32, with the first anchor member 2424 and the second anchor member 2434 in expanded states, the first anchor member 2424 is engaged with the first anatomical location 2320, and the second anchor member is engaged with the second anatomical location 2322. In order to axially displace the second anchor member 2430 relative to the first anchor member 2420, the actuators 2416a, 2416b, 2416c, are rotated in order to unscrew the actuators 2416a, 2416b, 2416c, from the threaded sheaths 2417a, 2417b, 2417c. The actuator 2416a is threaded within the threaded sheath 2417a, the actuator 2416b is threaded within the threaded sheath 2417b, and actuator 2416c is threaded within the threaded sheath 2417c. Since the actuators and threaded sheaths have complementary threads, the rotation of the actuators 2416a, 2416b, 2416c, causes the distance between the first anchor member 2420 and the second anchor member 2430 to increase. In some embodiments, once of the actuators 2416a, 2416b, 2416c, can be rotated more than the other actuators, causes a curved length $D_2$, which is greater than $D_1$, between the first anchor member 2420 and the second anchor member 2430.

In use, the curved length $D_2$ can be used to create tension on one side of the colon 2310, such as where the location of a tumor is located. Since the first anatomical location 2320 is engaged with the first anchor member 2420 by the expandable anchoring elements 2422, and the second anatomical location 232 is engaged with the second anchor member 2430 by the expandable anchoring elements 2432, when the actuators 2416a, 2416b, 2416c, are rotated and unthreaded, the second anatomical location 2322 is selectively repositioned relative to the first anatomical position 2320.

As illustrated in FIG. 32, the tissue wall 2324 is tensioned at a greater degree than the tissue wall 2326, arranged opposite the tissue wall 2324. By tensioning the tissue wall 2324, where the tumor 2308 is located on the colon 2310, the tumor can be visualized and removed by laparoscopically arranged instruments 2332, 2334. Additionally, to further help visualize the tumor 2308, an endoscope 2330 is arranged within the central lumen 2404 of the tubular member 2402.

Sensing Surgical Instruments

During certain surgical procedures, it may be advantageous to be able to track the location and orientation of certain surgical instruments within a patient's body. For example, during a colon resection, the mobilized portion of the colon must be aligned and connected to the rectum in order to reattach the colon to the rectum. In certain surgical systems, at least one of the surgical instruments can include integrated tracking and coordinating means that identifies a location of the surgical instruments relative to each other.

In some embodiments, a surgical instrument can include one or more markers (e.g., attachable or integrated markers) that can be used to track the surgical instrument. This can allow the surgical instrument to directly cooperate with the dual sensing and cooperative control systems. As a result, the surgical instrument can be directly inserted into the body (e.g., into a natural orifice) without a scope (e.g., an endoscope) and used similarly to a scope for.

Figure 33:
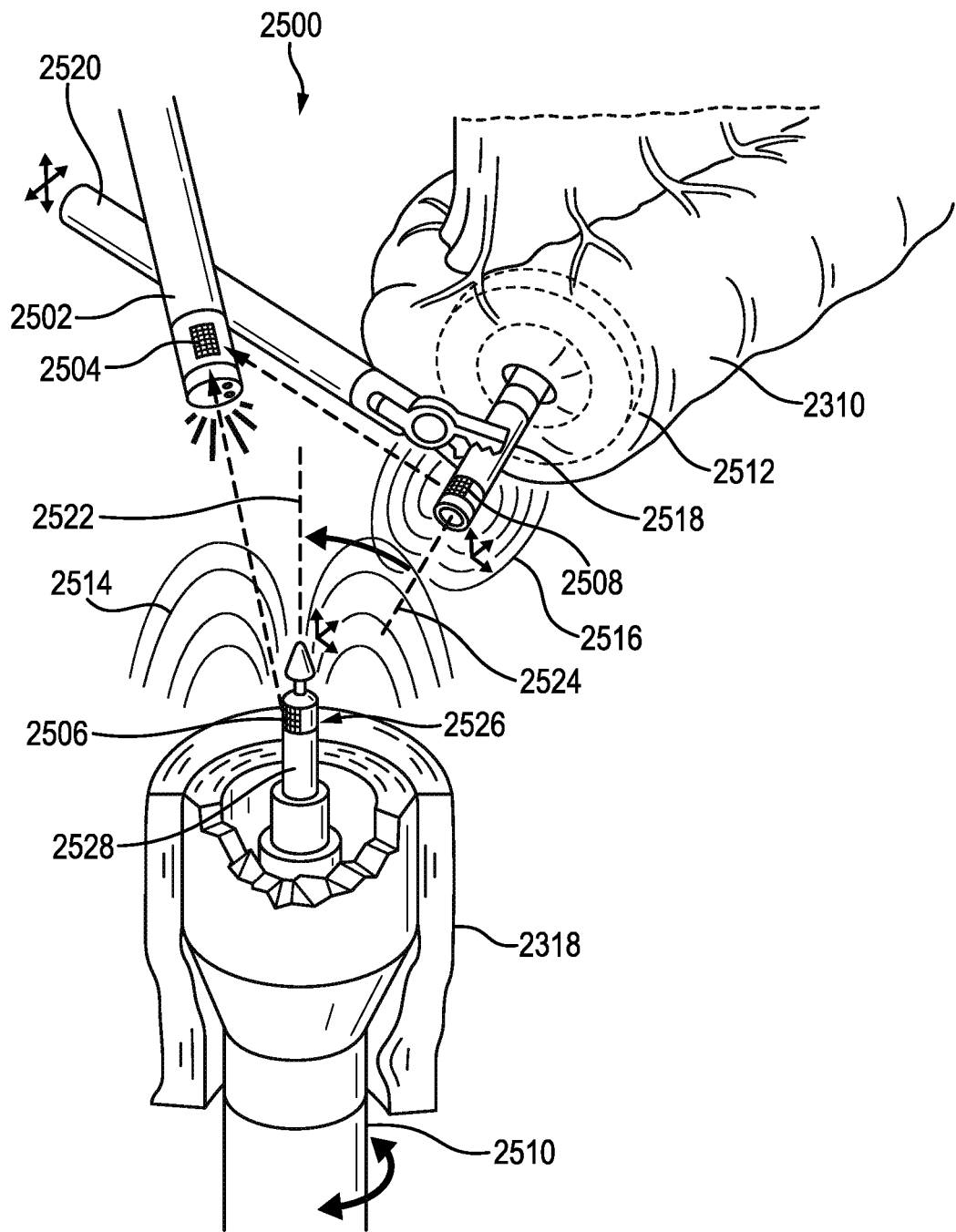
FIG. 33 is a schematic view of another embodiment of a surgical anchoring system having a circular stapler and anvil, each having a tracking means, showing the surgical anchoring system inserted through rectum and into a colon with a portion the circular stapler passing through the rectum and into the colon and the anvil passing through a mobilized portion of the colon.

FIG. 33 illustrates another embodiment of a surgical anchoring system 2500. The surgical anchoring system 2500 includes attachable or integrated markers and a sensing means for use with an instrument introduced through a natural orifice without another scope that would enable it to cooperate with the dual sensing and cooperative control systems.

The surgical anchoring system 2500 includes a laparoscopically arranged instrument 2502 having a sensing array 2504. The sensing array 2504 is configured to interact wirelessly with a first collar 2506 and a second collar 2508 in order to align a circular stapler 2510 arranged within the rectum 2318 with the anvil 2512 arranged within the remainder of the colon 2310. The first collar 2506 is arranged within the circular stapler 2510 and emits a magnetic field 2514. The second collar 2508 is arranged on the anvil 2512 and emits a magnetic field 2516. Both the magnetic fields 2514, 2516 are detectable by the sensing array 2504. The magnetic fields 2514, 2516 are configured to relay location and orientation data about the circular stapler 2510 and the anvil 2512 in order to align the colon 2310 with the rectum 2318.

The anvil 2512 include a post 2518, which is grasped by an instrument 2520 in order to mobilize the colon 2310. As the anvil 2512 is moved by the instrument 2520, the sensing array 2504 collects magnetic field data and determines the distance and misalignment of the stapler trocar axis 2522 and the anvil trocar axis 2524. When the stapler trocar axis 2522 is aligned with the anvil trocar axis 2524, the anvil 2512 can be positioned over the post 2526 of the circular stapler 2510. The post 2526 can include alignment features 2528 as the post 2518 is arranged over the post 2526. In certain embodiments, the circular stapler 2510 can be rotated once the posts 2518, 2526 are aligned with each other, coupling the anvil 2512 to the circular stapler 2510 so that the colon 2310 can be stapled to the rectum 2318.

The instrument 2502 can include an optical sensor arranged on the distal end thereof in order to visualize the treatment area to an external screen in view of a user, aiding them in adjusting and aligning the circular stapler to the correct location for anvil attachment from the laparoscopic side.

The surgical anchoring system disclosed herein can be designed to be disposed of after a single use, or they can be designed to be used multiple times. In either case, however, the surgical anchoring system can be reconditioned for reuse after at least one use. Reconditioning can include any combination of the steps of disassembly of the surgical anchoring system, followed by cleaning or replacement of particular pieces and subsequent reassembly. In particular, the surgical anchoring system can be disassembled, and any number of the particular pieces or parts of the surgical anchoring system can be selectively replaced or removed in any combination. Upon cleaning and/or replacement of particular parts, the surgical anchoring system can be reassembled for subsequent use either at a reconditioning facility, or by a surgical team immediately prior to a surgical procedure. Those skilled in the art will appreciate that reconditioning of a surgical anchoring system can utilize a variety of techniques for disassembly, cleaning/replacement, and reassembly. Use of such techniques, and the resulting reconditioned instrument, are all within the scope of the present application.

Instrument Control Imaging Systems

Devices, systems, and methods for multi-source imaging provided herein allow for cooperative surgical visualization. In general, in cooperative surgical visualization, first and second imaging systems (e.g., first and second scope devices) each gathering images of a surgical site are configured to cooperate to provide enhanced imaging of a surgical site. The cooperative surgical visualization may improve visualization of patient anatomy at the surgical site and/or improve control of surgical instrument(s) at the surgical site.

A surgical visualization system can allow for intraoperative identification of critical structure(s) (e.g., diseased tissue, anatomical structures, surgical instrument(s), etc.). The surgical visualization system may thus enable enhanced intraoperative decision making and improved surgical outcomes. The surgical visualization system can provide advanced visualization capabilities beyond what a medical practitioner sees with the "naked eye" and/or beyond what an imaging system can recognize and/or convey to the medical practitioner. The surgical visualization system can augment and enhance what a medical practitioner is able to know prior to tissue treatment (e.g., dissection, etc.) and, thus, may improve outcomes in various instances. As a result, the medical practitioner can confidently maintain momentum throughout the surgical procedure knowing that the surgical visualization system is tracking a critical structure, which may be approached during dissection, for example. The surgical visualization system can provide an indication to the medical practitioner in sufficient time for the medical practitioner to pause and/or slow down the surgical procedure and evaluate the proximity to the critical structure to prevent inadvertent damage thereto. The surgical visualization system can provide an ideal, optimized, and/or customizable amount of information to the medical practitioner to allow the medical practitioner to move confidently and/or quickly through tissue while avoiding inadvertent damage to healthy tissue and/or critical structure(s) and, thus, to minimize the risk of harm resulting from the surgical procedure.

The surgical systems provided herein generally include a first scope device configured to transmit image data of a first scene within its field of view, a second scope device configured to transmit image data of a second, different scene within its field of view, a tracking device associated with one of the first scope device or the second scope device and configured to transmit a signal indicative of a location of the one of the first scope device or the second scope device relative to the other one of the first scope device or the second scope device, a controller configured to receive the transmitted data and signal, determine the relative distance between the first and second scope devices and provide a merged image. The merged image can be at least a portion of at least the first scope device and the second scope device in a single scene, and at least one of the first scope device and the second scope device in the merged image is a representative depiction thereof. Thus, the merged image may thus provide two separate points of view of the surgical site, which can conveniently allow a medical practitioner to view only one display instead of multiple displays. Further, within that one display, the merged image allows a medical practitioner to coordinate relative location and/or orientation of at least the first and scope devices arranged at or proximate to the surgical site.

The first scope device is configured to be at least partially disposed within at least one of a natural body lumen and an organ (e.g., a lung, a stomach, a colon, or small intestines), and the second scope device is configured to be at least partially disposed outside of the at least one of the natural body lumen and the organ. In certain embodiments, the first scope device is endoscope and the second scope device is a laparoscope. The natural body lumen or organ can be any suitable natural body lumen or organ. Non-limiting examples include a stomach, a lung, a colon, or small intestines.

The surgical systems provided herein can also be used in various robotic surgical systems, such as those discussed above, and can incorporate various tracking and/or imaging mechanisms, such as electromagnetic (EM) tracked tips, fiber bragg grating, virtual tags, fiducial markers, use of probes, identification of known anatomy, various 3D scanning techniques such as using structured light, various sensors and/or imaging systems discussed previously, etc., to assist in tracking movement of the instruments, endoscopes, and laparoscopes relative to each other and/or the overall system. The tracking mechanisms can be configured to transmit tracking data from both a laparoscope and an endoscope so that the location of either scope can be determined relative to the other scope. Additionally, critical structures within the field of view of either scope (e.g., diseased tissue, surgical instruments, anatomical structures) can be tracked by the scope which has such critical structures within their field of view. In total, the surgical systems herein can track the objects within a field of view of each scope, and the relative position of each scope. Therefore, the totality of the tracking data allows the system to calculate the distance of a critical structure from a scope which does not have a critical structure in its field of view based on the tracking data collected by the other scope.

In some embodiments, the surgical system can include a tracking device associated with one of the first scope device or the second scope device and configured to transmit a signal indicative of a location of the one of the first scope device or the second scope device relative to the other one of the first scope device or the second scope device.

In various embodiments, the surgical systems provided herein includes a controller. The surgical system, the controller, a display, and/or the various instruments, endoscopes, and laparoscopes can also be incorporated into a number of different robotic surgical systems and/or can be part of a surgical hub, such as any of the systems and surgical hubs discussed above. The controller in general is configured to merge first and second scenes from an endoscope and a laparoscope, respectively, to visually create a merged image between the first and second scenes. The controller is configured to receive the tracking data detailed above, and in combination with the first and second scenes, generate the merged image containing a representative depiction of at least the endoscope or laparoscope, and any structures within field of view of the scope which is visually impaired by a tissue wall. For example, if the merged image was from a point-of-view of the endoscope, the merged image is the live image stream of what the endoscope is viewing, while including an overlay of the orientations and locations of laparoscopically arranged surgical instruments and a laparoscope, if present.

In some embodiments, the controller can be configured to receive the transmitted image data of the first and second scenes from the first and second scope devices and the transmitted signal from a tracking device, to determine, based on the transmitted signal, a relative distance between the first scope device and the second scope device, and to provide, based on the transmitted image data and relative distance between the first and second scopes, a merged image of at least a portion of at least the first scope device and the second scope device in a single scene, wherein at least one of the first scope device and the second scope device in the merged image is a representative depiction thereof.

An exemplary surgical system can include a variety of features as described herein and illustrated in the drawings. However, a person skilled in the art will appreciate that the surgical systems can include only some of these features and/or it can include a variety of other features known in the art. The surgical systems described herein are merely intended to represent certain exemplary embodiments. Moreover, while the surgical systems are shown and described in connection with stomach, a person skilled in the art will appreciate that these surgical systems can be used in connection with any other suitable natural body lumens or organs.

Surgery is the most common treatment for stomach cancer. When surgery is required for stomach cancer, the goal is to remove the entire tumor as well as a good margin of healthy stomach tissue around the tumor. Different procedures can be used to remove stomach cancer. The type of procedure used depends on what part of the stomach the cancer is located and how far it has grown into nearby areas. For example, endoscopic mucosal resection (EMR) and endoscopic submucosal dissection (ESD) are procedures on the stomach that can be used to treat some early-stage cancers. These procedures do not require a cut in the skin, but instead the surgeon passes an endoscope down the throat and into the stomach of the patient. Surgical tools (e.g., MEGADYNE™ Tissue Dissector or Electrosurgical Pencils) are then passed through the working channel of the endoscope to remove the tumor and some layers of the normal stomach wall below and around it.

Other surgical procedures include a subtotal (partial) or a total gastrectomy that can be performed as an open procedure (e.g., surgical instruments are inserted through a large incision in the skin of the abdomen) or as a laparoscopic procedure (surgical instruments are inserted into the abdomen through several small cuts). A laparoscopic gastrectomy procedure generally involves insufflation of the abdominal cavity with carbon dioxide gas to a pressure of around 15 millimeters of mercury (mm Hg). The abdominal wall is pierced and a 5-10 mm in diameter straight tubular cannula or trocar is then inserted into the abdominal cavity. A laparoscope connected to an operating room monitor is used to visualize the operative field and is placed through one of the trocar(s). Laparoscopic instruments are placed through two or more additional trocars for manipulation by the surgeon and surgical assistant(s) to remove the desired portion(s) of the stomach.

Figure 34:
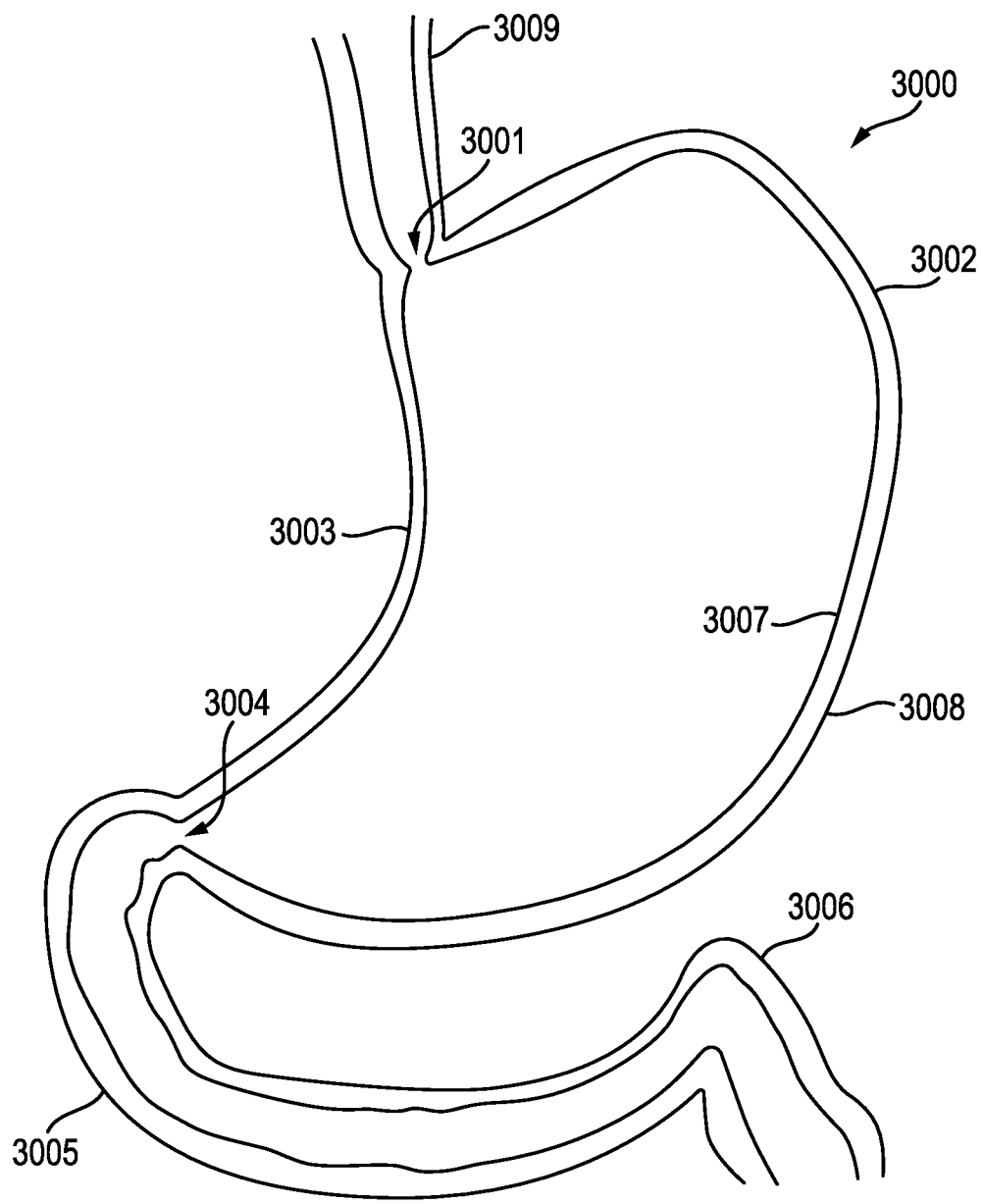
FIG. 34 is a schematic view of a stomach.

FIG. 34 illustrates a schematic depiction of a stomach 3000. The stomach 3000 can include an esophageal sphincter 3001, a greater curvature 3002, a lesser curvature 3003, a pyloric sphincter 3004, a duodenum 3005, and a duodenojejunal flexure 3006. Additionally, the stomach 3000 includes an inner tissue wall 3007 and an outer tissue wall 3008. The esophageal sphincter 3001 connects the stomach to the esophagus 3009, and allows an endoscope to be passed through a patient's mouth, down the esophagus 3009, and passed the esophageal sphincter 3001 in order to access the intraluminal space of the stomach 3000. The pyloric sphincter 3004, duodenum 3005, and duodenojejunal flexure 3006 connect the stomach 3000 to the small intestines (not shown).

Figure 35:
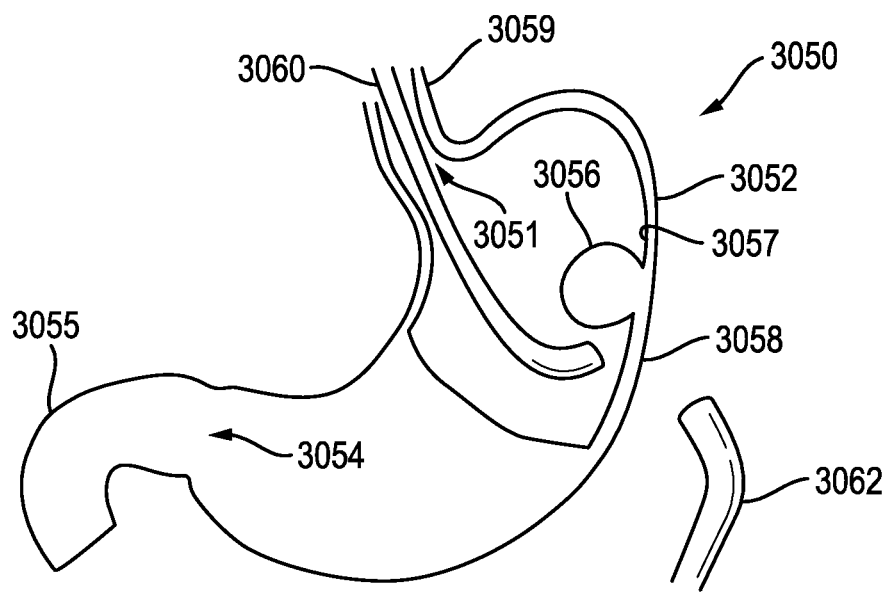
FIG. 35 is a schematic view of a conventional surgical system having a laparoscope and an endoscope, showing the laparoscope positioned outside of a stomach and an endoscope positioned within the stomach.
Figure 36:
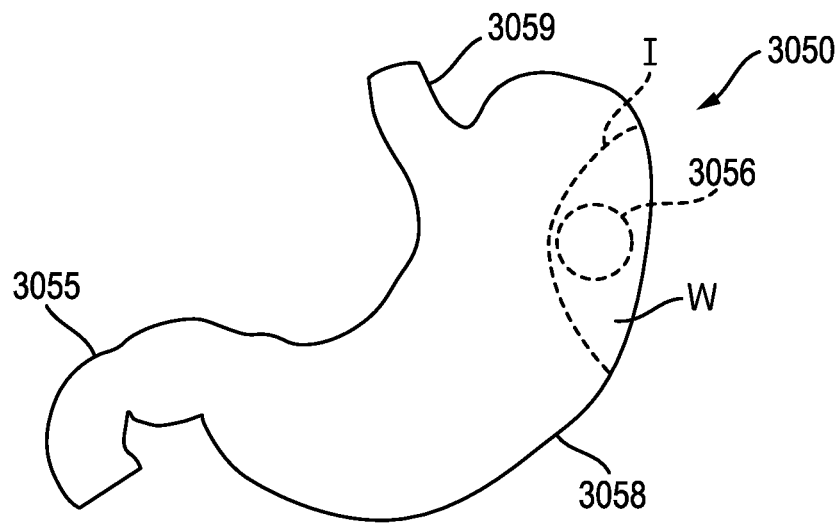
FIG. 36 is a schematic view of the stomach of FIG. 35, showing a conventional wedge resection to remove a tumor from the stomach using the surgical system of FIG. 35.

A conventional surgical procedure to remove a tumor from a stomach is called a wedge resection, where the portion of the stomach where the tumor is arranged is removed in full. FIG. 35 and FIG. 36 illustrate an exemplary embodiment of a conventional surgical system that is configured for endoluminal and laparoscopic access into a stomach 3050 to remove a tumor 3056. Similar to the stomach 3000, the stomach 3050 includes an esophageal sphincter 3051, a greater curvature 3052, a lesser curvature 3053, a pyloric sphincter 3054, a duodenum 3055, an inner tissue wall 3057, and an outer tissue wall 3058. As illustrated, the tumor 3056 is arranged on the inner tissue wall 3057 of the greater curvature 3052. The tumor 3056 is arranged away from the esophageal sphincter 3051 and esophagus 3059, and on the inner tissue wall 3057 of the greater curvature 3052. In order to remove the tumor 3056, an endoscope 3060 is arranged in the intraluminal space, and a laparoscope 3062 is arranged in the extraluminal space.

While both the endoscope 3060 and the laparoscope 3062 are providing image data to a display so that a surgeon can properly position the scopes and operate on the stomach 3050, the images from each scope are separate, requiring the surgeon to look at two different monitors, or a frame-in-frame arrangement. This is problematic when both the endoscope 3060 and the laparoscope 3062 must work cooperatively in order to create the incision line I to remove the wedge W with the tumor 3056 attached. The surgeon therefore typically relies on their experience or knowledge of the anatomy to ensure the endoscope 3060 and laparoscope 3062 are working cooperatively and arranged in the correct location on either side of the inner tissue wall 3057 and outer tissue wall 3058.

With conventional surgical systems, a unified visual image of a connected or joint surgical treatment site cannot be provided. Instead, a user is required either to monitor multiple displays at the same time and guess as to the orientation and distance between various surgical instruments and/or scopes visualized by different scopes involved in the same procedure or to incorporate an additional visual system into the procedure in an attempt to track the scopes and instruments. The surgical systems provided herein avoid these issues by integrating imaging from both an endoscope and a laparoscope into a single visual display to simplify alignment and deployment of various surgical instruments and scopes.

Figure 37:
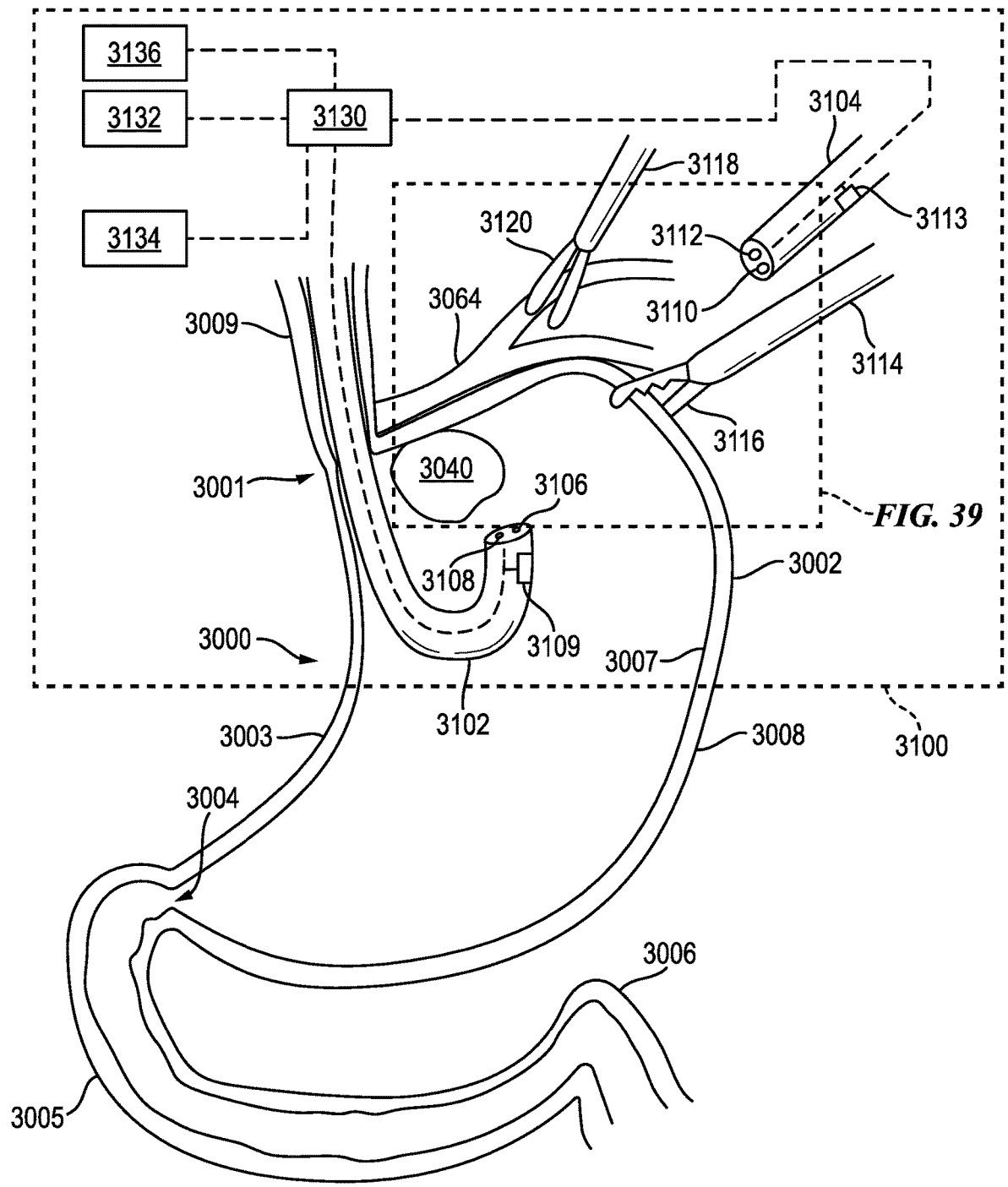
FIG. 37 is a schematic view of an embodiment of a surgical system having a laparoscope, laparoscopic instruments, and an endoscope, showing the laparoscope and laparoscopic instruments positioned outside of a stomach and the endoscope positioned within the stomach.

FIG. 37 illustrates an exemplary embodiment of a surgical system 3100 that is configured for endoluminal access into and laparoscopic access of the stomach 3000. As will be described in more detail below, the surgical system 3100 can transmit data from different scope devices in order to create a merged image of a single scene at the surgical site, which can include a representative depiction of at least one of the scope devices in the merged image. For purposes of simplicity, certain components of the surgical system 3100 and the stomach 3000 are not illustrated.

As shown, the stomach 3000 includes a tumor 3040 arranged on the greater curvature 3002. When operating on the stomach 3000, the blood vessels 3064 may need to be manipulated (e.g., mobilized) using laparoscopically arranged instruments in order to properly access the tumor 3040. In use, as described in more detail below, the surgical system 3100 can provide a merged image so that the endoscope and laparoscope can operate cooperatively while neither scope can visually see the other in their field of view (e.g., due to the stomach wall positioned therebetween).

The surgical system 3100 includes an endoscope 3102 that is configured for endoluminal access through the esophagus 3009 and into the stomach 3000. The endoscope 3102 can have a variety of configurations. For example, in this illustrated embodiment, the endoscope 3102 includes a first optical sensor 3106 (e.g., a camera) and lighting element 3108. Alternatively, or in addition, the endoscope 3102 can include a working channel (not shown) arranged along the length of the endoscope 3102 to pass an instrument endoluminally into the stomach 3000. In some embodiments, the endoscope 3102 can include an outer sleeve (not shown) configured to be inserted through a patient's mouth (not shown) and down the esophagus 3009. The outer sleeve can include a working channel that is configured to allow the endoscope 3102 to be inserted through the outer sleeve and access the stomach 3000. In certain embodiments, the endoscope 3102 can include a working channel extending therethrough. This working channel can be configured to receive one or more surgical instruments and/or allow fluid to pass therethrough to insufflate a lumen or organ (e.g., the stomach).

Further, the surgical system 3100 includes a laparoscope 3104 that is configured for laparoscopic access through the abdominal wall (not shown) and into the extraluminal anatomical space adjacent to the stomach 3000. The laparoscope 3104 can have a variety of configurations. For example, in this illustrated embodiment, the laparoscope 3104 includes a second optical sensor 3110 (e.g., a camera) and a lighting element 3112. Alternatively, or in addition, the laparoscope 3104 can include a working channel (not shown) arranged along the length of the laparoscope 3104 to pass an instrument laparoscopically into the extraluminal space. In some embodiments, the laparoscope 3104 can be inserted into the extraluminal anatomical space through a trocar or multi-port (not shown) positioned within and through a tissue wall. The trocar or multi-port can include ports for passing the laparoscope 3104 and/or other surgical instruments into the extraluminal anatomical space to access the stomach 3000.

As shown in FIG. 37, the endoscope 3102 includes a first tracking device 3109 disposed on or within the endoscope 3102. The first tracking device 3109 is configured to transmit (e.g., to controller 3130) a signal that is indicative of a location of the endoscope 3102 relative to the laparoscope 3004. Additionally, the laparoscope 3104 includes a second tracking device 3113 disposed on or within the laparoscope 3104. The second tracking device 3113 is configured to transmit (e.g., to controller 3130) a signal that is indicative of a location of the laparoscope 3104 relative to the endoscope 3102. In other embodiments, only one of the endoscope 3102 and the laparoscope 3104 include a tracking device.

Alternatively, or in addition, the transmitted signal (or an additional transmitted signal) from the first tracking device 3109 can be further indicative of an orientation of the endoscope 3102 relative to the laparoscope 3004. Alternatively, or in addition, the transmitted signal (or an additional transmitted signal) from the second tracking device 3113 can be further indicative of an orientation of the laparoscope 3004 relative to the first scope device.

In some embodiments, the first and second tracking devices 3109, 3113 are configured to use magnetic or radio frequency sensing to detect a location, an orientation, or both of the endoscope 3102 and laparoscope 3104, respectively (e.g., when the endoscope 3102 and laparoscope 3104 positioned on opposite sides of the tissue wall of the stomach 3000). Alternatively, the first and second tracking devices 3109, 3113 are configured to use common anatomic landmarks to detect a location, an orientation, or both of the endoscope 3102 and laparoscope 3104, respectively (e.g., when the endoscope 3102 and laparoscope 3104 positioned on opposite sides of the tissue wall of the stomach 3000). The first and second tracking devices 3109, 3113 can each transmit the signal(s) to a controller (like controller 3130). Various embodiments of magnetic fiducial markers and using magnetic fiducial markers in detecting location are discussed further, for example, in U.S. Pat. App No. 63/249, 658 entitled "Surgical Devices, Systems, And Methods For Control Of One Visualization With Another" filed on Sep. 29, 2021.

Figure 38:
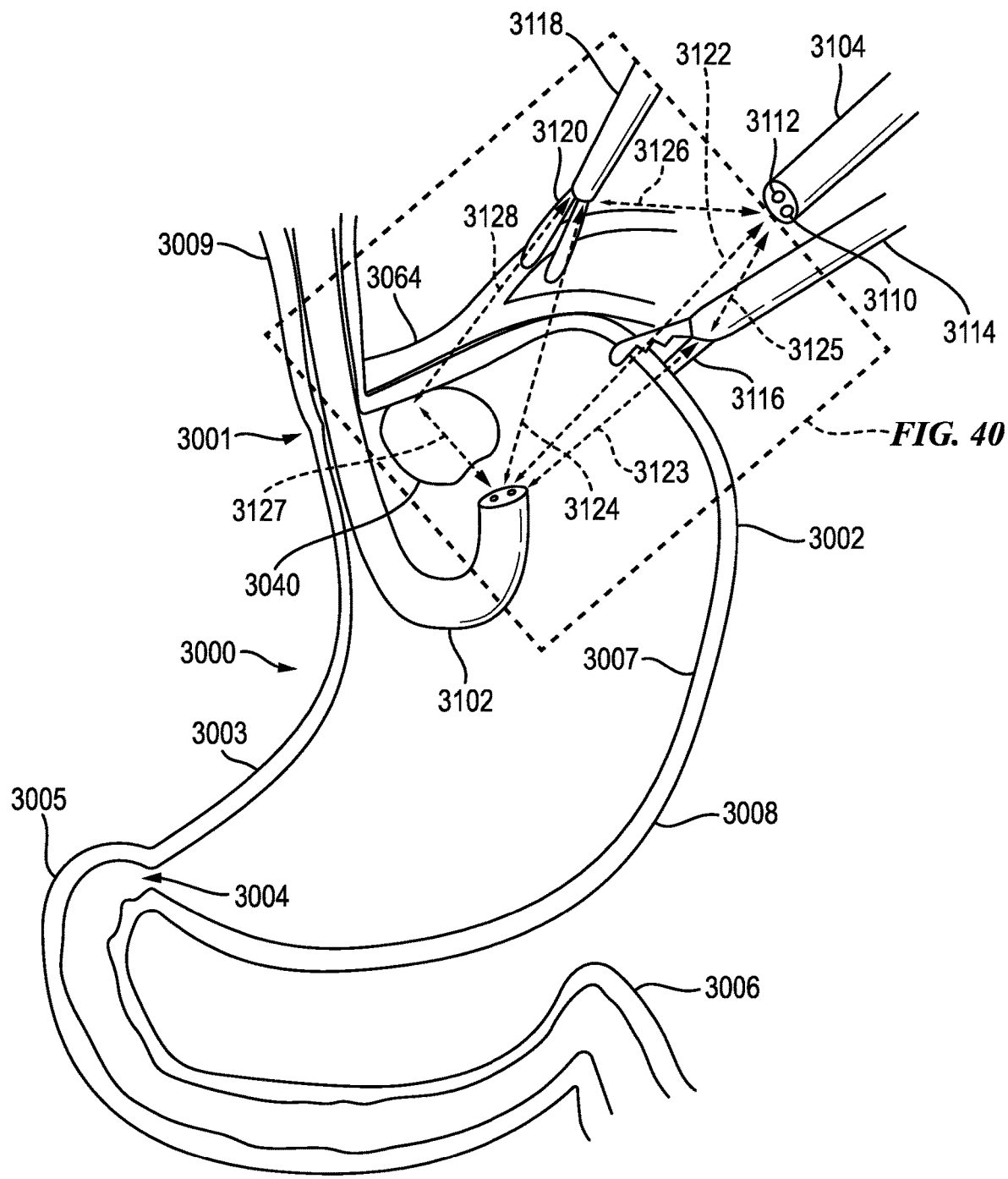
FIG. 38 is a schematic view of the surgical system of FIG. 37, showing the relative distances between the laparoscope, the laparoscopic instruments, the endoscope, and a tumor within the stomach.

As further shown in FIG. 37 and FIG. 38, the surgical system 3100 includes first and second surgical instruments 3114, 3118 that are each configured for laparoscopic access through the abdominal wall and into the extraluminal anatomical space surrounding the stomach 3000. The first and second surgical instruments 3114, 3118 can have a variety of configurations. For example, in this illustrated embodiment, the first and second surgical instruments 3114, 3118 each include a pair of jaws 3116, 3120, respectively, that are configured to manipulate the stomach 3000 from the laparoscopic side. While two surgical instruments 3114, 3118 are illustrated, in other embodiments, the surgical system 3100 can include one surgical instrument or more than two surgical instruments. In some embodiments, the first and second surgical instruments 3114, 3118 can be passed through ports of the same trocar and/or multi-port device that the laparoscope 3104 is positioned therethrough.

The surgical system 3100 also includes a controller 3130 communicatively coupled to the endoscope 3102 and the laparoscope 3104, and is configured to receive the transmitted image data of the first and second scenes from the first and second optical sensors 3106, 3110, respectively. The controller 3130 is also communicatively coupled to first and second tracking devices 3109, 3113 and is configured to receive the transmitted signals from the first and second tracking devices 3109, 3113, respectively. Once received, the controller 3130 is configured to determine at least the relative distance between the endoscope 3102 and the laparoscope 3104. In certain embodiments, the controller 3130 can also be configured to determine the relative orientation between endoscope 3102 and the laparoscope 3104.

As shown in FIG. 38, the relative distance between the endoscope 3102 and the laparoscope 3104 is illustrated in as dashed arrow 3122. Based on both the transmitted image data and the relative distance between endoscope 3102 and the laparoscope 3104, the controller 3130 is configured to provide a merged image to a display, for example, on a first display 3132, a second display 3134, or both of the surgical system 3100. In the merged image, at least one of the endoscope 3102 and the laparoscope 3104 is a representative depiction thereof.

The first and second displays 3132, 3134 can be configured in a variety of configurations. For example, in some embodiments, the first display can be configured to display the first scene and the second display can be configured to display the second scene, and the first display, the second display, or both, can be further configured to display the merged image. In another embodiment, the surgical system 3100 can include, a third display 3136 (FIG. 37) that can be used to display the merged image, and the first and second displays 3132, 3134 are used to only show the transmitted image data from the optical sensors 3106, 3110, respectively, without any modification. In this embodiment, a surgeon can access the real-time scenes from both the endoscope 3102 and the laparoscope 3104 on the first and second displays 3132, 3134, while also having access to the merged image on the third display 3136.

As stated above, the endoscope 3102 includes the first optical sensor 3106. The first optical sensor 3106 is configured to transmit image data of a first scene within a field of view of the endoscope 3102 to the controller 3130. In this illustrated embodiment, the tumor 3040 is arranged within the field of view of the endoscope 3102. As a result, the controller 3130, based on the transmitted image data can determine the relative distance between the endoscope 3102 and the tumor 3040. As shown in FIG. 38, the relative distance between the endoscope 3102 and the tumor 3040 is illustrated as dashed arrow 3127. In some embodiments, the relative distance 3127 can be determined by using structured light projected onto the tumor 3040 (e.g., via lighting element 3108) and tracked by the first optical sensor 3106. Further, in some embodiments, the controller 3130 based on the determined relative distances 3122 (between the endoscope 3102 and laparoscope 3104) and determined relative distance 3127 (between the endoscope 3102 and the tumor 3040), the controller can calculate the relative distance between the laparoscope 3104 and the tumor 3040.

Additionally, the laparoscope 3104 includes the second optical sensor 3110. The second optical sensor 3110 is configured to transmit image data of a second scene within a field of view of the laparoscope 3104 to the controller 3130. The first and second surgical instruments 3114, 3118 are arranged within the field of view of the laparoscope 3104. As a result, the controller 3130, based on the transmitted image data, can determine the relative distance between the laparoscope 3104 and each of the first and second surgical instruments 3114, 3118. In certain embodiments, the controller 3130 can also be configured to determine the relative orientation between the laparoscope 3104 and each of the first and second surgical instruments 3114, 3118.

As shown in FIG. 38, the relative distance between the laparoscope 3104 and the first surgical instrument 3114 is illustrated as dashed arrow 3125, and the relative distance between the laparoscope 3104 and the second surgical instrument 3118 is illustrated as dashed arrow 3126. In some embodiments, the relative distances 3125, 3126 can be determined by using structured light projected onto the surgical instruments 3114, 3118 (e.g., by lighting element 3112) and tracked by the second optical sensor 3110.

Based on the relative distance 3122 (between the endoscope 3102 and laparoscope 3104), the relative distance 3125 (between the laparoscope 3104 and the first surgical instrument 3114), 3126 (between the laparoscope 3104 and the second surgical instrument 3118), 3127 (between the endoscope 3102 and the tumor 3040), the controller 3130 can determine, for example, the relative distance between the endoscope 3102 and each of the first surgical instrument 3114 and the second surgical instrument 3118, the relative distance between the tumor 3040 and each of the first instrument 3114 and the second instrument 3118, etc. As shown in FIG. 38, the relative distance from the endoscope 3102 to the first surgical instrument 3114 is illustrated as dashed arrow 3123, the relative distance from the endoscope 3102 to the second surgical instrument 3118 is illustrated as dashed arrow 3124, and the relative distance from the tumor 3040 to the surgical second instrument 3118 is illustrated as dashed arrow 3128. Based on the determined relative distances 3123, 3124, 3128, and the transmitted image data (e.g., of the first scene, the second scene, or both), the controller can create a merged image that is projected onto the first display 3132, the second display 3134, or both. Since there is direct imaging of each of the instruments sets from their respective cameras, and because the system is able to determine the exact type of devices in use (e.g., graspers, cutters) since the instruments have been scanned into or identified in some form to the surgical hub to allow setup of the system for interaction with the devices, the system can create a 3D model recreation of each of the instruments. With the relative distances measured or at least one coupled 3D axis registration, the system could display the devices from the occluded camera and invert them in the necessary manner to show their location, orientation and status in real-time. These 3D models could even be modified with details directly imaged from the camera viewing the occluded cooperative image.

Further, in certain embodiments, the controller can also determine relative orientations between the endoscope 3102 and the laparoscope 3104, the first instrument 3114 and/or the second instrument 3118 relative to the endoscope 3102 and/or relative to the tumor 3040, etc. Based on the determined relative orientations and the transmitted image data (e.g., of the first scene, the second scene, or both), the merged image can also illustrate not only the locations, but also the orientations of one or more of the endoscope 3102, the laparoscope 3104, the first surgical instrument 3114, the second surgical instrument 3118, and the tumor 3040. As discussed above, the means to create a completely generated 3D model of the instrument that can be overlaid into the image of the system which cannot see the alternative view. Since the representative depiction is a generated image, various properties of the image (e.g., the transparency, color) can also be manipulated to allow the system to be clearly shown as not within the real-time visualization video feed, but as a construct from the other view. If the user where to switch between imaging systems, the opposite view could also have the constructed instruments within its field of view. In some embodiments, there is another way to generate these overlays. The obstructed image could isolate the instruments in its stream from the surrounding anatomy, invert and align the image to the known common axis point and then merely overlay a live image of the obstructed view into the non-obstructed view camera display feed. Like the other representative depiction above, the alternative overlay could be shaded, semi-transparent, or otherwise modified to insure the user can tell the directly imaged view from the overlaid view in order to reduce confusion. This could be done with key aspects of the anatomy as well (e.g., the tumor that can be seen by one camera but not the other). The system could utilize the common reference between the cameras and display the landmark, point of interest, or key surgical anatomy aspect and even highlight it to allow for better approaches and interaction even from the occluded approach of the key aspect.

Figure 39:
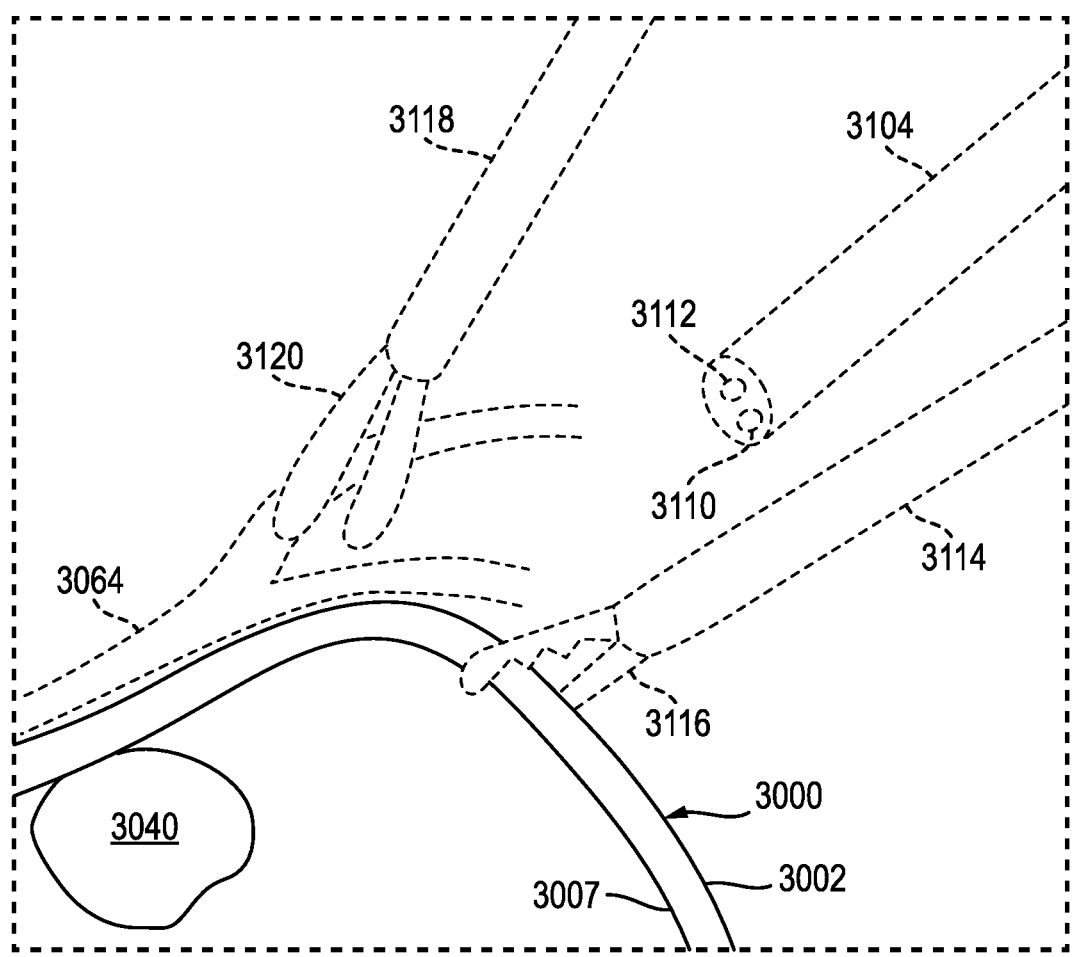
FIG. 39 is a schematic view of a merged image of the surgical system of FIG. 37 from the perspective of the endoscope.

FIG. 39 illustrates an exemplary embodiment of a merged image. The merged image illustrates a real-time first scene within the field of view of the endoscope 3102 with an overlaid representative depiction of a portion of the laparoscopic side of the stomach (e.g., the blood vessels 3064, the laparoscope 3104, and/or the surgical first and second instruments 3114, 3118). A person skilled in the art will understand that the phrase "representative depiction" as used herein refers to a virtual overlay on an actual depiction from a camera, where the virtual overlay corresponds to the location and orientation of objects which are arranged within the field of view of a camera, but not visible to the camera due to an obstacle being arranged between the camera and the objects, and that the phrase "actual depiction" as used herein refers to an unmodified, real-time image or video stream from a camera. Based on the transmitted image data of the first scene in combination with the determined relative distances 3122, 3123, 3124, the controller 3130 can provide the merged image from the point of view of the endoscope 3102, where the laparoscope 3104 and the surgical instruments 3114, 3118 are shown as representative depictions which correspond to their location in the extraluminal space in real-time. In the illustrated embodiment, the representative depictions are shown in dashed outlines of the corresponding blood vessels 3064, laparoscope 3104, and surgical instruments 3114, 3118. However, other forms of representative depictions can be used, such as simple geometric shapes to represent the non-visual instruments and anatomical structures within the intraluminal space.

Figure 40:
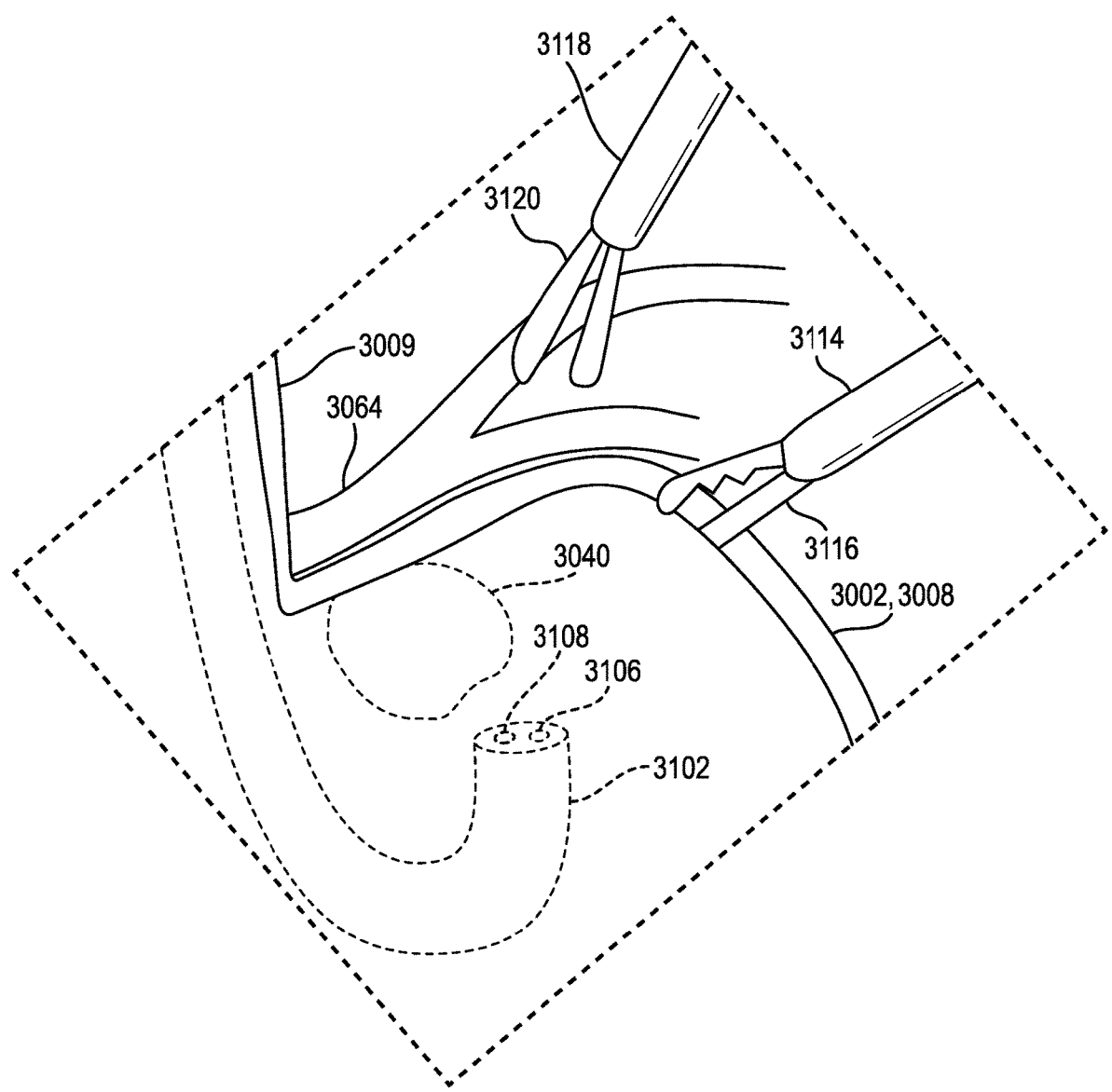
FIG. 40 is a schematic view of a merged image of the surgical system of FIG. 38 from the perspective of the laparoscope.

Alternatively, or in addition, the controller 3130 can generate a merged image from the perspective of the laparoscope 3104. For example, in FIG. 40, the merged image illustrates a the real-time second scene within the field of view of the laparoscope 3104 and an overlaid representative depiction of a portion of the endoscopic side of the stomach (e.g., the tumor 3040 and/or the endoscope 3102). Based on the transmitted image data of the second scene in combination with the determined, the controller 3130 can provide the merged image from the point of view of the laparoscope 3104, where the endoscope 3102 and the tumor 3040 are shown as representative depictions which correspond to their location in the intraluminal space in real-time. In the illustrated embodiment, the representative depictions are shown in dashed outlines of the corresponding tumor 3040 and endoscope 3102. However, other forms of representative depictions can be used, such as simple geometric shapes to represent the non-visual instruments and anatomical structures within the intraluminal space.

In some embodiments, monitoring of interior and exterior portions of interconnected surgical instruments can be performed in order to be image both the internal and external interactions of the surgical instruments with adjacent surgical instruments. In certain embodiments, the surgical instruments that include an articulation actuation system outside of the body. Additionally, the surgical instruments can be configured to be coupled to electromechanical arms of a robotic system. A tracking device can be used to ensure that robotic arms of different instruments do not contact one another outside of the body even though the internal instruments may not be contacting. This system can be used to control intended and prevent inadvertent interactions of laparoscopically arranged instruments by monitoring intracorporeal and extracorporeal aspects of the same instruments.

In other embodiments, the coordination of interior and exterior views of portions of surgical instruments can be accomplished by two separate imaging systems. This would enable the monitoring of the external interactions of multiple surgical instruments while controlling and tracking the internal interactions of those same surgical instruments. The system can minimize unintended external interactions between the surgical instruments while improving the internal operation envelop of the same surgical instruments.

Instrument Control Imaging Systems for Visualization of Upcoming Surgical Procedure Steps Devices, systems, and methods for multi-source imaging provided herein allow for cooperative surgical visualization that enable instrument coordination of the instruments based on a procedure plan for a specific operation. In general, the present surgical systems provide images of both the intraluminal anatomical space and the extraluminal anatomical space, and based on these images, provide a merged image in which certain surgical steps that are performed endoscopically can be coordinated with a known surgical site in a subsequent step performed laparoscopically, or vice versa.

For a surgical procedure, there is a corresponding procedure plan which a surgeon follows as the surgery progresses. The steps in a procedure plan can be performed in a linear fashion in order to achieve a desired outcome, such as removing a tumor from a stomach. Through the procedure plan, several steps are known in advance: (i) the tumor must be partially resected from the inner tissue wall of the stomach; (ii) the stomach must be flipped in order to access the tumor from the laparoscopic side in order to maintain the stomach in an upright orientation to prevent stomach acid from spilling out; and (iii) an incision must be made laparoscopically in order to access the tumor. These pieces of information suggest that two different incisions must be made on the stomach, one to partially remove the tumor, and one to create an opening in the stomach wall to access the tumor. Based on this knowledge that two separate incisions must be made in relatively the same location, an algorithm can calculate where the first and second incisions should be located to align the second incision with the first incision so that the incisions are as small as possible and efficiently made.

In one exemplary embodiment, the surgical systems can include an energy applying surgical instrument configured to apply energy to a natural body lumen or organ, a first scope device configured to transmit image data of a first scene within its field of view, a second scope device configured to transmit image data of a second scene within its field of view, and a controller configured to receive the transmitted image data of the first and second scenes and to provide a merged image of the first and second scenes. As a result, the merged image provides two separate points of view of the surgical site which allows a medical practitioner to coordinate a location of energy to be applied to an inner surface of a tissue wall at the surgical site relative to an intended interaction location of a second instrument on an outer surface of the tissue wall in a subsequent procedure step at the surgical site.

The controller is configured to generate a merged image of the first and second scenes. The controller receives the actual depiction from each of the first imaging system and second imaging system. The actual depiction can be a photo or a live video feed of what each of the imaging systems, which are attached to each of the scope devices, are seeing in real time. Each of the first and second scenes depict certain critical structures which are not visible by the other imaging system. For example, the first imaging system, arranged endoscopically can have a tumor and an energy applying surgical instrument within its field of view. Additionally, the second imaging system can include laparoscopic instruments arranged within its field of view. Further, as will be discussed in more detail, the merged image facilitates coordination of a location of energy to be applied by the energy applying surgical instrument to an inner surface of a tissue wall at a surgical site relative to an intended interaction location of a second instrument on an outer surface of the tissue wall in a subsequent procedure step at the surgical site.

In some embodiments, the system would need to couple "known" points. These known points would likely be either fixed aspects (e.g., instrument or scope features, since they are on rigid and predictable systems) or linked anatomic landmarks (e.g., a known anatomic sphincter, ligament, artery that can be seen from both systems directly). The tumor is likely visible or partially visible in one of imaging systems. In hollow organ surgeries, the tissue walls are usually thin and the tumors superficial to at least one side of the organ. An example would be lung cancer. In lung cancer the tumor would be present in either the dissected parenchyma (i.e. from the lap side) or in the bronchial wall (i.e. from the endoscopic approach). Then the system would only need to identify one scope with respect to the other in 3D space or identify an anatomic landmark that both scope can see from different points of view in order to overly the tumor from the side that can see it to the imaging system that cannot.

The first scope device is configured to be at least partially disposed within at least one of a natural body lumen and an organ (e.g., a lung, a stomach, a colon, or small intestines), and the second scope device is configured to be at least partially disposed outside of the at least one of the natural body lumen and the organ. In certain embodiments, the first scope device is endoscope and the second scope device is a laparoscope. The natural body lumen or organ can be any suitable natural body lumen or organ. Non-limiting examples include a stomach, a lung, a colon, or small intestines.

An exemplary surgical system can include a variety of features as described herein and illustrated in the drawings. However, a person skilled in the art will appreciate that the surgical systems can include only some of these features and/or it can include a variety of other features known in the art. The surgical systems described herein are merely intended to represent certain exemplary embodiments. Moreover, while the surgical systems are shown and described in connection with a stomach, a person skilled in the art will appreciate that these surgical systems can be used in connection with any other suitable natural body lumens or organs.

Figure 41:
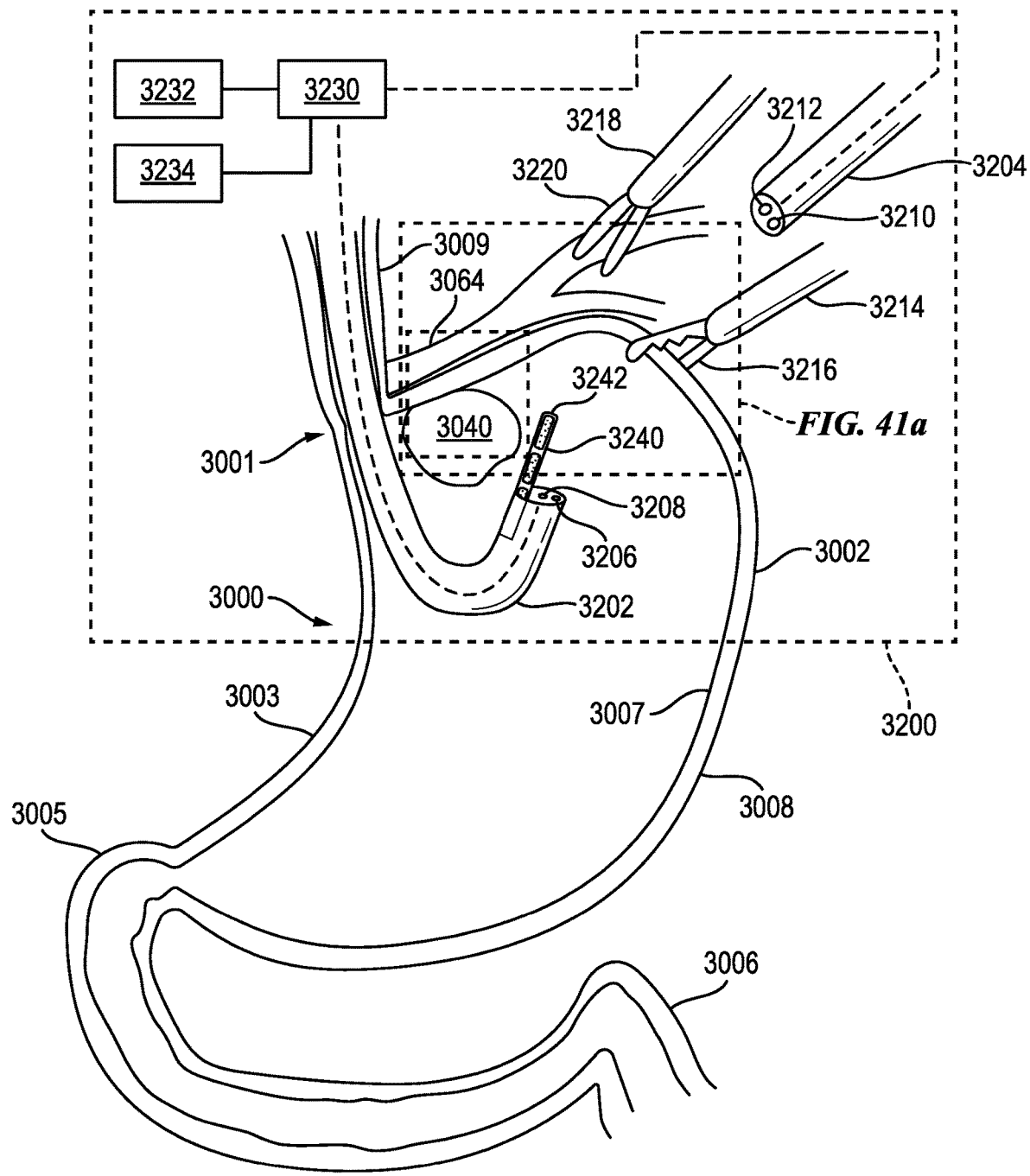
FIG. 41 is a schematic view of the surgical system of FIG. 40, showing a partial removal of a tumor arranged within the stomach by an endoscopically arranged instrument.
Figure 42:
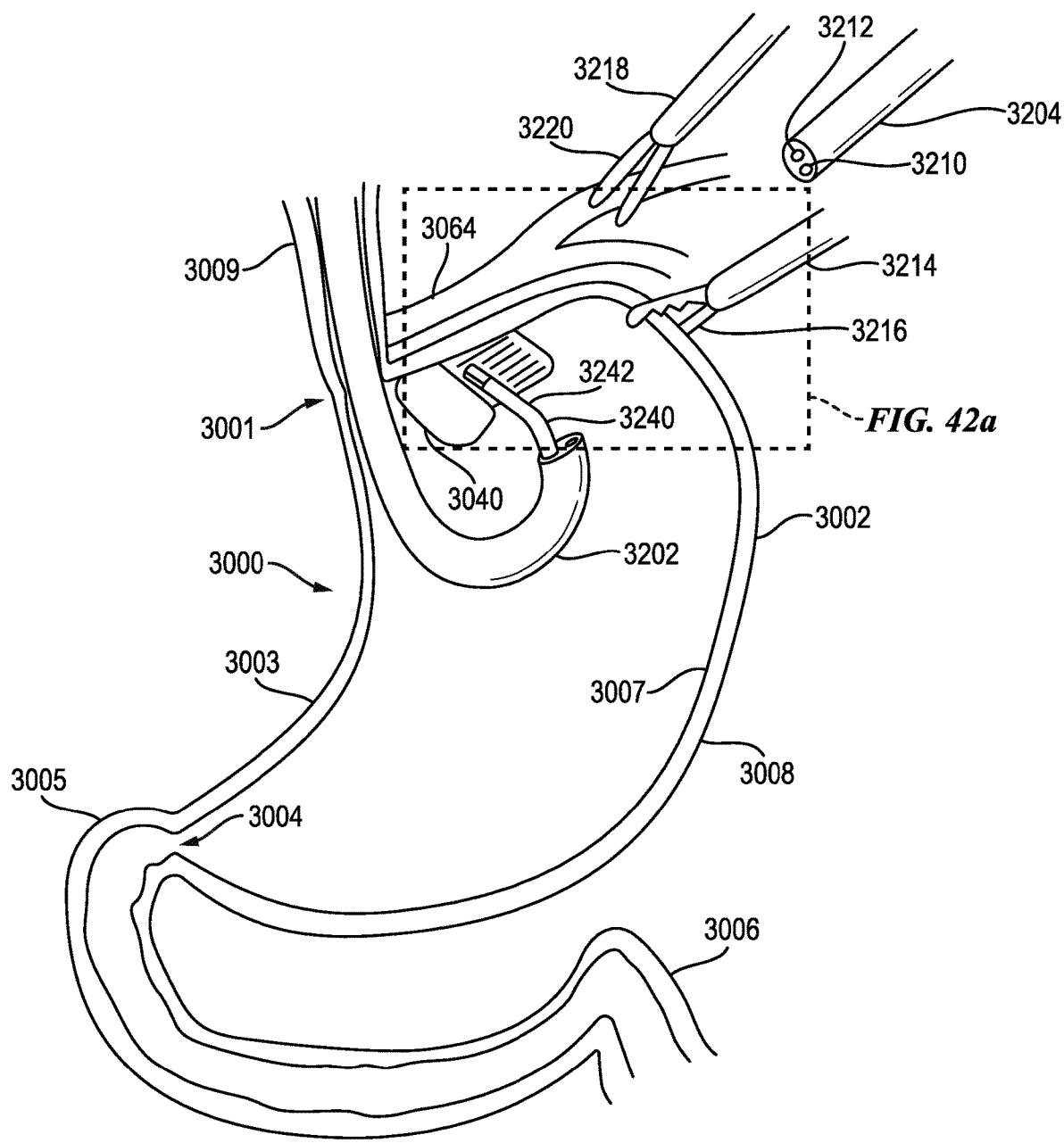
FIG. 42 is a schematic view of the surgical system of FIG. 41, showing the partial removal of a tumor from an inner tissue wall of a stomach.

FIG. 41 and FIG. 42 illustrate an exemplary embodiment of a surgical system 3100 that is configured for endoluminal access into and laparoscopic access of the stomach 3000. Aside from the differences described in detail below, the surgical system 3200 can be similar to surgical system 3100 (FIG. 37 and FIG. 38) and therefore common features are not described in detail herein. For purposes of simplicity, certain components of the surgical system 3200 and the stomach 3000 are not illustrated.

As shown, the stomach 3000 includes an esophageal sphincter 3001, a greater curvature 3002, a lesser curvature 3003, a pyloric sphincter 3004, a duodenum 3005, and a duodenojejunal flexure 3006. Additionally, the stomach includes an inner tissue wall 3007, and an outer tissue wall 3008. As illustrated, the stomach 3000 includes a tumor 3040 arranged on the greater curvature 3002. When operating on the stomach 3000, the blood vessels 3064 may need to be manipulated (e.g., mobilized) using laparoscopically arranged instruments in order to properly access the tumor 3040. In use, as described in more detail below, the surgical system 3200 can provide a merged image so that energy application and incisions in subsequent procedure steps can be coordinated and visualized.

The surgical system 3200 includes an endoscope 3202 configured for endoluminal access through the esophagus 3009 and into the stomach 3000. The endoscope 3202 can have a variety of configurations. For example, in this illustrated embodiment, the endoscope 3202 includes an optical sensor 3206 (e.g., a camera) and light element 3208. Further, the endoscope 3202 includes a working channel 3203 that is arranged along the length of the endoscope 3202. The working channel 3203 is configured to receive one or more surgical instruments and/or allow fluid to pass therethrough to insufflate a lumen or organ (e.g., the stomach). In some embodiments, the endoscope 3202 can include an outer sleeve (not shown) configured to be inserted through a patient's mouth (not shown) and down the esophagus 3009. The outer sleeve can include a working channel that is configured to allow the endoscope 3202 to be inserted through the outer sleeve and access the stomach 3000.

The surgical system 3200 also includes a laparoscope 3204 configured for laparoscopic access through the abdominal wall (not shown) and into the extraluminal anatomical space adjacent to the stomach 3000. The laparoscope 3204 can have a variety of configurations. For example, in this illustrated embodiment, the laparoscope 3204 includes an optical sensor 3210 (e.g., a camera) and lighting element 3212. Alternatively, or in addition, the laparoscope 3204 can include a working channel (not shown) arranged along the length of the laparoscope 3204 to pass an instrument laparoscopically into the extraluminal anatomical space. In some embodiments, the laparoscope 3204 can be inserted into the extraluminal anatomical space through a trocar or multi-port (not shown) positioned within and through a tissue wall. The trocar or multi-port can include ports for passing the laparoscope 3204 and/or other surgical instruments into the extraluminal anatomical space to access the stomach 3000.

As shown in FIG. 41 and FIG. 42, the surgical system 3200 includes an energy applying surgical instrument 3240 that passes through the working channel 3203 of the endoscope 3202 and into the stomach 3000. While the energy applying surgical instrument can have a variety of configurations, in this illustrated embodiment, the energy applying surgical instrument 3240 includes a blade 3242 at a distal end thereof. The blade 3242 can have a variety of configurations. For example, in some embodiments, the blade can be in the form of mono-polar RF blade or an ultrasonic blade. Exemplary embodiments of energy applying surgical instruments that can be used with the present systems are further described in U.S. Pat. No. 10,856,928, which is incorporated herein by reference in its entirety. A GEM blade is a Megadyne smart monopolar blade. It is an advanced monopolar blade capable of sensing the tissue and apply the appropriate RF energy need for the task, just like advanced bipolar or the smart ultrasonic controls. A person skilled in the art will appreciate that the type of surgical instrument and the structural configuration of the surgical instrument, including the end effector, depends at least upon the surgical site and the surgical procedure to be performed.

As further shown in FIG. 41, the energy applying surgical instrument 3202 includes a force sensor 3209 (e.g., the force sensor 3209 can be coupled to one or more motors (not shown) of the instrument 3202 or of a robotic arm (not shown) that is coupled to the instrument 3202). During use, the force sensor 3209 is configured to sense the amount of force being applied by the blade 3242 to the tissue of the stomach 3000 as the blade 3242 moves (e.g., cuts) through the tissue. The force sensor 3209 is further configured to transmit the force data to a controller 3230 of the surgical system 3200. The controller 3230 can aggregate the received feedback input(s) (e.g., force data), perform any necessary calculations, and provide output data to effect any adjustments that may need to be made (e.g., adjust power level, advancement velocity, etc.). Additional details on the force sensor 3209 and controller 3230 are further described in previously mentioned U.S. Pat. No. 10,856,928, which is incorporated herein by reference in its entirety. In some embodiments, the force sensor 3209 can be omitted.

Alternatively, or in addition, the controller 3230 is configured to calculate an insertion depth of the blade 3242 of the energy applying surgical instrument 3240 within tissue of the stomach 30 based on the transmitted image data from either the endoscope 3202 and/or the laparoscope 3204. For example, during endoscopic dissection of the stomach wall, the optical sensor 3206 of the laparoscope 3204 can monitor the dissection site from outside the stomach. Based on this image data that is transmitted to the controller 3230, the controller 3230 can determine the depth of the blade 3242. This can prevent inadvertent full thickness penetration which can result in a leak. Further, the laparoscope 3204 can also monitor heat (via IR wavelength) and collateral thermal damage (tissue refractivity & composition) of the stomach at the dissection site where the energy applying surgical instrument is active. This laparoscopic thermal and welding monitoring can be used to further prevent unnecessary damage to the stomach tissue (e.g., help trigger power adjustments to the energy applying surgical instrument). Various embodiments of thermal and welding monitoring in surgical systems to prevent unnecessary damage to tissue are discussed further, for example, in U.S. Pat. App No. 63/249,658 entitled "Surgical Devices, Systems, And Methods For Control Of One Visualization With Another" filed on Sep. 29, 2021.

The surgical system 3200 includes first and second surgical instruments 3214, 3218 that are each configured for laparoscopic access through the abdominal wall and into the extraluminal anatomical space surrounding the stomach 3000. The first and second surgical instruments 3114, 3118 can have a variety of configurations. For example, in this illustrated embodiment, the first and second surgical instruments 3114, 3118 each include a pair of jaws 3116, 3120, respectively, that are configured to manipulate the stomach 3000 from the laparoscopic side. While two surgical instruments 3114, 3118 are illustrated, in other embodiments, the surgical system 3100 can include one surgical instrument or more than two surgical instruments. In some embodiments, the first and second surgical instruments 3114, 3118 can be passed through ports of the same trocar and/or multi-port device that the laparoscope 3104 is positioned therethrough.

As stated above, the endoscope 3202 includes the first optical sensor 3206. The first optical sensor 3106 is configured to transmit image data of a first scene within a field of view of the endoscope 3102 to the controller 3130. In this illustrated embodiment, the tumor 3040 is arranged within the field of view of the endoscope 3102. As shown in FIG. 41, the energy applying surgical instrument 3240 is inserted into the working channel of the endoscope 3202 and the blade 3242 is advanced towards the tumor 3040. In conventional surgical systems, a surgeon would partially remove the tumor 3040 using the blade 3242 based on the endoscopic scene only, and then proceed to perform a partial stomach flip blindly (e.g., using only the laparoscopic scene) to remove the tumor 3040 laparoscopically through an incision in the stomach wall. The surgeon is not able to coordinate the endoscopic and laparoscopic incisions accurately, and instead approximates where the tumor is during the stomach flip, which could lead to inaccurate incisions which remove more tissue than required. However, in the present system 3200, since both the endoscope 3202 and laparoscope 3204 can provide image data of the surgical site from both the intraluminal anatomical space and the extraluminal anatomical space, the dissection margin (e.g., where the energy applying surgical instrument 3240 is going to apply energy to partially remove the tumor) can be coordinated with a second incision (e.g., where a laparoscopic cut will be made in a subsequent procedure step to remove or detach the tumor 3240 from the stomach.)

The surgical system 3200 also includes a controller 3230 communicatively coupled to the endoscope 3202 and the laparoscope 3204. The controller 3230 is configured to receive the transmitted image data of the first and second scenes from the first and second optical sensors 3206, 3210 and provide a merged image of first and second scenes. This merged image facilitates coordination of a location of energy to be applied by the energy applying surgical instrument 3240 to the inner tissue wall 3057 of the stomach at the surgical site 3245 relative to an intended interaction location of a second instrument (e.g., cutting instrument 3248 having end effectors 3250 in FIG. 43) on the outer tissue wall 3058 of the stomach in a subsequent procedure step at the surgical site 3245.

The controller 3230 is configured to provide a merged image to a display, for example, on a first display 3232, a second display 3234, or both of the surgical system 3200. The first and second displays 3232, 3234 can be configured in a variety of configurations. For example, in some embodiments, the first display can be configured to display the first scene and the second display can be configured to display the second scene, and the first display, the second display, or both, can be further configured to display the merged image. In another embodiment, the surgical system 3200 can include, a third display that can be used to display the merged image, and the first and second displays 3232, 3234 are used to only show the transmitted image data from the first and second optical sensors 3206, 3210, respectively, without any modification. In this embodiment, a surgeon can access the real-time scenes from both the endoscope 3202 and the laparoscope 3204 on the first and second displays 3232, 3234, while also having access to the merged image on the third display 3236.

Figure 41A:
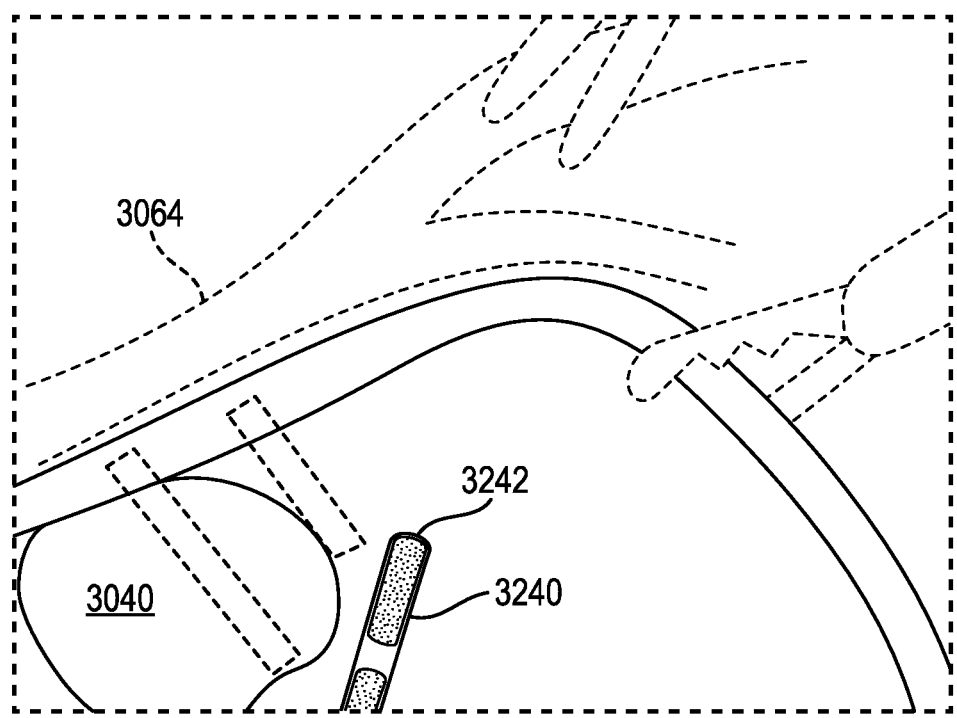
FIG. 41a is a schematic view of a merged image of the surgical system of FIG. 41 from the perspective of the endoscope.

As illustrated in FIG. 41a, the display 3232 depicts the scene from the endoscope 3202, where the optical sensor 3206 has the tumor 3040, energy applying surgical instrument 3240, and the blade 3242 in its field of view. Based on subsequent steps of the procedure plan, the controller 3230 can provide a merged image, where a first interaction location 3244, including a start location 3244a and an end location 3244b, is depicted in relation to the tumor 3040 as a representation of the intended interaction locations of the energy applying surgical instrument 3240. The start location 3244a corresponds to a start point of an incision to partially remove the tumor 3040 from the internal tissue wall 3007 of the stomach 3000, and the end location 3244b corresponds to an end point of the incision initiated at the start location 3244a. As such, a surgeon would be able to visualize where an incision should start and end, based on subsequent procedure steps. In some embodiments, one or more of the subsequent steps are based on the procedure plan. In certain embodiments, one or more of the subsequent procedure steps can be an adjusted based on the actual surgical steps relative to the procedure plan that have already been performed (e.g., GPS map destination directions recalculated based on user actions during the surgical procedure). In some embodiments, the blood vessels 3064 and surgical instruments 3216, 3220 can be shown in the merged image as representative depictions, similar to the merged images of FIG. 39.

Figure 42A:
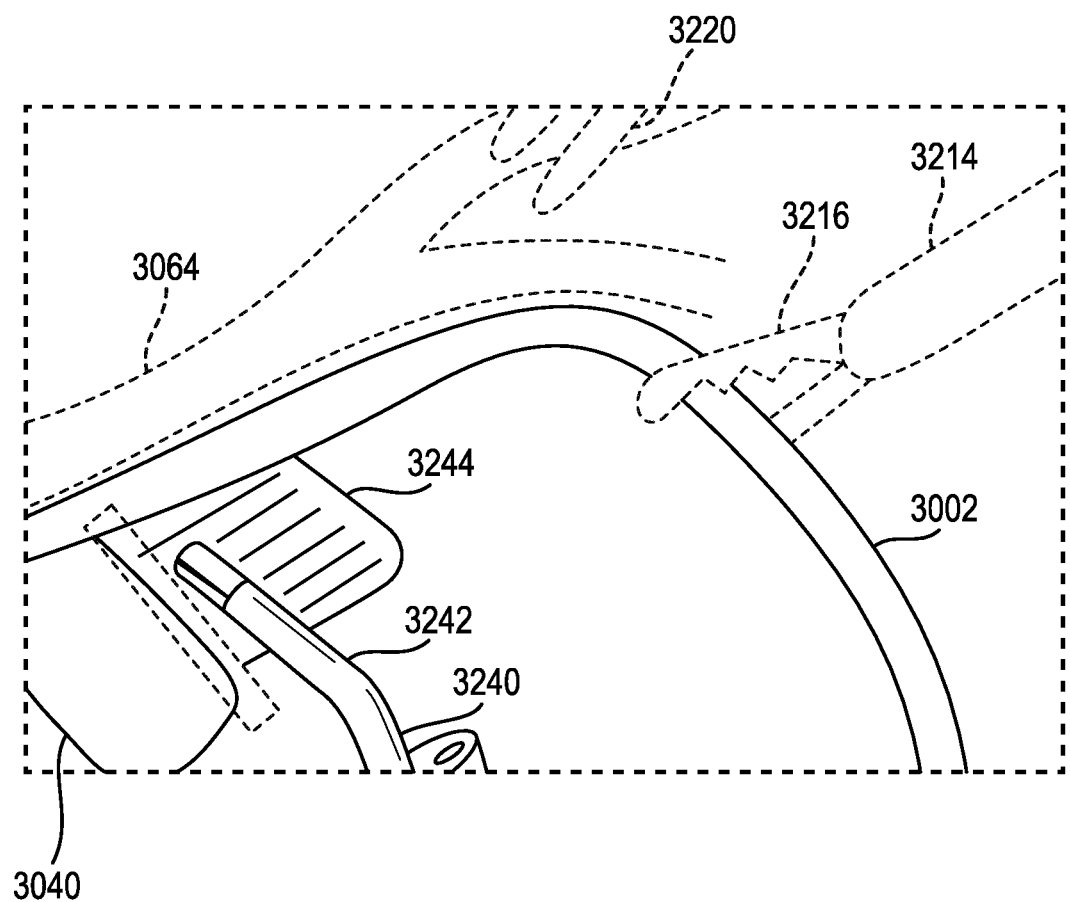
FIG. 42a is a schematic view of a merged image of the surgical system of FIG. 42 from the perspective of the endoscope.

As illustrated in FIG. 42, after energy applying surgical instrument is used to partially remove the tumor 3040 from the inner tissue wall 3007 of the stomach by applying the blade 3242 to the tissue surrounding the tumor 3040. As illustrated in FIG. 42a, the blade 3242 traverses from the first interaction location 3244a to the second interaction location 3244b. Once the blade 3242 has reached the second interaction location 3244b, the energy application is terminated as to not fully remove the tumor 3040 from the inner tissue wall 3007.

As stated above, the surgical system 3200 also includes a controller 3230 communicatively coupled to the endoscope 3202 and the laparoscope 3204, and is configured to receive the transmitted image data of the first and second scenes from the first and second optical sensors 3206, 3210, respectively. The controller 3230 is also communicatively coupled to first and second tracking devices 3252, 3254 arranged within the endoscope and laparoscope, similar to tracking device 3109, 3113, and is configured to receive the transmitted signals from the first and second tracking devices, respectively. Once received, the controller 3230 is configured to determine at least the relative distance between the endoscope 3202 and the laparoscope 3204. In certain embodiments, the controller 3230 can also be configured to determine the relative orientation between endoscope 3202 and the laparoscope 3204.

In some embodiments, the first and second tracking devices 3252, 3254 are configured to use magnetic or radio frequency sensing to detect a location, an orientation, or both of the endoscope 3202 and laparoscope 3204, respectively (e.g., when the endoscope 3202 and laparoscope 3204 positioned on opposite sides of the tissue wall of the stomach 3000). Alternatively, the first and second tracking devices 3252, 3254 are configured to use common anatomic landmarks to detect a location, an orientation, or both of the endoscope 3202 and laparoscope 3204, respectively (e.g., when the endoscope 3202 and laparoscope 3204 positioned on opposite sides of the tissue wall of the stomach 3000). The first and second tracking devices 3252, 3254 can each transmit the signal(s) to a controller (like controller 3230). Various embodiments of magnetic fiducial markers and using magnetic fiducial markers in detecting location are discussed further, for example, in U.S. Pat. App No. 63/249, 658 entitled "Surgical Devices, Systems, And Methods For Control Of One Visualization With Another" filed on Sep. 29, 2021.

Figure 43:
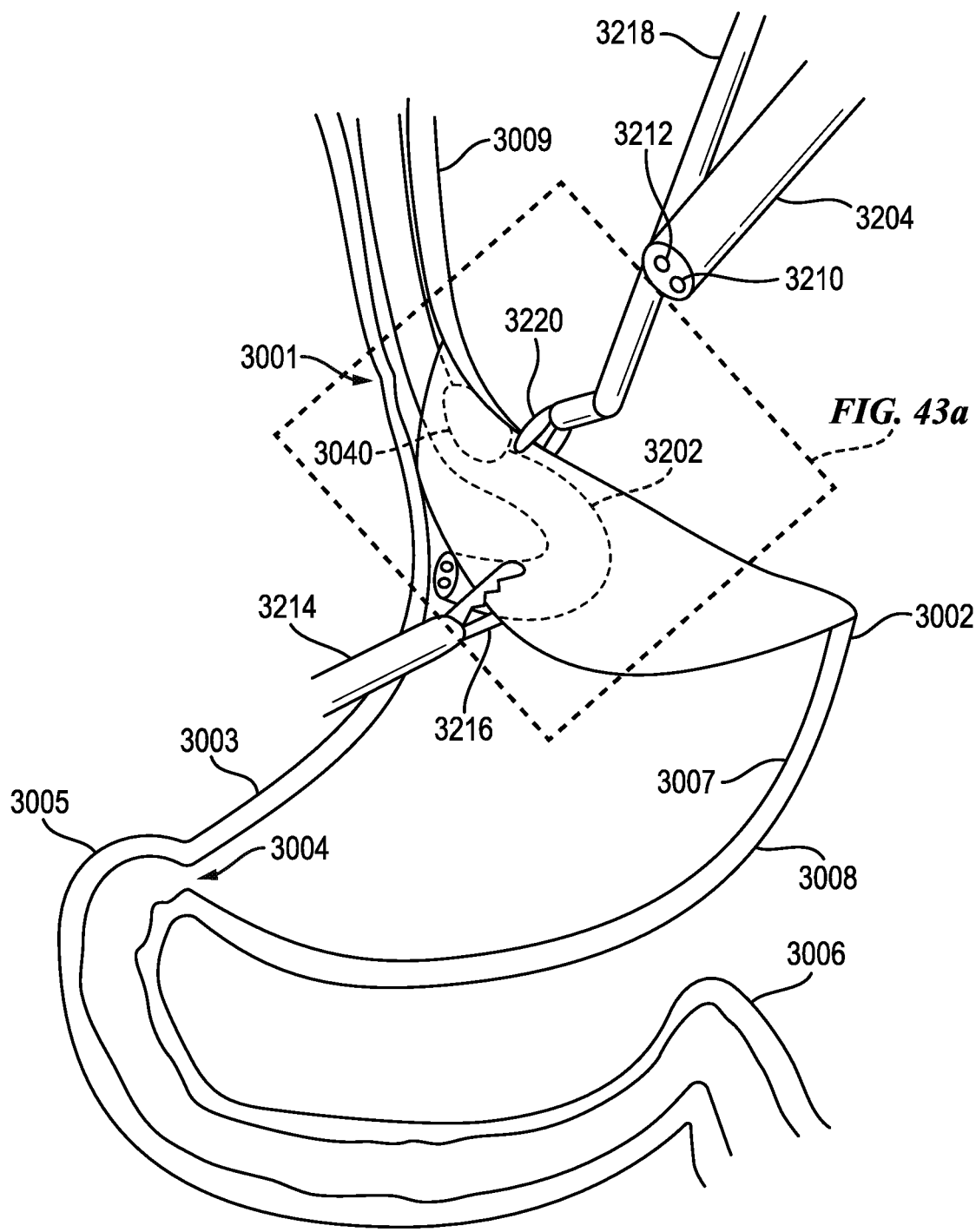
FIG. 43 is a schematic view of the surgical system of FIG. 42, showing mobilization of an upper portion of the stomach by the laparoscopically arranged instrument.

As shown in FIG. 43, the relative distance between the endoscope 3202 and the laparoscope 3204 is illustrated in as dashed arrow 3222. Based on both the transmitted image data and the relative distance between endoscope 3202 and the laparoscope 3204, the controller 3230 is configured to provide a merged image to a display, for example, on a first display 3232, a second display 3234, or both of the surgical system 3200. In the merged image, at least one of the endoscope 3202 and the laparoscope 3204 is a representative depiction thereof.

As stated above, the endoscope 3202 includes the first optical sensor 3206. The first optical sensor 3206 is configured to transmit image data of a first scene within a field of view of the endoscope 3202 to the controller 3230. In this illustrated embodiment, the tumor 3040 is arranged within the field of view of the endoscope 3202. As a result, the controller 3230, based on the transmitted image data can determine the relative distance between the endoscope 3202 and the tumor 3040. As shown in FIG. 43, the relative distance between the endoscope 3202 and the tumor 3040 is illustrated as dashed arrow 3227. In some embodiments, the relative distance 3227 can be determined by using structured light projected onto the tumor 3040 (e.g., via lighting element 3208) and tracked by the first optical sensor 3206. Further, in some embodiments, the controller 3230, based on the determined relative distances 3222 (between the endoscope 3202 and laparoscope 3204) and determined relative distance 3227 (between the endoscope 3202 and the tumor 3040), the controller can calculate the relative distance between the laparoscope 3204 and the tumor 3040.

Additionally, the laparoscope 3204 includes the second optical sensor 3210. The second optical sensor 3210 is configured to transmit image data of a second scene within a field of view of the laparoscope 3204 to the controller 3230. The cutting instrument 3248 is arranged within the field of view of the laparoscope 3204. As a result, the controller 3230, based on the transmitted image data, can determine the relative distance between the laparoscope 3204 and the cutting instrument 3248. In certain embodiments, the controller 3230 can also be configured to determine the relative orientation between the laparoscope 3204 and the cutting instrument 3248.

As shown in FIG. 43, the relative distance between the laparoscope 3204 and the cutting instrument 3248 is illustrated as dashed arrow 3225. In some embodiments, the relative distances 3225 can be determined by using structured light projected onto the cutting instrument 3248 (e.g., by lighting element 3212) and tracked by the second optical sensor 3210.

Based on the relative distance 3222 (between the endoscope 3202 and laparoscope 3204), the relative distance 3225 (between the laparoscope 3204 and the cutting instrument 3248), and the relative distance 3227 (between the endoscope 3202 and the tumor 3040), the controller 3230 can determine, for example, the relative distance between the tumor 3040 and cutting instrument 3248 and the cutting plane of the cutting instrument 3248. As shown in FIG. 43, the relative distance from the tumor 3040 to the cutting instrument 3248 is illustrated as dashed arrow 3223. Based on the determined relative distances 3223, and the transmitted image data (e.g., of the first scene, the second scene, or both), the controller can create a merged image that is projected onto the first display 3232, the second display 3234, or both. Since there is direct imaging of each of the instruments sets from their respective cameras, and because the system is able to determine the exact type of devices in use (e.g., graspers, cutters) since the instruments have been scanned into or identified in some form to the surgical hub to allow setup of the system for interaction with the devices, the system can create a 3D model recreation of each of the instruments. With the relative distances measured or at least one coupled 3D axis registration, the system could display the devices from the occluded camera and invert them in the necessary manner to show their location, orientation and status in real-time. These 3D models could even be modified with details directly imaged from the camera viewing the occluded cooperative image.

Figure 43A:
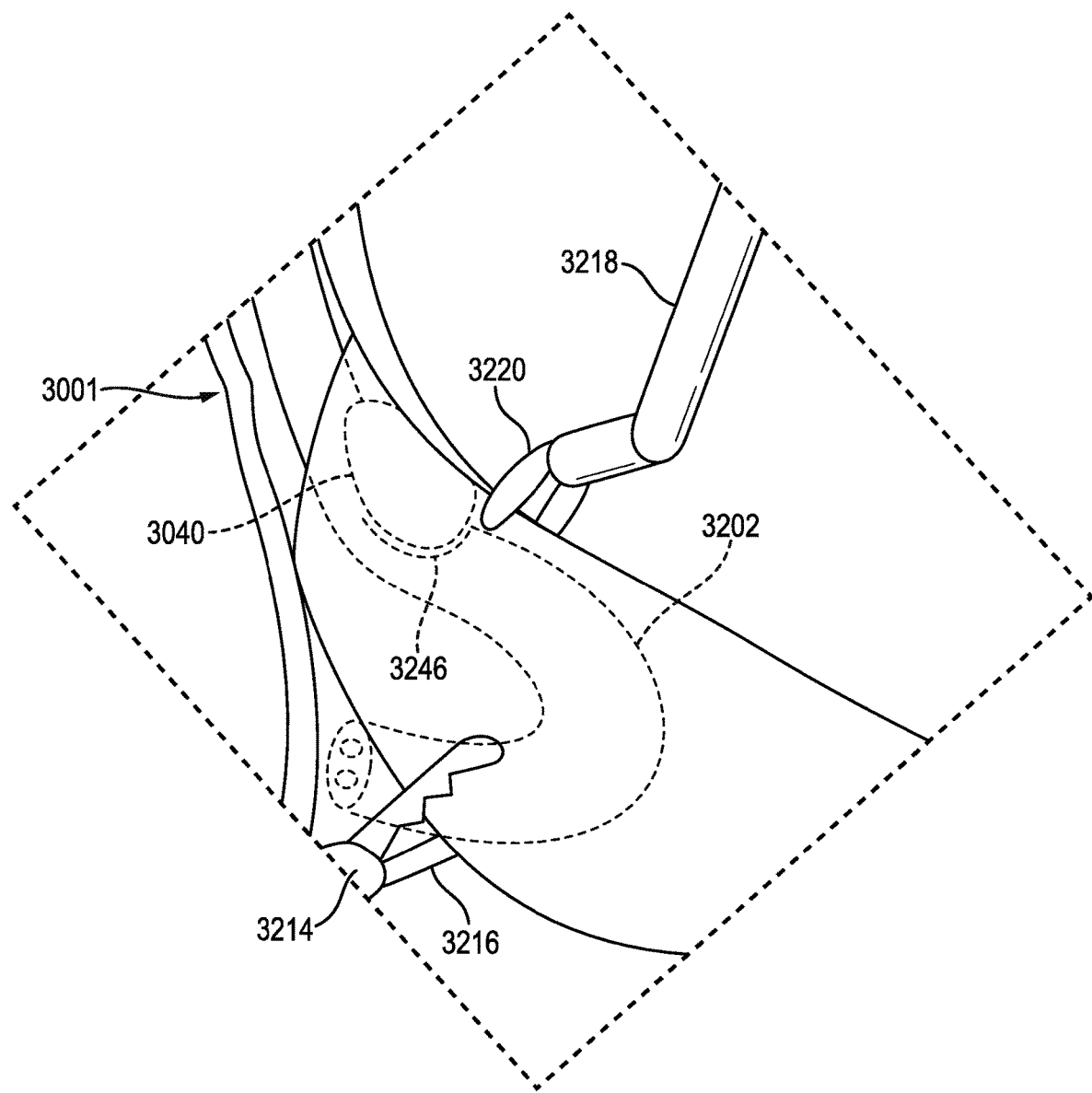
FIG. 43a is a schematic view of a merged image of the surgical system of FIG. 43 from the perspective of the endoscope.

As illustrated in FIG. 43a, the location of the first interaction location 3244 is coordinated with the location of a second interaction location 3246 so that the first interaction location 3244 abuts the second interaction location 3246. The controller 3230 can provide a merged image shown on the display 3234, where a second interaction location 3246 is depicted in relation to the tumor 3040 and the first interaction location 3244 as a representation of the intended interaction location of the surgical instrument 3218. In this illustrated embodiment, the second interaction location 3246 corresponds to an incision to open the stomach 3000 after a portion of the stomach has been flip procedure in order to remove the tumor 3040 from the stomach 30 laparoscopically.

Due to this coordination and alignment of the first interaction location 3244 and the second interaction location 3246, there is minimal damage to the surrounding tissue of the stomach 3000 when incisions are created using the interaction locations 3244, 3246 as guides. The second interaction location 3246 is able to be placed at the exact location of the tumor 3040, even though the tumor is not visible from the laparoscopic side. Due to the endoscope 3202 being able to visualize the tumor, and communicate with the controller 3230. In the illustrated embodiment, the interaction locations 3244, 3246 are shown in dashed outlines. However, other forms of representative depictions, such as simple geometric shapes, can be used.

Figure 44A:
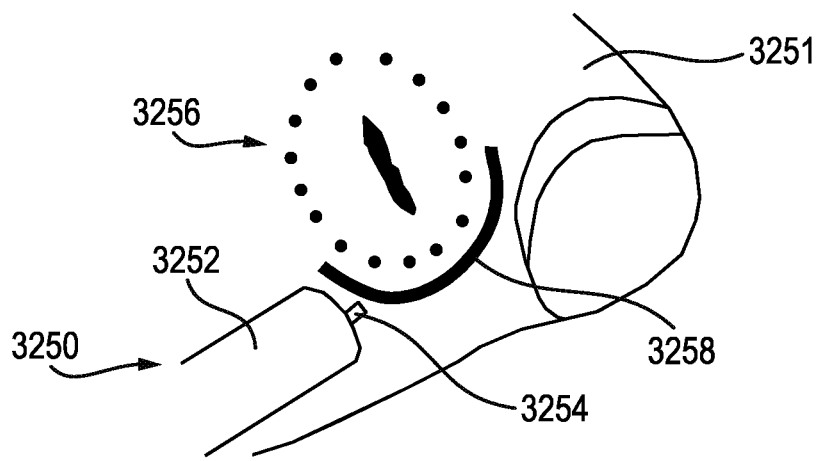
FIG. 44a is a detailed view of another embodiment of a surgical system, showing the removal of a damaged portion of tissue from a colon.

In some embodiments, coordination of lesion removal can be effected with externally supported orientation control via laparoscopic instruments or retractors. Alternatively, or in addition, coordination of lesion removal can be effected with internally supported balloon orientation control closure. For example, a surgical systems 3150 that is configured for lesion removal using an endoscopic and laparoscopic approach, in combination with an endoscopically supported balloon is illustrated in FIG. 44a, can be provided. This is an alternate procedure that has both intra luminal and extra luminal interactive operations. The submucosal dissection and separation is done within the colon. The dissection is stopped before full perimeter dissection is done. An incision is then made in the colon wall and the tumor flipped out into the extra luminal space. The endocutter is the brought into both seal/transect the tumor from the remaining attachment and to close the incision defect. This is done to minimize invasiveness and trauma and seal and remove the tumor since it is not really able to be done entirely intraluminal. This requires the same cooperation and interaction from devices and landmarks on both side of an organ wall that is only viewable from one side at a time.

Figure 44B:
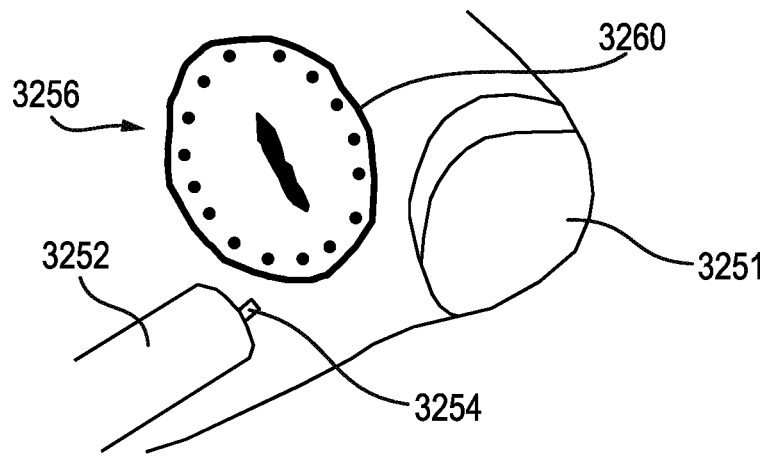
FIG. 44b is a detailed view of the surgical system of FIG. 44a, showing an incision in the seromuscular layer.
Figure 44C:
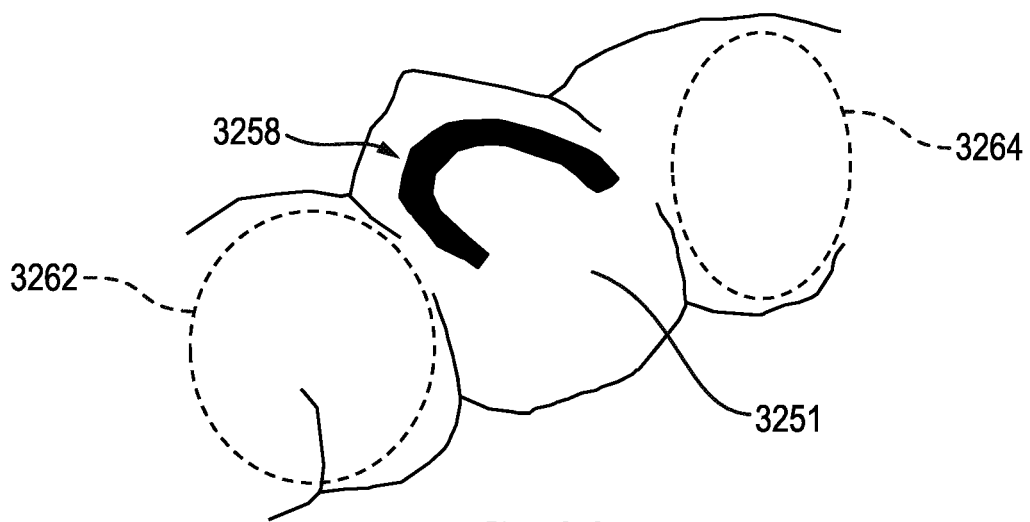
FIG. 44c is a detailed view of the surgical system of FIG. 44b, showing an endoscopic balloon inflation.
Figure 44D:
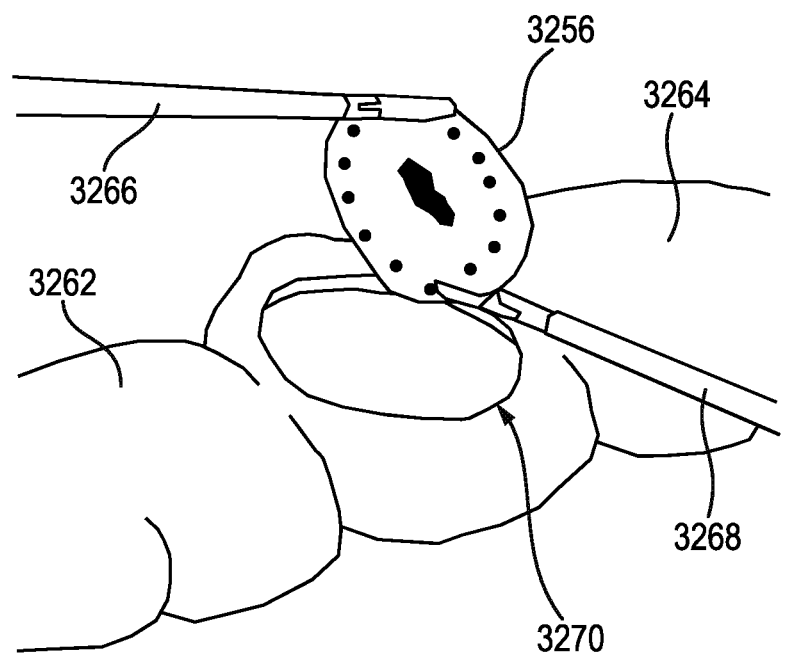
FIG. 44d is a detailed view of the surgical system of FIG. 44c, showing a lesion removal.
Figure 44E:
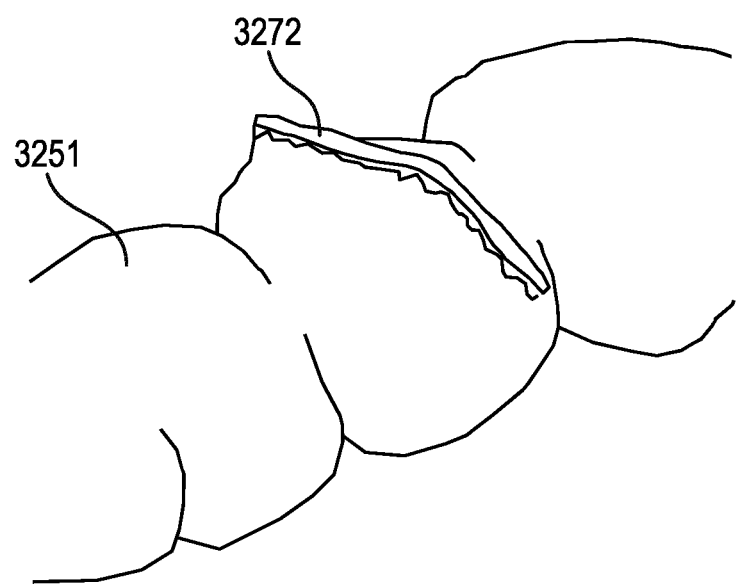
FIG. 44e is a detailed view of the surgical system of FIG. 44d, showing a sealing of the colon.

The surgical system 3150 includes a surgical instrument 3152 having a cutting tip 3154. The cutting tip 3154 is arranged at the distal end of the surgical instrument 3152. As illustrated in FIG. 44a, an initial mucosal incision 3158 can be made in the colon 3151 from the endoscopic side by the surgical instrument 3152. The mucosal incision 3158 is made around the lesion 3156 in order to prepare the lesion 3156 for removal, with the mucosal incision 3158 being only partially around the lesion 3156. As illustrated in FIG. 44b, an incision 3160 can be made in the seromuscular layer of the colon 3151 completely around the lesion 3156 after the mucosal incision 3158 is made. As illustrated in FIG. 44c, balloons 3162, 3164 are endoscopically arranged on either side of the area of the colon 3151 where the lesion 3156 is located. Even though not shown in the FIG. 44a and FIG. 44b, the balloons 3162, 3164 are present and inflated during the creation of the mucosal incision 3158 and the seromuscular incision 3160. The balloons 3162, 3164 provide tension to the colon 3151 to allow for a cleaner incision, and also reduce the likelihood that the lesion 3156 will contact the contents of the colon 3151 during removal through the "crown method." As illustrated in FIG. 44d, with the mucosal incision 3158 and the seromuscular incision 3160, the lesion 3156 can be removed by laparoscopically arranged instruments 3166, 3168. With the lesion 3156 removed, the hole 3170 left by the removal can be stapled closed by staples 3172, as illustrated in FIG. 44e.

Coordinated Instrument Control Systems

Surgical systems that allow for coordinated imaging, such as the surgical systems described above, can also include coordination of the instruments at a specific step of an operation. Since the surgical systems can provide images of both the intraluminal space and the extraluminal space, certain surgical steps which require both endoscopic and laparoscopic coordination with a known surgical site can be performed.

The surgical systems include surgical imaging systems described above, which can be used to track and locate various scopes and instruments arranged on opposite sides of a tissue wall, and provide a merged image. Since the merged image shows the orientation and location of instruments and scopes arranged on opposite sides of a tissue wall which are not visible to each scope, the instruments can be arranged on either side of the tissue wall in order to coordinate motion of the instruments from either side of the tissue wall.

For a surgical procedure, there may be a surgical step which requires coordination between instruments arranged endoscopically and laparoscopically. For example, during a procedure to remove a tumor from a stomach, an incision must be made laparoscopically to access the tumor, and then the tumor must be passed from the intraluminal space to the extraluminal space for removal. However, the endoscopically arranged instruments and the laparoscopically instruments used to pass the tumor through the incision cannot visually see the each other while the handoff is occurring. However, in combination with the imaging systems of the endoscope and laparoscope, the instruments can be coordinated to align with the incision in the stomach wall to pass the tumor through the incision since the instruments can be visualized through the stomach wall.

In one exemplary embodiment, the surgical system can include a first scope device configured to transmit image data of a first scene. Further, a second scope device is configured to transmit image data of a second scene, the first scene being different than the second scene. A tracking device is associated with one of the first scope device or the second scope device and configured to transmit a signal indicative of a location of one of the first scope device or the second scope device relative to the other one of the first scope device or the second scope device. A first surgical instrument is configured to interact with an internal side of a target tissue structure. A second surgical instrument is configured to interact an external side of the target tissue structure. A controller is configured to receive the transmitted image data and transmitted signal. Based on the transmitted signal and image data, the controller can determine on a first relative distance from the first scope device to the second scope device, a second relative distance from the first scope device to the first surgical instrument positioned within at least one natural body lumen and organ, and a third relative distance from the second scope to the second surgical instrument positioned outside of at least one natural body lumen and the organ. Relative movements of the instruments are coordinated based on the determined relative distances.

The controller is further configured to generate a merged image of the first and second scenes. The controller receives the actual depiction from each of the first imaging system and second imaging system. The actual depiction can be a photo or a live video feed of what each of the imaging systems, which are attached to each of the scope devices, are seeing in real time. Each of the first and second scenes depict certain critical structures that are not visible by the other imaging system. For example, the first imaging system, arranged endoscopically, can have a tumor and a surgical instrument within its field of view. Additionally, the second imaging system can include laparoscopic instruments arranged within its field of view. Further, as will be discussed in more detail, the merged image facilitates coordination of the relative movements of both endoscopic and laparoscopic instruments at a surgical site.

An exemplary surgical system can include a variety of features as described herein and illustrated in the drawings. However, a person skilled in the art will appreciate that the surgical systems can include only some of these features and/or it can include a variety of other features known in the art. The surgical systems described herein are merely intended to represent certain exemplary embodiments. Moreover, while the surgical systems are shown and described in connection with a stomach, a person skilled in the art will appreciate that these surgical systems can be used in connection with any other suitable natural body lumens or organs.

Figure 45:
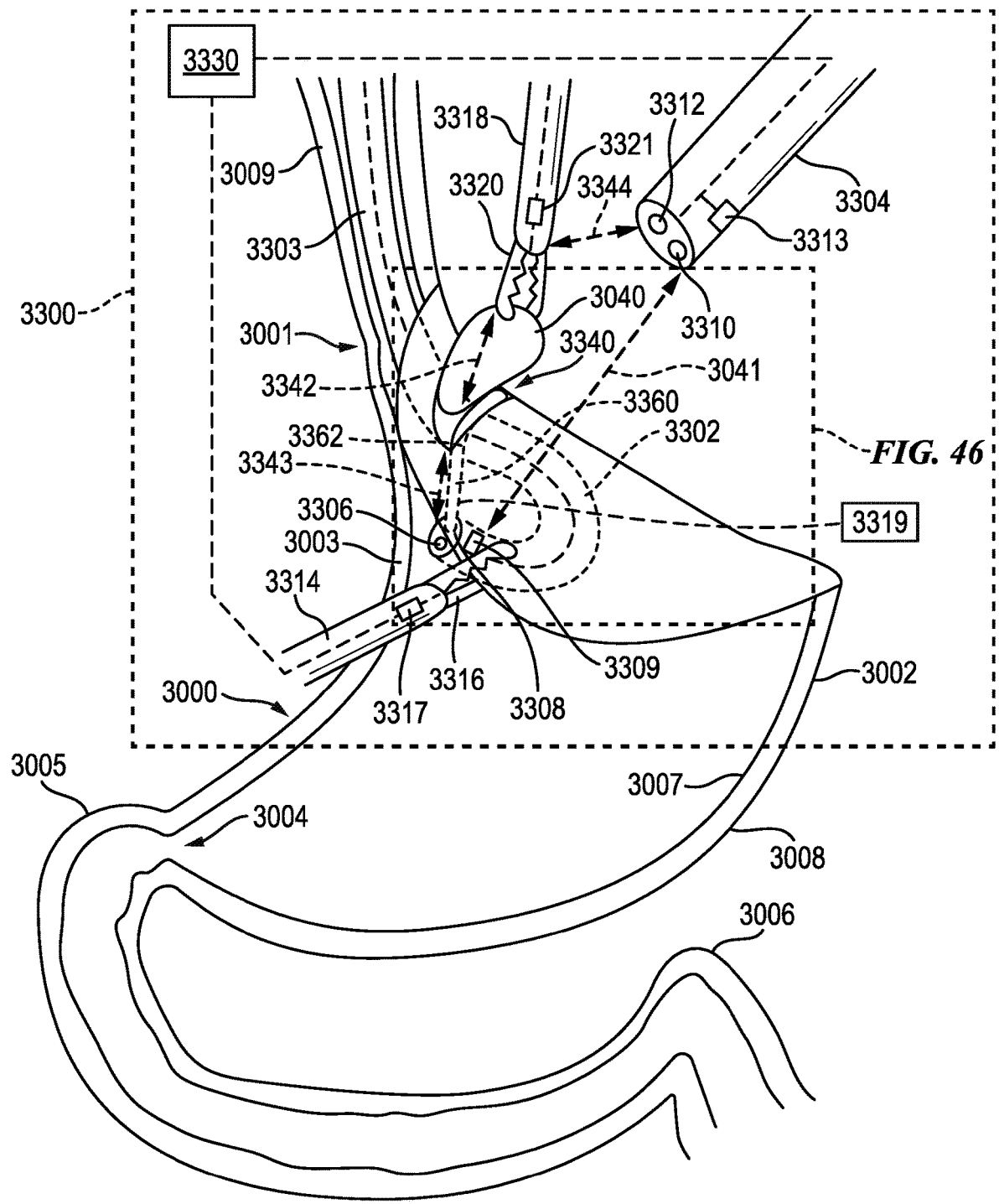
FIG. 45 is a schematic view of another embodiment of a surgical system, showing a removal of a tumor from a stomach by a laparoscopically arranged instrument.

FIG. 45 illustrates an exemplary embodiment of a surgical system 3300 that is configured for endoluminal access into and laparoscopic access of the stomach 3000. Aside from the differences described in detail below, the surgical system 3300 can be similar to surgical system 3100 (FIG. 37 and FIG. 38) and therefore common features are not described in detail herein. For purposes of simplicity, certain components of the surgical system 3300 and the stomach 3000 are not illustrated.

As shown, the stomach 3000 includes an esophageal sphincter 3001, a greater curvature 3002, a lesser curvature 3003, a pyloric sphincter 3004, a duodenum 3005, and a duodenojejunal flexure 3006. Additionally, the stomach includes an inner tissue wall 3007, and an outer tissue wall 3008. As illustrated, the stomach 3000 includes a tumor 3040 arranged on the greater curvature 3002. When operating on the stomach 3000, the blood vessels 3064 may need to be manipulated (e.g., mobilized), such as by using laparoscopically arranged instruments, to properly access the tumor 3040. In use, as described in more detail below, the surgical system 3200 can provide a merged image so that energy application and incisions in subsequent procedure steps can be coordinated and visualized.

The surgical system 3300 includes an endoscope 3302 configured for endoluminal access through the esophagus 3009 and into the stomach 3000. The endoscope 3302 can have a variety of configurations. For example, in this illustrated embodiment, the endoscope 3302 includes an optical sensor 3306 (e.g., a camera) and light element 3308. Further, the endoscope 3302 includes a working channel 3303 that is arranged along the length of the endoscope 3302. The working channel 3303 is configured to receive one or more surgical instruments and/or allow fluid to pass therethrough to insufflate a lumen or organ (e.g., the stomach). In some embodiments, the endoscope 3302 can include an outer sleeve (not shown) configured to be inserted through a patient's mouth (not shown) and into the esophagus 3009. The outer sleeve can include a working channel that is configured to allow the endoscope 3302 to be inserted through the outer sleeve and access the stomach 3000.

The surgical system 3300 also includes a laparoscope 3304 configured for laparoscopic access through the abdominal wall (not shown) and into the extraluminal anatomical space adjacent to the stomach 3000. The laparoscope 3304 can have a variety of configurations. For example, in this illustrated embodiment, the laparoscope 3304 includes an optical sensor 3310 (e.g., a camera) and lighting element 3312. Alternatively, or in addition, the laparoscope 3304 can include a working channel (not shown) arranged along the length of the laparoscope 3304 to pass an instrument laparoscopically into the extraluminal anatomical space. In some embodiments, the laparoscope 3304 can be inserted into the extraluminal anatomical space through a trocar or multi-port (not shown) positioned within and through a tissue wall. The trocar or multi-port can include ports for passing the laparoscope 3304 and/or other surgical instruments into the extraluminal anatomical space to access the stomach 3000.

The endoscope 3302 includes a tracking device 3309 arranged with the endoscope 3302. The tracking device 3309 is configured to transmit a signal indicative of a location of the endoscope 3302 relative to the laparoscope 3304. Additionally, laparoscope 3304 includes a tracking device 3313 associated with the laparoscope 3304. The tracking device 3313 is configured to transmit a signal indicative of a location of the laparoscope 3304 relative to the endoscope 3302. In some embodiments, the tracking devices 3309, 3313 are configured to use magnetic or radio frequency sensing to detect a location and orientation of the endoscope 3302 and laparoscope 3304 arranged opposite sides of the tissue wall of the stomach 3000. Alternatively, the tracking devices 3309, 3313 are configured to use common anatomic landmarks to detect a location and orientation of the endoscope 3302 and laparoscope 3304 arranged opposite sides of the tissue wall of the stomach 3000. The tracking devices 3309, 3313 can determine a relative distance represented by dashed arrow 3341, which is indicative of the location of one of the endoscope 3302 and laparoscope 3304 relative to the other scope device.

In some embodiments, the first and second tracking devices 3309, 3313 are configured to use magnetic or radio frequency sensing to detect a location, an orientation, or both, of the endoscope 3302 and laparoscope 3304, respectively (e.g., when the endoscope 3302 and laparoscope 3304 positioned on opposite sides of the tissue wall of the stomach 3000). Alternatively, the first and second tracking devices 3309, 3313 are configured to use common anatomic landmarks to detect a location, an orientation, or both, of the endoscope 3302 and laparoscope 3304, respectively (e.g., when the endoscope 3302 and laparoscope 3304 positioned on opposite sides of the tissue wall of the stomach 3000). The first and second tracking devices 3309, 3313 can each transmit the signal(s) to a controller (like controller 3330). Various embodiments of magnetic fiducial markers and using magnetic fiducial markers in detecting location are discussed further, for example, in U.S. Pat. App No. 63/249,658 entitled "Surgical Devices, Systems, And Methods For Control Of One Visualization With Another" filed on Sep. 29, 2021.

As shown in FIG. 45, the surgical system 3300 includes a surgical instrument 3360 that passes through the working channel 3303 of the endoscope 3302 and into the stomach 3000. While the surgical instrument can have a variety of configurations, in this illustrated embodiment, the surgical instrument 3360 includes graspers 3362 at a distal end thereof. A person skilled in the art will appreciate that the type of surgical instrument and the structural configuration of the surgical instrument, including the end effector, depends at least upon the surgical site and the surgical procedure to be performed. While only one surgical instrument 3360 is illustrated, in other embodiments, the surgical system 3300 can include more than one surgical instrument arranged in the working channel of the endoscope.

As further shown in FIG. 45, the surgical instrument 3360 includes a force sensor 3319 (e.g., the force sensor 3319 can be coupled to one or more motors (not shown) of the instrument 3360 or of a robotic arm (not shown) that is coupled to the instrument 3360). During use, the force sensor 3319 is configured to sense the amount of force being applied by the graspers 3362 to the tissue of the stomach 3000 as the graspers 3362 manipulate the tissue. The force sensor 3319 is further configured to transmit the force data to a controller 3330 of the surgical system 3300. The controller 3330 can aggregate the received feedback input(s) (e.g., force data), perform any necessary calculations, and provide output data to effect any adjustments that may need to be made (e.g., adjust power level, advancement velocity, etc.). Additional details on the force sensor 3319 and controller 3330 are further described in previously mentioned U.S. Pat. No. 10,856,928, which is incorporated herein by reference in its entirety. In some embodiments, the force sensor 3319 can be omitted.

The surgical system 3300 includes first and second surgical instruments 3314, 3318 that are each configured for laparoscopic access through the abdominal wall and into the extraluminal anatomical space surrounding the stomach 3000. The first and second surgical instruments 3314, 3318 can have a variety of configurations. For example, in this illustrated embodiment, the surgical instruments 3314, 3318 include graspers 3316, 3320, respectively. While two surgical instruments 3314, 3318 are illustrated, in other embodiments, the surgical system 3300 can include more than two surgical instruments. The surgical instruments 3314, 3318 are configured to be inserted through the abdominal wall and into the extraluminal space to manipulate and/or operate on the stomach 3000 from the laparoscopic side. In some embodiments, the first and second surgical instruments 3314, 3318 can be passed through ports of the same trocar and/or multi-port device that the laparoscope 3304 is positioned therethrough.

The surgical instrument 3314 includes a force sensor 3317 arranged with the surgical instrument 3314. The force sensor 3317 is configured to sense an applied force to the target tissue structure by the surgical instrument 3314. Additionally, the surgical instrument 3318 includes a force sensor 3321 arranged with the surgical instrument 3318. The force sensor 3321 is configured to sense an applied force to the target tissue structure by the surgical instrument 3318. The controller 3330 is further configured to determine an amount of strain that is applied to the stomach 3000 by at least one of the surgical instruments 3314, 3318 via the force sensors 3317, 3321.

As stated above, the endoscope 3302 includes the optical sensor 3306. The optical sensor 3306 is configured to transmit image data of a first scene within a field of view of the endoscope 3302 to the controller 3330. As shown in FIG. 45, the surgical instrument 3340 is inserted into the working channel of the endoscope 3302 and advanced towards the tumor 3040. In conventional surgical systems, a surgeon would perform a partial stomach flip blindly (e.g., using only the laparoscopic scene) to remove the tumor 3040 laparoscopically through an incision in the stomach wall. The surgeon is not able to coordinate the endoscopic and laparoscopic instruments accurately, and instead approximates the location of the tumor and instruments during the stomach flip, potentially leading to inaccurate removal of the tumor and the removal more tissue than needed. However, in the present system 3300, since both the endoscope 3302 and laparoscope 3304 can provide image data of the surgical site from both the intraluminal anatomical space and the extraluminal anatomical space, the handoff of the tumor through the incision from the intraluminal space to the extraluminal space can be coordinated between both sets of instruments.

As shown in FIG. 45, the endoscope 3302 can determine the location of the tumor 3040 and incision 3340 based on the relative distance 3343, and the location of the surgical instrument 3360, which is sensed by the optical sensor 3306 and determined by the controller 3330. In some embodiments, the relative distance 3343 is determined using structured light projected onto the tumor 3040 and/or surgical instrument 3360 and tracked by the optical sensor 3306. Additionally, the laparoscope 3304 includes the optical sensor 3310. The optical sensor 3310 is configured to transmit image data of a second scene within a field of view of the laparoscope 3304. The surgical instruments 3314, 3318 are arranged within the field of view of the laparoscope 3304. As shown in FIG. 45, the laparoscope 3304 can determine the location of the surgical instruments 3318 based on the relative distance 3344, which is measured by the optical sensor 3310 and determined by the controller 3330. In some embodiments, the relative distance 3344 is determined by using structured light projected onto the surgical instrument 3318 and tracked by the optical sensor 3310.

The surgical system 3300 also includes a controller 3330 communicatively coupled to the endoscope 3302 and the laparoscope 3304. The controller 3330 is configured to receive the transmitted image data of the first and second scenes from the optical sensors 3306, 3310. The controller 3330 is also configured to determine, based on the transmitted signals, a relative distance from the endoscope 3302 to the laparoscope device 3304 represented by dashed arrow 3341, a relative distance from the tumor 3040 to the surgical instrument 3318 represented by dashed arrow 3342, a relative distance from the endoscope 3302 to the tumor 3040 represented by dashed arrow 3343, and a relative distance from the laparoscope 3304 to the surgical instrument 3318 positioned outside of at least one natural body lumen and the organ represented by dashed arrow 3344.

Figure 46:
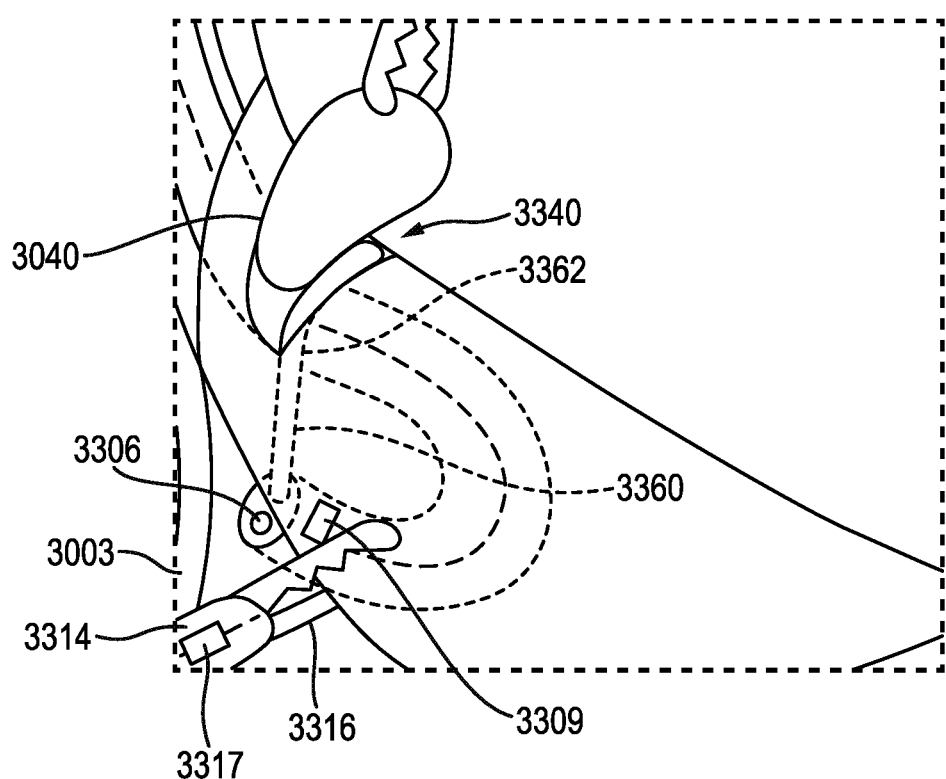
FIG. 46 is a schematic view of a merged image of the surgical system of FIG. 45 from the perspective of the laparoscope.

As illustrated in FIG. 46, based on the determined relative distances, a merged image is provided by the controller 3330 to depict the scene within the field of view of the laparoscope 3304, while also overlaying a representative depiction of the objects arranged only within view of the endoscope 3302 such as the tumor and the surgical instrument 3360. The optical sensor 3310 has the surgical instruments 3314, 3318 and the outer tissue wall 3007 in its field of view, and cannot visually detect the tumor 3040, endoscope 3302, or the surgical instrument 3360.

The controller 3330 is configured to provide a merged image to a display. The displays can be configured in a variety of configurations. For example, in some embodiments, a first display can be configured to display the first scene and a second display can be configured to display the second scene, and the first display, the second display, or both, can be further configured to display the merged image. In another embodiment, the surgical system 3300 can include, a third display that can be used to display the merged image, and the first and second displays are used to only show the transmitted image data from the first and second optical sensors 3306, 3310, respectively, without any modification. In this embodiment, a surgeon can access the real-time scenes from both the endoscope 3302 and the laparoscope 3304 on the first and second displays while also having access to the merged image on the third display.

Based on the relative distances 3341, 3342, 3343, 3344 determined by the controller 3330, the controller 3330 can provide the merged image from the point of view of the laparoscope 3304, where the endoscope 3302 and the surgical instrument 3360 are shown as representative depictions which correspond to their location in the intraluminal space in real-time. In the illustrated embodiment, the representative depictions are shown in dashed outlines of the endoscope 3302 and surgical instrument 3360. However, other forms of representative depictions can be used, such as simple geometric shapes to represent the non-visual instruments and anatomical structures within the intraluminal space. By using the merged image, a surgeon can arrange the surgical instruments in a proper position in order to operate on the stomach 3000. With the mobilized tumor 3040 produced in the merged image, along with the endoscope 3302 and surgical instrument 3360, the surgical instrument 3360 can be coordinated through movement commands input by a user to align the partially removed tumor 3040 with the incision made in the stomach wall. The surgical instrument 3318 can also be coordinated through movement commands input by the user to align the surgical instrument 3318 with the incision 3340 on the laparoscopic side. As such, when the tumor 3040 is at least partially passed through the incision 3340 by the surgical instrument 3360 from the intraluminal space to the extraluminal space, the surgical instrument 3318 can grasp the tumor 3040 and aid in removing the tumor 3040 from the stomach 3000.

In use, the controller 3330 can be configured to restrict movement of the surgical instrument 3314 and the surgical instrument 3318 relative to each other at the target tissue structure (e.g., tumor 3040) based on the transmitted image data of the first and second scenes and the relative distances 3341, 3342, 3342 through the robotic arms which the surgical instruments are attached to.

Figure 47:
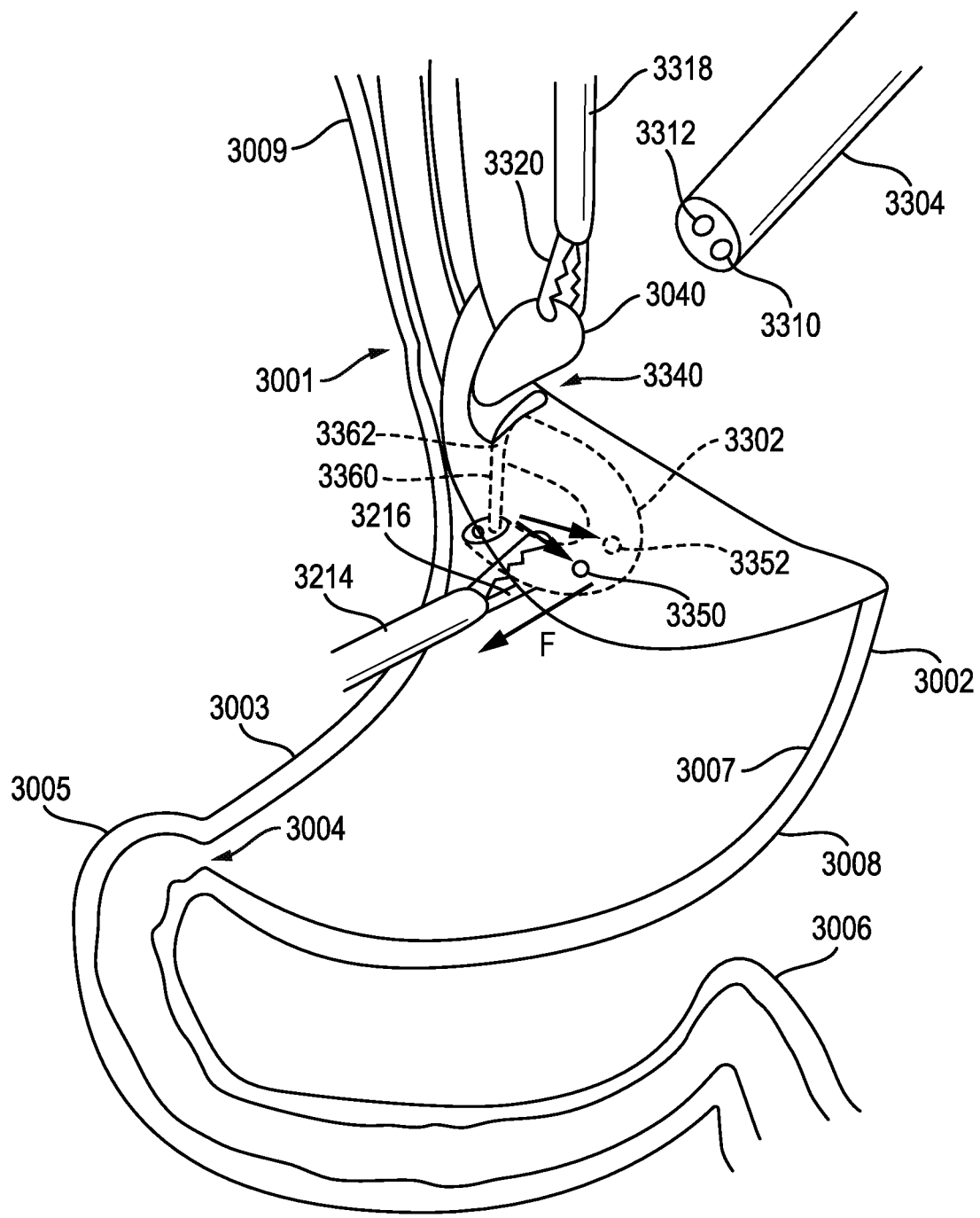
FIG. 47 is a schematic view of the surgical system of FIG. 45, showing a tissue strain measurement using markers arranged on the inner tissue surface of the stomach.

As illustrated in FIG. 47, the controller 3330 is further configured to determine an amount of strain that is applied to the stomach 3000 by at least one of the surgical instruments 3314, 3318 with the use of visual markers 3350, 3352 associated with the stomach 3000. The visual markers 3350, 3352 are at least one of one or more local tissue markings on the stomach 30, one or more projected light markings on the stomach 3000, or one or more anatomical aspects of at least one of the stomach 3000. The visual markers 3350, 3352 are detected by the optical sensor 3306 of the endoscope 3302 or the optical sensor 3310 of the laparoscope 3304. In use, the optical sensor 3306 or optical sensor 3310 senses the movement of the visual marker 3350 as it transitions to the visual marker 3352.

Figure 48:
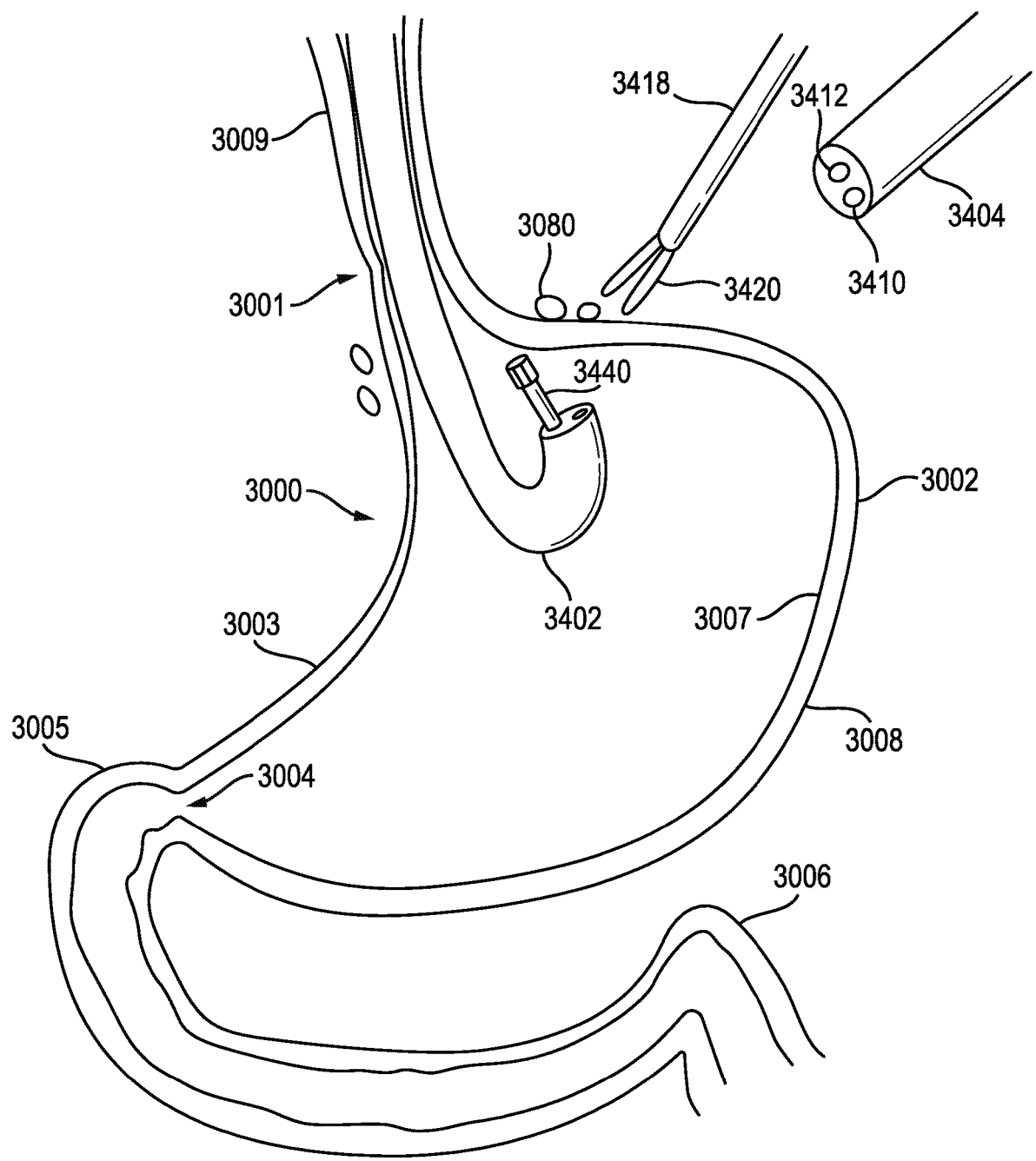
FIG. 48 is a schematic view of another embodiment of a surgical system, showing the removal of lymph nodes from the outer tissue wall of a stomach.

As illustrated in FIG. 48, the surgical system 3400 can be used for optical temperature sensing methods in order to sense the external temperature of the stomach 3000 while an ablation is occurring internally to ensure that certain layers of the stomach 3000 are not damaged. Aside from the differences described in detail below, the surgical system 3400 can be similar to surgical system 3300 (FIG. 45) and therefore common features are not described in detail herein. The temperature monitoring methods can be used to restrict the application of energy by an energy applying surgical instrument 3440 endoscopically. For example, an energy applying surgical instrument 3440 is endoscopically arranged through the endoscope 3402. Additionally, a laparoscope 3404 and a surgical instrument 3418 are laparoscopically arranged in the extraluminal space. The laparoscope 3404 includes an optical sensor 3410 and a light 3412.

In use, in order to remove lymph nodes 3080, the energy applying surgical instrument 3440 can apply an energy to the internal wall 3007 of the stomach 3000. The laparoscopically arranged surgical instrument 3418 can be arranged to grasp the lymph nodes 3080. As the energy applying instrument applies energy to the lymph nodes, the optical sensor 3410 can detect the temperature of the tissue of the stomach 3000, and reduce the amount of energy applied if the temperature becomes too high in order to prevent tissue damage.

In some embodiments, the surgical system 3400 can be used for control of mid-thickness ablation (e.g., thermal, electrical, or microwave) controlled by one imaging access system by coordinating it with a second system viewing from a different point-of-view, similar to surgical system 3000. Additionally, after removal of a tumor, the final ablation from the endoscopic side could be used to expand the margin around the site of the tumor to insure complete removal of the cancer. For example, where a cancerous tumor is close to the esophageal sphincter, maintenance of the sphincter is important to preventing acid reflux from occurring and thus it is useful to maintain as much healthy tissue as possible avoid unnecessary expansive dissection and resection.

The surgical systems disclosed herein can be designed to be disposed of after a single use, or they can be designed to be used multiple times. In either case, however, the surgical systems can be reconditioned for reuse after at least one use. Reconditioning can include any combination of the steps of disassembly of the surgical systems, followed by cleaning or replacement of particular pieces and subsequent reassembly. In particular, the surgical systems can be disassembled, and any number of the particular pieces or parts of the surgical systems can be selectively replaced or removed in any combination. Upon cleaning and/or replacement of particular parts, the surgical systems can be reassembled for subsequent use either at a reconditioning facility, or by a surgical team immediately prior to a surgical procedure. Those skilled in the art will appreciate that reconditioning of a surgical systems can utilize a variety of techniques for disassembly, cleaning/replacement, and reassembly. Use of such techniques, and the resulting reconditioned instrument, are all within the scope of the present application.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. It will be appreciated that the terms "proximal" and "distal" are used herein, respectively, with reference to the top end (e.g., the end that is farthest away from the surgical site during use) and the bottom end (e.g., the end that is closest to the surgical site during use) of a surgical instrument, respectively. Other spatial terms such as "front" and "rear" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Values or ranges may be expressed herein as "about" and/or from/of "about" one particular value to another particular value. When such values or ranges are expressed, other embodiments disclosed include the specific value recited and/or from/of the one particular value to another particular value. Similarly, when values are expressed as approximations, by the use of antecedent "about," it will be understood that here are a number of values disclosed therein, and that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value or within 2% of the recited value.

For purposes of describing and defining the present teachings, it is noted that unless indicated otherwise, the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety. Any patent, publication, or information, in whole or in part, that is said to be incorporated by reference herein is only to the extent that the incorporated material does not conflict with existing definitions, statements, or other disclosure material set forth in this document. As such the disclosure as explicitly set forth herein supersedes any conflicting material incorporated herein by reference.

Selective Re-Inflation for Visualization or Operation

In one aspect the present disclosure relates to a surgical system having a surgical instrument configured for endoluminal access (e.g., an endoscope) that includes instrument sealing element(s) that allow for selective inflation, or re-inflation, of a portion of a natural body lumen or organ (e.g., a lung, a stomach, a colon, or small intestine), such as for visualization or operational purposes. In some embodiments, the natural body lumen or organ is inflated from a collapsed state (e.g., a deflated configuration relative to a normal configuration), whereas in other embodiments, the natural body lumen or organ is inflated from a non-collapsed state (e.g., a normal configuration).

In certain exemplary aspects, the surgical instrument includes a fluid channel that extends through the surgical instrument and at least one deployable sealing element that is configured to form a first seal at a portion of a natural body lumen or organ, and. The fluid channel is configured to allow fluid ingress and egress distal to the portion of the natural body lumen or organ while the at least one deployable sealing member is in an expanded state. As a result, the natural body lumen distal to the portion can be selectively pressurized. That is, unlike conventional systems (e.g., systems that re-inflate the entire collapsed natural body lumen or organ), the present surgical systems are designed to selectively distend only a portion of the natural body lumen or organ. This distention can increase the surgical working space at the treatment site to thereby improve instrument access and movement (e.g., for dissection and resection), reposition the portion of the natural body lumen or organ or tumor, if present, in such a way that can result in the intra-operative imaging to substantially, or completely, match the pre-operative imaging, allow for pressure testing at the surgical site (e.g., to check for leaks after an anastomosis), or control the environment (e.g., temperature, humidity) within the natural body lumen or organ to increase surgical efficiency (e.g., for dissection).

The terms "filled" or "expanded" are intended to mean that the sealing element(s) has/have fluid therein or added thereto in a desired amount or pressure. These terms are not intended to mean that the sealing element(s) is/are necessarily entirely or 100% filled with a fluid when the sealing element(s) are "expanded" (however, such embodiments are within the scope of the term "filled"). Similarly, the term "unexpanded" does not necessarily mean that the sealing element(s) is/are entirely empty or at 0 pressure. There may be some fluid and the sealing element(s) may have a non-zero pressure in an "unexpanded" state. An "uninflated" sealing element(s) is/are intended to mean that the sealing element(s) does/do not include fluid in an amount or at a pressure that would be desired after the sealing element(s) is/are filled.

An exemplary surgical system can include a variety of features as described herein and illustrated in the drawings. However, a person skilled in the art will appreciate that the surgical systems can include only some of these features and/or it can include a variety of other features known in the art. The surgical systems described herein are merely intended to represent certain exemplary embodiments. Moreover, while the surgical systems are shown and described in connection with a lung and a colon, a person skilled in the art will appreciate that these surgical systems can be used in connection with any other suitable natural body lumen or organ.

A method of inflating a lung to increase visualization and access during a lung surgical procedure is to selectively inflate and deflate a portion of the lung. Similar to the procedure for manipulating the lungs, a bronchoscope is passed through the trachea of a patient and into a respective bronchi of the lung. A sealing element, which can be arranged on the distal end of the scope, can be inflated to locally seal off the scope relative to the bronchus. The scope can then be used to re-inflate a portion of the organ distal to the scope, such as a singular lobe of a lung.

Figure 49:
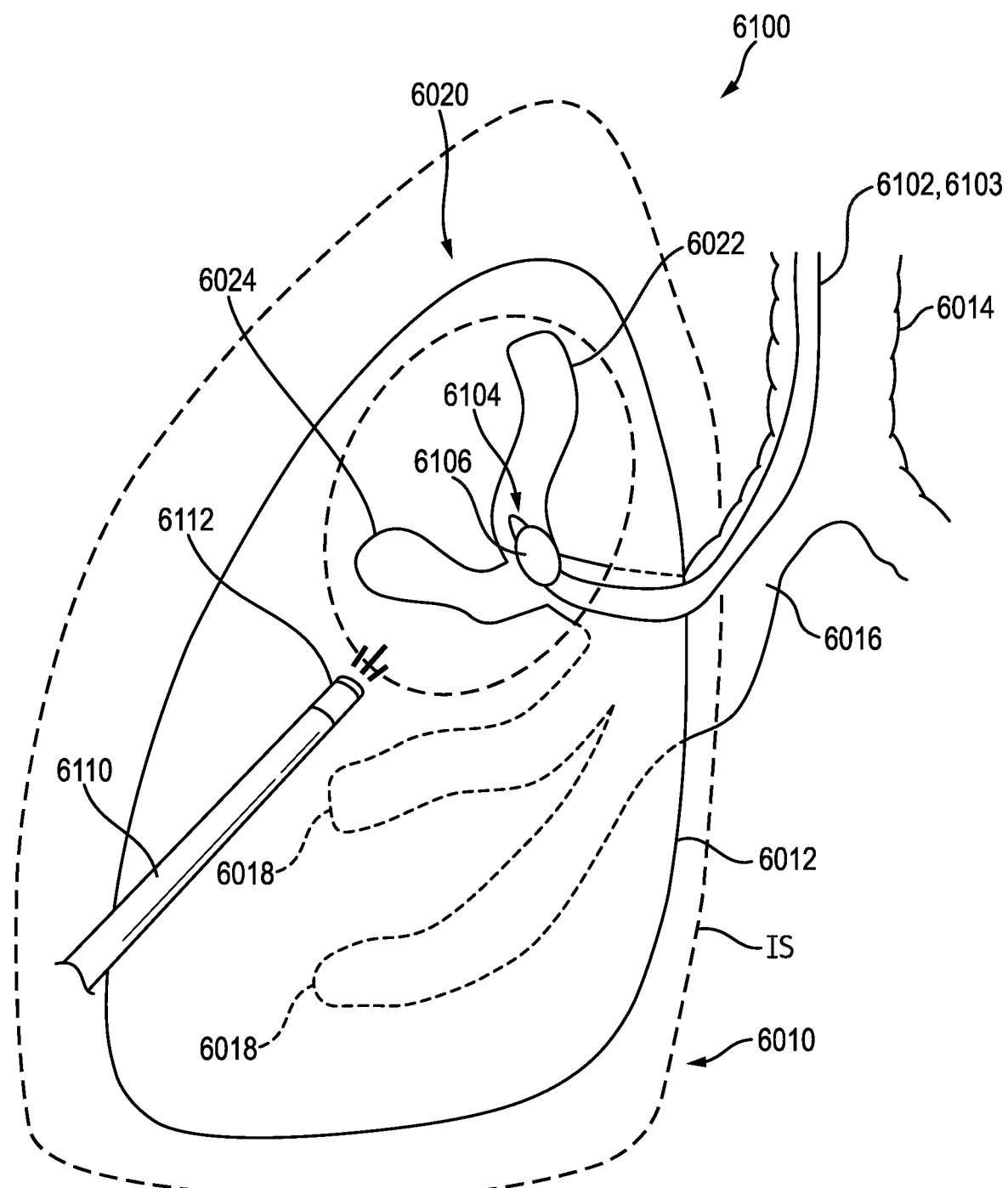
FIG. 49 is a schematic view of one embodiment of a surgical system.
Figure 50:
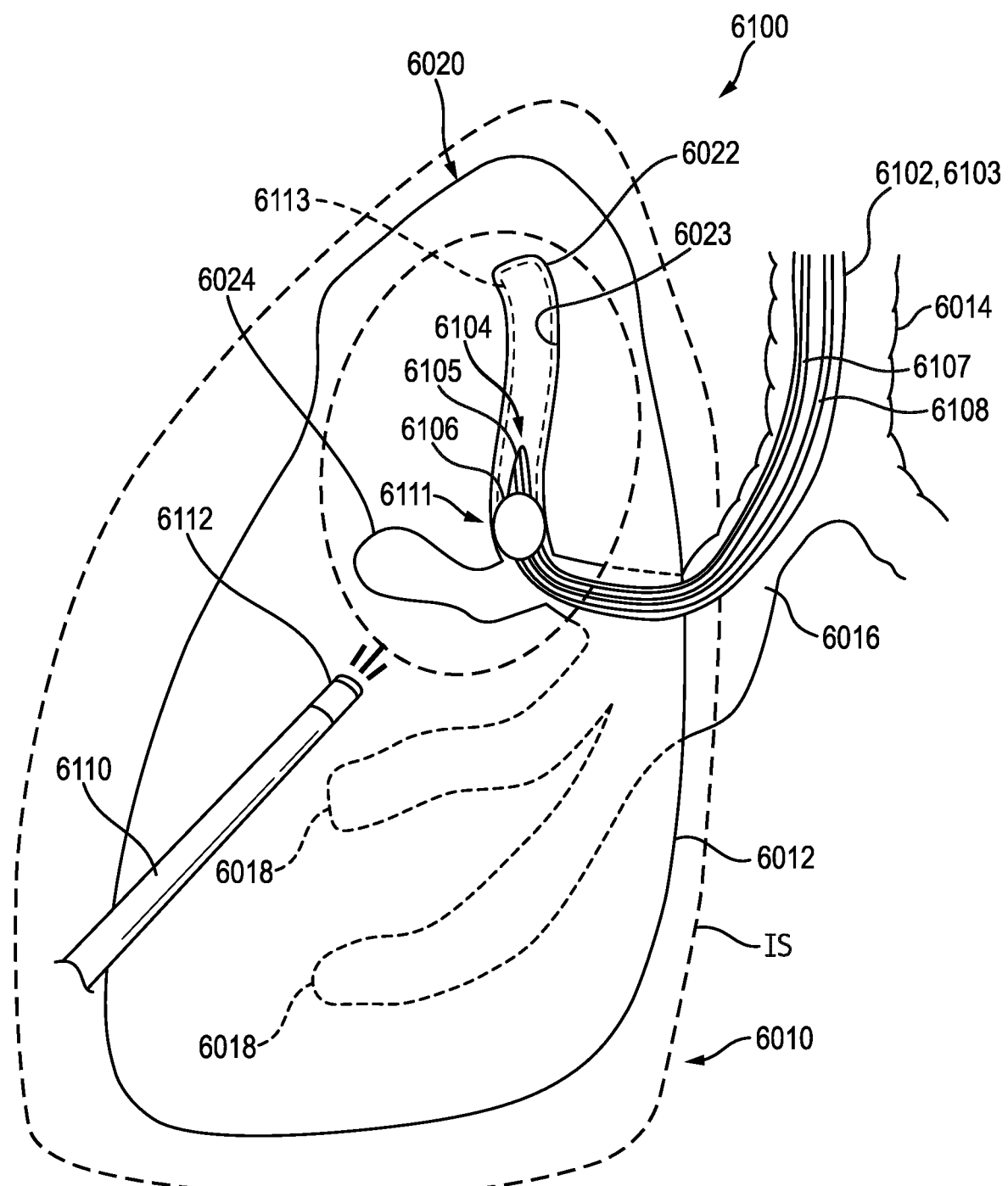
FIG. 50 is a schematic view of the embodiment of the surgical system of FIG. 49.

FIG. 49 and FIG. 50 illustrate one embodiment of a surgical system 6100 that is configured for endoluminal access into a lung 6010 and partial inflation thereof. As will be described in more detail below, the surgical system 6100 is used to selectively pressurize a natural body lumen (e.g., first bronchiole 6022) within the lung 6010. For purposes of simplicity, certain components of the surgical system 6100 and the lung 6010 are not illustrated. As shown, the lung 6010 includes an outer tissue surface 6012, a trachea 6014, a right bronchus 6016, and bronchioles 6018. The trachea 6014, right bronchus 6016, and the bronchioles 6018 are fluidly coupled together. Additionally, the lung 6010 includes an upper lobe 6020, which includes first and second bronchioles 6022 and 6024. As illustrated in FIG. 50, the lung 6010 is in a collapsed state, with the inflated state being represented as a dashed-line border IS. When operating in the thoracic cavity, the lung 6010 is collapsed to provide sufficient working space between the rib cage and the lungs such that the laparoscopically arranged instruments 6110 can easily access and manipulate the lung 6010. In use, as described in more detail below, the surgical system 6100 can partially inflate a portion of the lung 6010.

The surgical system 6100 includes a surgical instrument 6102 configured for endoluminal access through the trachea 6014 and into the lung 6010. In some aspects, the surgical instrument 6102 can have a flexible body 6103 with a distal tip 6104 that configured to be endoscopically inserted through a patient's mouth (not shown) and down the trachea 6014. In use, as shown in FIG. 22 and FIG. 23, the distal tip 6104 is then passed into the lung 6010 through the right bronchus 6016, and into the first bronchiole 6022 of the upper lobe 6020 The distal tip 6104 can have a variety of configurations. In some embodiments, the distal tip 6104 can be tapered to help navigate through the lung.

As further shown in FIG. 49 and FIG. 50, the surgical instrument 6102 includes at least one deployable sealing element 6106 operatively coupled to the surgical instrument 6102. The at least one deployable sealing element 6106 can be arranged on or proximal to the distal tip 6104 of the surgical instrument 6102 such that the deployable sealing element 6106 is positioned within the first bronchiole 6022 when the distal tip 6104 is inserted therein. The at least one deployable sealing element 6106 is configured to move between unexpanded and expanded states. The at least one deployable sealing element 6101 can have a variety of configurations. For example, in some embodiments, the at least one deployable sealing element 6106 can be an inflatable balloon. In other embodiments, the at least one deployable sealing element can be a mechanically expandable stent.

In use, when in the expanded state, the at least one deployable sealing element 6106 is configured to form a first seal 6111 within the first bronchiole 6022. More specifically, as shown in FIG. 50, when the at least one deployable sealing element 6106 is expanded into its expanded state within the first bronchiole 6022, the at least one deployable sealing element 6106 contacts an internal surface 6023 of the first bronchiole 6022. This contact forms the first seal 6111 therebetween. The at least one deployable sealing element 6106 can alternate between its unexpanded and expanded states by passing fluid into or removing fluid from the at least one deployable sealing element 6106 through a first fluid channel 6108 that passes through the length of the surgical instrument 6102. The fluid passed into or out of the at least one deployable sealing element 6106 can be any suitable fluid (e.g., saline, carbon dioxide gas, and the like). The fluid system used to control the ingress or egress of fluid into the deployable sealing element 6106 can include a pump and a fluid reservoir. The pump creates a pressure which pushes the fluid into the deployable sealing element 6106, to expand the deployable sealing element 6106, and creates a suction that draws the fluid from the deployable sealing element 6106 in order to collapse the deployable sealing element 6106.

The surgical instrument 6102 also includes a fluid channel 6107 that extends therethrough. The fluid channel 6107 terminates at an opening 6105 within the distal tip 6104. The opening 6105, in combination with the fluid channel 6107, are configured to allow fluid ingress and egress into and from the sealed portion 6113 of the first bronchiole 6022 (e.g., the portion of the first bronchiole 6022 distal to the first seal 6111). This allows the sealed portion 6113 to be selectively pressurized. The fluid system used to control the ingress or egress of fluid into the sealed portion 6113 can include a pump and a fluid reservoir arranged outside of the body. The pump is configured to create a pressure which forces the fluid into the sealed portion 6113, which thereby pressurizes the sealed portion 6113. Additionally, when pressurization of the sealed portion 6113 is no longer needed, the pump can create a suction that draws the fluid from the sealed portion 6113 and into the fluid reservoir in order to collapse the sealed portion 6113. Thus, in use, once the first seal 6111 within the first bronchiole 6022 is created, the upper lobe 6020 of the lung 6010 can then be at least partially re-inflated via the injection of fluid through the fluid channel 6107 and the opening 6105 and into the first bronchiole 6022. As a result, the inflated upper lobe 6020 is closer to its pre-deflated shape (see FIG. 51), and thus, the intra-operative imagining thereof is similar to that of the pre-operative imagining. Further, the fluid can then be subsequently drawn out of the first bronchiole 6022 through opening 6105 and the fluid channel 6107.

The surgical instrument 6102 can further include an optical sensor arranged at the distal tip 6104. The optical sensor can be configured to allow a user to determine the location of the surgical instrument 6102 within the lung 6010 and to help the user position the distal tip 6104 into the desired bronchiole, such as first bronchiole 6022. Views from the optical sensor can be provided in real time to a user (e.g., a surgeon), such as on a display (e.g., a monitor, a computer tablet screen, etc.).

Further, in use, another surgical instrument 6110 can be introduced laparoscopically within the thoracic cavity in order to visual/and or operate on the lung 6010 from the extraluminal space. The surgical instrument 6110 can include a variety of surgical tools, such as graspers, optical sensors, and/or electrosurgical tools. In an exemplary embodiment, where the surgical instrument 6110 is or includes an optical sensor, a user (e.g., a surgeon) can visually inspect the partially inflated lung 6010 (FIG. 24) to determine if a leak is present (e.g., in combination with use of a contrast or fluorescing agent mixed with the inflation fluid), identity inadvertent tears and tissue trauma for repair, or both.

Figure 51:
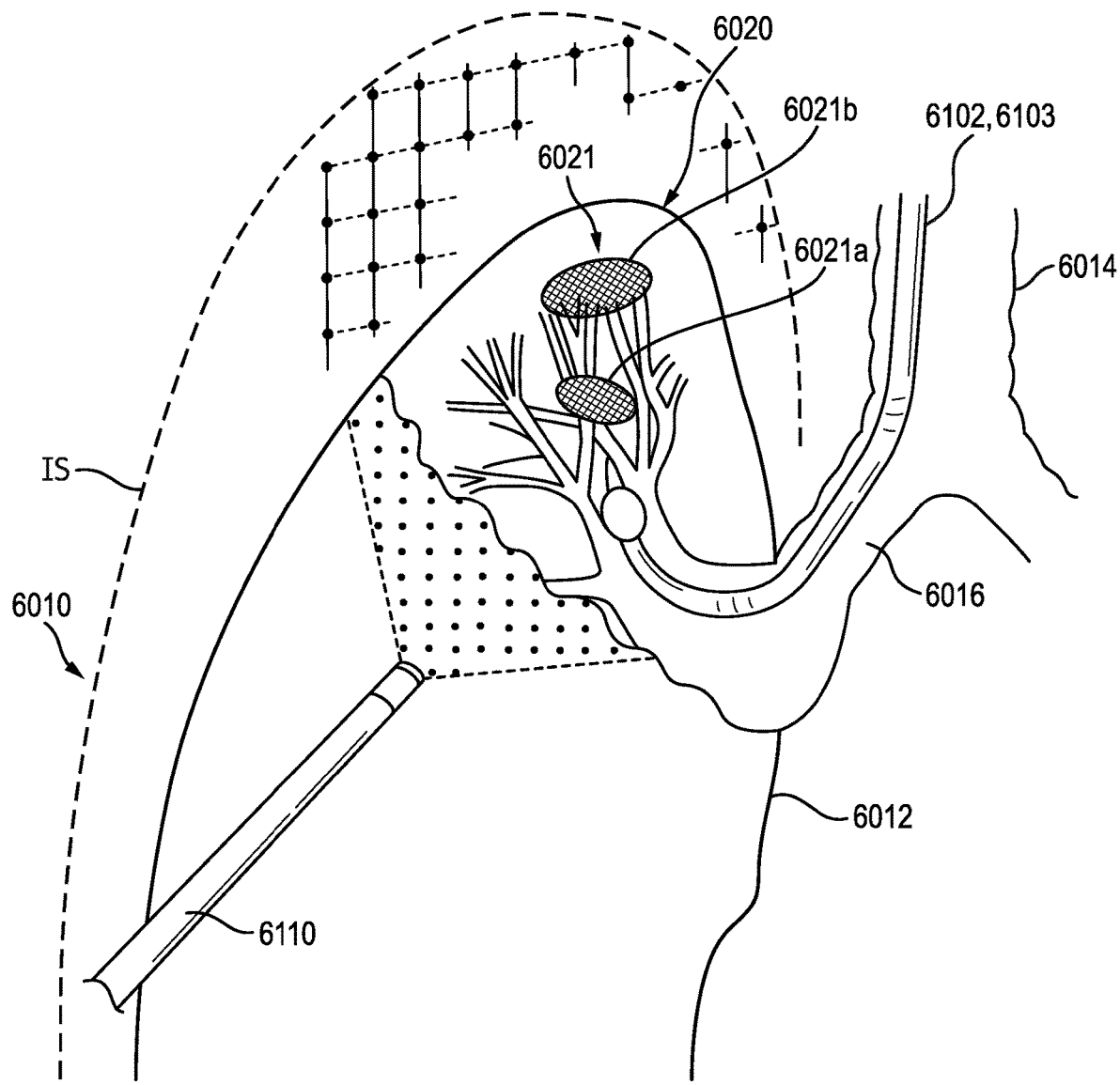
FIG. 51 is a schematic view of the embodiment of the surgical system of FIG. 49.

FIG. 51 illustrates a schematic view of the lung 6010 depicting a tumor in both a pre-collapsed position and a collapsed position. In order for a medical practitioner to plan the surgical procedure, multiple pre-operative scans (e.g., MRI, CAT Scan, X-Rays) are performed to determine the location of the tumor 6021 as well as the surrounding healthy tissue, which cannot be removed. However pre-operative scans are performed when the lung is inflated and the patient is awake. During surgery, the lung is collapsed, which results in the lung shrinking considerably relative to its original size. This can render the pre-operative scans useless since the tumor 6021 may be in a completely different location. As shown in FIG. 51, with the lung deflated, the tumor 6021 is arranged at location 6021a, which is in a lower position within the upper lobe 6020. When the lung 6010 is selectively pressurized, the tumor 6021 will be located in location 6021b, which is at a higher position within the upper lobe relative to location 6021a. This would place the tumor 6021 within the first bronchiole 6022 closer to its original spot when compared to pre-operative scans.

In some embodiments where a portion of the lung is removed (e.g., an upper lobe 6020 that is distal to the end of the first bronchiole 6022), the remaining portion of the lung can be pressure tested to ensure that the lung is properly sealed after completion of the surgical dissection, thus helping to identity inadvertent tears and tissue trauma in need of subsequent repair. In some embodiments, a contrast or fluorescing agent can be mixed into the fluid that can help enable real-time visualization of the airways (e.g., with the use of a laparoscopic camera 6112). This real-time visualization can allow for clearer cooperative surgical intervention within the lung that would not otherwise be available in instances where the entire lung is inflated.

In some embodiments, the surgical instrument can include two or more deployable sealing elements arranged on the flexible body. This arrangement can allow two or more portions of the lung to be pressurized (e.g., two or more portions of the first bronchiole 6022). In other embodiments, the flexible body can have channel arms extending outward from a distal end of the flexible body in which each channel arm includes at least one deployable sealing element arranged on or proximal to a respective distal end. Each channel arm can be independently manipulated so that each respective sealing element can be advanced into a respective separate bronchiole. This arrangement can enable multiple portions of the lung to be selectively inflated or deflated through the inflation and deflation of the separate bronchioles while also allowing the mechanical manipulation of the surgical instrument. The cooperative selective inflation and articulation using multiple sealing element can be used to bend or fold the lung, improving access to the surgical site.

In another embodiment, local embolization using a fluid (e.g., saline, carbon dioxide gas, or the like) to expand a local portion of a deflated natural body lumen or organ (e.g., the first bronchiole 6022 in FIG. 49) can enable tissue plane separation or dissection of a tumor, if present. In an embodiment where the fluid is saline, a local saline injection could also change the conductivity and contrast properties of the tissue. This change in conductivity and contrast could improve visualization and/or locally advanced energy ablation and cauterization.

In other embodiments, a sealing element can include a laparoscopically deployed portion in addition to an endoscopically arranged sealing element within a natural body lumen or organ. An example of a laparoscopically arranged portion can be a surgical instrument that operates in cooperation with the endoscopically arranged sealing element. The surgical instrument can apply a wrap or band on the external surface of the natural body lumen or organ at the same location as the endoscopically arranged sealing element to prevent over distention of the sealing element.

In other embodiments, sealing one or more ends of a portion of a natural body lumen to be selectively pressurized, and thus inflated, can be accomplished by applying a local concentric suction to an inner surface of the natural body lumen or organ. In order to generate a sufficient seal at one or more ends during a leak test, the suction pressure is greater than the leak test pressure (e.g., the pressure used to inflate the natural body lumen, such as during a leak test). This arrangement can prevent over distension of the natural body lumen or organ since the portion of the natural body lumen has had a partial vacuum applied prior to pressurizing, lowering the required max leak pressure.

As noted above, the present surgical systems can be configured to selectively pressurize other natural body lumens or organs. For example, as discussed below, the present surgical systems can be configured to partially inflate one or more portions of the colon.

Figure 52:
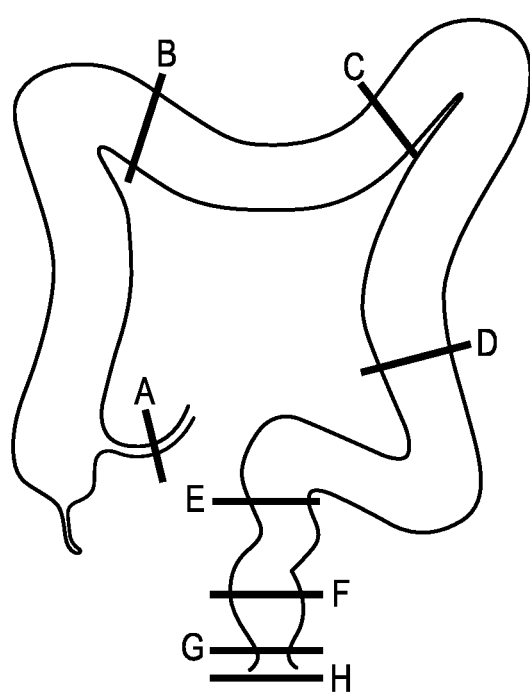
FIG. 52 is a schematic view of a colon.

Surgery is often the primary treatment for early-stage colon cancers. The type of surgery used depends on the stage (extent) of the cancer, its location in the colon, and the goal of the surgery. Some early colon cancers (stage 0 and some early stage I tumors) and most polyps can be removed during a colonoscopy. However, if the cancer has progressed, a local excision or colectomy, a surgical procedure that removes all or part of the colon, may be required. In certain instances, nearby lymph nodes are also removed. A hemicolectomy, or partial colectomy, can be performed if only part of the colon is removed. In a segmental resection of the colon the surgeon removes the diseased part of the colon along with a small segment of non-diseased colon on either side. Usually, about one-fourth to one-third of the colon is removed, depending on the size and location of the cancer. Major resections of the colon are illustrated in FIG. 52, in which (i) A-B is a right hemicolectomy, A-C is an extended right hemicolectomy, B-C is a transverse colectomy, C-E is a left hemicolectomy, D-E is a sigmoid colectomy, D-F is an anterior resection, D-G is a (ultra) low anterior resection, D-H is an abdomino-perineal resection, A-D is a subtotal colectomy, A-E is a total colectomy, and A-H is a total proctocolectomy. Once the resection is complete, the remaining intact sections of colon are then reattached.

A colectomy can be performed through an open colectomy, where a single incision through the abdominal wall is used to access the colon for separation and removal of the affected colon tissue, and through a laparoscopic-assisted colectomy. With a laparoscopic-assisted colectomy, the surgery is done through many smaller incisions with instruments and a laparoscope passing through the small incisions to remove the entire colon or a part thereof. At the beginning of the procedure, the abdomen is inflated with gas, e.g., carbon dioxide, to provide a working space for the surgeon. The laparoscope transmits images inside the abdominal cavity, giving the surgeon a magnified view of the patient's internal organs on a monitor. Several other trocars are inserted to allow the surgeon to access the body cavity to work inside the body cavity and remove the appropriate part(s) of the colon. Once the diseased parts of the colon are removed, the remaining ends of the colon are attached to each other, e.g., via staples or sutures. The entire procedure may be completed through the cannulas or by lengthening one of the small cannula incisions.

Following a colectomy and reattachment of the colon, it can be beneficial to test for leaks of the colon at the connection site. With conventional systems, leak testing is typically carried out by laparoscopically arranging clamps to the colon to create a seal at the rectum and at the distal end of the colon, and once the seals are created, inflating the entire colon. However, inflation of the entire colon can reduce the working volume space within the abdominal cavity and can be inefficient. As will be described in more detail below, unlike the conventional systems, the present surgical systems can be configured to inflate one or more sections of the colons for leak testing and/or identifying unanticipated tissue damage. While the following discussion is with respect to the colon, a person skilled in the art will appreciate that the present surgical systems can be used in connection with other suitable natural body lumens or organs for leak testing and/or identifying unanticipated tissue damage.

Figure 53:
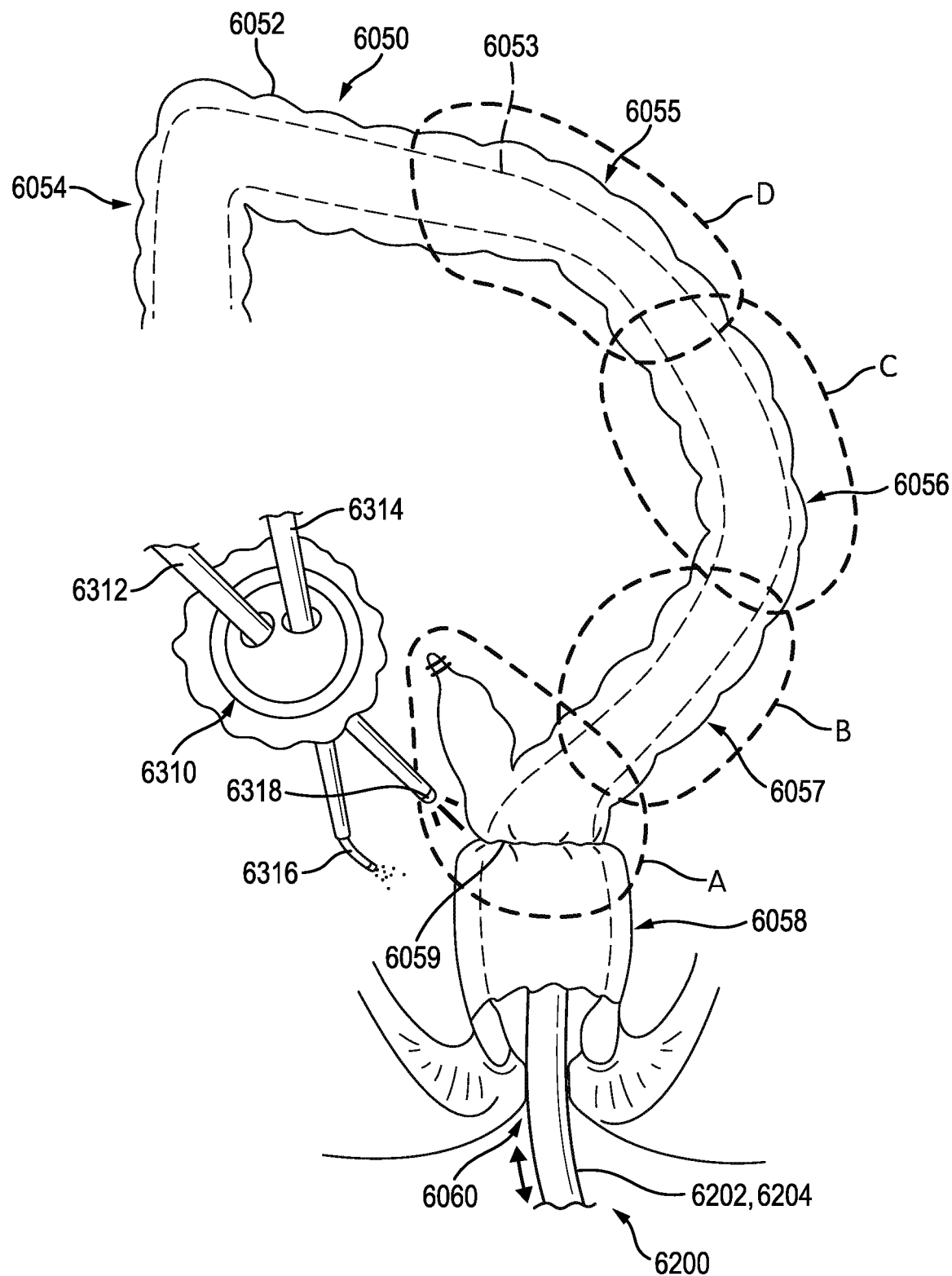
FIG. 53 is a schematic view of another embodiment of a surgical system.
Figure 54:
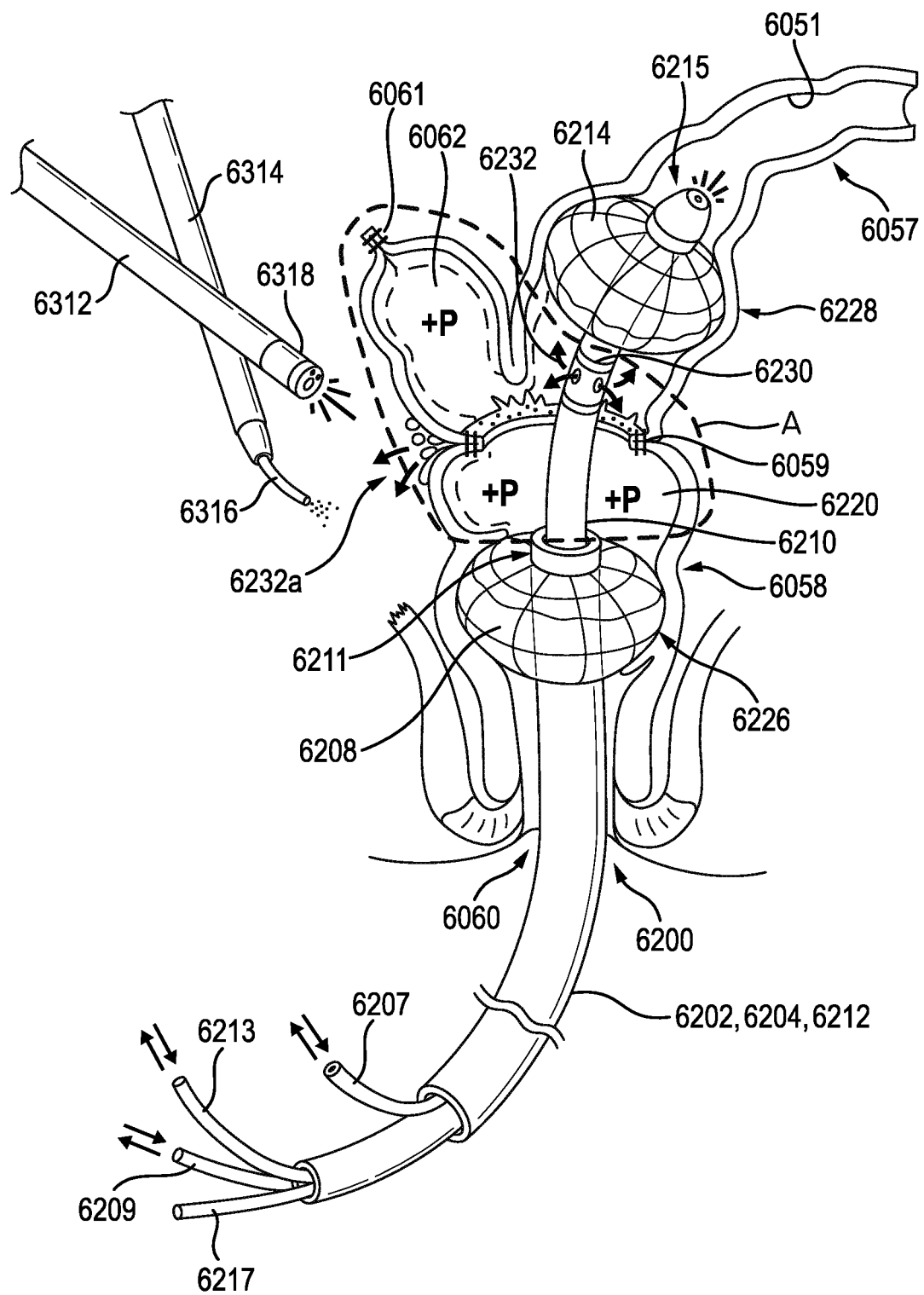
FIG. 54 is a schematic view of the embodiment of the surgical system of FIG. 53.

FIG. 53 and FIG. 54 illustrate one embodiment of a surgical system 6200 that is configured for endoluminal access into and partial inflation of a colon 6050. As will be described in more detail below, the surgical system 6200 is used to selectively pressurize a portion of the colon 6050

(e.g., section A). For purposes of simplicity, certain components of the surgical system 6200 and the colon 6050 are not illustrated. While this surgical system 6200 is shown and described in connection with inflation of section A of the colon 6050, a person skilled in the art will appreciate that the surgical system 6200 can be used to additionally, or in the alternative, inflate other sections of the colon 6050.

As shown in FIG. 26, the colon 6050 includes an intestinal wall 6052 defining a passageway 6053 through the colon 6050. The intestinal wall 6052 further defines different segments of the colon (e.g., cecum, not shown, ascending colon 6054, transverse colon 6055, descending colon 6056, sigmoid colon 6057, and rectum 6058). The rectum 6058 is connected to and extends from a natural orifice 6060 to the sigmoid colon 6050. As illustrated in FIG. 53, the colon 6050 has undergone a segmental resection in which a portion of the rectum 6058 and sigmoid colon 6057 has been removed and the remaining portions thereof attached at connection point 6059 (e.g., by sutures, staples, or other suitable attachment mechanism(s)). Further, after the segmental resection, the surgical system 6200 can be used to identify any leaks or tissue damage (e.g., at the connection site 6059 or within any one or more segment of the colon, such as segment A, which includes the connection site 6059, segment B, segment C, or segment D illustrated in FIG. 53).

The surgical system 6200 can have a variety of configurations. In some embodiments, as shown in FIG. 26, the surgical system 6200 includes a surgical instrument 6202 configured for endoluminal access through the natural orifice 6060 and into the colon 6050. The surgical instrument, which is shown in more detail in FIG. 54, includes a flexible body 6204 having an inner tube 6210 and an outer tube 6212 that is disposed about at least a portion of the inner tube 6210. In other embodiments, the flexible body can have other suitable configurations and shapes.

The surgical instrument 6202 can include at least one deployable sealing element. In this illustrated embodiment, the surgical system 6200 includes two deployable sealing elements 6208, 6214. The first deployable sealing element 6208 is coupled to the outer tube 6212 and positioned proximal to the distal end 6211 of the outer tube 6212. The second deployable sealing element 6214 is coupled to the inner tube 6210 and positioned proximal to the distal end 6215 of the inner tube 6210. In this illustrated embodiment, the inner tube 6210 extends through the outer tube 6212 and can move relative to the outer tube 6212.

Due to this arrangement, the second deployable sealing element 6214 can be distally spaced from the sealing element 6208 to allow a sealed portion 6220 between the two sealing elements 6208 and 6214. In order to form the sealed portion 6220, the inner tube 6210 and outer tube 6212 are inserted together as surgical instrument 6202. Once the first deployable sealing element 6208 is in position, the first deployable sealing element 6208 is deployed to contact the internal surface 6051. With the first deployable sealing element 6208 in position, the inner tube 6210 is further inserted into the colon 6050 to place the second sealing element 6214 in a position distal to the first deployable sealing element 6208. When the second deployable sealing element 6214 is in position, the second deployable sealing elements 6214 can be expanded to contact the inner wall 6051. A camera 6222 is arranged in the distal tip 6215 of the inner tube 6210 in order to allow navigation within the colon 6050.

The first and second deployable sealing elements 6208, 6214 are configured to move between respective unexpanded and expanded states. When in the expanded state, the first deployable sealing element 6208 is configured to form a first seal 6226 within the inner tissue surface 6051 of the colon 6050. Similarly, when in an expanded state, the second deployable sealing element 6214 is configured to form a second seal 6228 within the inner tissue surface 6051 at a location distal to the first seal 6226. The first and second deployable sealing elements 6208, 6214 can have a variety of configurations. For example, in some embodiments, the first deployable sealing element 6208, the second deployable sealing elements 6214 can be in the form of an inflatable balloon, or a mechanically expanding stent. In this illustrated embodiment, both the first deployable sealing element 6208 and the second deployable sealing element 6214 are each in the form of an inflatable balloon.

Each of the first and second deployable sealing elements 6208, 6214 can move between respective unexpanded and expanded states. In this illustrated embodiment, the first deployable sealing element 6208 can move between an unexpanded state and an expanded state (FIG. 54) by passing fluid (e.g., saline, gas, or any other suitable fluid(s)) into the sealing elements 6208 through a first fluid channel 6207 that is in fluid communication with the first deployable sealing and extends through the outer tube 6212. To move the first deployable sealing element 6208 from an expanded state to an unexpanded state, fluid is removed from the sealing element 6208 though the first fluid channel 6207. Similarly, the second deployable sealing element 6214 can move from an unexpanded state to an expanded state (FIG. 54) by passing fluid (e.g., saline, gas, or any other suitable fluid(s)) into the second deployable sealing element through a second fluid channel 6209 that is in fluid communication with the second sealing element and extends through the inner tube. To move the second deployable sealing element from an expanded state to an unexpanded state, fluid is removed from the sealing element 6214 though the second fluid channel 6209.

In use, once the unexpanded first deployable sealing element is positioned at a desired location within the colon, fluid can be passed into the first sealing element to cause it to expand to form a first seal, and thus move from an unexpanded state to an expanded state. Similarly, once an unexpanded second deployable sealing element is positioned at a desired location within the colon, fluid can be passed into the second deployable sealing element to cause the second deployable sealing element to expand to form a second seal, and thus move from an unexpanded state to an expanded state. By creating a seal with the first deployable sealing element at the distal end relative to the colon anastomosis, and creating a seal with the deployable second sealing element proximal end relative to the colon anastomosis, the targeted section of the colon can then be pressurized with a fluid. The fluid can include a dye, contrast agent, or florescence agent, and be passed into the sealed section at a controllable pressure that would allow for the leak testing of the surgical site. Using a laparoscope already inserted from the colectomy, the connection site can be observed for leaking fluid. Additionally, an endoscopy which has multiple sealing elements can be used to isolate the targeted area and locally control temperature, humidity, pressure and/or fluids within the targeted location. Altering these parameters could modify the local environment allowing for improvements for therapeutic treatment either prior, during or after the procedure. This local modifications would allow for better performance to the tissue based on conditions and/or after the intended treatment to reduce inflammation and/or promote blood flow to improve recovery.

When the first and second deployable sealing elements 6208, 6214 are deployed into the colon and expanded, they create a sealed segment 6062 within the colon 6050. Once the sealed segment 6062 is created, a leak test evaluation can be performed thereon. As shown in FIG. 54, the sealed segment 6062 is located in section A of the colon. However, a person skilled in the art will appreciate that the sealed segment can be positioned in other sections of the colon (e.g., in section B, C, or D in FIG. 53), and thus the following discussion is also applicable to such instances.

In use, once the sealed segment 6062 is created, section A of the colon, which includes the connection site 6059, can be inflated to assess for any leaks therein (e.g., at the connection site 6059). As shown, a fluid channel 6213 extends through the inner tube 6210 of the surgical instrument 6202 and has an opening 6230 arranged between the first and second deployable sealing elements 6208, 6214. The opening 6230 is distal to the first seal 6226 created between the inner surface 6051 of the colon 6050 and the first deployed sealing element 6208, and proximal to the second seal 6228 created between the inner surface 6051 of the colon 6050 and the deployed second sealing element 6214. The opening 6230 is configured to allow fluid to pass into and out of the sealed portion 6220, thereby selectively pressurizing section A of the colon 6050. The fluid used to pressurize the sealed portion 6220 can be pressurized fluid that is introduced through a fluid channel 6213 that is in fluid communication with the opening 6230. As a result, the pressurized fluid is expelled into the sealed portion through the opening 6230. In certain embodiments, the fluid is expelled at a controllable rate.

In some embodiments, the fluid 6232 can include a leak assessment fluid (a dye, contrast agent, or florescence agent) that would be visually detectable outside of the colon. In such instances, a first laparoscopic instrument 6312 inserted through a port 630 and into the abdominal cavity can be positioned proximal to the colon 6050 and used to identify any discharge of the leak assessment fluid from the inflated section A of the colon. For example, as illustrated in FIG. 53 and FIG. 54, the first laparoscopic instrument 6312 can include a camera 6318 configured to detect any leak assessment fluid outside of the colon. For example, the camera 6318 can be used to visually detect (e.g., by a surgeon) any of the leak assessment fluid that passes through the connection 6058. In another embodiment, the camera 6318 can be configured to emit a multi-spectrum wavelength (e.g., near-infrared) if the leak assessment fluid is a florescence agent which must be excited in order to be located. A multi-spectrum wavelength must be applied first to excite the agent within the leak assessment fluid so it becomes visible to the camera. The presence of leak assessment fluid outside the colon can be used to highlight the location of the leak(s) and, in some instances, also highlight the magnitude of the leak(s).

In some embodiments, as shown in FIG. 54, a second laparoscopic instrument 6314 can be positioned proximal to the colon 6050 and configured to apply agent (e.g., a clot-inducing agent) to one or more leak areas of the colon to form a respective outer seal. The clot-inducing agent can be biologically inert or stable, and have an agent within the fluid, which in direct contact with an agent within the fluid 6232 applied from within the colon 6050, will activate the clot-inducing agent. For example, a platelet rich plasma can be introduced with leak assessment fluid 6232, and in the event a leak is identified from the laparoscopic side, an oxidized regenerated cellulose (ORC) with or without a freeze dried fibrin and/or thrombin powder could be placed at the leak location via the second laparoscopic instrument 6314. As a result, the plasma would then activate the ORC and the fibrin to form a resilient gel seal. This seal would be treated by the body like a clot or scab and therefore would be remodeled as the body heals. Alternatively, or in addition, an adjunct can be applied laparoscopically to one or more leak area(s) to form a respective outer seal.

As illustrated in FIG. 54, an observed amount of liquid assessment fluid 6232a is located on the outside of the colon at, and therefore has leaked through the connection site 6059. This leak is detected by the camera 6318. However, the connection 6061 is not leaking any fluid 6232 while pressurized. In an exemplary embodiment, where a leak is present, the pressure from the fluid 6232 can be relieved and re-applied, or the sealed portion 6062 can remain pressurized, while the adjunct therapy is applied (such as a clotting agent) to insure the adjunct therapy is capable of resisting that level of pressure.

Further, in use, the camera 6215 is arranged endoscopically within the colon 6050 in order to visual/and or operate on the colon 6050 from the intraluminal space. In an exemplary embodiment, a user (e.g., a surgeon) can visually inspect the colon 6050 to determine if a leak is present (e.g., in combination with use of a contrast or fluorescing agent mixed with the inflation fluid), identity inadvertent tears and tissue trauma for repair, or both.

Figure 55:
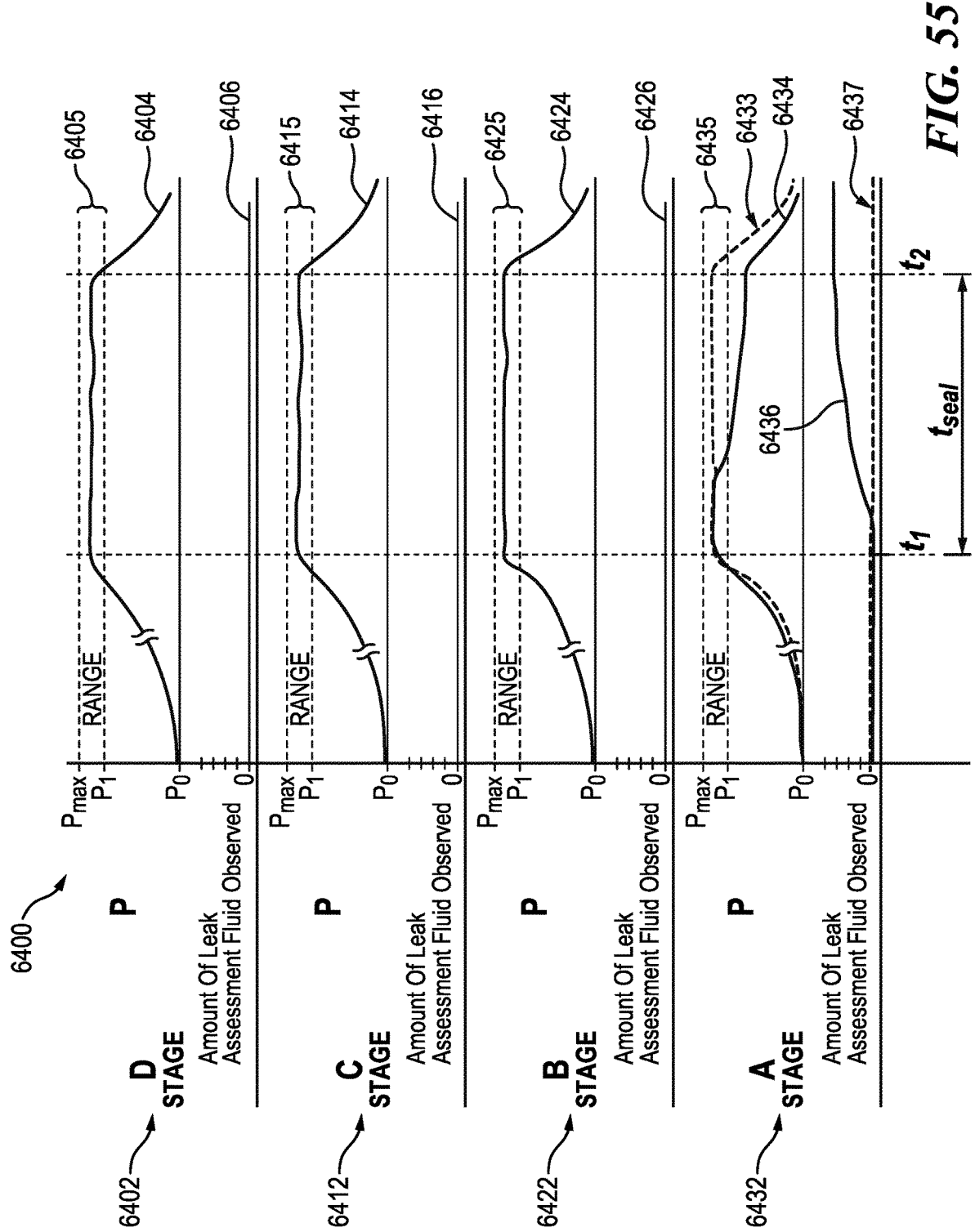
FIG. 55 is a graph depicting the pressurization testing of the surgical system of FIG. 53.

FIG. 55 illustrates a compilation of graphs which are representative of an exemplary leak test evaluation for sections A, B, C, and D of the colon 6050 in FIG. 53 and FIG. 54. Graph 6402 is representative of the exemplary leak test evaluation on section D of the colon 6050. Line 6404 represents the pressure within section D over the course of the evaluation, a pressure range 6405 is defined between $P_1$ and $P_{max}$ and represents the acceptable pressure range for pressurizing section D during the evaluation over time interval $t_{seal}$, and line 6406 represents the amount of leak assessment fluid observed outside of the colon during the evaluation. Time interval $t_{seal}$ represents an acceptable duration period to access whether any leaks are present within section D. As illustrated in graph 6402, over time interval $t_{seal}$, section D was maintained at a pressure within the pressure range 6405 and no leak assessment fluid was observed outside of section D and therefore no leaks were detected within section D. Graph 6412, which is a representative of section B of the colon 6050 in FIG. 53, and Graph 6422, which is representative of section C of the colon 6050 in FIG. 53 are similar to graph 6402. That is, lines 6414, 6426 represent the pressure within section C and section B, respectively, over the course of the evaluation, pressure ranges 6415, 6425 represent the acceptable pressure range for pressurizing section C and Section B, respectively over the time interval $t_{seal}$, and lines 6416, 6426 represent the amount of leak assessment fluid observed outside of the colon during the evaluation. For the same reasons as section D, no leaks were detected in section C and section B.

Graph 6432 represents the exemplary leak test evaluation of section A of colon 6050 in FIG. 54. Line 6433 represents the desired pressure within section A over the course of the evaluation, a pressure range 6435 is defined between $P_1$ and $P_{max}$ and represents the acceptable pressure range for pressurizing section A during the evaluation over time interval $t_{seal}$, and line 6437 represents the desired amount of leak assessment fluid observed outside of the colon during the evaluation. Time interval $t_{seal}$ represents an acceptable duration period to access whether any leaks are present within section A. As illustrated in graph 6432, over time interval $t_{seal}$, section A did not maintain the desired pressure within the pressure range 6435 and leak assessment fluid was observed outside of section A. Line 6434 represents the actual pressure within section A over the course of the evaluation, and line 6436 represents the actual amount of leak assessment fluid observed outside of the colon during the evaluation. As shown in graph 6432, as the pressure 6434 decreased, the observed leak assessment fluid 6436 increased.

In some embodiments, the first laparoscopic instrument 6312, along with the camera 6316, can be configured to detect over-distension of the sealed portion 6062 when a leak test evaluation is being performed. In such embodiments, the over-distension can be measured by 3D structured light scan of colon 6050 prior to pressurization, which can provide a diameter delta limit for 3D surface change of the colon 6050 to prevent inadvertent tissue damage.

In another exemplary embodiment, the arrangement of the sealing elements 6208, 6214 creating a sealed portion 6062 can enable controlled introduction of a fluid or gas within the sealed portion 6062 in order to alter the environment for optimal surgical conditions. Surgical conditions which can affect the efficiency of a procedure can include temperature, pressure, and humidity in order to optimize the environment for tissue dissection. Tissue property values are highly variable, and dependent on time, history, temperature, pressure and hydration. Variations exist between young and old, healthy, diseased and irradiated tissues, which can lead to inefficiencies if constant changes to equipment must be made.

An example of increasing efficiency of a surgical task with a sealed region by altering the conditions within an organ can include the use of bi-polar or mono polar energy applied to tissue for dissection and/or sealing. For bi-polar energy, power is delivered while monitoring the impedance of the tissue, the impedance will go through 3 phases, initially it will decrease impedance for a period of time, then stay at a near constant impedance for a period of time during the desiccating tissue phase until vaporization has occurred and a rapid increase in impedance occurs at which power is stopped. During this type of procedure, tissue that is low in moisture due to a condition of patient, trauma, disease and/or previously treated or altered from treatment can cause the energy cycle to be too short which would reduce the seal and/or alter the intended therapeutic treatment. Modifying the local environmental characteristics (e.g., temperature or humidity) prior or during treatment could improve the efficiency of the energy application and improve sealing and/or dissection optimization of the energy applying instrument.

Another example of increasing surgical efficacy through controlling environmental parameters includes altering the temperature of a region to increase blood flow. Tissue that has low blood flow can alter coagulation properties of that tissue. By modifying the local environments characteristics (e.g., temperature) prior or during treatment could improve the blood flow and improve sealing and/or dissection optimization of an energy applying instrument. Additionally, modifying the local temperature could be done during treatment to reduce blood flow during treatments or targeted areas in which is prone to heavy bleeding.

The instruments disclosed herein can be designed to be disposed of after a single use, or they can be designed to be used multiple times. In either case, however, the instrument can be reconditioned for reuse after at least one use. Reconditioning can include any combination of the steps of disassembly of the instrument, followed by cleaning or replacement of particular pieces and subsequent reassembly. In particular, the instrument can be disassembled, and any number of the particular pieces or parts of the instrument can be selectively replaced or removed in any combination. Upon cleaning and/or replacement of particular parts, the instrument can be reassembled for subsequent use either at a reconditioning facility, or by a surgical team immediately prior to a surgical procedure. Those skilled in the art will appreciate that reconditioning of an instrument can utilize a variety of techniques for disassembly, cleaning/replacement, and reassembly. Use of such techniques, and the resulting reconditioned instrument, are all within the scope of the present application.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "rear" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Values or ranges may be expressed herein as "about" and/or from/of "about" one particular value to another particular value. When such values or ranges are expressed, other embodiments disclosed include the specific value recited and/or from/of the one particular value to another particular value. Similarly, when values are expressed as approximations, by the use of antecedent "about," it will be understood that here are a number of values disclosed therein, and that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value or within 2% of the recited value.

For purposes of describing and defining the present teachings, it is noted that unless indicated otherwise, the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety. Any patent, publication, or information, in whole or in part, that is said to be incorporated by reference herein is only to the extent that the incorporated material does not conflict with existing definitions, statements, or other disclosure material set forth in this document. As such the disclosure as explicitly set forth herein supersedes any conflicting material incorporated herein by reference.

Surgical Sealing Devices for a Natural Body Orifice

In certain embodiments, surgical sealing devices are provided that are configured to allow surgical access into a body cavity through a natural body orifice (e.g., a trachea, a rectum, and the like). In general, the present surgical sealing devices include a seal housing that is configured to be at least partially disposed within a natural body orifice and at least one retention element configured to affix the seal housing to the natural body orifice. Unlike conventional surgical sealing devices that are typically inserted into an incision, the present surgical sealing devices are designed to be inserted into a natural body orifice. As a result, the present surgical sealing devices provide a less traumatic and more direct access point to a natural body lumen or organ (e.g., for introduction and extraction of surgical instruments, fluid exchange, breathing apparatuses, smoke evacuation apparatuses, etc.) that would not otherwise be available through the use of conventional surgical sealing devices.

In use, as discussed in more detail below, the surgical sealing devices disclosed herein can be used to provide access to a natural body lumen, such as a colon, through a natural body orifice associated therewith. That is, the seal housing can be at least partially positioned within a natural body orifice. Given the contractive nature of a natural body orifice, however, it can be difficult maintain the seal housing within the natural body office. As a result, the surgical sealing devices include at least one retention element (e.g., arranged on an exterior surface of the seal housing) that enables and maintains fixation of the seal housing to the natural body orifice during device use. The at least one retention element can be configured to be deployed inside or outside of the patient's body.

The seal housing can be positioned and affixed to the natural body orifice in such a way in which a distal portion of the seal housing extends into the natural body orifice, and a proximal portion extends out of the natural body orifice and into the ambient environment (e.g., positioned adjacent to and in contact with an exterior surface of the patient's body, such as the patient's skin. Alternatively, the seal housing can be designed to be entirely positioned within the natural body orifice.

Further, the seal housing generally includes one or more ports arranged within the seal housing to allow instruments to pass into the natural body lumen from the ambient environment through the natural body orifice. The one or more ports arranged through the seal housing can form pathway(s) into and through the natural body orifice. This can enable controlled fluid exchange through the natural body orifice, and consequently, into and/or out of the natural body lumen associated therewith, introduction and extraction of surgical instruments through the natural body orifice, and the like. As a result, the natural body lumen can be accessed without the need for an incision through the patient's skin.

Figure 56:
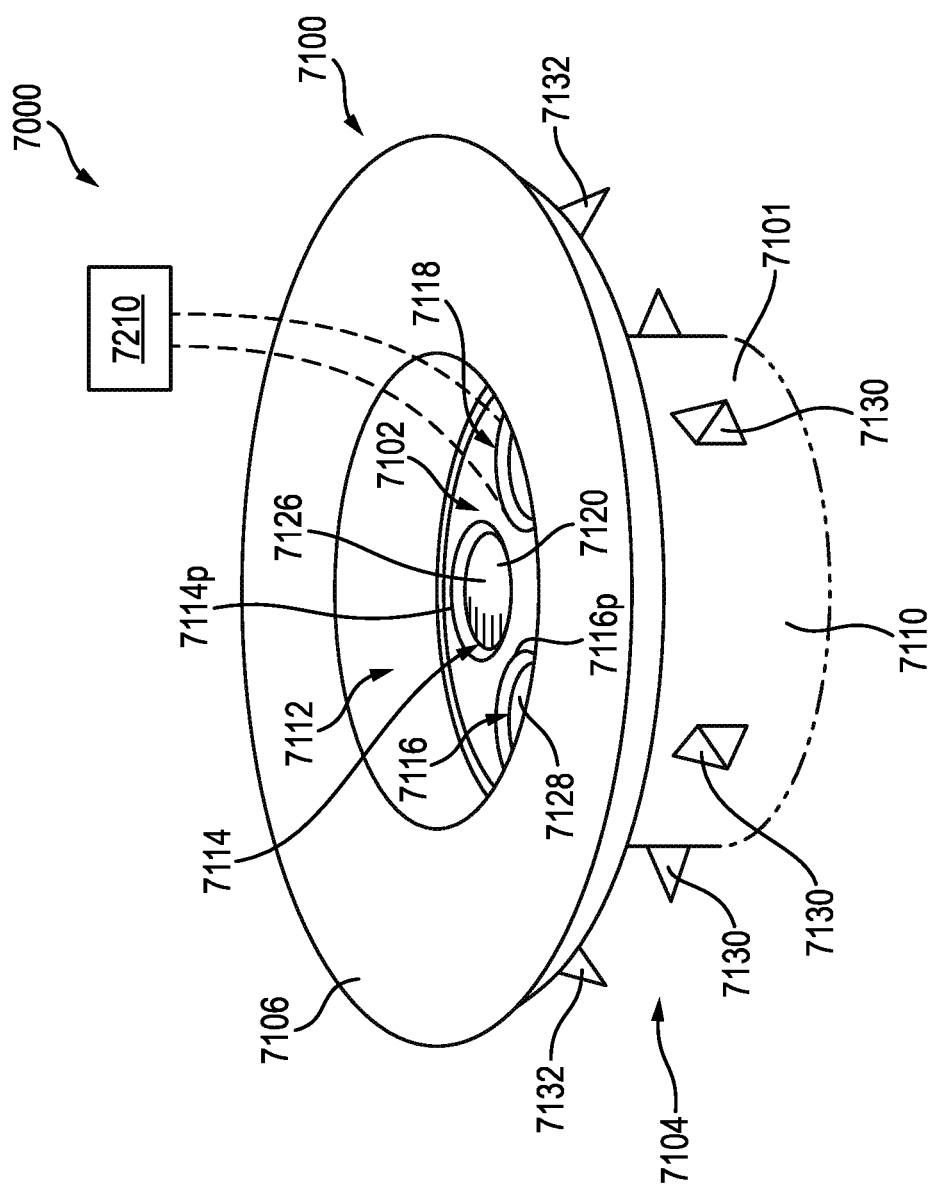
FIG. 56 is a schematic view of an exemplary embodiment of a surgical sealing device.
Figure 57:
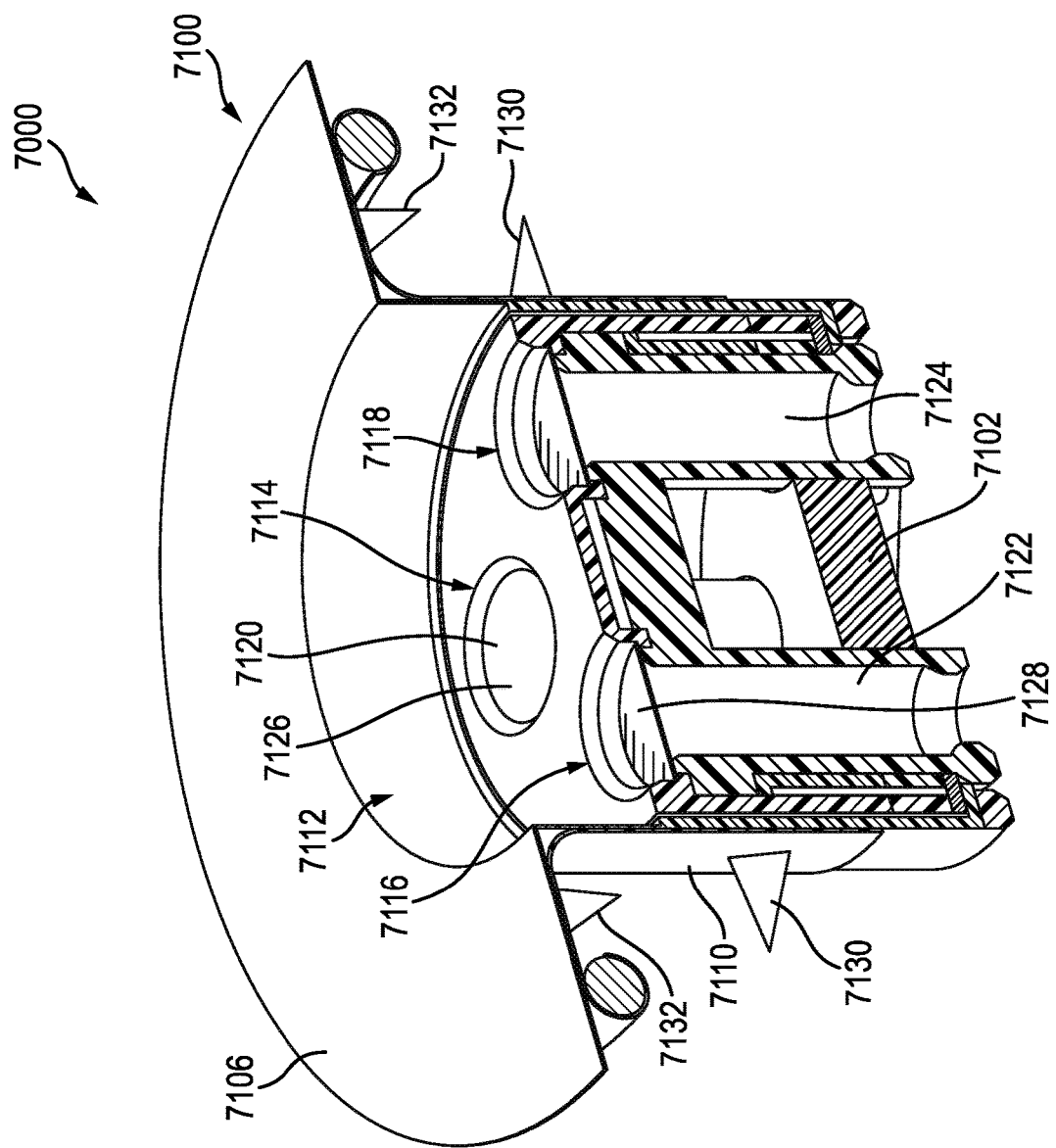
FIG. 57 is a cross-sectional view of the surgical sealing device of FIG. 56.

FIG. 56 and FIG. 57 illustrate one embodiment of a surgical sealing device 7000 that is configured to provide access into a natural body lumen or organ (e.g., a lung, a stomach, a colon, or small intestines) through a natural body orifice (e.g., esophagus, rectum, and the like). Therefore, at least a portion of the surgical sealing device 7000 is configured to be inserted into and stabilized within a natural body orifice.

The sealing device 7000 includes a seal housing 7100 with ports extending therethrough and at least one retention element on the exterior surface 7101 of the seal housing 7100. While the at least one retention element can have a variety of configurations, in this illustrated embodiment, the at least one retention element includes first retention elements 7130 and second retention elements 7132. The first and second retention elements 7130, 7132 are configured to secure the seal housing 7100 within a natural body orifice.

In use, the surgical sealing device 7000 can be positioned within a natural body orifice, such as by deforming the seal housing 7100, or a portion thereof (e.g., the outer body member 7104) and inserting the seal housing 7100 in the natural body orifice. The insertion of the seal housing can be performed by hand or by using an insertion tool. The at least one retention element is releasably positioned to thereby affix the seal housing to the natural body orifice. In some embodiments, the at least one retention element can be deployed inside the natural body lumen, whereas in other embodiments, the at least one retention element can be deployed outside of the natural body lumen. The at least one retention member can be releasably positioned concurrently with or subsequently after the sealing housing is positioned at least partially within the natural body lumen. To withdraw the surgical sealing device 7000 from the natural body orifice, a portion of the seal housing 7100 (e.g., the outer body member 7104) can be gripped with one or both hands (such as at opposite sides of the outer body member 7104) or by a removal instrument, or both, and the seal housing 7100 may be pulled proximally to withdraw the seal housing 7100 from natural body orifice. Prior to gripping the seal housing, the at least one retention element can be moved or otherwise disengaged from tissue defining the natural body orifice or tissue positioned proximate to the natural body orifice.

As shown in FIG. 56 and FIG. 57, the first and second retention elements 7130, 7132 are arranged on and extend from the exterior surface 7101 of the seal housing 7100. The first and second retention elements 7130, 7132 can have a variety of configurations. In some embodiments, the first and second retention elements can have the same or similar configurations. In other embodiments, the first and second retention elements can have different structural configurations relative to each other. It is also contemplated herein that in certain embodiments, the first retention elements or the second retention elements can be omitted.

In this illustrated embodiment, the first and second retention elements 7130, 7132 are each in the form of barbs that are configured to penetrate into the tissue to affix the seal housing 7100 to the natural body orifice. Further, the retention elements 7130, 7132 can allow for twisting and deformation of the natural body orifice, which can occur naturally, while also keeping the seal housing 7100 securely lodged within the natural body orifice.

In other embodiments, the at least one retention element can have a structural configuration that is configured to contact and engage the tissue surrounding or adjacent to the natural body orifice without penetration. That is, the at least one retention element can have a structural configuration that is configured to frictionally engage with the tissue so to prevent the seal housing from further movement within the natural body orifice during use. By way of example, in some embodiments, the at least one retention element can be in the form of an expandable element (e.g., inflatable balloons), as illustrated in Figure X. In use, once the seal housing is inserted (e.g., partially or fully) within the natural body orifice, the expandable element(s) can be inflated, and when the seal housing is to be removed from the natural body orifice, the expandable element(s) can be deflated.

In some embodiments, when one or more retention elements are expandable elements, these retention elements can configured to be expanded within the natural body orifice (e.g., after at least a portion of the seal housing is inserted into the natural body orifice). In other embodiments one or more retention elements can be configured to be deployed outside of the natural body lumen (e.g., after at least a portion of the seal housing is inserted into the natural body orifice). Alternatively, in certain embodiments, at least one retention element can be configured to be deployed within the natural body orifice, and at least another one retention element can be configured to be deployed outside the natural body orifice. A person skilled in the art will appreciate that the deployable position of the retention elements depends at least upon the position of the retention elements relative to the seal housing 7100 and the position of the seal housing 7100 relative to the natural body orifice when the seal housing 7100 is inserted therein.

Figure 58:
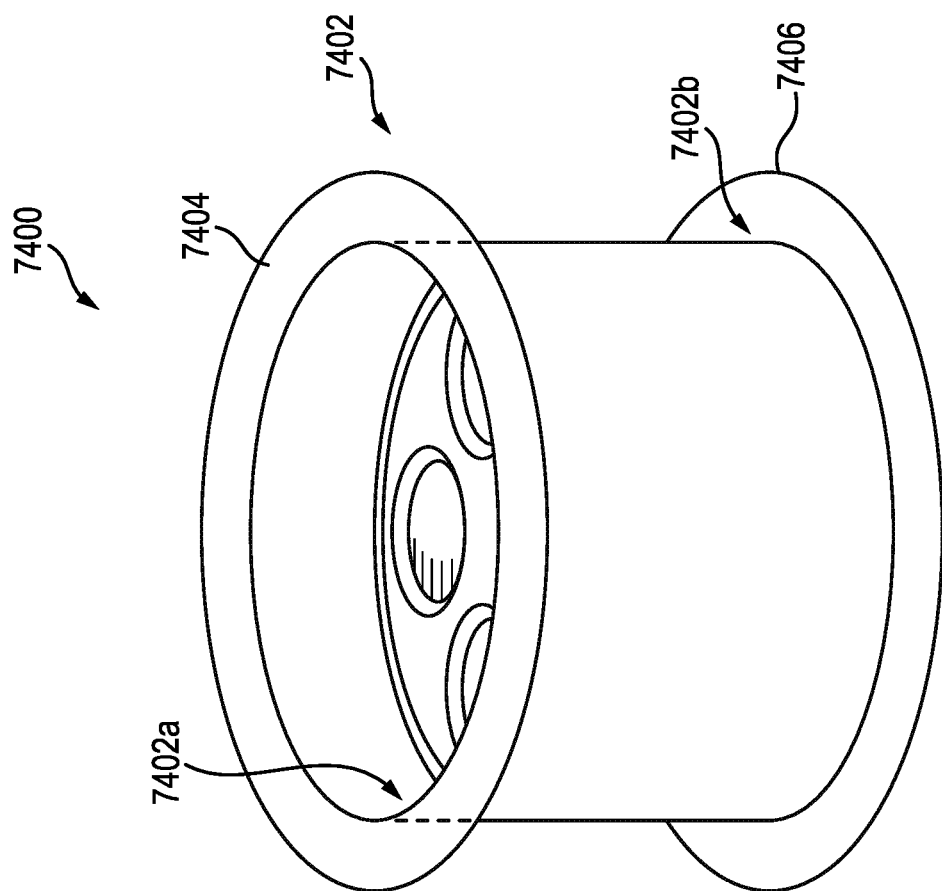
FIG. 58 is a cross-sectional view of another exemplary embodiment of a surgical sealing device.

FIG. 58 illustrates an exemplary embodiment of a surgical sealing device 7400 that includes a sealing housing 7402 and two retention elements 7404, 7406 that are in the form of inflatable balloons. The two retention elements 7404, 7406 are each configured to move from an unexpanded to an expanded state (FIG. 58). Aside from the differences described in detail below, sealing device 7400 can be similar to sealing device 7000 (FIG. 56 and FIG. 57) and therefore common features are not described in detail herein. As shown, the first retention element 7404 is positioned at a first end 7202*a* of the seal housing 7402 and the second retention element 7406 is positioned at a second end 7202*b* of the seal housing 7402. Further, when both the first and second retention elements 7404, 7406 are in their expanded state, as illustrated in FIG. 58, they are configured to contact and frictionally engage an internal surface of the natural body orifice. In embodiments where only a portion of the surgical sealing device 7400 is positioned within the natural body orifice, the second end 7402*b* of the seal housing 7402 can be positioned outside the natural body orifice (e.g., outside of the body of the patient). In such embodiments, the second retention element 7406 can be configured to contact and frictionally engage the outer tissue surface surrounding or adjacent to the natural body orifice (e.g., an external surface of the natural body orifice).

Referring back to FIG. 56 and FIG. 57, the seal housing 7100 of surgical sealing device 7000 can have a variety of configurations. For example, in this illustrated embodiment, the seal housing 7100 has an inner body member 7102 and an outer body member 7104 that is positioned about the inner body member 7102. In other embodiments, the outer body member can designed so as to extend distally from one end of the inner body member. In certain embodiments, the outer body member can be omitted.

The inner body member 7102 and the outer body member 7104 can each have a variety of configurations. In this illustrated embodiment, the inner body member 7102 has a generally cylindrical configuration. The outer body member 7104 includes an annular flange 7106 with an elongated cylindrical base 7110 extending therefrom. Further, the base 7110 defines a lumen 7112 extending therethrough. The lumen 7112, as shown in FIG. 56 and FIG. 57, at least partially houses the inner body member 7102. A person skilled in the art will appreciate that the inner body member and/or the outer body member, and/or portions thereof, can have other suitable shapes and sizes (e.g., oval, elliptical, ovoid, and any combination thereof) and therefore their configurations are not limited to what is shown in the figures.

The inner body member 7102 and the outer body member 7104 can formed as a unitary structure, permanently coupled to each other, or releasably coupled to each other. For example, in some embodiments, the inner body member 7102 can be configured to be inserted into and/or removed from the lumen 7112 (e.g., while the outer body member 7104 is at least partially positioned within a natural body orifice). In certain embodiments, the outer body member 7104 can be configured to provide assistance in preventing the inner body member 7102 from be pushed through the sealing housing 7100 (e.g., and into the body of the patient), and to assist in removing the inner body member 7102 from the seal housing 7100. For example, during surgery, removal of the inner body member 7102 may be needed for removing damaged or diseased tissue through the lumen 7112 of the outer body member 7104. Further, in addition, or alternatively, the outer body member 7104 can be configured to help prevent the inner body member 7102 from being torn or otherwise damaged by surgical instrument(s) that is/are inserted therethrough (e.g., during surgery).

As further shown in FIG. 56 and FIG. 57, the inner body member 7102 includes ports that extend therethrough, and thus, through the seal housing 7100. While the inner body 7102 can include two or more ports, in this illustrated embodiment the inner body member 7102 includes three ports: a first port 7114, a second port 7116, a third port 7118. Each port 7114, 7116, 7118 defines a respective passageway 7120, 7122, 7124 through the seal housing 7100. The ports 7114, 7116, 7118 can be designed as a variety of different ports that serve different functions (e.g., fluid exchange into and/or out of the natural body lumen, sealing instruments inserted therethrough, preventing fluid from escaping out of the natural body orifice and into the ambient environment, and/or the like).

In some embodiments, at least one port can be configured to form a seal (e.g., around an instrument inserted therethrough) and at least another one port can be configured to control the ingress and/or egress of fluid (e.g., liquid, gas, or a combination thereof) between an interior volume of the natural body orifice and an ambient environment. In certain embodiments, at least one port can be configured to seal and control ingress and/or egress of fluid. For purposes of this discussion, the first and second ports 7114, 7116 are each configured to form a respective seal around an instrument inserted therethrough and the third port 7118 is configured to control the fluid ingress and egress. A person skilled in the art that any of these ports can configured to control fluid ingress and/or egress (e.g., air into and/or out of the natural body orifice, e.g., for breathing or insufflation) and/or to form a seal (e.g., around an instrument inserted therethrough and/or when an instrument is absent, for preventing loss of fluid therethrough).

In some embodiments, sealing element(s) can be positioned within the first port and/or second port to form a seal therein. In some embodiments, the sealing element(s) can be in the form of a thin membrane formed of a flexible material which can be punctured or otherwise pierced by a surgical instrument. In addition, or alternatively, zero closure sealing elements such as a duck bill seal or other suitable seals for sealing in the absence of instrument can be used in association with the ports. The sealing elements can be positioned at any suitable location within the port.

As shown in FIG. 56 and FIG. 57, a first sealing element 7126 is positioned within the passageway 7120 of the first port 7114 and a second sealing element 7128 is positioned within the passageway of the second port 7116. In some embodiments, the first and second sealing elements 7126, 7128 can the same, whereas in other embodiments, the first and second sealing elements 7126, 7128 can be different. The first and second sealing elements 7126, 7128 can be positioned in a variety of different locations within the respective passageways. In this illustrated embodiment, the first sealing element 7126 is positioned proximate to the proximal end 7114$p$ (e.g., the end closest to the ambient environment during use) of the first port and the second sealing element 7128 is positioned proximate to the proximal end 7116$p$ (e.g., the end closest to the ambient environment during use) of the second sealing port 7116. In other embodiments, the first sealing element, the second sealing element, or both, can be positioned at a distal end of the second port and the third port, respectively.

In some embodiments, the first sealing element 7126, the second sealing element 7128, or both can be further configured to limit the direction of airflow while also providing sealed access for the surgical instruments through the seal housing 7100. This can prevent contamination from aerosolized viruses or contagions during treatment due to the advancement and extraction of surgical instruments through the first port 7114 and/or the second port 7116. Additionally, the first sealing element, the second sealing element, or both can be a one-way valve to allow exhaust to be vented to a fluid trap and particulate filter to control the expiration of contagions. In another exemplary embodiment, the surgical sealing device 7000 can have a small higher pressure inlet and a larger exhaust port for controlling exhaust gases being expelled from the natural body lumen.

In addition to the insertion and extraction of one or more surgical instruments through the first and second ports 7114, 7116, fluid exchange can occur through the third port 7118 of the surgical sealing device 7000. That is, in this illustrated embodiment, the third port 7118 is designed to allow the ingress and egress of fluid between an interior volume of the natural body orifice and an ambient environment.

In certain embodiments, as shown in FIG. 56, the third port 7118 can be operatively connected to a valve 7210. The valve 7210 can be configured to monitor a parameter that can be used to control a fluid transfer rate through the third port 7118. The monitored parameter can be a fluid transfer pressure, a fluid transfer volume, and/or a direction of the fluid transfer therethrough. For example, the valve can include a sensor that is configured to sense the pressure, volume, or flow direction of the fluid as it passes through the valve, and transmit the sensed data to a controller (not shown). If at any time during use, the controller determines that the sensed data is outside of a predetermined range(s), the controller can alter the valve position (e.g., partially close or open the valve relative to its current position) to change the pressure, volume, or flow direction of the fluid therethrough, and consequently, through the third port 7118. Non-limiting examples of suitable sensors include pressure, temperature, and flow sensors. In other embodiments, a controller can be omitted, and the valve can be structurally configured to control the fluid flow therethrough by itself, and therefore alter the pressure, volume, or flow direction, if needed.

During an electrosurgical procedure, energy devices can delivery mechanical and/or electrical energy to target tissue in order to treat the tissue (e.g., to cut the tissue, cauterize blood vessels and/or coagulate the tissue within and/or near the targeted tissue). The cutting, cauterization, and/or coagulation of tissue can result in fluids and/or particulates being released into the air. Such fluids and/or particulates emitted during a surgical procedure can constitute smoke, for example, which can comprise carbon particles and/or other particles suspended in air. As a result, electrosurgical systems typically employ a surgical evacuation system that captures the resultant smoke from a surgical procedure, and directs the captured smoke through a filter and a smoke exhaust port away from the clinician(s) and/or from the patient(s).

For example, surgical procedures on a lung can require inhalation and expulsion of breathable air and exhaustion of smoke that is generated during the procedure. In such instances, cooperative control of the smoke evaluation and breathing apparatus can be helpful. As such, the surgical sealing devices disclosed herein can be configured to enable simultaneous trans-seal system use. That is, the present surgical sealing devices can be configured to provide smoke evacuation control of a fluid exchange system that allows cooperative flow of fluid such that, during surgery, the body can continue to receive the intended flow of fluid (e.g., breathable air) while also allowing extraction of a portion of the fluid through a different path to direct the smoke extraction from the patient.

In some embodiments, the smoke exhaust port can be its own separate port within the seal housing or it can be combined with another port of the seal housing (e.g., a port that is connected to a breathing apparatus that inflates and deflates the lung with breathable air and/or configured for insertion and extraction of surgical instruments), or the smoke evacuator passage can be a working passage of a flexible endoscope inserted through a port of the seal housing for controlling the ingress and egress of lung gasses as needed for breathing and smoke evacuation. If the smoke evacuation is activated when the body is breathing, an additional airflow inlet can be configured as a port of the seal housing to offset the smoke evacuation air flow, resulting in enough air for lung inflation while cooperatively extracting smoke and air form the lung. In some embodiments, the smoke evacuation system can be configured to pass the smoke to an externally connected smoke evacuator pump and filters, while in other embodiments, the smoke evacuation system can be arranged to use the same filters as a primary breathing exhaust system coupled to the breathing passage port of the seal housing. Exemplary smoke evacuator systems suitable for use with the present disclosure are described, for example, in U.S. Pat. No. 11,051,876 entitled "Surgical Evacuation Flow Paths" issued Jul. 6, 2021, U.S. Patent Publication No. 2019/0201088 entitled "Surgical Evacuation System With A Communication Circuit For Communication Between A Filter And A Smoke Evacuation Device" published Jul. 4, 2019, and U.S. Patent Publication No. 2019/0204201 entitled "Adjustments Based On Airborne Particle Properties" published Jul. 4, 2019, the disclosures of which are incorporated herein by reference in their entireties.

Figure 59:
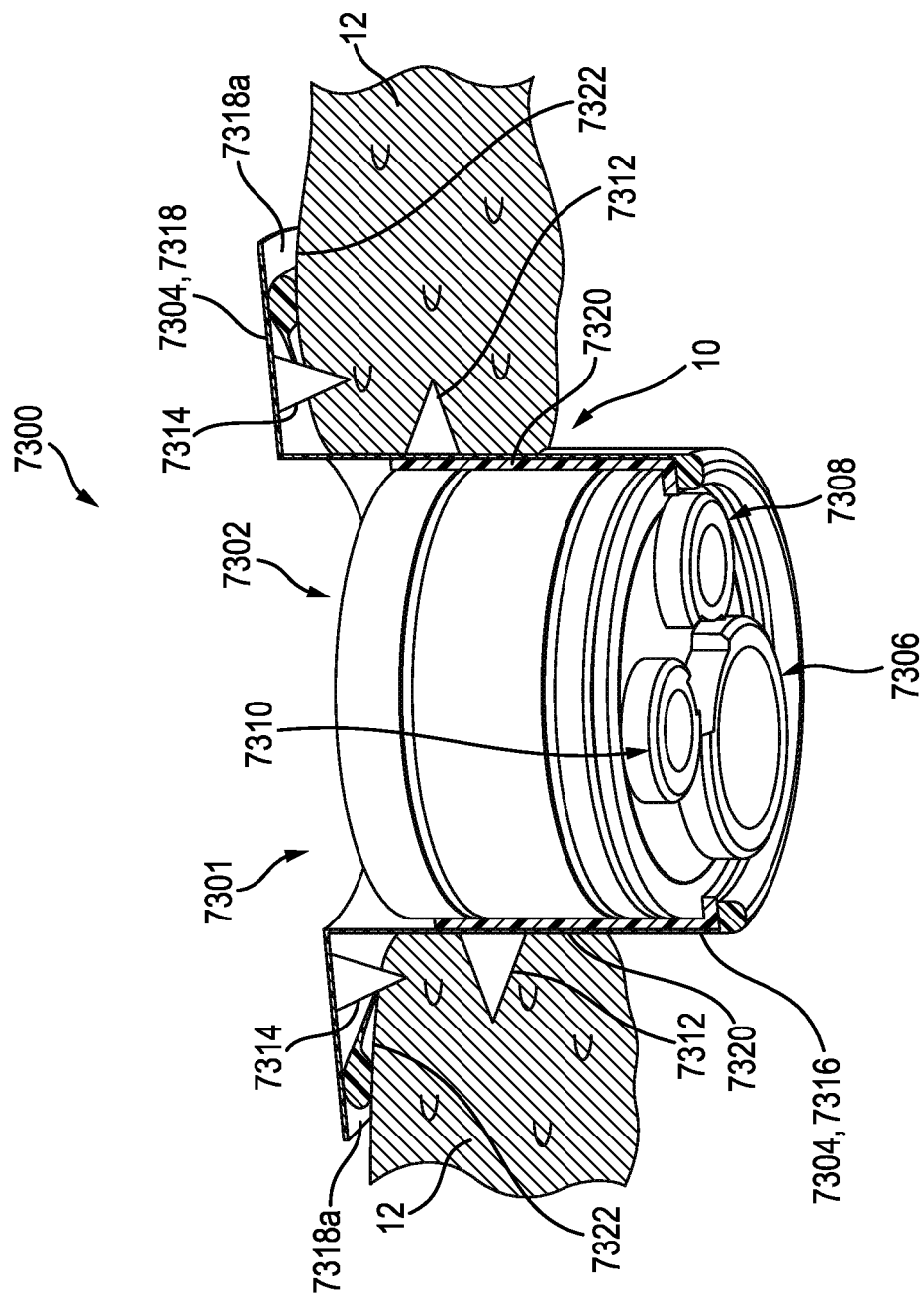
FIG. 59 is a cross-sectional view of another exemplary embodiment of a surgical sealing device, showing the device inserted into a natural body orifice.

FIG. 59 illustrates another embodiment of a surgical sealing device 7300. Aside from the differences described in detail below, the surgical sealing device 7300 can be similar to surgical sealing device 7000 (FIG. 56 and FIG. 57) and therefore common features are not described in detail herein. The surgical sealing device 7300 is shown at least partially inserted within a natural body orifice 10 formed by tissue 12. The surgical sealing device 7300 includes a seal housing 7301 having an inner body member 7302 and an outer body member 7304 that is positioned about the inner body member 7302. The inner body member 7302 has three ports 7306, 7308, 7310 extending therethrough. While different numbers and sizes of ports can be used, the illustrated three ports 7306, 7308, 7310 include one relatively larger port 7306 (e.g., to receive an endoscope or other relatively larger diameter device), and two relatively smaller ports 7308, 7310 (e.g., to receive relatively smaller devices, such as graspers, clip appliers, or the like).

Further, the seal housing 7301 includes first retention elements 7312 and second retention elements 7314. As shown, the first retention elements 7312 extend outward from the elongated cylindrical base 7316 of the outer body member 7304 and the second retention elements 7314 extend from a bottom surface 7318a of the annular flange 7318 of the outer body member 7304. The first retention elements 7312 engage with an internal surface 7320 of the natural body orifice 10 and penetrate portions of the tissue 12 that define such internal surface 7320. Since the surgical sealing device 7300 is only partially inserted into the natural body orifice 10, the annular flange 7318 of the seal housing 7300 is positioned outside of the natural body orifice 10. As a result, the second retention elements 7314 engage an outer tissue surface 7322 surrounding the natural body orifice 10 and penetrate portions of the tissue 12 that define such outer surface 7322 (e.g., external surface of the natural body lumen). This penetration by both the first and second retention elements 7312, 7314 into the tissue 12 affix the seal housing 7301 to the natural body orifice 10 so as to allow one or more surgical instruments to be inserted and extracted through the natural body orifice 10 and/or fluid transfer to occur through the natural body orifice 10.

In some embodiments, the surgical sealing device can include wound protectors for use with natural body orifices that enable introduction and extraction of instruments while limiting instrument to tissue interaction. This limiting of interaction between the tissue and instruments can provide reduced friction between the body wall and the insertion forces of the instruments. The arrangement can minimize damage to the surrounding tissue during manipulation or advancing or retracting of the instruments through the sealing device.

In some embodiments, the seal housing of the surgical sealing device can be configured as a mechanical fixation point for a flexible scope and/or instruments passing through the seal housing. The seal housing can be arranged such that a fixation point is formed by the seal housing being secured within the natural body orifice, which provides the flexible scope and/or instruments passing through the seal housing a resistive fixation point from which to resist internally generated forces, motions and actions from the instruments manipulating tissue within the body. The fixation point for the instruments would prevent inappropriate loads on the patient during movement of the instruments within the sealing device. The fixation point could be outside of the body and prevent excessive torque from being applied to the body by the instruments through the sealing device.

While the seal housings 7100, 7402, 7301 in FIG. 56 and FIG. 57, FIG. 58, and FIG. 59 are illustrated as a separate device which to be inserted into a natural body orifice and allows instruments to be inserted therethrough and into a natural body lumen, in other embodiments a seal housing can be arranged on an instrument, such as a gastroscopic bougie, as the instrument is inserted into a natural body orifice. A gastroscopic bougie is commonly understood to be a thin cylinder of rubber, plastic, metal or another material that a medical practitioner inserts into or through a body passageway, such as the esophagus, to diagnose or treat a condition. A bougie may be used to widen a passageway, guide another instrument into a passageway, or dislodge an object. The gastroscopic bougie can include a seal housing having retention elements which are configured to be deployed in the esophagus prior to the stomach. This arrangement would allow laparoscopic access to the stomach while the abdominal cavity is insufflated for procedures such as a tumor resection within the stomach. By arranging the seal housing in the esophagus, the laparoscopic insufflation is prevented from escaping endoluminally, while also allowing bougie to manipulate the stomach and tumor through four-wire control.

Surgical Systems with Port Devices for Instrument Control

In certain embodiments, surgical systems that enable control of surgical instrument interactions between separate port devices are provided. In general, these systems have two or more port devices (e.g., multi-port devices) that include respective housings that are each configured to allow instruments from respective sets of instruments to be inserted therethrough. The two or more port devices are each designed to provide individualized resistive forces to respective inserted instruments and to allow the inserted instruments to work cooperatively together (e.g., for at least one surgical step of a surgical procedure or at one or more surgical sites, etc.). The two or more port devices are interconnected to each other (e.g., electrically or mechanically) to create an interrelationship between the inserted instruments. This interrelationship enables these instruments to work in combination (e.g., move concurrently or sequentially in the same or different direction relative to each other or in groups) to provide the force(s), retraction, access angle(s), and the like to carry out at least one surgical step (e.g., to provide the intended medial therapy). As a result, these cooperative movements between at least a portion of the inserted instruments can provide a more collaborative surgical environment within the same port or among different ports that can increase precision and help prevent collisions (e.g., of surgical instruments and/or robotic arms).

A person skilled in the art will understand that the phrase "work cooperatively together" as used herein refers to coordinated movement between two or more inserted instruments in the same port, in separate ports, or a combination thereof based on a location, an orientation, or a motion of at least one inserted instrument of the two or more inserted instruments. Similarly, a person skilled in the art will understand that the coordinated movement between the two or more inserted instruments can occur in the same direction at the same time, in the same direction at different times, opposing directions at the same time, opposing directions at different times, in the same plane at the same time, in the same plane at different times, in two separate planes at the same time, in two different planes at different times, or any combination thereof.

Each port device is configured to be at least partially disposed with a body. For example, a first port device can be partially inserted into a body (e.g., through a natural orifice or an opening made by an incision) and a second port device can be partially inserted into the (e.g., through a natural orifice or an opening made by an incision). The first and second port devices can be partially inserted within the same physiological space or different physiological spaces. In some embodiments, the first port device can bridge the ambient environment with a first physiological space inside the body (e.g., thoracic cavity or abdomen cavity and the second port device can bridge the ambient environment and a second physiological space that is not directly connected to the first physiological space (e.g., through a natural orifice to inside the colon, esophagus or other physiologic tract). In other embodiments, the first and second physiological spaces are directly connected to each other. For example, in one embodiment, the first port device can be partially inserted into a first abdominal quadrant and the second port device can be partially inserted into a second abdominal quadrant that is different than the first abdominal quadrant.

The housing of each port device can be positioned and affixed to body in such a way in which a distal portion of the housing extends into the body (e.g., a physiological space), and a proximal portion extends out of the body and into the ambient environment (e.g., positioned adjacent to and in contact with an exterior surface of the patient's body, such as the patient's skin). Alternatively, the housing can be designed to be entirely positioned within the body.

Further, the housing of each port device generally includes ports arranged within the housing that allow instruments to be inserted therethrough into the body (e.g., a physiological space, such as a one or more cavities within the body) from the ambient environment through a natural body orifice or an opening made by an incision. The ports arranged through the housing can form pathway(s) into and through the body.

In some embodiments, at least one port of at least one port device can be configured to form a seal around an inserted instrument. In one embodiment, at least one port of the first port device can be configured to form a seal around a respective inserted instrument of a first set of instruments. Alternatively, or in addition, at least one port of the second port device can be configured to form a seal around a respective inserted instrument of a second set of instruments.

In certain embodiments, sealing element(s) can be positioned within the at least one port to form a seal therein. The sealing element(s) can have a variety of configurations. In some embodiments, the sealing element(s) can be in the form of a thin membrane formed of a flexible material which can be punctured or otherwise pierced by a surgical instrument. Alternatively, or in addition, zero closure sealing elements such as a duck bill seal or other suitable seals for sealing in the absence of instrument can be used in association with the at least one port. The sealing elements can be positioned at any suitable location within the at least one port.

In some embodiments, when first and second instruments are inserted into respective ports of the first port device, the first port device can be configured to allow the first instrument to move within a first range of motion relative to the first port device and to allow the second instrument to move within a second range of motion relative to the first port device that is at least partially overlaps with the first range of motion. Alternatively, or in addition, when first and second instruments are inserted into respective ports of the second port device, the second port device can be configured to allow the first instrument to move within a first range of motion relative to the second port device and to allow the second instrument to move within a second range of motion relative to the second port device that at least partially overlaps with the first range of motion.

In use, as discussed in more detail below, the respective port device provides resistive inter-device forces to respective inserted instruments (e.g., to prevent unintended contact between inserted instruments). That is, during movement of an inserted instrument, the port device can restrain movement of the inserted instrument relative to other inserted instruments in the same port device, in at least one other port device, or a combination thereof. The port device(s) of the surgical system are configured to interact at least one inserted instrument in such a way that limits one or more instrument motions. This limitation can be based on, for example, at least one of a location, orientation, and a motion of at least one other instrument of the same set of inserted instruments, at least one other instrument of a different set of inserted instruments, or both.

The location, orientation, motion, or any combination thereof, of an inserted instrument can be determined, for example, by using one or more tracking device(s) or a tracking system. In some embodiments, the system can include a tracking device that can be associated with one of the first port device or the second port device. The tracking device can be configured in a variety of ways. In certain embodiments, the tracking device can be configured to transmit a signal indicative of a location of the first port device relative to the second port device. Alternatively, or in addition, the tracking device can be configured to transmit a signal indicative of at least one of a location, an orientation, and a motion of at least one inserted instrument in the first port device relative to the second port device. Alternatively, or in addition, the tracking device can be configured to transmit a signal indicative of at least one of a location, an orientation, and a motion of at least one inserted instrument in the second port device relative to the first port device.

The transmitted signal(s) from the tracking device can be received by a controller. In general, depending on the data of the received signal, the controller can determine at least one or more of the following: a relative location of the first port device and the second port device, at least one of the location, the orientation, and the motion of at least one inserted instrument in the first port device relative to the second port device, or at least one of the location, the orientation, and the motion of the at least one inserted instrument of in the second port device relative to the first port device based on the respective transmitted signal. This information is used as guidance for movement of the inserted instruments individually, as a single group, or as multiple groups. This guidance in combination with the resistive forces applied by the respective port devices can control instrument interaction between the inserted instruments such that the inserted instruments can work cooperatively together at one or more surgical sites and/or to perform at least one surgical step of a surgical procedure.

An exemplary surgical system can include a variety of features as described herein and illustrated in the drawings. However, a person skilled in the art will appreciate that the surgical systems can include only some of these features and/or it can include a variety of other features known in the art. The surgical systems described herein are merely intended to represent certain exemplary embodiments. Moreover, while the surgical systems are shown and described in connection with a colon, a person skilled in the art will appreciate that these surgical systems can be used in connection with any other suitable natural body lumens or organs.

Figure 60:
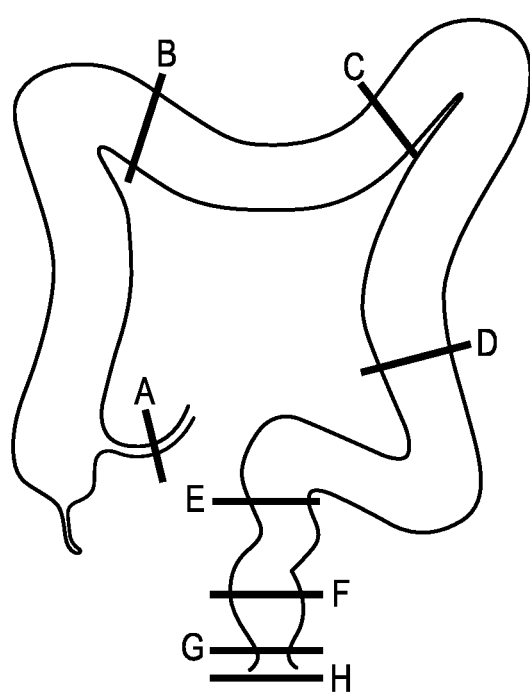
FIG. 60 is an exemplary image of a colon.

Surgery is often the primary treatment for early-stage colon cancers. The type of surgery used depends on the stage (extent) of the cancer, its location in the colon, and the goal of the surgery. Some early colon cancers (stage 0 and some early stage I tumors) and most polyps can be removed during a colonoscopy. However, if the cancer has progressed, a local excision or colectomy, a surgical procedure that removes all or part of the colon, may be required. In certain instances, nearby lymph nodes are also removed. A hemicolectomy, or partial colectomy, can be performed if only part of the colon is removed. In a segmental resection of the colon the surgeon removes the diseased part of the colon along with a small segment of non-diseased colon on either side. Usually, about one-fourth to one-third of the colon is removed, depending on the size and location of the cancer. Major resections of the colon are illustrated in FIG. 60, in which (i) A-B is a right hemicolectomy, A-C is an extended right hemicolectomy, B-C is a transverse colectomy, C-E is a left hemicolectomy, D-E is a sigmoid colectomy, D-F is an anterior resection, D-G is a (ultra) low anterior resection, D-H is an abdomino-perineal resection, A-D is a subtotal colectomy, A-E is a total colectomy, and A-H is a total proctocolectomy. Once the resection is complete, the remaining intact sections of colon are then reattached.

During a laparoscopic-assisted colectomy procedure, it is often difficult to obtain an adequate operative field. Often times, dissections are made deep in the pelvis which makes it difficult to obtain adequate visualization of the area. As a result, the lower rectum must be lifted and rotated to gain access to the veins and arteries around both sides of the rectum during mobilization. During manipulation of the lower rectum, bunching of tissue and/or overstretching of tissue can occur. Additionally, a tumor within the rectum can cause adhesions in the surrounding pelvis, and as a result, this can require freeing the rectal stump and mobilizing the mesentery and blood supply before transection and removal of the tumor.

After a colectomy, the remaining healthy portions of the colon must be reattached to one another to create a path for waste to leave the body. However, when using laparoscopic instruments to perform the colectomy, one single entry port device may not have a large enough range of motion to move the one end of the colon to connecting portion. As such, a second entry port device is therefore needed to laparoscopically insert instruments to help mobilize the colon and/or purchase the one end of the colon from a laparoscopic instrument of the first entry port device and move the one end to the connecting portion. The multiple port devices having multiple instrument inserted therethrough to carry out at least one surgical step or site can increase the chance of surgical errors and collisions between surgical instruments or robotic arms.

The present surgical systems include multiple port devices (e.g., multi-port devices) that interconnect multiple groups of surgical instruments that can move together while also providing individualized resistive inter-device forces and motions to the surgical instruments. For example, a first port device can be configured to receive a first set of instruments (e.g., two or more instruments) and a second port device can be configured to receive a second set of instruments (e.g., two or more instruments), and when at least one instrument from the first set and from the second set are inserted into the first and second port devices, respectively, these instruments can move together as a single group. Alternatively, or in addition, at least one inserted instrument of the first set can move with at least one instrument of the second set, or vice versa.

Figure 61:
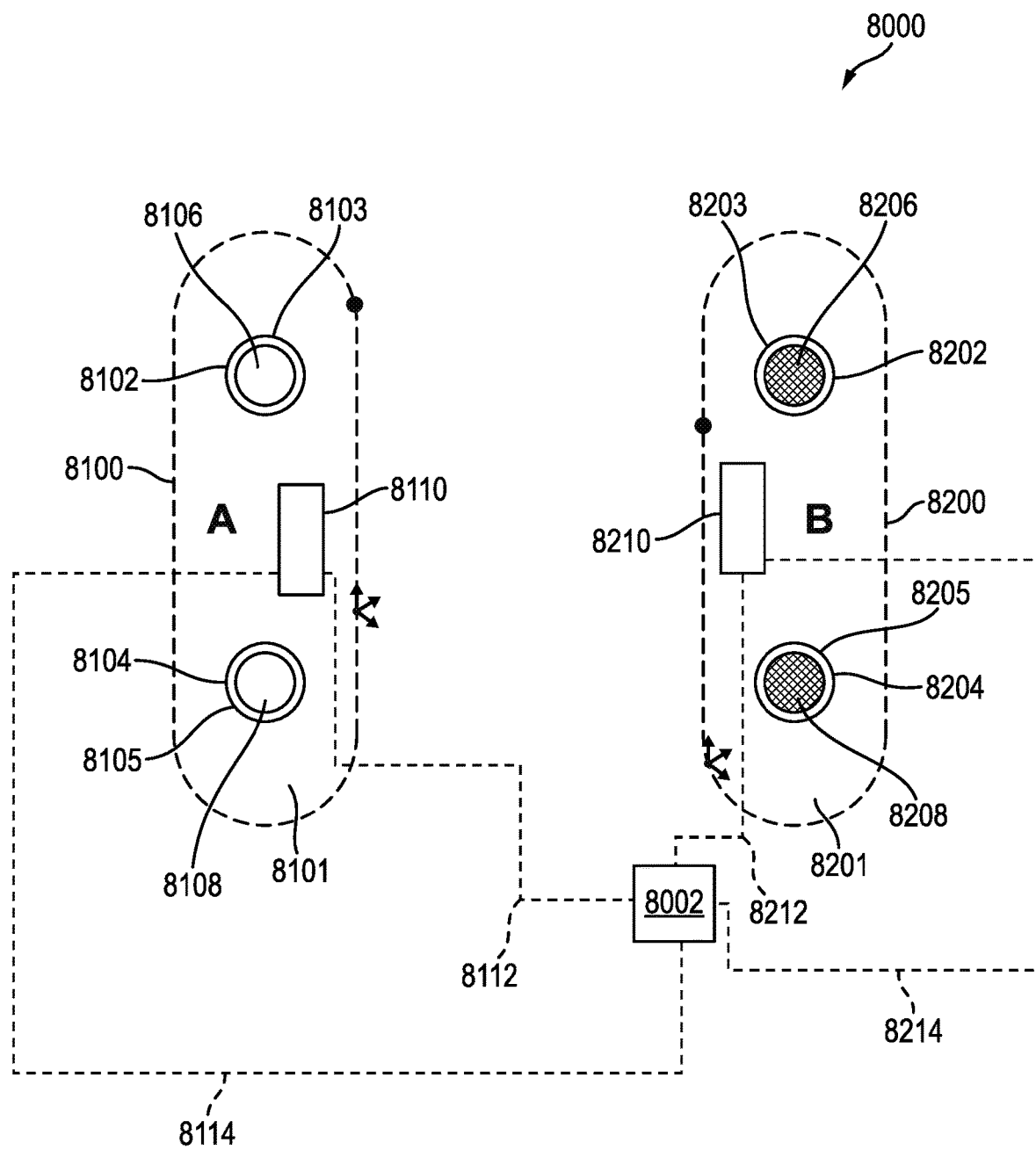
FIG. 61 is a schematic view of an exemplary embodiment of a surgical system having first and second multi-port devices.

FIG. 61 illustrates an exemplary embodiment a surgical system 8000 that is configured to for laparoscopic and/or endoscopic access into a body through two or more interconnected multi-port devices. FIG. 28 schematically illustrates the surgical system 8000 being used in a surgical resection procedure on a colon 10. For purposes of simplicity, certain components of the surgical system 8000 are not illustrated.

As shown, the surgical system 8000 includes a first multi-port device 8100 and a second multi-port device 8200, in which each multi-port device 8100, 8200 is configured to be at least partially disposed within the body. In other embodiments, the surgical system can include more than two multi-port devices. It is also contemplated herein that in addition to the multi-port devices, the surgical system can include one or more single port devices.

Figure 62:
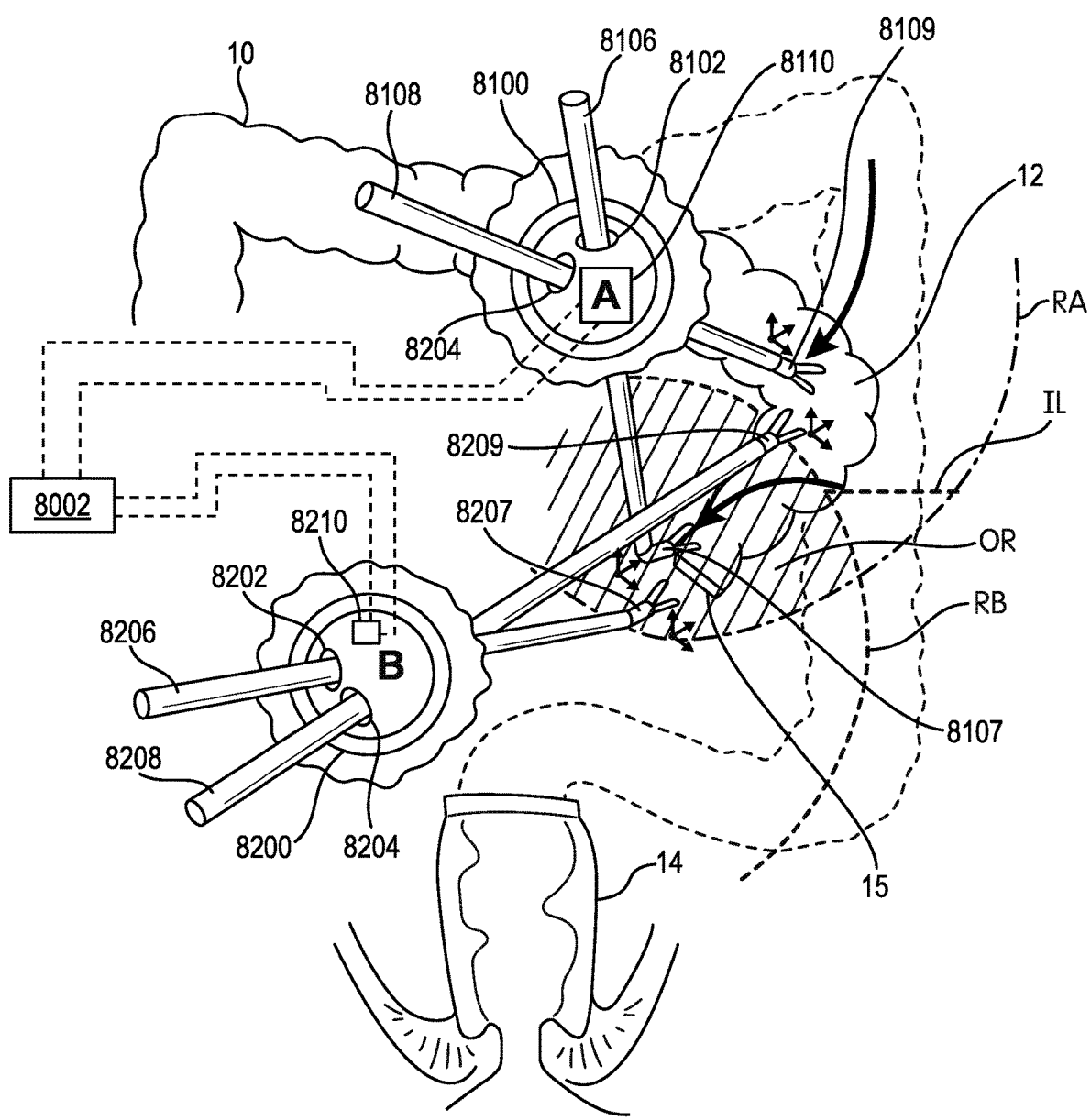
FIG. 62 is a schematic view of the surgical system of FIG. 27, showing the first and second multi-port devices partially inserted within an abdominal cavity.

The first multi-port device 8100 can have a variety of configurations. For example, in some embodiments, as shown in FIG. 61 and FIG. 62, the first multi-port device 8100 includes a first housing 8101 with a first port 8102 and a second port 8104 defined therein. The first and second ports 8102, 8104 are each configured to allow a respective surgical instrument to be inserted therethrough. For example, a first instrument 8106 (shown in more detail in FIG. 62) can be inserted into the first port 8102 and a second instrument 8108 (show in more detail in FIG. 62) can be inserted into the second port 8104. The first and second instruments 8106, 8108 are collectively referred to herein as "a first set of instruments."

In use, the first multi-port device 8100 interacts with the first instrument 8106, the second instrument 8108, or both. The first multi-port device 8100 can be configured to interact with the first instrument 8106 and the second instrument 8108 concurrently, separately, or both. By way of example, the first multi-port device 8100 interacts with the first instrument 8106, and during the interaction, the first multi-port device 8100 applies resistive forces to the first instrument 8106. These resistive forces limit one or more motions of the first instrument 8106 based on at least one of a location, orientation, and a motion of the second instrument 8108. A person skilled in the art will understand that the first multi-port device 8100 is configured to have a similar interaction with the second instrument 8108.

The first housing 8101 can be formed of one or more suitable material(s). In some embodiments, a first portion of the first housing can be formed of at least one first material and a second portion of the first housing can be formed of at least one second material. In such embodiments, the first portion can be more flexible than the second portion or vice versa. In other embodiments, the first housing is uniformly formed of one or more suitable material(s). A person skilled in the art will understand that the amount and type of resistive forces the first multi-port device applies to any inserted instrument will depend at least upon the material(s) and structural configuration of the first housing and the amount of force and the direction of force applied to the respective port by the inserted instrument.

The first and second ports 8102, 8104 can be configured to form a seal around an instrument inserted therethrough. For example, a first sealing element 8103 and a second sealing element 8105 can be positioned within the first port 8102 and the second port 8104, respectively. The sealing elements 8103, 8105 can be formed of any suitable material(s). A person skilled in the art will understand that the amount and type of resistive forces the first multi-port device applies to any inserted instrument will depend at least upon the material(s) and structural configuration of any sealing element(s) disposed within the first and second ports of the first housing.

In use, the first and second sealing elements 8103, 8105 form a seal around first and second instruments 8106, 8108, respectively. This can allow the physiological space inside the body to remain insufflated as the first and second instruments 8106, 8108 and/or other suitable instrument(s) are inserted and removed from the first multi-port device 8100. In certain embodiments, one or more of the inserted instruments of the first multi-port device 8100 can pivotally move relative to the first housing 8101.

The second multi-port device 8200 can have a variety of configurations. For example, in some embodiments, as shown in FIG. 61, the second multi-port device 8200 includes a second housing 8201 with a third port 8202 and a fourth port 8204 defined therein. The third and fourth ports 8202, 8204 are each configured to allow a respective instrument to be inserted therethrough. For example, a third instrument 8206 (shown in more detail in FIG. 62) can be inserted into the third port 8202 and a fourth instrument 8208 (shown in more detail in FIG. 62) can be inserted into the fourth port 8204. The third and fourth instruments 8206, 8208 are collectively referred to herein as "a second set of instruments."

In use, the second multi-port device 8200 interacts with the third instrument 8206, the fourth instrument 8208, or both. The second multi-port device 8200 can be configured to interact with the third instrument 8206 and the fourth instrument 8208 concurrently, separately, or both. By way of example, the second multi-port device 8200 can interact with the third instrument 8206, and during this interaction, the second multi-port device 8200 applies resistive forces to the third instrument 8206. These resistive forces limit one or more motions of the third instrument 8206 based on at least one of a location, orientation, and a motion of the fourth instrument 8208. A person skilled in the art will understand that the second multi-port device 8200 is configured to have a similar interaction with the fourth instrument 8208.

The second housing 8201 can be formed of one or more suitable material(s). In some embodiments, a first portion of the second housing can be formed of at least one first material and a second portion of the second housing can be formed of at least one second material. In such embodiments, the first portion can be more flexible than the second portion or vice versa. In other embodiments, the second housing is uniformly formed of one or more suitable material(s). A person skilled in the art will understand that the amount and type of resistive forces the second multi-port device applies to any inserted instrument will depend at least upon the material(s) and structural configuration of the second housing and the amount of force and the direction of force applied to the respective port by the inserted instrument.

The third and fourth ports 8202, 8204 can be configured to form a seal around an instrument inserted therethrough. For example, a third sealing element 8203 and a fourth sealing element 8205 can be positioned within the third port 8202 and the fourth port 8204, respectively. The third and fourth sealing elements 8203, 8205 can be formed of any suitable material(s). A person skilled in the art will understand that the amount and type of resistive forces the second multi-port device applies to any inserted instrument will depend at least upon the material(s) and structural configuration of any sealing element(s) disposed within the third and fourth ports of the second housing.

In use, the third and fourth sealing elements 8203, 8205 form a seal around third and fourth instruments 8206, 8208, respectively. This can allow the physiological space inside the body to remain insufflated as the third and fourth instruments 8206, 8208 and/or other suitable instrument(s) are inserted and removed from the second multi-port device 8200. In certain embodiments, one or more of the inserted instruments of the second multi-port device 8200 can pivotally move relative to the second housing 8201.

Further, the first multi-port device 8100 and/or the second multi-port device 8200 can incorporate various tracking mechanisms, such as electromagnetic (EM) tracked tips, fiber bragg grating, various sensors, etc., to assist in tracking orientation, location, and movement of the instruments. For example, the first multi-port device 8100 and the second multi-port device can include a first tracking device 8110 and a second tracking device 8210, respectively. Each of the first and second tracking devices 8110, 8210 can be configured to transmit a variety of signals that can be used to determine the relative location of the first and second multi-port devices 8100, 8200, at least one of a location, an orientation, and a motion of at least one instrument inserted into one of the first or second multi-port devices 8100, 8200 relative to the other one of the first or second multi-port devices 8100, 8200 or relative to at least one instrument inserted into the other one of the first or second multi-port devices 8100, 8200, or a combination thereof.

In use, with respect to the first tracking device 8110, as the third and fourth instruments 8206, 8208 are inserted into the second multi-port device and moved within the body, the first tracking device 8110 is configured to transmit a first signal 8112 to a controller 8002 that includes sensed data associated with the third instrument 8206, the fourth instrument 8208, or the second set of instruments. That is, the first tracking device 8110 is configured to sense, or otherwise track, the third instrument 8206, the fourth instrument 8208, or both (e.g., the second set of instruments), as such instrument(s) is/are inserted into and moved in the body with or relative to the second multi-port device 8200. Alternatively, or in addition, the first signal 8112 or an additional signal can include sensed data associated with the second multi-port device 8200. The first tracking device 8110 is also configured to transmit a second signal 8114 to the controller 8002 that includes sensed data associated with the first set of instruments and/or the first multi-port device 8100 itself.

Once the first and second transmitted signals 8112, 8114 are transmitted to and received by the controller 8002, the controller 8002, based on these signals, can calculate location, position, or motion of the third instrument 8206, the fourth instrument 8208, or both, relative to the first set of instruments and/or the first multi-port device 8100 itself. This creates one or more interrelationships between the first and second sets of instruments, and as a result, at least a portion of the first and second sets of instruments can work cooperatively together at one or more surgical sites and/or to carry out at least one surgical step of a surgical procedure. As shown in FIG. 62, and as described in more detail below, the first instrument 8106 and the third instrument 8206 are working cooperatively together to handoff the free end 15 of the colon 10, and the second instrument 8108 and the fourth instrument 8208 are shown working cooperatively together to purchase the same area of the colon 10.

Similarly, with respect to the second tracking device 8210, in use, as the first and second instruments 8106, 8108 are arranged within the body, the second tracking device 8210 is configured to transmit a third signal 8212 to the controller 8002 that includes sensed data associated with the first instrument 8106, the second instrument 8108, or the first set of instruments. That is, the second tracking device 8210 is configured to sense, or otherwise track, the first instrument 8106, the second instrument 8108, or both (e.g., the first set of instruments), as such instrument(s) is/are inserted into and moved within the body with or relative to the first multi-port device 8100. Alternatively, or in addition, the third signal 8212 or an additional signal can include sensed data associated with the first multi-port device 8100. The second tracking device 8210 is also configured to transmit a fourth signal 8214 to the controller 8002 that includes sensed data associated with the second set of instruments and/or the second multi-port device 8200 itself.

Once the third and fourth transmitted signals 8212, 8214 are transmitted to and received by the controller 8002, the controller 8002, based on these signals, can calculate location, position, or motion of the first instrument 8106, the second instrument 8108, or both, relative to the second set of instruments and/or the second multi-port device 8200 itself. This also creates one or more additional interrelationships between the first and second sets of instruments, and as a result, at least a portion of the first and second sets of instruments can work cooperatively together at one or more surgical sites and/or to carry out at least one surgical step of a surgical procedure.

The tracking mechanism of the first and second tracking devices 8110, 8210 can be any suitable mechanism. For example, the first tracking device 8110 can be configured to use magnetic sensing to detect a location, an orientation, or a motion of the third instrument 8206, the fourth instrument 8208, or both relative to the first multi-port device 8100 and/or to determine a location of the second multi-port device 8200 relative to the first multi-port device 8100. In such instances, the third instrument 8206, the fourth instrument 8208, or both and/or the second multi-port device 8200 includes a respective magnetic fiducial marker (not shown) that is configured to emit a respective magnetic field that can be detected by the first tracking device 8110. Alternatively, or in addition, the second tracking device 8210 can be configured to use a similar magnetic sensing mechanism to detect a location, an orientation, or a motion of at least one of the first and second instruments 8106, 8108 relative to the second multi-port device 8200 and/or to determine a location of the first multi-port device 8100 relative to the second multi-port device 8200. In some embodiment, a magnetic tracking system is configured to output a defined directional field relative to the magnet, its orientation, and near-by metallic systems. When the magnet is a permanent magnet, the field is of a predefined intensity, size, and orientation. Since the field is vector directional, a magnetic sensor within the directional field is configured to sense from the intensity, direction of the magnet vectors, and change of those measures over time where the sensor is within the directional field and orientation of the sensor with respect to the magnet. When the magnet is an electro-magnet, the intensity and field direction can be alternated and changed as directed, which mitigates metal impacts on the field and interferences as well as increase accuracy. "DESIGN OF A MAGNETIC FIELD-BASED MULTI DEGREE-OF-FREEDOM ORIENTATION SENSOR USING THE DISTRBUTED-MULTIPLE-POLE MODEL" from Proceedings of IMECE2007 2007 ASME International Mechanical Engineering Congress and Exposition Nov. 11-15, 2007, Seattle, Wash., USA illustrates and describes multi-degree freedom magnetic field tracking.

For another example, the first tracking device 8110 can be configured to use common anatomic landmarks to detect a location, an orientation, or a motion of the third instrument 8206, the fourth instrument 8208, or both relative to the first multi-port device 8100 and/or a location of the second multi-port device 8200 relative to the first multi-port device 8100. Alternatively, or in addition, the second tracking device 8210 can be configured to use common anatomic landmarks to detect a location, an orientation, or a motion of at least one of the first and second instruments 8106, 8108 relative to the second multi-port device and/or a location of the first multi-port device 8100 relative to the second multi-port device 8200. In some embodiments, the use of physiologic landmarks, and the distances and focal aspects of these landmarks with respect to an imaging system enable the imaging system to use the same imaging and distance measurements to determine the location and orientation of the instruments with respect to the anatomic location. These "reference" points would enable the system to using imaging & pre-operative imaging to scale the measures allowing them to more accurately correct for focus or depth measures of the system. In certain embodiments, 3D imaging systems and/or Lidar imaging systems can both be used to enhance or replace the optical measurements with respect to the surgical sites.

For yet another example, a structured light scan can be used to create a 3D map. Electromagnetic tracking of the first multi-port device 8100, the second multi-port device 8200 and the instruments 8106, 8108, 8206, 8208 (e.g., using one or more fiducial markers) provides 3D registration of the map. A perimeter can then be created around a critical structure using manual line or guides by confocal laser endomicroscopy to provide real time histology guidance. A line as registered in space can be communicated to the first multi-port device 8100 and the first and second instruments 8106, 8108 located in a different quadrant of an abdominal cavity than the second multi-port device 8200 and third and fourth instruments 8206, 8208, for mobilizing the colon 10 between the quadrants. Alternatively, or in addition, a line as registered in space can be communicated to the second multi-port device 8200 and the third and fourth instruments 8206, 8208 for mobilizing the colon 10 between the quadrants.

Alternatively, for yet another example, the physical mechanical linkage angles between robotic arms holding the surgical instruments and their predefined lengths can be used to enhance a visual system's calculation of depth and focal distance between surgical instruments and a surgical site. By using the linkage angles and predefined length, the system can achieve triangulation of the instruments within a patient in order to "calibrate" or compensate for optical losses by the imaging system.

For still another example, the first tracking device 8110 can be an optical sensor that can be configured to detect a fiducial marker on the third instrument, the fourth instrument, and/or the second multi-port device. Alternatively, or in addition, the second tracking device can be an optical sensor that is configured to detect a fiducial marker on the first instrument, the second instrument, and/or the first multi-port device. Any number of multi-ports and/or surgical instruments can be tracked in this way during performance of a surgical procedure.

In some embodiments, controlling cooperative surgical instrument interactions includes using smart device location cooperatively with scope tracking. In general, a non-magnetic sensing system can be used for 3D tracking to provide X, Y, Z coordinates using a single receiver and at least one emitter. A time-of-flight distance sensor system, discussed above, may thus be used.

For example, the non-magnetic sensing system can include ultrasonic sensor technology and radiofrequency (RF) sensor technology. A time of flight system can include an emitter and a receiver. To facilitate controlling cooperative surgical imaging interactions, the emitter includes an ultrasonic sensor (ultrasonic beacon) configured to transmit ultrasonic pulses, and the receiver includes an RF receiver configured to transmit an RF signal that commands the emitter to begin transmitting the ultrasonic pulses. The ultrasonic pulses are reflected back by object(s) within their range. The RF receiver is configured to record the ultrasonic pulses and to, based on the recorded ultrasonic pulses, calculate 3D coordinates (X, Y, Z) of the emitter. The sound propagation time of the ultrasonic pulses allows the RF receiver to calculate the 3D coordinates and to calculate distance to objects.

FIG. 62 illustrates a schematic view of the surgical system 8000 being used during a colon resection procedure. As explained above, the first tracking device 8110 of the first multi-port device 8100 can track the third instrument 8206, the fourth instrument 8208, or both, and the second tracking device 8210 of the second multi-port device 8200 can track the location of first instrument 8106, the second instrument 8108, or both, while the instruments are inserted into their respective port devices and arranged within the body. Further, the first and second instruments 8106, 8108 can include first and second graspers 8107, 8109, respectively, and third and fourth instruments 8206, 8208 can include third and fourth graspers 8207, 8209, respectively, to grasp the colon 10 and the mobilized section 12 thereof and help reattach the mobilized section 12 to the rectum 14.

As shown in FIG. 62, the first and second instruments 8106, 8108 passing through the first multi-port device 8100 are arranged in the upper left quadrant of the abdominal cavity to mobilize the transverse and descending colon 10. The third and fourth instruments 8206, 8208 passing through the second multi-port device 8200 are arranged in the lower left quadrant of the abdominal cavity to mobilize and create an incision along line IL to remove a tumor in the descending colon or sigmoid. Each set of instruments is accessing the abdominal cavity together through respective multi-port devices 8100, 8200, which allow for interrelating the instrument motions for each multi-port within its own quadrant. As illustrated, the first and second instruments 8106, 8108 have a first range of motion shown as dashed line RA, and the third and fourth instruments 8206, 8208 have a second range of motion shown as dashed line RB.

Due to the location of the first and second multi-port devices 8100, 8200 relative to each other and the resistive forces that are applied to the respective first and second sets of instruments during use, there is an overlapping range of motion shown as OR in which both sets of instruments can move within. As a result, based on the overlapping range of motion relative to the position of the colon, the instruments 8106, 8108, 8206, 8208 can interact during the handoff of the mobilization and retraction of the mobilized section 12 of the colon 10 transiting from the upper left quadrant to the lower right quadrant. Prior to and/or during the handoff, the first tracking device 8110 transmits the first and second signals 8112, 8114 to the controller 8002 and/or the second tracking device 8210 transmits the third and fourth signals 8212, 8214 to the controller 8002. The resulting interrelationship between the first and second multi-port devices 8100, 8200 (e.g., by way of the first and/or second tracking devices) enables triangulation and opposed motion of the instruments 8106, 8108, 8206, 8208 within their respective quadrant, as well as coordinated movement amongst at least a portion of the first and second set of instruments. As a result, the first and second sets of instruments work cooperatively together to interface with each other to control and/or stabilize the colon, or a portion thereof and/or to move the free end 15 toward the rectum for attachment. More specifically, as shown in FIG. 62, the second instrument 8108 and the fourth instrument 8208 are purchasing the same area of the colon 10, and the third instrument 8206 is ready to grasp the free end 15 of the colon 10 from the first instrument 8106 to move the free end 15 towards the rectum 14.

Any one or more of the exemplary surgical systems, port devices and related methods described herein, and variations thereof, can be implemented in conventional surgical procedures conducted by a medical professional as well as in robotic-assisted surgical procedures. Various teachings herein may be readily incorporated into a robotic surgical system such as one or more of the DAVINCI™ systems by Intuitive Surgical, Inc., of Sunnyvale, Calif., including their SP™ surgical system. Exemplary robotic surgical systems and related features, which may be combined with any one or more of the exemplary surgical access devices and methods disclosed herein, are disclosed in the following: U.S. Pat. No. 8,068,649, entitled "Method and Apparatus for Transforming Coordinate Systems in a Telemanipulation System," issued Nov. 29, 2011; U.S. Pat. No. 8,517,933, entitled "Retraction of Tissue for Single Port Entry, Robotically Assisted Medical Procedures," issued Aug. 27, 2013; U.S. Pat. No. 8,545,515, entitled "Curved Cannula Surgical System," issued Oct. 1, 2013; U.S. Pat. No. 8,551,115, entitled "Curved Cannula Instrument," issued Oct. 8, 2013; U.S. Pat. No. 8,623,028, entitled "Surgical Port Feature," issued Jan. 7, 2014, the disclosure of which is incorporated by reference herein; U.S. Pat. No. 8,771,180, entitled "Retraction of Tissue for Single Port Entry, Robotically Assisted Medical Procedures," issued Jul. 8, 2014, the disclosure of which is incorporated by reference herein; U.S. Pat. No. 8,888,789, entitled "Curved Cannula Surgical System Control," issued Nov. 18, 2014; U.S. Pat. No. 9,254,178, entitled "Curved Cannula Surgical System," issued Feb. 9, 2016; U.S. Pat. No. 9,283,050, entitled "Curved Cannula Surgical System," issued Mar. 15, 2016; U.S. Pat. No. 9,320,416, entitled "Surgical Instrument Control and Actuation," issued Apr. 26, 2016, the disclosure of which is incorporated by reference herein; U.S. Pat. No. 9,339,341, entitled "Direct Pull Surgical Gripper," issued May 17, 2016; U.S. Pat. No. 9,358,074, entitled "Multi-Port Surgical Robotic System Architecture," issued Jun. 7, 2016; U.S. Pat. No. 9,572,481, entitled "Medical System with Multiple Operating Modes for Steering a Medical Instrument Through Linked Body Passages," issued Feb. 21, 2017; U.S. Pat. No. 9,636,186, entitled "Multi-User Medical Robotic System for Collaboration or Training in Minimally Invasive Surgical Procedures," issued May 2, 2017; U.S. Pat. Pub. No. 2014/0066717, entitled "Surgical Port Feature," published Mar. 6, 2014, issued as U.S. Pat. No. 10,245,069 on Apr. 2, 2019, the disclosure of which is incorporated by reference herein; U.S. Pat. Pub. No. 2017/0128041, entitled "Laparoscopic Ultrasound Robotic Surgical System," published May 11, 2017; and U.S. Pat. Pub. No. 2017/0128144, entitled "Laparoscopic Ultrasound Robotic Surgical System," published May 11, 2017, the disclosure of which is incorporated by reference herein; and U.S. Pat. Pub. No. 2017/0128145, entitled "Laparoscopic Ultrasound Robotic Surgical System," published May 11, 2017. The disclosure of each of these references is incorporated by reference herein.

Surgical Sealing Systems for Instrument Stabilization

In various surgical procedures, a surgeon may need to direct two or more surgical instruments into a body cavity simultaneously in order to gain access to and provide effective treatment to tissue. It is generally desirable, however, to minimize the number of surgical openings that need to be formed in the patient (e.g., in a patient's abdominal wall) to thereby mitigate tissue trauma, cosmetic damage, and post-operation recovery time for the patient. Accordingly, surgical sealing systems are provided that generally include a sealing device having a seal housing with ports for receiving surgical instruments.

In general, the ports of the seal housing are designed to control or limit the motions of at least one instrument inserted through a respective port such that the instrument can stabilize another instrument inserted through a respective other port. Each of the ports can have a nominal size and shape and each can be configured to assume a selected size and/or shape that is different from the nominal size and/or shape. A person skilled in the art will understand that a nominal size and a nominal shape refer to a size and shape of a port without a force applied thereto. Similarly, a person skilled in the art will understand that a selected size and a selected shape of a port refers to a size and shape of a port when a force is applied to the port, such as by an instrument being inserted therethrough. It will be further understood by a person skilled in the art that the selected size and the selected shape will depend on the amount of force and the direction of force applied to the port, such as by the instrument.

The selected size and/or shape of each port can be constrained by the size and shape of each of the other plurality of ports. As a result, forces applied to one port can affect the size and shape of the other ports. The force can be applied by an instrument that is disposed within one port of the plurality of ports. The force applied thereto is therefore effective to change the size and/or shape of the ports based on the movement, direction, and force of the instrument. Since the ability to alter to the nominal shape of any one port is therefore constrained or limited by the size and/or shape of the other ports, a force applied to one instrument positioned within one of the plurality of ports is configured to stabilize at least one other instrument positioned within others of the plurality of ports.

Figure 63:
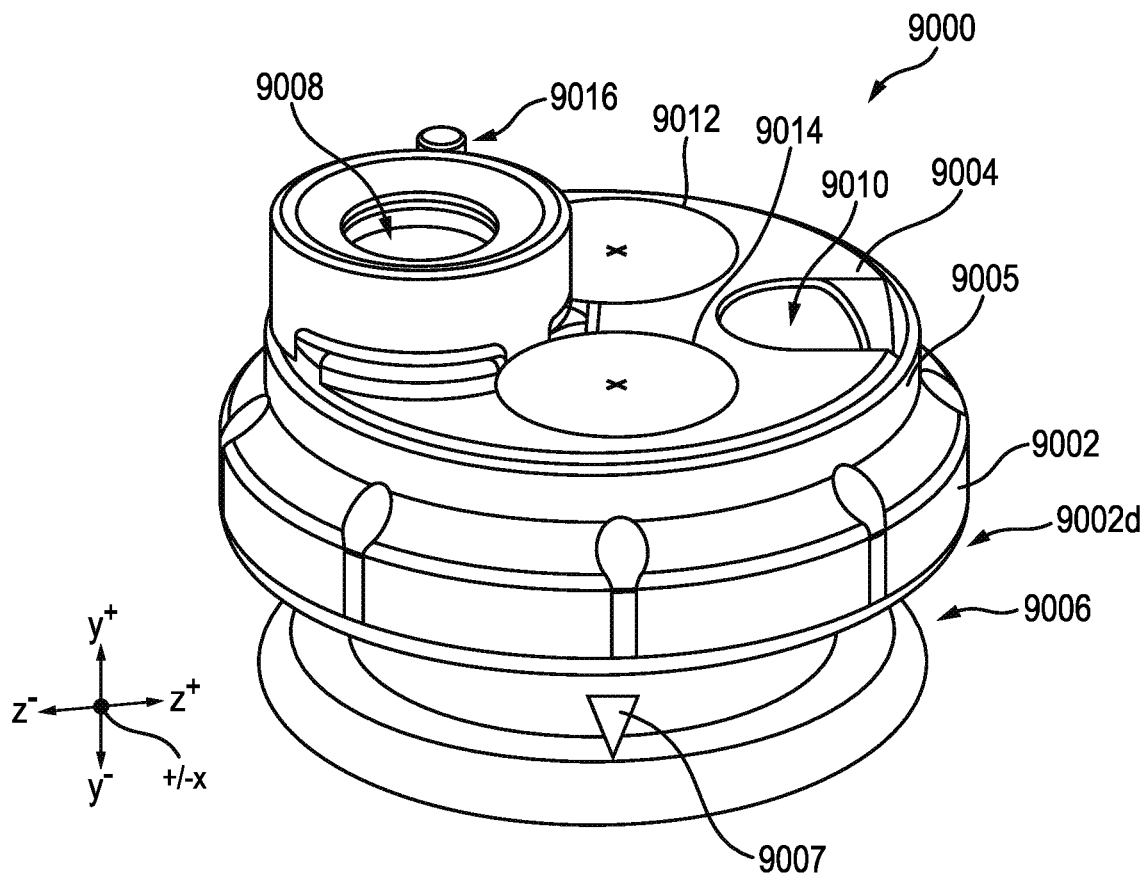
FIG. 63 is a schematic view of an exemplary embodiment of a surgical sealing system having a sealing device with ports extending therethrough.
Figure 64:
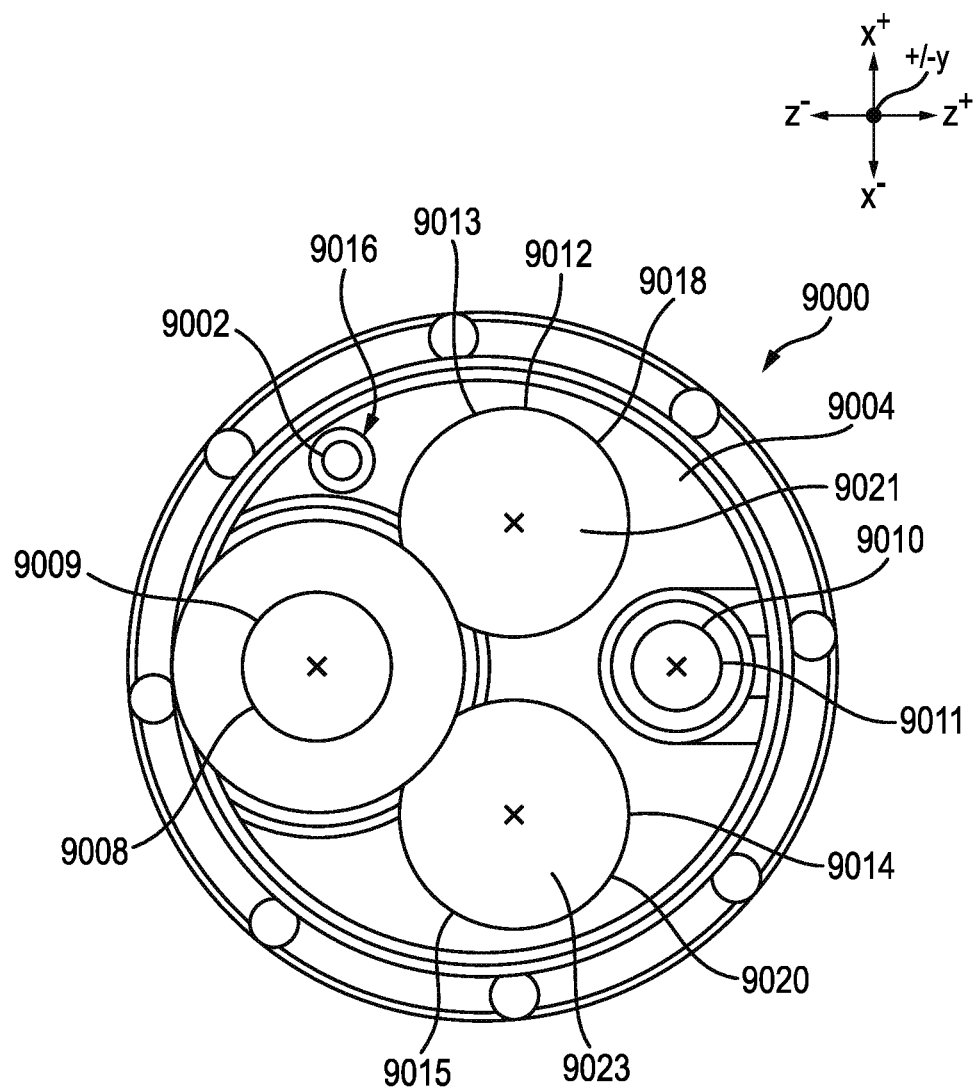
FIG. 64 is a top view of the sealing device of FIG. 29.

FIG. 63 and FIG. 64 illustrate a surgical sealing device 9000 that includes a seal housing 9002 with a predetermined size and shape and ports 9008, 9010, 9012, 9014 extending therethrough before any external force is applied to the ports. As shown in FIG. 63 and FIG. 64, the seal housing 9002 is illustrated in its predetermined size and shape. The seal housing 9002 can have a variety of configurations. For example, in this illustrated embodiment, the seal housing 9002 has an inner body member 9004 and an outer body member 9005 that is positioned about the inner body member 9004. In certain embodiments, the inner body member 9004 can be flexible relative to the outer body member 9005 or vice versa. Stated differently, the outer body member 9005 can be rigid relative to the inner body member 9004 or vice versa. In one embodiment, the inner body member and the outer body member are formed of the same material.

While any number of ports can be formed in the seal housing 9002, in this illustrated embodiment, four ports 9008, 9010, 9012, 9014 extend through sealing housing 9002. The ports can be formed in any suitable portion(s) of the seal housing 9002. For example, as shown in FIG. 63 and FIG. 64, all the ports 9008, 9010, 9012, 9014 extend through the inner body member 9004 of the seal housing 9002. Further, the ports 9008, 9010, 9012, 9014 can be movable with respect to the seal housing 9002 and each other, as discussed in more detail below. Such a configuration can help prevent interference between surgical instruments inserted through the various ports 9008, 9010, 9012, 9014 and can facilitate instrument positioning in a body cavity to which the surgical sealing device 9000 provides access thereto.

In some embodiments, as shown in FIG. 63 and FIG. 64, the sealing device 9000 can include a retractor 9006 that couples to and extends from a distal end 9002d of the seal housing 9002. The retractor 9006 can be configured to be placed in any opening within a patient's body, whether a natural body orifice or an opening made by an incision. As such, the retractor 9006 can function as a support structure for the seal housing 9002 and form a pathway through the opening in a patient's body so that surgical instruments can be inserted through the ports 9008, 9010, 9012, 9014 and into the interior body cavity or natural body lumen of the patient. Further, the retractor can additionally function as a retention element that is configured to affix the seal housing to tissue. In certain embodiments, in order to secure the seal housing within an incision or natural body orifice, a separate retention element 9007 can be used arranged on the exterior surface of retractor 9006, as shown in FIG. 63, and/or the exterior surface of the seal housing 9100.

The ports 9008, 9010, 9012, 9014 can be configured to form a seal around a surgical instrument inserted therethrough. For example, in some embodiments, at least one or more of the ports can include a sealing element, which can be positioned within the channel of the respective port. A sealing element can include at least one instrument seal and/or at least one channel seal, and can generally be configured to contact an instrument inserted through the sealing element's associated sealing port. For example, the port 9012 can include a sealing element 9021 arranged within the channel 9013 of the port 9012, and the port 9014 can include a sealing element 9023 arranged within the channel 9015 of the port 9014. While not illustrated, a person skilled in the art will appreciate that one or more of the other ports can include a sealing element (e.g., sealing element(s) structurally similarly to sealing elements 9021, 9023).

In some embodiments, the sealing element(s) can be in the form of a thin membrane formed of a flexible material which can be punctured or otherwise pierced by a surgical instrument. In addition, or alternatively, zero closure sealing elements such as a duck bill seal or other suitable seals for sealing in the absence of instrument can be used in association with the ports. The sealing elements can be positioned at any suitable location within the port.

The surgical sealing device 9000 can also include an insufflation port 9016 supported by the seal housing 9002, although a person skilled in the art will appreciate that the insufflation port 9016 can be located in other locations. A person skilled in the art will also appreciate that the insufflation port 9016 can have a variety of configurations. Generally, the insufflation port 9016 can be configured to pass an insufflation fluid into and/or out of a body cavity to which the surgical sealing device 9000 provides access to.

Figure 65:
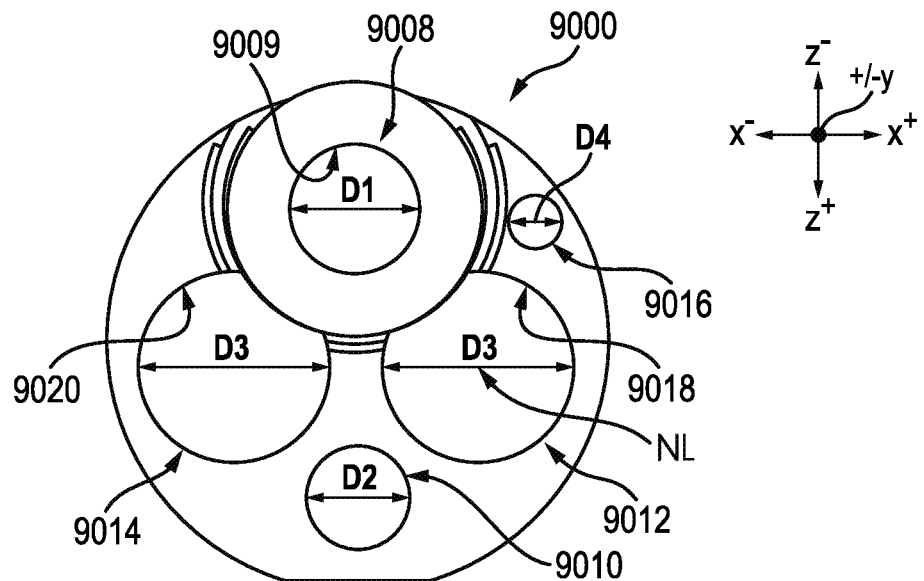
FIG. 65 is a schematic view of the ports of the surgical sealing port of FIG. 63.
Figure 66:
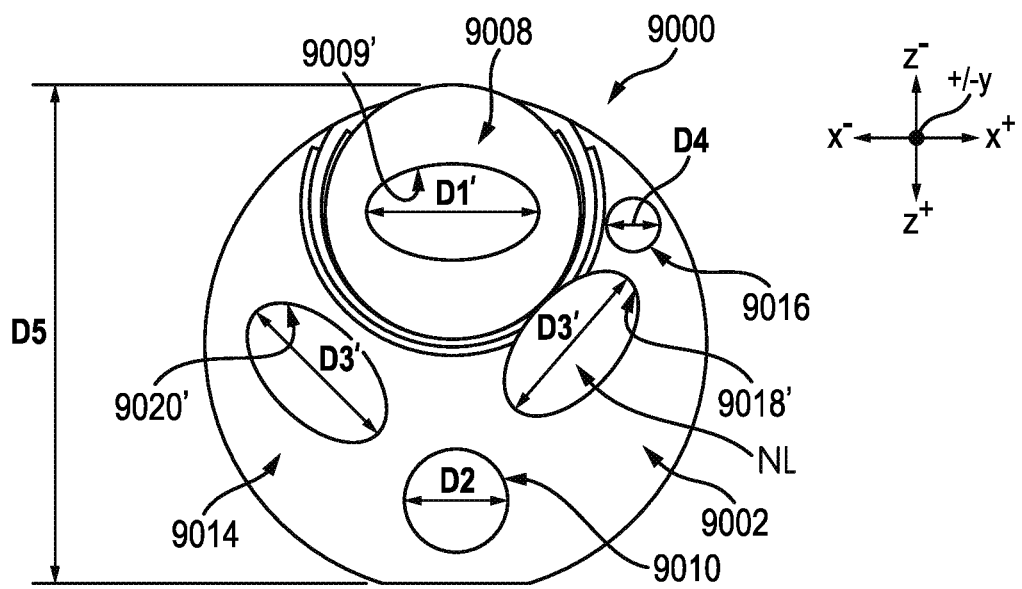
FIG. 66 is a schematic view of the altered ports of the surgical sealing port of FIG. 65.

FIG. 65 and FIG. 66 are schematic bottom views of the surgical sealing device 9000 with the retractor 9006 and the sealing elements 9021, 9023 removed. As stated above, the ports 9008, 9010, 9012, 9014 can have any combination of sizes and shapes. The port 9008 can have a diameter D1, port 9010 can have a diameter D2, and ports 9012, 9014 can have a diameter D3. The insufflation port opening 9016 can have any diameter D4. The diameter D3 of the ports 9012, 9014 can define a diameter of an orbital path of instruments arranged within the ports 9012, 9014.

When an instrument is inserted into one of the ports 9008, 9010, 9012, 9014, and a force is applied to the instrument, the port can adjust from a nominal size and shape to a selected size and shape based on the movement, direction, and force of the instrument. As shown in FIG. 65, the ports 9012, 9014 can include a nominal shape 9018, 9020, respectively. The nominal shape 9018, 9020 of the ports 9012, 9014 is the size and shape of the ports when no instrument is arranged therein and applying a force to the ports. Additionally, the port 9008 has a nominal size and shape 9009 when no instrument is arranged therein. In certain embodiments, the seal housing 9100 can have a diameter D5, which can be fixed or adjustable.

Each of the plurality of ports 9012, 9014 has a nominal size and shape 9018, 9020 and diameter D3, and each is configured to assume a selected size and/or shape 9018', 9020' that is different from the nominal size and shape 9018, 9020, wherein the selected size and/or shape 9018', 9020' of each port is constrained by the size and shape of each of the other plurality of ports. Additionally, the altered diameter D3' of the ports 9012, 9014 can further limit the planes in which an instrument can move. For example, as shown in FIG. 66, the ports 9012, 9014 have become narrower and oval shape, limiting an instrument within the ports to only be moveable in plane parallel to the diameter D3' of each port 9012, 9014. Since the limiting planes for ports 9012, 9014 are non-parallel, the instruments within the ports 9012, 9014 can be used to stabilize a third instrument within the port 9010.

An example of how the ports 9008, 9012, 9014 are altered from their nominal size and shapes 9009, 9018, 9020 to their selected size and shapes 9009', 9018', 9020' is as follows. An instrument (not shown) is inserted into each respective port 9008, 9010, 9012, 9014 parallel to the Y-axis. As the instrument arranged within the port 9008 is pivoted along the X-axis, the port 9008 changes from a nominal size and shape 9009 to a selected size and shape 9009' as a result of the instrument applying a force to the port 9008, causing the port 9008 react and change to an elongated shape along the X-axis. As the port 9008 is in the selected size and shape 9009', the instrument in the port 9012 can be moved along the Z-axis. However, due to the port 9008 already being elongated along the X-axis, the port 9012 will change from the nominal size and shape 9018 to the selected size and shape 9018'. As illustrated in FIG. 66, the port 9012 becomes elongated at an approximately 45° angle from the Z-axis, which was the intended axis of travel for the instrument. If the port 9008 was not in the selected size and shape 9009', then the selected size and shape of the port 9012 can be parallel to the Z-axis since the port 9008 would not be blocking the movement of the port 9012.

Additionally, the port 9014 operates similarly to the port 9012 where the intended direction of an instrument within the port 9014 is parallel to the Z-axis. However, similar to the port 9012, the selected size and shape 9020' of the port 9014 is limited by the selected size and shape 9009' of the port 9008. This forces the port 9014 to elongate at approximately a 135° angle relative to the Z-axis when moving from the nominal size and shape 9020 to the selected size and shape 9020'.

In certain embodiments, if the selected size and shape 9018' of the port 9012 was instead parallel to the X-axis, and the selected size and shape 9009' of the port 9008 remained parallel to the X-axis, then the selected size and shape of the port 9014 would be limited to moving only in the +Z axis and the +X-axis since the −Z axis would be blocked by the port 9008 and the −X-axis would be blocked by the port 9012.

In some embodiments, the sealing device can include restraining elements that can further control some but not all the movements and forces of the instruments inserted into the sealing device. For example, as shown in FIG. 64, port 9010 can includes a rigid structure 9011 encapsulated by the inner body member 9004. In other embodiments, one or more ports can include rigid restraining elements while one or more other ports can include flexible restraining elements that allows some movement in predefined directions of the ports with respect to each other while preventing other movements. In certain embodiments, the seal housing includes restraining features positioned in at least some directions tangential to the ports to substantially prevent stretching or movement of one port relative to another. This can be done in multiple planes for the same port or in selective directions to allow the port to float in other directions to improve maintenance of the seal around the instrument being inserted through the sealing device.

Figure 67:
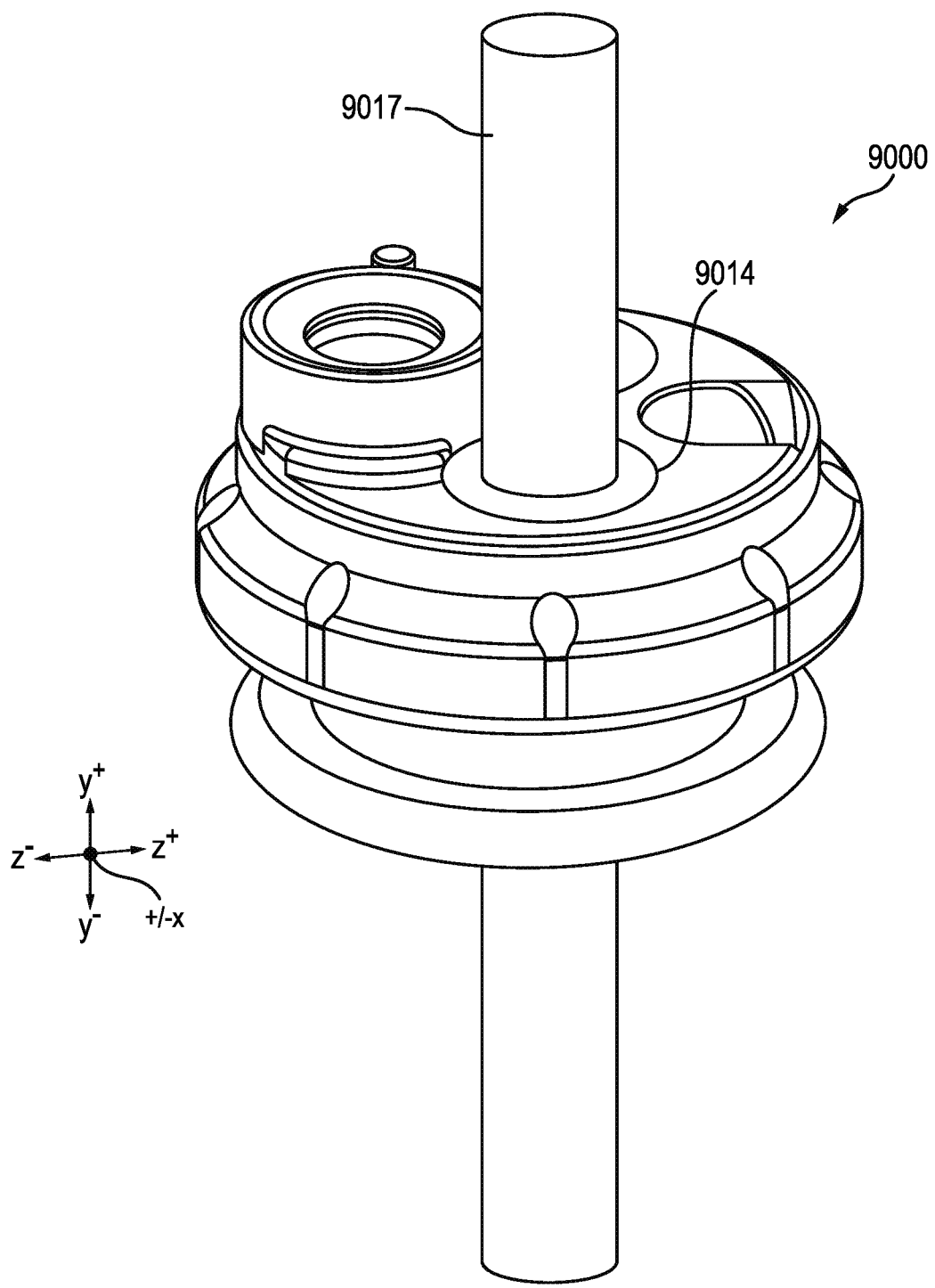
FIG. 67 is the sealing device of FIG. 29, showing an instrument inserted into one port of the sealing device.

In certain embodiments, one of the inserted instruments within one of the ports of the seal housing can function as a central anchoring tool. The central anchoring tool can be a designated instrument within one of the ports of the seal housing which supports the remaining instruments passing through other ports within the seal housing. In some embodiments, the central anchoring tool can be an instrument that does not interact with tissue directly, such as a camera or scope device passing through a port. Alternatively, the central anchoring tool can be an instrument (e.g., graspers, electrosurgical tool, etc.) that interacts with the tissue so that the additional instruments can be manipulated and supported without altering the anchor point of the seal housing. FIG. 67 illustrates an exemplary central anchor tool 9017 inserted into port 9014 of sealing device 9000.

Figure 68:
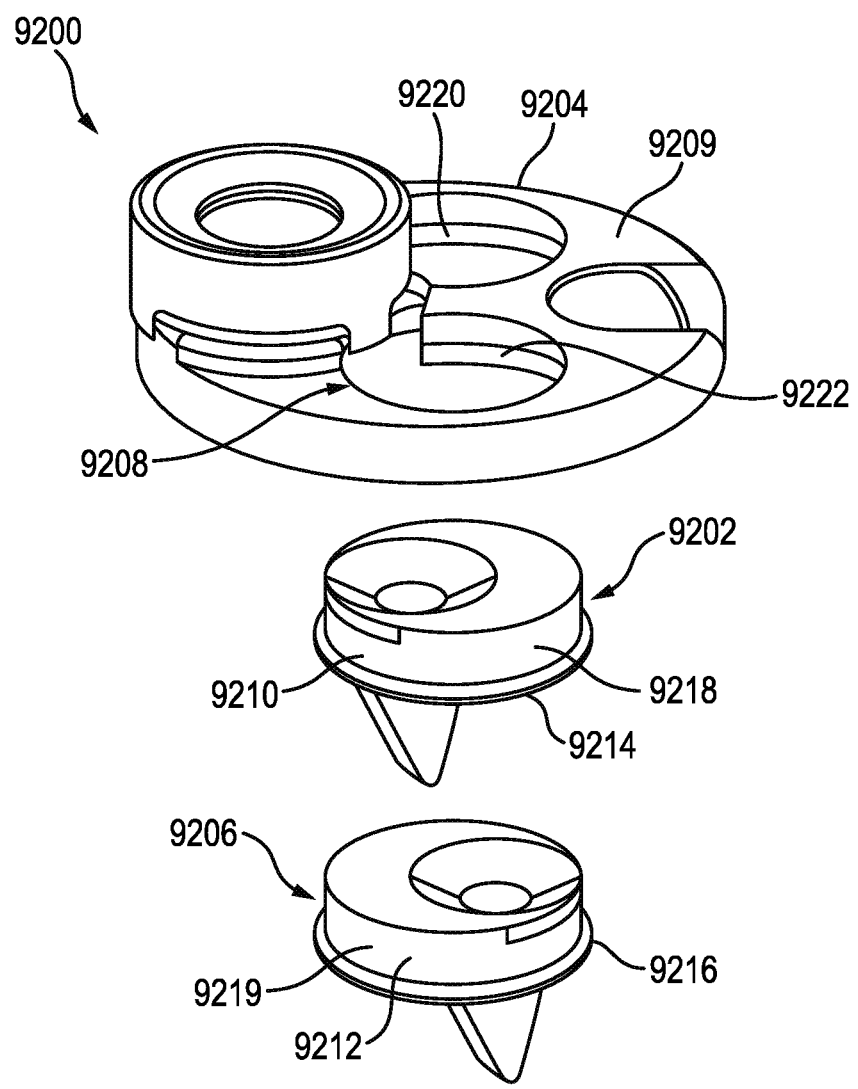
FIG. 68 is a schematic view of an exemplary embodiment of a surgical sealing system having threaded restraints.

In certain embodiments, at least one of the ports can include a threaded restraint arranged within a respective port, for example, as illustrated in FIG. 68. Aside from the differences described in detail below, sealing device 9200 can be similar to sealing device 9000 (FIG. 63) and therefore common features are not described in detail herein. As shown a first threaded restraint 9202 is configured to be arranged in a first port 9204 and a second threaded restraint 9206 is configured to be arranged in second port 9208. Each threaded restraint 9202, 9206 is configured to fixate an instrument arranged within each respective port 9204, 9208 to the seal housing 9209 and each of the threaded restraints 9202, 9206 is configured to contact the outer surface of the instrument. While the threaded restraints 9202, 9206 can have a variety of configurations, in this illustrated embodiment, each of the first and second threaded restraints 9202, 9206 includes a generally cylindrical body 9210, 9212 with threads 9214, 9216 on its outer surface 9218, 9219. The threads 9214, 9216 are configured to threadably engage corresponding threads 9220, 9222 on each respective first and second ports 9204, 9208.

During use, as an instrument is inserted into and rotated within the first port 9204 or the second port 9208, the respective first or second threaded restraint 9202, 9206 also rotates, thereby tightening the respective first or second threaded restraint 9202, 9206 relative to the seal housing 9209. As the threaded restraint 9202, 9206 tightens, the range of motion available to the inserted instrument decreases. Once the threaded restraint 9202, 9206 is fully tightened, the instrument is fixated to the seal housing 9209. While fixated, the instrument can serve as an anchor for the other instruments within the other ports 9204, 9208 of the seal housing 9209.

In other embodiments, the sealing systems can include integrated mechanism or electronic activated restriction systems to provide selective support or floating (e.g., moving) operation. For example, a fluidic coupling cylinder with a selectively sizeable valve can be employed on or in the seal housing to inhibit motion. In certain embodiments, a solenoid valve can be used to inhibit circular fluid motion.

In some embodiments, the ports can be configured to change shape and size in response to an external energy being applied to the ports. For example, each of the plurality of ports 9012, 9014 can be formed of a ferromagnetic material that is configured to be structurally altered in response to exposure to an electromagnet. During use, the electromagnet can apply a magnetic flux to the ports 9012, 9014 to cause the ports 9012, 9014 to alter their at least their shape compared to their shape when the electromagnet is switched off.

Any one or more of the exemplary surgical sealing systems, devices and related methods described herein, and variations thereof, can be implemented in conventional surgical procedures conducted by a medical professional as well as in robotic-assisted surgical procedures. Various teachings herein may be readily incorporated into a robotic surgical system such as one or more of the DAVINCI™ systems by Intuitive Surgical, Inc., of Sunnyvale, Calif., including their SP™ surgical system. Exemplary robotic surgical systems and related features, which may be combined with any one or more of the exemplary surgical access devices and methods disclosed herein, are disclosed in the following: U.S. Pat. No. 8,068,649, entitled "Method and Apparatus for Transforming Coordinate Systems in a Telemanipulation System," issued Nov. 29, 2011; U.S. Pat. No. 8,517,933, entitled "Retraction of Tissue for Single Port Entry, Robotically Assisted Medical Procedures," issued Aug. 27, 2013; U.S. Pat. No. 8,545,515, entitled "Curved Cannula Surgical System," issued Oct. 1, 2013; U.S. Pat. No. 8,551,115, entitled "Curved Cannula Instrument," issued Oct. 8, 2013; U.S. Pat. No. 8,623,028, entitled "Surgical Port Feature," issued Jan. 7, 2014, the disclosure of which is incorporated by reference herein; U.S. Pat. No. 8,771,180, entitled "Retraction of Tissue for Single Port Entry, Robotically Assisted Medical Procedures," issued Jul. 8, 2014, the disclosure of which is incorporated by reference herein; U.S. Pat. No. 8,888,789, entitled "Curved Cannula Surgical System Control," issued Nov. 18, 2014; U.S. Pat. No. 9,254,178, entitled "Curved Cannula Surgical System," issued Feb. 9, 2016; U.S. Pat. No. 9,283,050, entitled "Curved Cannula Surgical System," issued Mar. 15, 2016; U.S. Pat. No. 9,320,416, entitled "Surgical Instrument Control and Actuation," issued Apr. 26, 2016, the disclosure of which is incorporated by reference herein; U.S. Pat. No. 9,339,341, entitled "Direct Pull Surgical Gripper," issued May 17, 2016; U.S. Pat. No. 9,358,074, entitled "Multi-Port Surgical Robotic System Architecture," issued Jun. 7, 2016; U.S. Pat. No. 9,572,481, entitled "Medical System with Multiple Operating Modes for Steering a Medical Instrument Through Linked Body Passages," issued Feb. 21, 2017; U.S. Pat. No. 9,636,186, entitled "Multi-User Medical Robotic System for Collaboration or Training in Minimally Invasive Surgical Procedures," issued May 2, 2017; U.S. Pat. Pub. No. 2014/0066717, entitled "Surgical Port Feature," published Mar. 6, 2014, issued as U.S. Pat. No. 10,245,069 on Apr. 2, 2019, the disclosure of which is incorporated by reference herein; U.S. Pat. Pub. No. 2017/0128041, entitled "Laparoscopic Ultrasound Robotic Surgical System," published May 11, 2017; and U.S. Pat. Pub. No. 2017/0128144, entitled "Laparoscopic Ultrasound Robotic Surgical System," published May 11, 2017, the disclosure of which is incorporated by reference herein; and U.S. Pat. Pub. No. 2017/0128145, entitled "Laparoscopic Ultrasound Robotic Surgical System," published May 11, 2017. The disclosure of each of these references is incorporated by reference herein.

Figure 69:
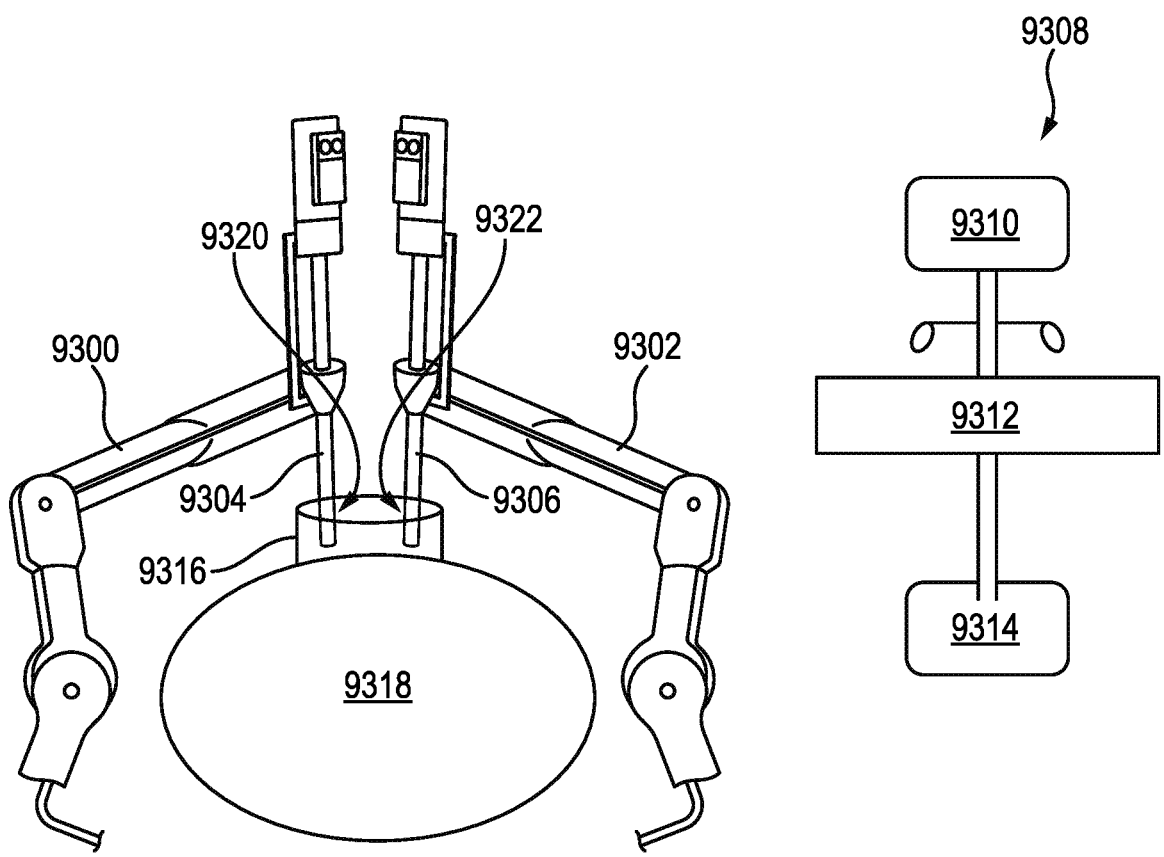
FIG. 69 is a schematic of an exemplary embodiment of a surgical robotic system that includes electromechanical arms each having a surgical instrument mounted thereto, and being wirelessly coupled to a control system.

FIG. 69 illustrates an exemplary embodiment of two robotic arms 9300, 9302, each having a surgical instrument 9304, 9306 attached thereto. The robotic arms 9300, 9302 can be wirelessly coupled to a control system 9308 having a console, with a display 9310, a controller 9312, and a user input device 9314. As shown, seal housing 9316 is partially inserted into a patient's body 9318, and each surgical instrument 9304, 9306 is inserted into a respective port 9320, 9322 of the seal housing 9316. In certain embodiment, the robotic arm(s) 9300, 9302 can be configured to create a compression loading around the ports to the prevent motion of the surgical instruments 9304, 9306.

In some embodiments, the controller 9312 is configured to receive a force reading from at least one of the plurality of ports 9008, 9010, 9012, 9014 (see FIG. 32) based on the movement, direction, and force of an instrument. For example, a force sensor (not shown) can be arranged on each robotic arm 9300, 9302 such that the force applied by each arm can be measured and sent to the controller 9312. Based on the measured force readings, the controller 9312 can determine a selected size and shape 9018', 9020' of ports 9012, 9014 (see FIG. 32) based on the amount of force the inserted instruments 9304, 9306 is applying to such ports 9012, 9014. Based on the determined selected size and shape 9018', 9020', the robotic arm(s) 9300, 9302 can be moved by the user in such a way that can alter the size and shape of the ports 9012, 9014 to stabilize at least one other instrument (not shown) positioned within at least one of the other ports 9008, 9010.

In certain embodiments, a tool driver restraint of a trocar access port can be used in combination with the surgical sealing device 9000. The trocar access port can be used to limit the force applied to an instrument shaft, allowing for a robotic arm to control the forces. The robotic arm restraint of the trocar access port can be used to allow the tool driver restraint to provide a stabilizing force to the surgical sealing device 9000, and not instruments inserted through the ports. In this embodiment, the diameter of the trocar access port is the key rigidity factor, rather than the diameter D5 of the surgical sealing device 9000. In certain embodiments, a cannula from which multiple instruments are deployed from does not have a static end lumen. Instead, the cannula is segmented into two or more curved members. The curved members can be driven to different depths within tissue to provide for a local force reaction to the instrument that is against that respective cannula segment.

In certain embodiments, one of the ports can further include a locking arm configured to lock a position of the at least one port relative to the seal housing. FIG. 70 illustrates an exemplary embodiment of a seal housing 9402 having a slot 9403 arranged therein such that a locking arm 9404 can pass through the slot 9403 and into the seal housing 9402. As shown, the locking arm 9404 include locking tabs 9406, which are configured to be selectively depressed to allow the locking arm 9405 to move relative to the seal housing 9402. Arranged at a distal end of the locking arm 9404 is a port 9412, with an instrument 9410 arranged within the port 9412. Due to the arrangement of the locking arm 9404, the port 9412 can be moved relative to the seal housing 9402. Other suitable configurations of a locking arm are also contemplated herein. For example, another configuration of the locking arm can include a base member having a plurality of rotatable rings. A top rotatable ring can contain a flexible sealing member, and one or more other rotatable rings each can have sealing arms extending therefrom and can be stacked one on top of the other beneath the sealing member. Each ring can be individually rotatable relative to the other rings and relative to the sealing member. Each of the sealing arms can include a sealing element positioned at one end thereof and configured to form a seal around an instrument inserted therethrough.

FIG. 71 and FIG. 72 illustrate an exemplary embodiment of a locking seal 9500 arranged within at least one port 9502 of a seal housing 9504. The locking seal 9500 can be in the form of a honeycomb locking structure which interacts with an instrument 9510 passing therethrough. The shape of the locking seal 9500 can be adjusted through the application of external energy, such as heat, light, or electrical current. As illustrated in FIG. 72, after exposure to external energy, the locking seal 9500 can deform into a first portion 9506 and a second portion 9508. When deformed, the second portion 9508 can contact the instrument 9510 so that the instrument 9510 is locked in position to the seal housing 9504.

In certain embodiments, a surgical sealing device can further include changeable ports as restraining means to control some, but not all movements and forces of instruments inserted therethrough the ports of the surgical sealing device. The ports of the surgical sealing device can include sections that are formed from 4D printed material and then over molded into an elastomer section of a seal with a port. 4D printing is an additive manufacturing process through which a 3D printed object includes transformable components (e.g., hydrogel, shape memory polymer) such that the 3D printed object transforms itself into another structure over the influence of external energy input as temperature, light or other environmental stimuli. 4D printing is similar to 3D printing in the sense that an object is also built layer by layer, but the object can then change over time after its initial manufacture. The object will change because it is printed with materials that have the ability to change when exposed to certain factors: such as heat, magnetic, water, light or another source of energy.

In some embodiments, the ports including a 4D printed material initially can be in a flexible condition to allow for introduction and manipulation of instruments through the ports. At defined conditions, the surgical sealing device can have an external energy applied thereto to alter the structure of the 4D printed material thus changing the geometry of the seal interface with respect to the instrument and/or lock to the seal itself. Additionally, the 4D printed material can interlock all the ports of a surgical sealing device and instruments inserted therein to create rigid restraints allowing some movement of the instruments in predefined directions with respect to each other while preventing some movements of the instruments in other directions. The prevention of movement in some directions allows for an instrument interacting with the 4D printed material to stabilize the other instruments within the surgical sealing device.

An example of how a 4D printed material would interact with an instrument within a port is as follows. A honeycomb structure can be formed of 4D printed material and integrated with the pivotal seals within each of the ports of the surgical sealing device. The honeycomb structure can be in a triangular or hexagonal pattern that allows an instrument shaft to freely pass through the seal. When needed or activated by heat, pressure, light or an energy source, the honeycomb structure alters its form for to make contact with the instrument shaft. Contact is made by the triangular or hexagonal honeycomb bending inward towards the instrument shaft, compressing the honeycomb structure and/or seal material against the shaft.

In certain embodiments, the surgical sealing device can include a 3D printed housing support structure having an elastomer structural member. The elastomer structural member can be pneumatically actuated between a fix and no fixed state in order to fixate instrument inserted through the ports of the surgical sealing system.

The surgical devices disclosed herein can be designed to be disposed of after a single use, or they can be designed to be used multiple times. In either case, however, the surgical devices can be reconditioned for reuse after at least one use. Reconditioning can include any combination of the steps of disassembly of the surgical devices, followed by cleaning or replacement of particular pieces and subsequent reassembly. In particular, the surgical devices can be disassembled, and any number of the particular pieces or parts of the surgical devices can be selectively replaced or removed in any combination. Upon cleaning and/or replacement of particular parts, the surgical devices can be reassembled for subsequent use either at a reconditioning facility, or by a surgical team immediately prior to a surgical procedure. Those skilled in the art will appreciate that reconditioning of a surgical device can utilize a variety of techniques for disassembly, cleaning/replacement, and reassembly. Use of such techniques, and the resulting reconditioned instrument, are all within the scope of the present application.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. It will be appreciated that the terms "proximal" and "distal" are used herein, respectively, with reference to the top end (e.g., the end that is farthest away from the surgical site during use) and the bottom end (e.g., the end that is closest to the surgical site during use) of a surgical instrument, respectively, that is configured to be mounted to a robot. Other spatial terms such as "front" and "rear" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Values or ranges may be expressed herein as "about" and/or from/of "about" one particular value to another particular value. When such values or ranges are expressed, other embodiments disclosed include the specific value recited and/or from/of the one particular value to another particular value. Similarly, when values are expressed as approximations, by the use of antecedent "about," it will be understood that here are a number of values disclosed therein, and that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value or within 2% of the recited value.

For purposes of describing and defining the present teachings, it is noted that unless indicated otherwise, the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety. Any patent, publication, or information, in whole or in part, that is said to be incorporated by reference herein is only to the extent that the incorporated material does not conflict with existing definitions, statements, or other disclosure material set forth in this document. As such the disclosure as explicitly set forth herein supersedes any conflicting material incorporated herein by reference.

Surgical Systems with Hybrid Intraluminal and Extraluminal Devices

In certain embodiments, surgical systems are configured to allow one or more endoluminal instruments to be introduced into an organ using a laparoscopic approach. That is, unlike conventional systems (e.g., systems with endoluminal instruments that are introduced through a natural orifice), the present surgical systems include endoluminal instruments that, when in use, approach and enter an organ (e.g., colon, bladder, stomach, and the like) through the laparoscopic side of the organ. This can provide bi-manual capability with reduced technical complexity.

Further, in some embodiments, laparoscopic instruments (e.g., grasper) and/or features (e.g., seals or stent-like structures) can be introduced into the extraluminal anatomical space and configured to provide local support for a portion (e.g., distal portion) of the endoluminal instrument(s). This local support can improve the intraluminal reaction load capabilities of the endoluminal instrument. That is, the local support can allow movement under load of the endoluminal instrument to enable rotating, longitudinal advancement, and contact between the end effector of the endoluminal instrument (e.g., ablation element or jaws) and the different intraluminal walls of the surgical site.

In one exemplary embodiment, the surgical system can generally include a first scope device having a first portion configured to be inserted into and positioned within an extraluminal anatomical space and a second portion distal to the first portion and configured to be positioned within an intraluminal anatomical space, and a second instrument configured to be inserted into the extraluminal anatomical space and configured to couple to and move the first portion of the first scope device within the extraluminal anatomical space to facilitate movement of the second portion of the first scope device while the second portion is positioned within the intraluminal anatomical space. In some embodiments, the first scope device can have a flexible body with a working channel extending therethrough and a first imaging system at a distal end thereof. The working channel being configured to enable a distal end of a first instrument to be inserted into and through the extraluminal anatomical space and into the intraluminal anatomical space such that the first instrument is present in both the extraluminal and intraluminal spaces.

During use, in general, the first portion of the first device scope is inserted into the extraluminal anatomical space, and the second portion of the first scope device is further inserted into an intraluminal anatomical space. A first instrument is then inserted through the working channel to position the first instrument within both the extraluminal and intraluminal spaces. Further, the second instrument is inserted into the extraluminal anatomical space. The second instrument can be inserted into the extraluminal anatomical space, prior to, concurrently with, or subsequent to the insertion of the first device scope or the insertion of the first instrument. After insertion, the second instrument is moved to cause the inserted second portion of the first scope device to move within the intraluminal anatomical space. Prior to insertion of any one of the first scope device, the first instrument, or the second instrument, the extraluminal space, the intraluminal space, or both, can be insufflated, e.g., via a fluid port operatively coupled to the first portion of the first scope device.

In another exemplary embodiment, the surgical system can generally include an anchor member configured to be positioned within an extraluminal anatomical space and in contact with a tissue wall that at least partially defines an intraluminal anatomical space, and a cannula having a first portion configured to be inserted into and positioned within the extraluminal anatomical space and a second portion distal to the first portion that is configured to be positioned within an intraluminal anatomical space, and a selectively deployable stabilizing member arranged on the first portion of the cannula in the extraluminal anatomical space that is configured to couple to the anchor member. In some embodiments, the cannula can be configured to allow a distal end of a first instrument to be inserted into and through the extraluminal anatomical space and into the intraluminal anatomical space such that the first instrument is present in both the extraluminal and intraluminal anatomical spaces. Further, the selectively deployable stabilizing member, when in a deployed state, can be configured to provide an anchor point for the first instrument to facilitate pivotal movement of the first instrument within the intraluminal anatomical space.

An exemplary surgical system can include a variety of features as described herein and illustrated in the drawings. However, a person skilled in the art will appreciate that the surgical systems can include only some of these features and/or it can include a variety of other features known in the art. The surgical systems described herein are merely intended to represent certain exemplary embodiments. Moreover, while the surgical systems are shown and described in connection with a colon, a person skilled in the art will appreciate that these surgical anchoring systems can be used in connection with any other suitable body cavities or organs.

Figure 73:
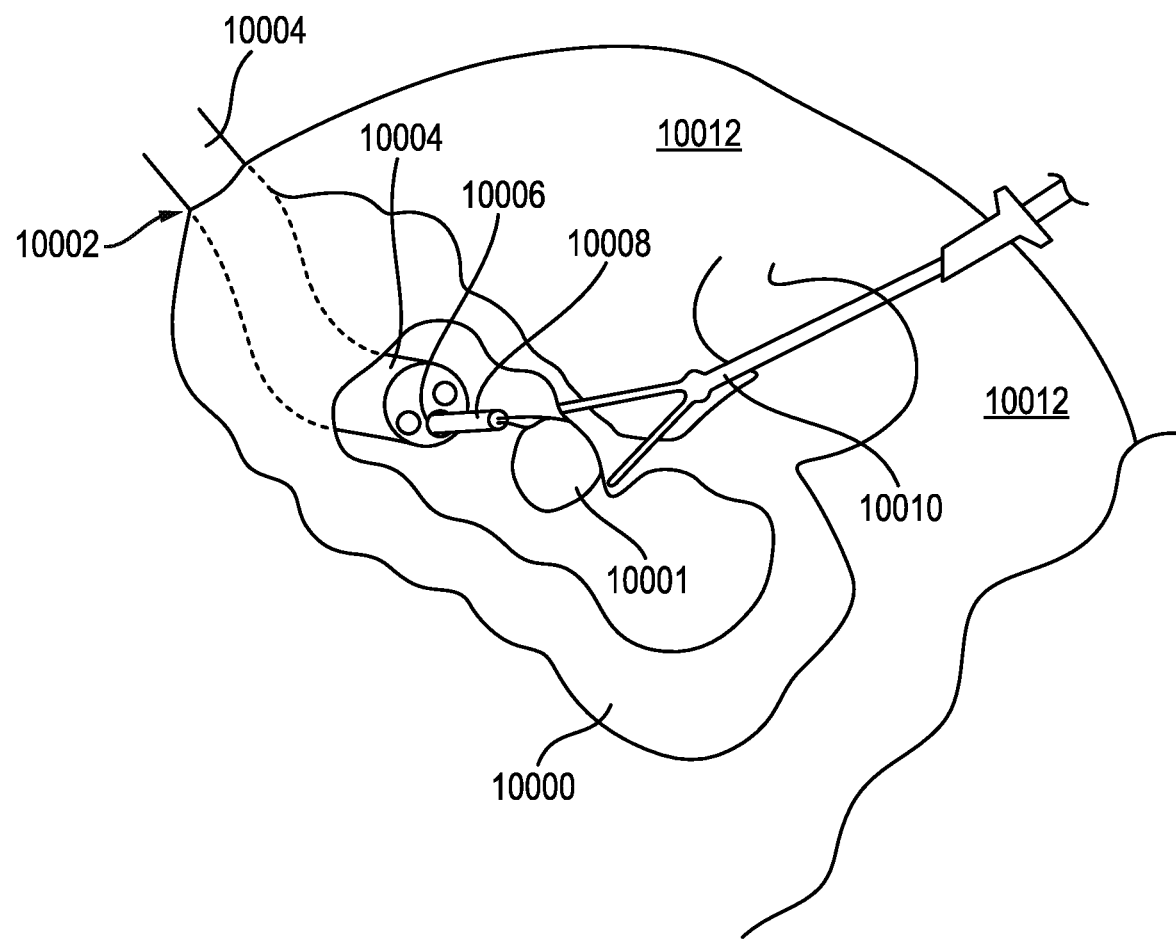
FIG. 73 is a schematic view of a conventional surgical system having endoscopic and laparoscopic instruments, showing a partial cut-away view of a colon with the endoscopic instrument inserted into the colon through a natural orifice and the laparoscopic instrument inserted through an abdominal cavity and interacting with the outer surface of the colon.

A surgical resection of a partial tissue wall thickness tumor is conventionally performed through a natural orifice. For example, as illustrated in FIG. 73, a colon 10000 includes a partial tissue wall tumor 10001. As shown, the conventional surgical system includes an endoscope 10004 that is inserted into the colon 10000 through the rectum 10002, and a first instrument 10008 that is passed through the working channel 10006 of the endoscope 10004. The first instrument 10008 engages the tumor 10001 for subsequent removal. A laparoscopic instrument 10010 (e.g., graspers) is inserted through an abdominal cavity 10012 and interacts with the colon 10000 to assist in stabilization of the tumor 10001 or to position the colon 10000 for tumor removal. As will discussed below in more detail, unlike these conventional surgical systems and procedures, the surgical systems disclosed herein are designed to remove diseased tissue (e.g., lesions or tumors) using endoluminal instruments that approach the natural lumen or organ from the laparoscopic side rather than through a natural orifice.

Figure 74:
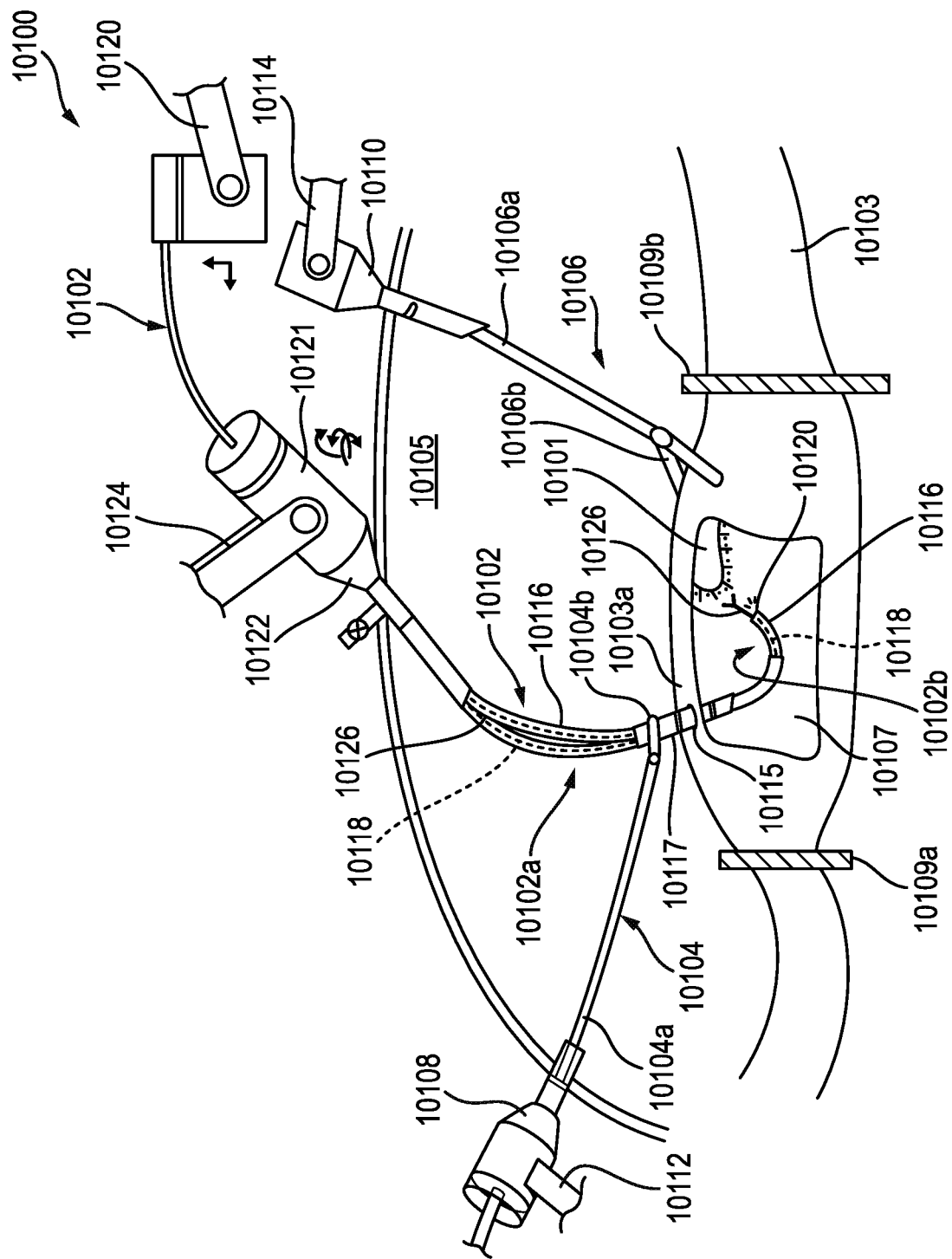
FIG. 74 is a schematic view of an exemplary embodiment of a surgical system having a laparoscopic instrument and an endoluminal instrument, showing the endoluminal instrument being inserted into a colon through a laparoscopic approach.

FIG. 74 illustrates an exemplary embodiment of a surgical system 10100 having a first scope device 10102 and first and second laparoscopic instruments 10104, 10106, which are being used in a surgical resection of a partial tissue wall thickness tumor 10101 located in a colon 10103. For purposes of simplicity, certain components of the surgical system 10010 are not illustrated.

The first and second laparoscopic instruments 10104, 10106 are each inserted into an abdominal cavity 10105 (e.g., an extraluminal anatomical space) through a respective first and second trocar 10108, 10110. The first and second trocar 10108, 10110 are each coupled to a respective robotic arm 10112, 10114. While the first and second laparoscopic instruments 10104, 10106 can have a variety of configuration, in this embodiment, each laparoscopic instrument 10104, 10106 has an elongate shaft 10104a, 10106a with an end effector 10104b, 10106b at a distal end thereof. While each end effector 10104b, 10106b can have a variety of configurations, in this illustrated embodiment, each end effector 10104b, 10106b is the form of a set of movable jaws. Further, while two laparoscopic instruments are shown, in other embodiments, any number of laparoscopic instruments can be used (e.g., one, three, four, etc.).

The first scope device 10102 includes a flexible body 10116 with a working channel extending 10118 therethrough and a first imaging system 10120 (e.g., a camera) at a distal end thereof. The flexible body can be formed of any suitable flexible material(s). As shown, during use, a proximal end of the first scope device 10102 is coupled to a first robotic arm 10120 and the first scope device 10102 extends into and through a trocar 10122 coupled to a second robotic arm 10124 and into the abdominal cavity 10105 (e.g., an extraluminal anatomical space). The trocar 10122 includes a fluid port 10123 that is configured to insufflate the abdominal cavity 10105 prior to or currently with the insertion of any devices or instruments into the abdominal cavity 10105. In other embodiments, the abdominal cavity 10105 can be insufflated using trocar 10112, 10114, or any other suitable insufflating mechanisms and devices.

The first scope device 10102 is further inserted through a wall 10103a of the colon 10103 and into a colon cavity 10107 (e.g., intraluminal anatomical space). While the first scope device 10102 can be inserted directly through an otomy 10115 made in the colon wall 10103a, in this illustrated embodiment, a lumen of a cannula 10117 that is inserted through the otomy 10115 and partially into the colon cavity 10107. As such, the first scope device 10102 is inserted into the colon cavity 10107 through the lumen of the cannula 10117.

As shown, the first scope device 10102 has a first portion 10102a that is present within the abdominal cavity 10105 and a second portion 10102b that is distal to the first portion 10102a and present within the colon cavity 10107. That is, the first scope device 10102 is designed to be introduced into the colon 10103 through a laparoscopic approach. Prior to insertion of the second portion of the first scope device, the colon can be insufflated, e.g., by introduction of fluid through a fluid port (not shown) or lumen (not shown) previously inserted into the colon. After insufflation, sealing clips 10109a and 10109b can be positioned on opposing ends of the insufflated region of the colon 10103.

In some embodiments, the trocar 10122 can provide structural support for the first portion 10102a of the first scope device 10102. Further, the first portion 10102a of the first scope device 10102 can be driven from the one or more tool drivers (now shown) positioned within the motor housing 10121 positioned between the robotic arm 10124 and the trocar 10122.

Since the first scope device 10102 has a flexible body 10116 that is present within both the abdominal cavity 10105 and the colon cavity 10107, a cooperative support element is needed such that the second portion 10102b of the first scope device 10102 can move within the colon cavity 10107. In this illustrated embodiment, the cooperative support element is the first laparoscopic instrument 10104. That is, as shown, the jaws of the end effector 10104b grasp to, and thus couple the first laparoscopic instrument 10104 to the first portion 10102a of the first scope device 10102.

While the jaws of the end effector can grasp the first portion 10102a of the first scope device 10104 at various locations, in this illustrated embodiment, the first laparoscopic instrument 10104 is coupled to the first portion 10102 at a predefined location that is within the abdominal cavity 10105 (e.g., an extraluminal anatomical space) and directly adjacent the colon wall 10103a. More specifically, the predefined location is proximate to the otomy 10115 made in the colon wall 10103a. In this embodiment, the elongate shaft 10104a of the first laparoscopic instrument 10104 is rigid and therefore can provide support to the first scope device and move the first portion of the first scope device within the abdominal cavity (e.g., an extraluminal space) to facilitate movement of the second portion of the first scope device 10102 within the colon cavity 10107 (e.g., an intraluminal anatomical space).

In some embodiments, the fixation provided by the first laparoscopic instrument 10104 can keep the otomy 10115 upright to prevent escape of the colon contents into the abdominal cavity 10105. Alternatively, or in addition, the jaws of the end effector 10104b can be configured to act as a wound protector that can prevent the first scope device 10102 from applying inappropriate loads to the otomy edges.

As further shown in FIG. 74, once the second portion 10102b of the first scope device 10102 is positioned within the colon cavity 10107, an instrument 10126 can be inserted through the working channel 10118 of the first scope device 10102 and into the colon cavity 10107. Once inserted, the instrument 10126 can interact with the tumor 10102 for subsequent removal. Further, the jaws of the end effector 10106b of the second laparoscopic device 10106 can interact with the colon 10103 to help stabilize the colon 10103 for removal of the tumor 10102.

Figure 75:
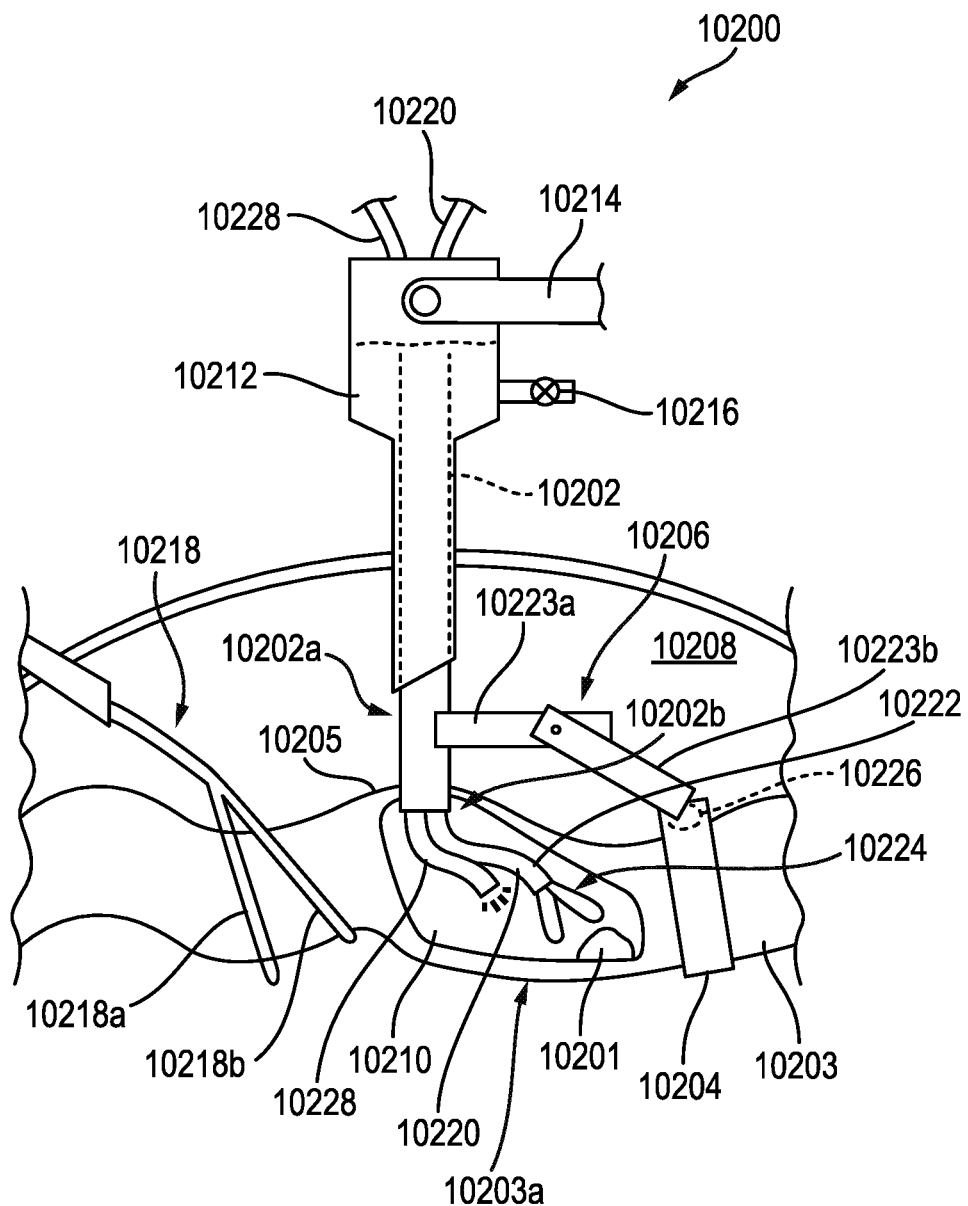
FIG. 75 is a schematic view of an exemplary embodiment of a surgical system having a laparoscopic instrument and two endoluminal instruments, showing the endoluminal instruments being inserted into a colon through a laparoscopic approach.

In some embodiments, localized mechanical docking can be used as a mechanism for stabilizing a flexible endoluminal device or instrument or device, for example, as illustrated in FIG. 75.

FIG. 75 illustrates an exemplary embodiment of a surgical system 10200 that is configured to allow laparoscopic access to an endoluminal surgical site. The surgical system 10200 includes a cannula 10202, an anchor member 10204, and a selectively deployable stabilizing member 10206, which are being used in a surgical resection of a partial tissue wall thickness tumor 10201 located in a colon 10203.

The cannula 10202 can have a variety of different configurations. In this illustrated embodiment, the cannula 10202 has a first portion 10202a configured to be inserted into and positioned within an abdominal cavity 10208 (e.g., an extraluminal anatomical space) and a second portion 10202b distal to the first portion 10202a that is configured to be positioned within a cavity 10210 of the colon 10203 (e.g., an intraluminal anatomical space). The cannula 10202 can be formed of any suitable material. As shown, during use, the cannula 10202 is inserted through a trocar 10212 that is coupled to a robotic arm 10214 and into the abdominal cavity 10208. The trocar 10212 includes a fluid port 10216 that is configured to insufflate the abdominal cavity 10208 prior to or currently with the insertion of any devices or instruments into the abdominal cavity 10208. In other embodiments, the abdominal cavity 10208 can be insufflated using another trocar or any other suitable insufflating mechanisms and devices.

The cannula 10202 is further inserted through a wall 10205 of the colon 10203 and into the colon cavity 10210 (e.g., an intraluminal anatomical space). Thus, the cannula 10202 is designed to be introduced into the colon 10203 through a laparoscopic approach. Further, once the first and second portions 10202a, 10202b are positioned within the abdominal cavity 10208 and the colon cavity 10201, respectively, a first instrument 10220 can be inserted therethrough such that a distal end of the first instrument 10220 can be positioned within the colon cavity 10210 and used to remove the tumor 10201.

As shown, the cannula 10202 allows a distal end of the first instrument 10220 to be introduced into the colon 10203 through the abdominal cavity 10208, and therefore the first instrument 10220 is present in both the abdominal cavity 10208 and the colon cavity 10210. While the first instrument 10220 can have a variety of configurations, in this illustrated embodiment, the first instrument 10220 includes a flexible shaft 10222 with a pair of jaws 10224 at a distal end thereof. The pair of jaws 10224 are configured to interact with the tumor 10201.

Prior to insertion of the second portion 10202b of the cannula 10202, the colon 10203 can be insufflated, e.g., by introduction of fluid through a fluid port (not shown) or lumen (not shown) previously inserted into the colon. After insufflation, the insufflated region 10203a can be sealed. For example, in this illustrated embodiment, the insufflated region 10203a is sealed by jaws 10218a, 10218b of a laparoscopic device 10218 that is inserted into the abdominal cavity 10208 with the jaws 10218a, 10218b grasping one end of the region and by the anchor member 10204 clipped about an opposing end of the region. As such, in this illustrated embodiment, the anchor member 10204 can function as both an anchor and a seal. In other embodiments, a separate sealing element can be used.

The anchor member 10204 can have a variety of configurations. In this illustrated embodiment, the anchor member 10202 is the form of a clip that is positioned within the abdominal cavity (e.g., an extraluminal anatomical space) and is in contact with the outer surface of the tissue wall 10203a of the colon 10203. Prior to, concurrently with, or subsequent to the insertion of the cannula 10202, the anchor member 10204 can be inserted into the abdominal cavity 10208 and placed in contact with the colon wall 10205 (e.g., arranged about a portion of the colon 10203).

As further shown in FIG. 75 the selectively deployable stabilizing member 10206 is arranged on the first portion 10202a of the cannula 10202, and thus within the abdominal cavity 10208 (e.g., an extraluminal anatomical space). The selectively deployable stabilizing member 10206 can have a variety of configurations. In this illustrated embodiment, the selectively deployable stabilizing member 10206 includes first and second links 10223a, 10223b pivotally connected to other, in which the first link 10223a is directly coupled to the cannula 10202. As such, the selectively deployable stabilizing member 10206 can move from an undeployed state to a deployed state (FIG. 75).

In use, when in a deployed state (FIG. 75), the selectively deployable stabilizing member 10206 is configured to couple to the anchor member 10204. This coupling provides an anchor point for the first instrument 10220 that is inserted through the cannula 10202. Since the first instrument 10220 includes a flexible shaft 10222, the anchor point allows the first instrument 10220 to pivotally move within the colon cavity 10210 with respect to the cannula 10202.

The selectively deployable stabilizing member 10206 can be coupled to the anchor member 10204 in a variety of ways. For example, in certain embodiments, the anchor member 10204 can include a magnet 10226 that is configured to couple the selectively deployable stabilizing member 10206 to the anchor member 10204 when the selectively deployable stabilizing member 10206 is in a deployed state. In other embodiments, any other suitable coupling mechanisms can be used.

Further, additional instruments or devices can be inserted through the cannula 10202 (e.g., through one or more lumens of the cannula). For example, as shown in FIG. 75, a first scope device 10228 can be inserted into and through the cannula 10202 such that a first portion of the first scope device 10228 is present in the abdominal cavity (e.g., an extraluminal anatomical space), and a second portion of the first scope device 10228 that is distal to the first portion is positioned in the colon cavity (e.g., an intraluminal anatomical space).

Figure 76:
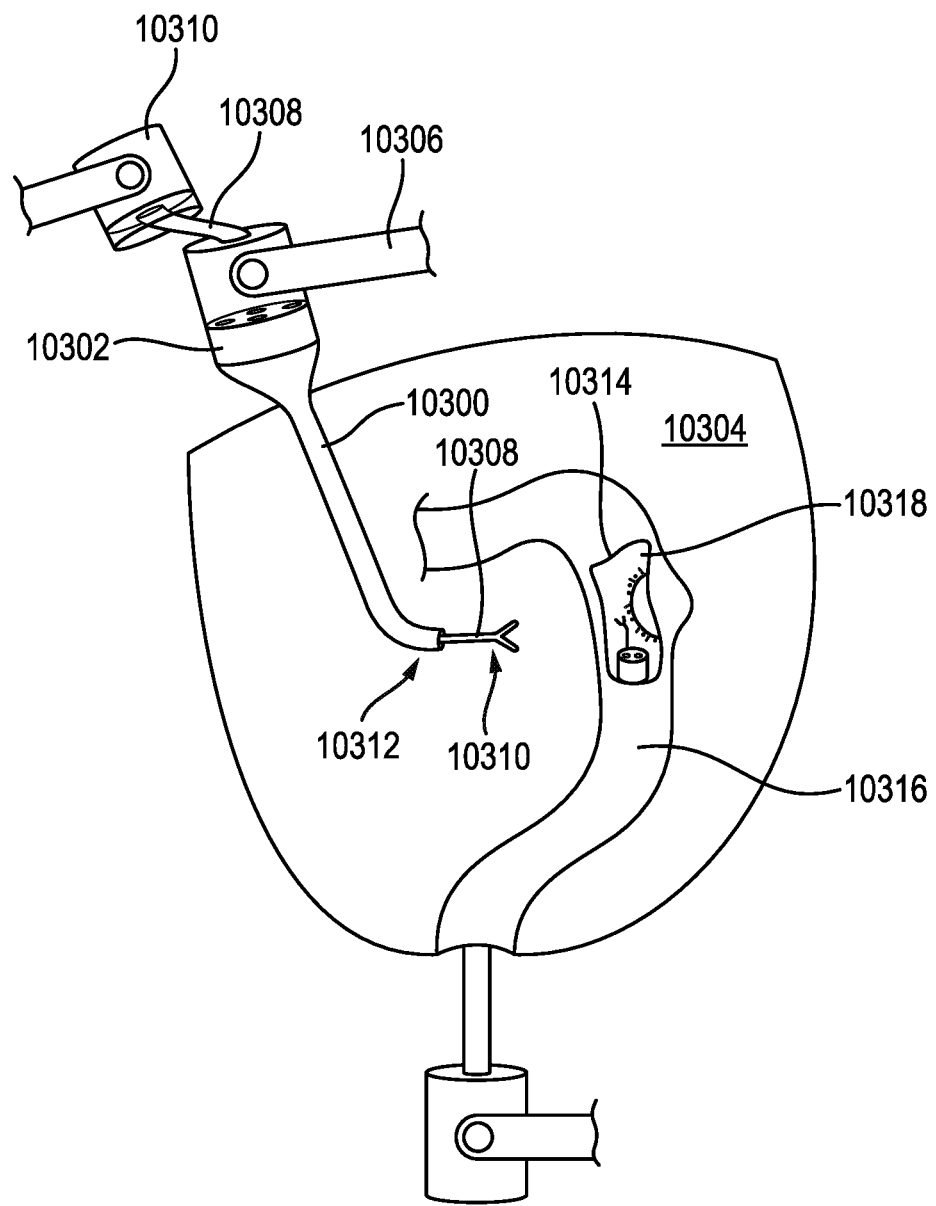
FIG. 76 is schematic view of an exemplary embodiment of a surgical system.

In other embodiments, a robotically steerable and lockable cannula can be used to introduce an endoluminal instrument into an intraluminal anatomical space using an laparoscopic approach. For example, as illustrated in FIG. 76, a robotically steerable and lockable cannula 10300 can be inserted through a first trocar 10302 and into an extraluminal anatomical space 10304 (e.g., an abdominal cavity). The first trocar 10302 is coupled to a first robotic arm 10306. As further shown, a first instrument 10308 can be coupled to a second robotic arm 10310 and inserted through the first trocar 10302. The first instrument 10308 can be inserted further through the robotically steerable and lockable cannula 10300 such that a distal end 10310 of the first instrument 10308 extends through a distal end 10312 of the cannula 10300. As a result, the first instrument 10308 is structurally guided and supported by the steerable and lockable distal end 10302 of the cannula 10300. The movement of the cannula 10300 (e.g., by the first robotic arm 10306) can therefore guide the distal end 10312 of the first instrument 10308 through an otomy 10314 made in an organ 10316 and into the organ cavity 10318, and the movement of the second robotic arm 10310 can cause the distal end 10312 of the first instrument 10308 to move within the organ cavity 10318 relative to the distal end 10312 of the cannula 10300.

Surgical Systems with Intraluminal and Extraluminal Cooperative Instruments

Devices, systems, and methods for multi-source imaging provided herein allow for cooperative surgical visualization. In general, in cooperative surgical visualization, first and second imaging systems (e.g., first and second scope devices) each gathering images of a surgical site are configured to cooperate to provide enhanced imaging of a surgical site. The cooperative surgical visualization may improve visualization of patient anatomy at the surgical site and/or improve control of surgical instrument(s) at the surgical site.

In certain embodiments, surgical systems are configured to be arranged within two separate anatomical areas for conducting one or more surgical tasks. A surgical visualization system can allow for intraoperative identification of critical structure(s) (e.g., diseased tissue, anatomical structures, surgical instrument(s), etc.). The surgical visualization system may thus enable enhanced intraoperative decision making and improved surgical outcomes. The surgical visualization system can provide advanced visualization capabilities beyond what a medical practitioner sees with the "naked eye" and/or beyond what an imaging system can recognize and/or convey to the medical practitioner. The surgical visualization system can augment and enhance what a medical practitioner is able to know prior to tissue treatment (e.g., dissection, etc.) and, thus, may improve outcomes in various instances. As a result, the medical practitioner can confidently maintain momentum throughout the surgical procedure knowing that the surgical visualization system is tracking a critical structure, which may be approached during dissection, for example. The surgical visualization system can provide an indication to the medical practitioner in sufficient time for the medical practitioner to pause and/or slow down the surgical procedure and evaluate the proximity to the critical structure to prevent inadvertent damage thereto. The surgical visualization system can provide an ideal, optimized, and/or customizable amount of information to the medical practitioner to allow the medical practitioner to move confidently and/or quickly through tissue while avoiding inadvertent damage to healthy tissue and/or critical structure(s) and, thus, to minimize the risk of harm resulting from the surgical procedure.

In general, the surgical systems provided herein generally include a first scope device configured to be positioned in both the intraluminal and extraluminal anatomical spaces and to transmit image data of a first scene within its field of view, a second scope device configured to be inserted into the extraluminal anatomical space and transmit image data of a second, different scene within its field of view, and a controller configured to receive the transmitted data and determine the relative distance between the first and second scope devices to provide a merged image. The merged image can be at least a portion of at least the first scope device and the second scope device in a single scene, and at least one of the first scope device and the second scope device in the merged image is a representative depiction thereof. Thus, the merged image may thus provide two separate points of view of the surgical site, which can conveniently allow a medical practitioner to view only one display instead of multiple displays. Further, within that one display, the merged image allows a medical practitioner to coordinate relative location and/or orientation of at least the first and scope devices arranged at or proximate to the surgical site. In certain embodiments, a surgical system can include a tracking device associated with one of the first scope device or the second scope device and configured to transmit a signal indicative of a location of the one of the first scope device or the second scope device relative to the other one of the first scope device or the second scope device.

The surgical systems provided herein can also be used in various robotic surgical systems, such as those discussed above, and can incorporate various tracking and/or imaging mechanisms, such as electromagnetic (EM) tracked tips, fiber bragg grating, virtual tags, fiducial markers, use of probes, identification of known anatomy, various 3D scanning techniques such as using structured light, various sensors and/or imaging systems discussed previously, etc., to assist in tracking movement of the instruments, endoscopes, and laparoscopes relative to each other and/or the overall system. The tracking mechanisms can be configured to transmit tracking data from both a laparoscope and an endoscope so that the location of either scope can be determined relative to the other scope. Additionally, critical structures within the field of view of either scope (e.g., diseased tissue, surgical instruments, anatomical structures) can be tracked by the scope which has such critical structures within their field of view. In total, the surgical systems herein can track the objects within a field of view of each scope, and the relative position of each scope. Therefore, the totality of the tracking data allows the system to calculate the distance of a critical structure from a scope which does not have a critical structure in its field of view based on the tracking data collected by the other scope.

In one exemplary embodiment, the surgical system also includes a first instrument and a second instrument. The first instrument is configured to be inserted into and through the extraluminal anatomical space and into the intraluminal anatomical space such that the first instrument is present in both the extraluminal and intraluminal anatomical spaces. The second instrument is configured to be inserted into the extraluminal anatomical space.

Further, in some embodiments, an imaging system (e.g., a camera) can be arranged on the second portion of the first scope device and configured to transmit image data of a scene within a field of view of the first scope device. Alternatively, or in addition, an imaging system (e.g., a camera) can be arranged on the second scope device and configured to transmit image data of a scene within a field of view of the second scope device. This can allow cooperative visualization between the instruments working in the extraluminal anatomical space and instruments working in the intraluminal anatomical space, and further enable the instruments to work cooperatively together on a single surgical site.

In various embodiments, the surgical systems provided herein includes a controller. The surgical system, the controller, a display, and/or the various instruments, endoscopes, and laparoscopes can also be incorporated into a number of different robotic surgical systems and/or can be part of a surgical hub, such as any of the systems and surgical hubs discussed above. The controller in general is configured to merge first and second scenes from an endoscope and a laparoscope, respectively, to visually create a merged image between the first and second scenes. The controller is configured to receive the tracking data detailed above, and in combination with the first and second scenes, generate the merged image containing a representative depiction of at least the endoscope or laparoscope, and any structures within field of view of the scope which is visually impaired by a tissue wall. For example, if the merged image was from a point-of-view of the endoscope, the merged image is the live image stream of what the endoscope is viewing, while including an overlay of the orientations and locations of laparoscopically arranged surgical instruments and a laparoscope, if present.

During use, in general, the first portion of the first scope device scope is inserted into an extraluminal anatomical space, and a second portion (e.g., a portion that is distal to the first portion) of the first scope device is inserted into an intraluminal anatomical space. Further, the second scope device is inserted into the extraluminal anatomical space. Further, the first instrument is inserted into and through the extraluminal anatomical space and into the intraluminal anatomical space such that the first instrument is present in both the extraluminal and intraluminal anatomical spaces. For example, the first instrument can be inserted through a working channel of the first scope device to position the first instrument within both spaces. Further, the second instrument is inserted into the extraluminal anatomical space. The second instrument can be inserted into the extraluminal anatomical space, prior to, concurrently with, or subsequent to the insertion of the first device scope or the insertion of the first instrument.

An exemplary surgical system can include a variety of features as described herein and illustrated in the drawings. However, a person skilled in the art will appreciate that the surgical systems can include only some of these features and/or it can include a variety of other features known in the art. The surgical systems described herein are merely intended to represent certain exemplary embodiments. Moreover, while the surgical systems are shown and described in connection with a colon, a person skilled in the art will appreciate that these surgical systems can be used in connection with any other suitable body cavities or organs.

FIG. 77 illustrates an exemplary embodiment of a surgical system 10400 having a first scope device 10412 and a second scope device 10414, which are being used in a surgical resection of a partial tissue wall thickness tumor 10401 located in a colon 10402. For purposes of simplicity, certain components of the surgical system 10400 are not illustrated.

The first scope device 10412 includes a flexible body 10422 with first and second working channels 10424, 10426 extending therethrough and a first imaging system 10428 (e.g., a camera) at a distal end thereof. The flexible body 10422 can be formed of any suitable flexible material(s).

During use, a proximal end of the first scope device 10412 is coupled to a first robotic arm 10430 and the first instrument 10432 is coupled to a second robotic arm 10434. The first scope device 10412 is inserted into an abdominal cavity 10405 (e.g., an extraluminal anatomical space) through a first trocar 10436. The first trocar 10436 is coupled to a robotic arm 10438. The first scope device 10412 is further inserted through a lumen of a sealing port 10440, with the sealing port 10440 being arranged within a wall 10406 of the colon 10402, and into a colon cavity 10407 (e.g., intraluminal anatomical space). The first scope device 10412 can be inserted into and through the first trocar 10436 and sealing port 10440 such that a first portion 10412a of the first scope device 10412 is present in the abdominal cavity 10405 (e.g., an extraluminal anatomical space), and a second portion 10412b of the first scope device 10412 that is distal to the first portion 10412a is positioned in the colon cavity 10407 (e.g., an intraluminal anatomical space). In some embodiments, the sealing port 10440 can be omitted such that the first scope device 10412 is directly inserted through an otomy made in the colon wall 10402a.

As shown, the first scope device 10412 has a first portion 10412a that is present within the abdominal cavity 10405 and a second portion 10412b that is distal to the first portion 10412a and present within the colon cavity 10407. That is, the first scope device 10412 is designed to be introduced into the colon 10402 through a laparoscopic approach. Prior to or after insertion of the second portion 10412b of the first scope device 10412, sealing clips 10409a and 10409b can be positioned on opposing ends of the insufflated region of the colon 10402.

In some embodiments, the first portion 10412a of the first scope device 10412 can be driven from the one or more tool drivers (not shown) within the motor housing 10421, which is positioned between the robotic arm 10438 and the first trocar 10436.

As further shown in FIG. 77, once the second portion 10412b of the first scope device 10412 is positioned within the colon cavity 10407, a first instrument 10432 can be inserted through the first working channel 10424 of the first scope device 10412 such that the distal end of the first instrument is positioned the colon cavity 10407. As a result, the first instrument 10432 is present within both the abdominal cavity (e.g., an extraluminal anatomical space) and the colon cavity 10407 (e.g., intraluminal anatomical space). Once inserted, the end effector 10433 (of the first instrument 10432 can interact with the tumor 10401 for subsequent removal. While the end effector 10433 can have a variety of configurations, in this illustrated embodiment, the end effector 10433 is the form of a set of movable jaws. In some embodiments, at least one of the first and second working channels 10424, 10426 are configured to allow for the interchanging of instruments without compromising the position of the first scope device 10412 within at least one of the abdominal cavity 10405 and the colon cavity 10407. This can also maintain the field of view of the first imaging system 10428.

The surgical system 10400 also includes a controller 10470 communicatively coupled to the endoscope 10412 and the laparoscope 10414, and is configured to receive the transmitted image data of the first and second scenes from the first and second optical sensors 10428, 10458, respectively. In some embodiments, the controller 10470 is also communicatively coupled to a first and second tracking devices 10482, 10484 arranged within the endoscope 10412 and the laparoscope 10414, respectively, and is configured to receive the transmitted signals from the first and second tracking devices. Once received, the controller 10470 is configured to determine at least the relative distance between the endoscope 10412 and the laparoscope 10414. In certain embodiments, the controller 10470 can also be configured to determine the relative orientation between endoscope 10412 and the laparoscope 10414.

As further shown in FIG. 77, the second scope device 10414 is laparoscopically arranged within the abdominal cavity 10405. The second scope device includes a flexible body 10452 with third and fourth working channels 10454, 10456, extending therethrough and a second imaging system 10458 (e.g., a camera) at a distal end thereof. The flexible body 10452 can be formed of any suitable flexible material(s).

The second scope device 10414 is inserted into an abdominal cavity 10405 (e.g., an extraluminal anatomical space) through a second trocar 10466 arranged within the abdominal wall 10403. The second trocar 10466 is coupled to a second robotic arm 10468. The second scope device 10414 is inserted into and positioned in the abdominal cavity 10405 (e.g., an extraluminal anatomical space). In some embodiments, the flexible body 10452 of the second scope device 10414 can be driven from the one or more tool drivers (not shown) within the motor housing 10451, which is positioned between the second robotic arm 10468 and the second trocar 10466.

As shown, during use, a proximal end of the second scope device 10414 is coupled to a first robotic arm 10460 and a second instrument 10462 is coupled to a second robotic arm 10464. The second instrument 10462 extends into and through the third working channel 10454 and into the abdominal cavity 10405 (e.g., an extraluminal anatomical space). While the second instrument 10462 can have a variety of configuration, in this illustrated embodiment, the second instrument 10462 has an elongate shaft 10462a with an end effector 10463 at a distal end thereof. In some embodiments, the second instrument 10462 is configured to aid in manipulating the colon 10402 from the abdominal cavity 10405 (e.g., an extraluminal anatomical space) in order to arrange the first instrument 10432 in the colon cavity 10407 (e.g., an intraluminal anatomical space). Further, the end effector 10463 of the second instrument 10462 can interact with the colon 10402 to help stabilize the colon 10402 for removal of the tumor 10401. While the end effector 10463 can have a variety of configurations, in this illustrated embodiment, the end effector 10463 is the form of a set of movable jaws. In some embodiments, the end effector 10463 can be used to create a seal within the colon cavity 10407 (e.g., by clamping the colon 10402).

As shown in FIG. 77, a fiducial marker 10480 can be arranged on the first portion 10412a of the endoscope 10412. The fiducial marker 10480 is within the field of view of the optical sensor 10458 of the laparoscope 10414. The fiducial marker 10480 is fixed on the outer surface of the first portion of the endoscope 10412 such that the position of the second portion 10412b of the endoscope 10412 can be determined through visualization of the fiducial marker 10480 by the optical sensor 10458. Based on both the transmitted image data from the optical sensor 10458 identifying the fiducial marker 10480, the controller 10470 is configured to provide a merged image to a display, for example, on a first display 10471, a second display 10472, or both of the surgical system 10400. In the merged image, at least one of the endoscope 10412 and the laparoscope 10414 is a representative depiction thereof. Various embodiments of magnetic fiducial markers and using magnetic fiducial markers in detecting location are discussed further, for example, in U.S. Pat. App No. 63/249,658 entitled "Surgical Devices, Systems, And Methods For Control Of One Visualization With Another" filed on Sep. 29, 2021.

In some embodiments, the fiducial marker is a physical symbol which can be visually identified. In other embodiments, the fiducial marker can be a light emitting device, or an electromagnet emitting device which can be identified by the laparoscope in order to track the endoscope. Additionally, there can be multiple fiducial markers arranged on the outer surface of the first portion of the endoscope, where the optical sensor of the laparoscope can identify which fiducial markers are within the extraluminal space.

The first and second displays 10471, 10472 can be configured in a variety of configurations. For example, in some embodiments, the first display can be configured to display the first scene and the second display can be configured to display the second scene, and the first display, the second display, or both, can be further configured to display the merged image. In another embodiment, the surgical system 10400 can include, a third display 10473 that can be used to display the merged image, and the first and second displays 10471, 10472 are used to only show the transmitted image data from the optical sensors 10428, 10458, respectively, without any modification. In this embodiment, a surgeon can access the real-time scenes from both the endoscope 10412 and the laparoscope 10414 on the first and second displays 10471, 10472, while also having access to the merged image on the third display 10473.

As stated above, the endoscope 10412 includes the first optical sensor 10428. The first optical sensor 10428 is configured to transmit image data of a first scene within a field of view of the endoscope 10412 to the controller 10470. In this illustrated embodiment, the tumor 10401 and surgical instrument 10432 are arranged within the field of view of the endoscope 10412. In some embodiments, the relative distance between the endoscope 10412 and the laparoscope 10414 can be determined by using structured light projected onto the first portion 10412a and the fiducial marker 10480 (e.g., via a lighting element) and tracked by the second optical sensor 10458. Further, in some embodiments, based on the determined relative distances between the endoscope 10412 and laparoscope 10414 and determined relative distance between the endoscope 10412 and the tumor 10401, the controller can calculate the relative distance between the laparoscope 10414 and the tumor 10401.

Additionally, the laparoscope 10414 includes the second optical sensor 10458. The second optical sensor 10458 is configured to transmit image data of a second scene within a field of view of the laparoscope 10414 to the controller 10470. The surgical instrument 10462 is arranged within the field of view of the laparoscope 10414. As a result, the controller 10470, based on the transmitted image data, can determine the relative distance between the surgical instrument 10462 and the surgical instrument 10432.

Figure 77A:
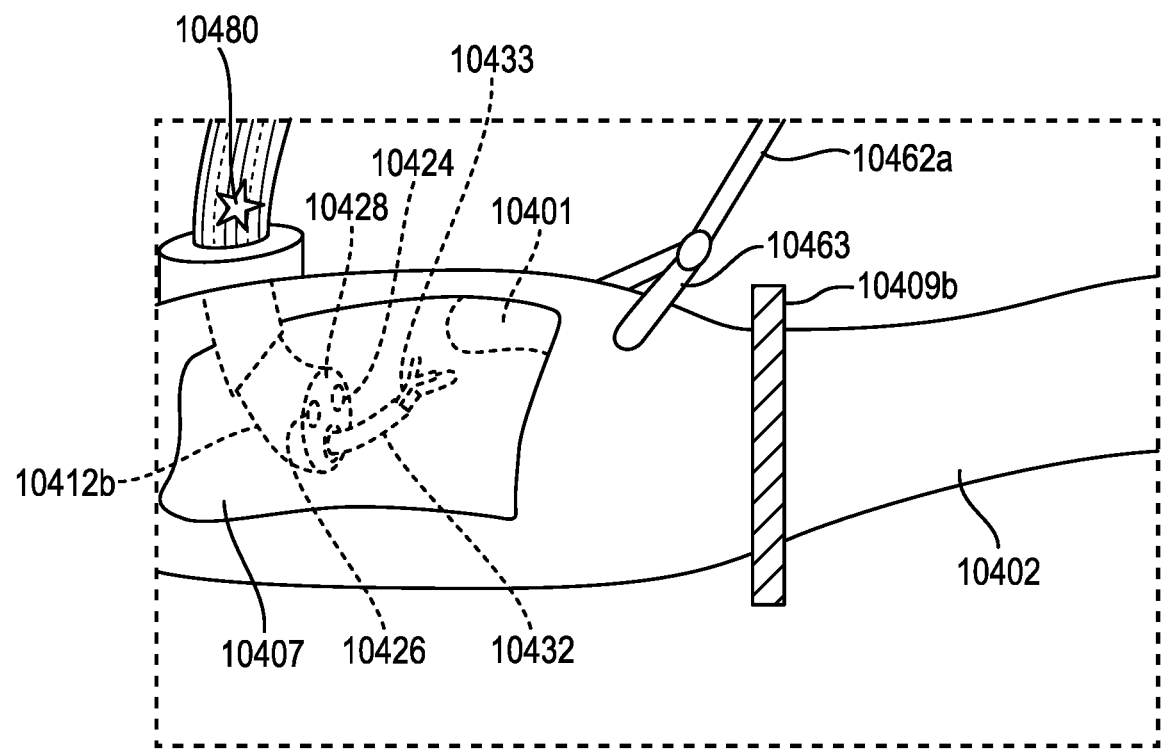
FIG. 77a is a schematic view of a merged image of the surgical system of FIG. 77 from the perspective of the laparoscope.
Figure 77B:
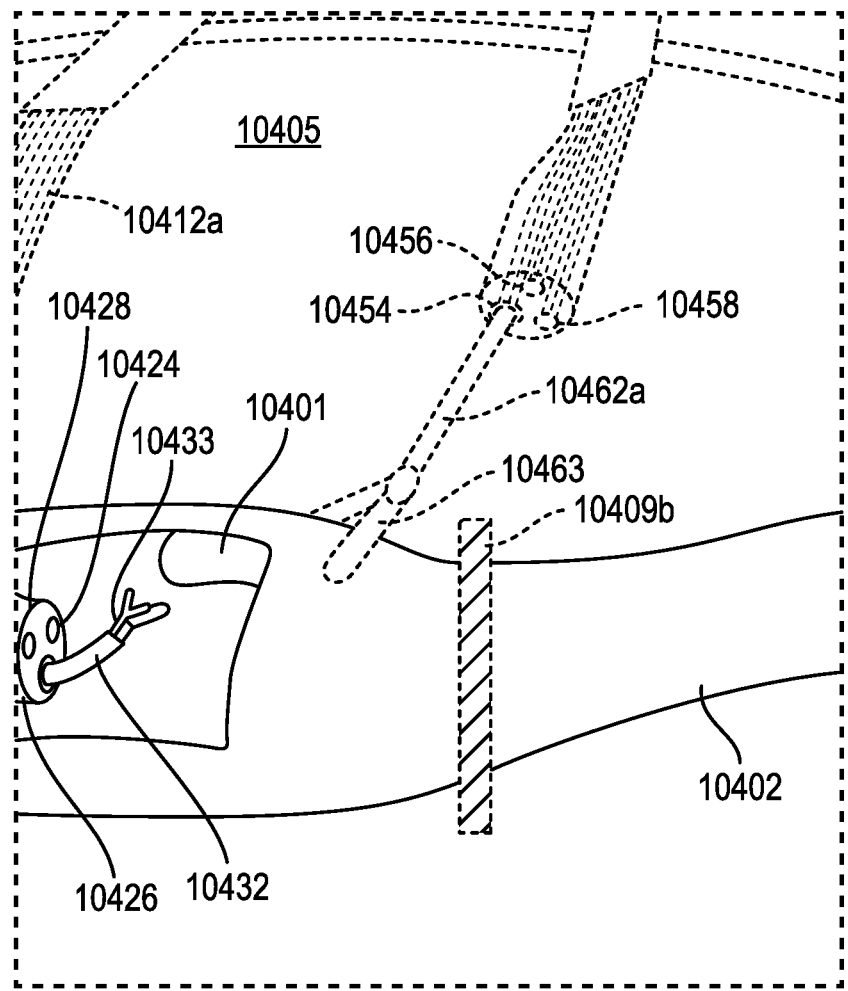
FIG. 77b is a schematic view of a merged image of the surgical system of FIG. 77 from the perspective of the endoscope.

FIG. 77a illustrates an exemplary embodiment of a merged image. The merged image illustrates a real-time second scene within the field of view of the laparoscope 10414 and an overlaid representative depiction of a portion of the endoscopic side of the colon 10402 (e.g., the tumor 10401 and/or the endoscope 10412). Based on the transmitted image data of the second scene in combination with the fiducial marker 10480, the controller 10470 can provide the merged image from the point of view of the laparoscope 10414, where the endoscope 10412 and the tumor 10401 are shown as representative depictions which correspond to their location in the intraluminal space in real-time. In the illustrated embodiment, the representative depictions are shown in dashed outlines of the corresponding tumor 10401 and endoscope 10412. However, other forms of representative depictions can be used, such as simple geometric shapes to represent the non-visual instruments and anatomical structures within the intraluminal space.

Alternatively, or in addition, the controller 10470 can generate a merged image from the perspective of the endoscope 10412. For example, in FIG. 77b, the merged image illustrates a real-time first scene within the field of view of the endoscope 10412 with an overlaid representative depiction of a portion of the laparoscopic side of the colon 10402 (e.g., the laparoscope 10414, and/or the surgical instrument 10462). A person skilled in the art will understand that the phrase "representative depiction" as used herein refers to a virtual overlay on an actual depiction from a camera, where the virtual overlay corresponds to the location and orientation of objects which are arranged within the field of view of a camera, but not visible to the camera due to an obstacle being arranged between the camera and the objects, and that the phrase "actual depiction" as used herein refers to an unmodified, real-time image or video stream from a camera. Based on the transmitted image data of the optical sensor 10428 in combination with the fiduciary marker 10480, the controller 10470 can provide the merged image from the point of view of the endoscope 10412, where the laparoscope 10414 and the surgical instrument 10462 are shown as representative depictions which correspond to their location in the extraluminal space in real-time. In the illustrated embodiment, the representative depictions are shown in dashed outlines of the laparoscope 10414 and surgical instrument 10462. However, other forms of representative depictions can be used, such as simple geometric shapes to represent the non-visual instruments and anatomical structures within the intraluminal space.

In certain embodiments, the movements between the instruments in both intraluminal and extraluminal spaces can be coordinated since both sets of instrument can be visualized by the other. For example, a cooperative defect repair (e.g., suturing an incision) can be accomplished by inserting needle hook from the laparoscopic side with an instrument, and then passing the needle hook into the intraluminal space, where the endoscopically arranged instrument can grab the hook needle. The hook needle can then be passed back through the colon to the extraluminal space, with the process being repeated until the incision is sutured closed.

In other embodiments, the position of the endoscope and laparoscope can be tracked relative to each other through a time-based approach. Once the scope devices cannot visually identify each other, that point in time can become a reference point. The movements of each scope device by the robotic arms can be recorded, and the position of each scope device can be determined over time as the scope devices are moved within an anatomical space.

Surgical Systems for Independently Insufflating Two Separate Anatomic Spaces

In certain embodiments, surgical systems are configured to independently insufflate two separate anatomical areas for conducting one or more surgical tasks. In general, the present surgical systems include a first access port(s) that is/are configured to provide access to and enable insufflation of a first cavity (e.g., an extraluminal anatomical space) and a second access port(s) that is/are configured to provide access to and enable insufflation of a separate cavity (e.g., an intraluminal anatomical space) through the first cavity. This can provide separate anatomical working volumes for different instruments and further enable these different instruments to work together on a single surgical site.

In one exemplary embodiment, a surgical system can generally include a first scope device that is configured to be positioned in both the intraluminal and extraluminal anatomical spaces and a second scope device that is configured to be inserted into the extraluminal anatomical space. The first scope device has a first insufflation port (e.g., a fluid port) operatively coupled to the first scope device and configured to insufflate the intraluminal anatomical space into a first insufflated space, and the second scope device has a second insufflation port (e.g., a fluid port) operatively coupled to the second scope device and configured to insufflate the extraluminal anatomical space into a second insufflated space. As such, the first insufflated space and the second insufflated space are both independently pressurized, and thus, generated to provide separate working volumes for different instruments.

The surgical system also includes a first instrument and a second instrument. The first instrument is configured to be inserted into and through the extraluminal anatomical space and into the intraluminal anatomical space such that the first instrument is present in both the extraluminal and intraluminal anatomical spaces. The second instrument is configured to be inserted into the extraluminal anatomical space.

In some embodiments, the surgical system can include a sealing port arranged in a tissue wall separating the extraluminal anatomical space from the intraluminal anatomical space. In certain embodiments, the sealing port is configured to allow the second portion of the first scope device to pass into the intraluminal anatomical space.

Further, in some embodiments, an imaging system (e.g., a camera) can be arranged on the second portion of the first scope device and configured to transmit image data of a scene within a field of view of the first scope device. Alternatively, or in addition, an imaging system (e.g., a camera) can be arranged on the second scope device and configured to transmit image data of a scene within a field of view of the second scope device. This can allow cooperative visualization between the instruments working in the extraluminal anatomical space and instruments working in the intraluminal anatomical space, and further enable the instruments to work cooperatively together on a single surgical site. Moreover, cooperative visualization can be used to when adjustments may need to be made to the first insufflated area, the second insufflated space, or both during a specific surgical task or step or the entire surgical procedure. An imaging system can include multiple cameras which the surgeon can use to achieve a better perspective on a surgical treatment site within a patient's body.

During use, in general, the first portion of the first scope device scope is inserted into an extraluminal anatomical space, and a second portion (e.g., a portion that is distal to the first portion) of the first scope device is inserted into an intraluminal anatomical space. Further, the second scope device is inserted into the extraluminal anatomical space. Prior to, concurrently with, or subsequent to, the insertion of the first scope device, the first insufflation port can be used to insufflate the intraluminal anatomical space to a first pressure thereby creating the first insufflated space. Further, prior to, concurrently with, or subsequent to insertion of the first device scope, insufflation of the intraluminal anatomical space, and/or the insertion of the second device scope, the extraluminal anatomical space can be insufflated to a second pressure via the second insufflation port thereby creating the second insufflated space.

Further, the first instrument is inserted into and through the extraluminal anatomical space and into the intraluminal anatomical space such that the first instrument is present in both the extraluminal and intraluminal anatomical spaces. For example, the first instrument can be inserted through a working channel of the first scope device to position the first instrument within both spaces. The first instrument can be inserted prior to, concurrently with, or subsequent to the insufflation of the intraluminal anatomical space, the extraluminal space, or both. Further, the second instrument is inserted into the extraluminal anatomical space. The second instrument can be inserted into the extraluminal anatomical space, prior to, concurrently with, or subsequent to the insertion of the first device scope, the insertion of the first instrument, insufflation of the intraluminal anatomical space, or insufflation of the extraluminal space.

An exemplary surgical system can include a variety of features as described herein and illustrated in the drawings. However, a person skilled in the art will appreciate that the surgical systems can include only some of these features and/or it can include a variety of other features known in the art. The surgical systems described herein are merely intended to represent certain exemplary embodiments. Moreover, while the surgical systems are shown and described in connection with a colon, a person skilled in the art will appreciate that these surgical systems can be used in connection with any other suitable body cavities or organs.

Figure 78:
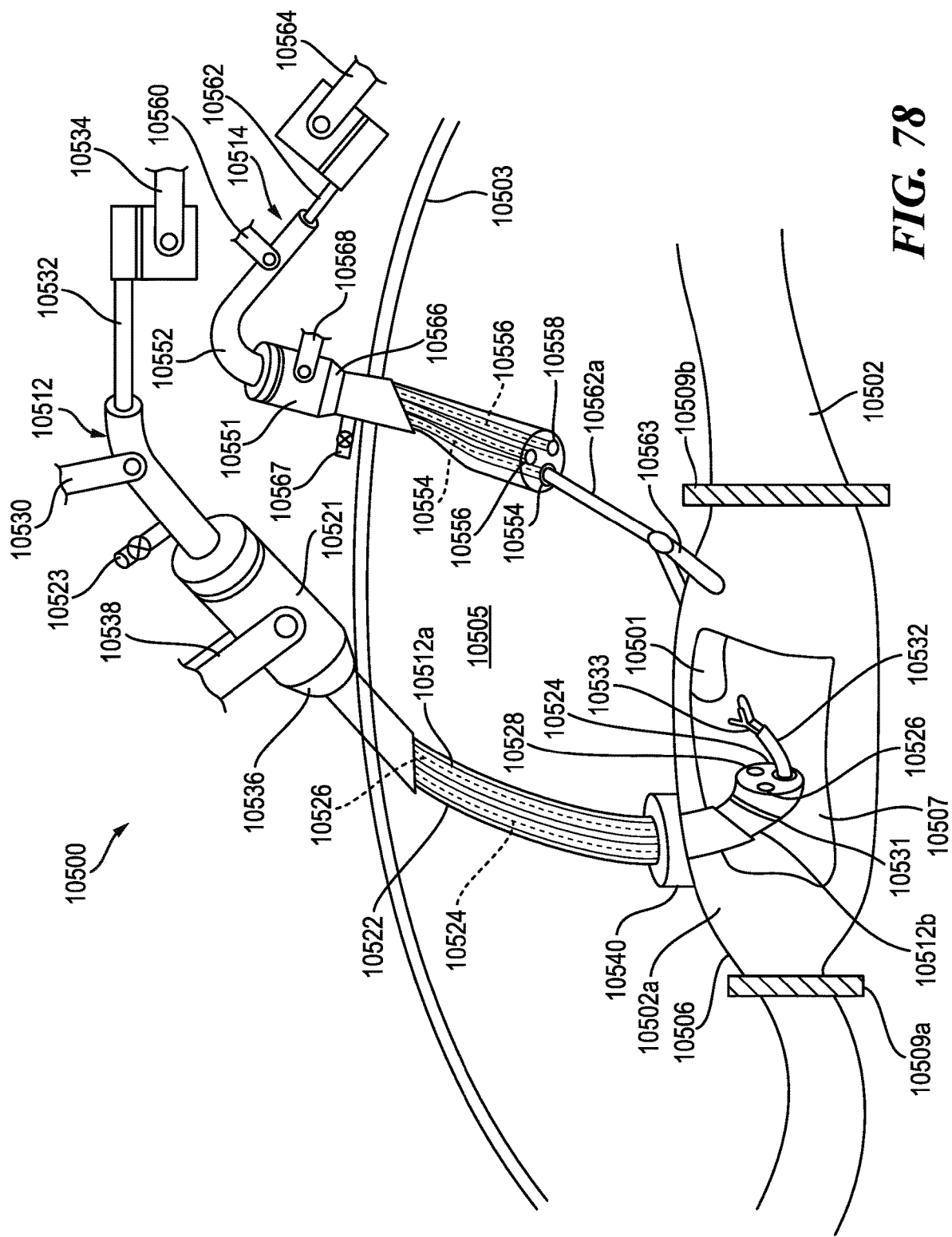
FIG. 78 is a schematic view of an exemplary embodiment of a surgical system having a laparoscopic instrument and an endoluminal instrument, showing the endoluminal instrument being inserted into a colon through a laparoscopic approach.

FIG. 78 illustrates an exemplary embodiment of a surgical system 10500 having a first scope device 10512 and a second scope device 10514, which are being used in a surgical resection of a partial tissue wall thickness tumor 10501 located in a colon 10502. For purposes of simplicity, certain components of the surgical system 10500 are not illustrated.

The first scope device 10512 includes a flexible body 10522 with first and second working channels 10524, 10526 extending therethrough and a first imaging system 10528 (e.g., a camera) at a distal end thereof. The flexible body 10522 can be formed of any suitable flexible material(s).

During use, a proximal end of the first scope device 10512 is coupled to a first robotic arm 10530 and the first instrument 10532 is coupled to a second robotic arm 10534. The first scope device 10512 is inserted into an abdominal cavity 10505 (e.g., an extraluminal anatomical space) through a first trocar 10536. The first trocar 10536 is coupled to a robotic arm 10538. The first scope device 10512 is further inserted through a lumen of a sealing port 10540, with the sealing port 10540 being arranged within a wall 10506 of the colon 10502, and into a colon cavity 10507 (e.g., intraluminal anatomical space). The first scope device 10512 can be inserted into and through the first trocar 10536 and sealing port 10540 such that a first portion 10512*a* of the first scope device 10512 is present in the abdominal cavity 10505 (e.g., an extraluminal anatomical space), and a second portion 10512*b* of the first scope device 10512 that is distal to the first portion 10512*a* is positioned in the colon cavity 10507 (e.g., an intraluminal anatomical space). In some embodiments, the sealing port 10540 is configured to prevent the contents of the colon cavity 10507 from escaping into the abdominal cavity 10505 during an insufflation procedure. In other embodiments, the sealing port 10540 can be omitted such that the first scope device 10512 is directly inserted through an otomy made in the colon wall 10502*a*.

As shown, the first scope device 10512 has a first portion 10512*a* that is present within the abdominal cavity 10505 and a second portion 10512*b* that is distal to the first portion 10512*a* and present within the colon cavity 10507. That is, the first scope device 10512 is designed to be introduced into the colon 10502 through a laparoscopic approach. Prior to or after insertion of the second portion 10512*b* of the first scope device 10512, sealing clips 10509*a* and 10509*b* can be positioned on opposing ends of the insufflated region of the colon 10502.

The first scope device 10512 includes a first insufflation port 10523 that is configured to insufflate the colon cavity 10507 prior to or concurrently with the insertion of any devices or instruments into the colon cavity 10507. In this illustrated embodiment, the first insufflation port 10523 is in fluid communication with the second working channel 10526 of the first scope device 10512. As a result, the first insufflation port 10523 can be used to control the ingress or egress of fluid to and from the colon cavity 10507 so as to insufflate or desufflate the colon cavity 10507. While not shown the first insufflation port 10523 is connected to a fluid system. The fluid system can include a pump and a fluid reservoir. The pump creates a pressure which pushes the fluid into and inflates (e.g., pressurizes) the colon cavity 10507, and creates a suction that draws the fluid from the colon cavity 10507 in order to deflate (e.g., depressurizes) the colon cavity 10507. The fluid passed into or out of the colon cavity 10507 can be any suitable fluid (e.g., saline, carbon dioxide gas, and the like). In other embodiments, the colon cavity 10507 can be insufflated and desufflated using any other suitable insufflating mechanisms and devices.

In some embodiments, the first portion 10512*a* of the first scope device 10512 can be driven from the one or more tool drivers (not shown) within the motor housing 10521, which is positioned between the robotic arm 10538 and the first trocar 10536.

As further shown in FIG. 78, once the second portion 10512*b* of the first scope device 10512 is positioned within the colon cavity 10507, a first instrument 10532 can be inserted through the first working channel 10524 of the first scope device 10512 such that the distal end of the first instrument is positioned the colon cavity 10507. As a result, the first instrument 10532 is present within both the abdominal cavity (e.g., an extraluminal anatomical space) and the colon cavity 10507 (e.g., intraluminal anatomical space). Once inserted, the end effector 10533 (of the first instrument 10532 can interact with the tumor 10501 for subsequent removal. While the end effector 10533 can have a variety of configurations, in this illustrated embodiment, the end effector 10533 is the form of a set of movable jaws. In some embodiments, at least one of the first and second working channels 10524, 10526 are configured to allow for the interchanging of instruments without compromising the position of the first scope device 10512 within at least one of the abdominal cavity 10505 and the colon cavity 10507. This can also maintain the field of view of the first imaging system 10528.

In some embodiments, the first scope device 10512 can be configured to create a seal within the colon cavity 10507. For example, as shown in FIG. 78, the first scope device 10512 includes a sealing element 10531 that is positioned at or proximate to a distal end of the first scope device 10512. While the sealing element 10531 can have a variety of configurations, in this illustrated embodiment, the sealing element 10531 is in the form of an inflatable annular ring positioned about the first scope device 10512. While the first scope device 10512 is advanced through the abdominal cavity 10505 and into the colon cavity 10507, the sealing element 10531 is in a deflated state. Once in the colon cavity 10507, the sealing element 10531 can be inflated to thereby create a seal as it engages the inner tissue wall of the colon 10502. Further, in certain embodiments, the sealing element 10531, when in an inflated state, can also function as a fixation point for the first scope device 10512 within the colon cavity 10507.

As further shown in FIG. 78, the second scope device 10514 is laparoscopically arranged within the abdominal cavity 10505. The second scope device includes a flexible body 10552 with third and fourth working channels 10554, 10556, extending therethrough and a second imaging system 10558 (e.g., a camera) at a distal end thereof. The flexible body 10552 can be formed of any suitable flexible material(s).

The second scope device 10514 is inserted into an abdominal cavity 10505 (e.g., an extraluminal anatomical space) through a second trocar 10566 arranged within the abdominal wall 10503. The second trocar 10566 is coupled to a second robotic arm 10568. The second scope device 10514 is inserted into and positioned in the abdominal cavity 10505 (e.g., an extraluminal anatomical space). The second trocar 10566 includes a second insufflation port 10567 that is configured to insufflate the abdominal cavity 10105 prior to or concurrently with the insertion of any devices or instruments into the abdominal cavity 10105. In this illustrated embodiment, the second insufflation port 10567 is in fluid communication with the fourth working channel

10556. As a result, the second insufflation port 10567 can be used to control the ingress or egress of fluid into and out of the abdominal cavity 10505 so as to insufflate or desufflate the abdominal cavity 10505. While not shown the second insufflation port 10567 is connected to a fluid system. The fluid system can include a pump and a fluid reservoir. The pump creates a pressure which pushes the fluid into and inflates (e.g., pressurizes) the abdominal cavity 10105, and creates a suction that draws the fluid from the abdominal cavity 10105 in order to deflate (e.g., depressurizes) the abdominal cavity 10105. The fluid passed into or out of the abdominal cavity 10105 can be any suitable fluid (e.g., saline, carbon dioxide gas, and the like). In other embodiments, the abdominal cavity 10105 can be insufflated and desufflated using any other suitable insufflating mechanisms and devices.

In some embodiments, the flexible body 10552 of the second scope device 10514 can be driven from the one or more tool drivers (not shown) within the motor housing 10551, which is positioned between the second robotic arm 10568 and the second trocar 10566.

As shown, during use, a proximal end of the second scope device 10514 is coupled to a first robotic arm 10560 and a second instrument 10562 is coupled to a second robotic arm 10564. The second instrument 10562 extends into and through the third working channel 10554 and into the abdominal cavity 10505 (e.g., an extraluminal anatomical space). While the second instrument 10562 can have a variety of configuration, in this illustrated embodiment, the second instrument 10562 has an elongate shaft 10562*a* with an end effector 10563 at a distal end thereof. In some embodiments, the second instrument 10562 is configured to aid in manipulating the colon 10502 from the abdominal cavity 10505 (e.g., an extraluminal anatomical space) in order to arrange the first instrument 10532 in the colon cavity 10507 (e.g., an intraluminal anatomical space). Further, the end effector 10563 of the second instrument 10562 can interact with the colon 10502 to help stabilize the colon 10502 for removal of the tumor 10501. While the end effector 10563 can have a variety of configurations, in this illustrated embodiment, the end effector 10563 is the form of a set of movable jaws. In some embodiments, the end effector 10563 can be used to create a seal within the colon cavity 10507 (e.g., by clamping the colon 10502).

In use, the colon cavity 10507 is pressurized to a first pressure via fluid ingress through the first insufflation port 10523 and the second working channel 10526. Additionally, the abdominal cavity 10505 is pressurized to a second pressure via fluid ingress through second insufflation port 10567 and the fourth working channel 10556. In some embodiments, the first pressure is different than the second pressure. Alternatively, the first pressure and the second pressure can be identical.

The first pressure and second pressure can be adjusted independently to alter the working volume space within the abdominal cavity 10505, the colon cavity 10507, or both. For example, the working volume space within the abdominal cavity 10505 can be increased by increasing the pressure in the abdominal cavity 10505, decreasing the pressure in the colon cavity 10507, or both. Similarly, the working volume space within the abdominal cavity 10505 can be decreased by decreasing the pressure in the abdominal cavity 10505, increasing the pressure in the colon cavity 10507, or both. Further, the working volume space within the colon cavity 10507 can be increased by increasing the pressure in the colon cavity 10507 and can be decreased by decreasing the pressure in the colon cavity 10507.

While not illustrated, the first and second imaging systems 10528, 10558 are connected to one or more displays that provide a snapshot and/or a live video feed of the surgical site(s). The snapshot and/or live video feed on the displays can permit a medical practitioner to observe a surgical site from multiple angles and approaches, for example. As a result, the first and second imaging systems 10528, 10558 can provide information to the medical practitioner that can be used in determining effective working volume spaces for the first and second instruments for a particular surgical task or step or throughout the entire surgical procedure and what, if any, adjustments need to be made to the first insufflated space, the second insufflated space, or both.

The surgical systems disclosed herein can be designed to be disposed of after a single use, or they can be designed to be used multiple times. In either case, however, the surgical systems can be reconditioned for reuse after at least one use. Reconditioning can include any combination of the steps of disassembly of the surgical devices, followed by cleaning or replacement of particular pieces and subsequent reassembly. In particular, the surgical systems can be disassembled, and any number of the particular pieces or parts of the surgical systems can be selectively replaced or removed in any combination. Upon cleaning and/or replacement of particular parts, the surgical systems can be reassembled for subsequent use either at a reconditioning facility, or by a surgical team immediately prior to a surgical procedure. Those skilled in the art will appreciate that reconditioning of a surgical device can utilize a variety of techniques for disassembly, cleaning/replacement, and reassembly. Use of such techniques, and the resulting reconditioned instrument, are all within the scope of the present application.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. It will be appreciated that the terms "proximal" and "distal" are used herein, respectively, with reference to the top end (e.g., the end that is farthest away from the surgical site during use) and the bottom end (e.g., the end that is closest to the surgical site during use) of a surgical instrument, respectively, that is configured to be mounted to a robot. Other spatial terms such as "front" and "rear" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Values or ranges may be expressed herein as "about" and/or from/of "about" one particular value to another particular value. When such values or ranges are expressed, other embodiments disclosed include the specific value recited and/or from/of the one particular value to another particular value. Similarly, when values are expressed as approximations, by the use of antecedent "about," it will be understood that here are a number of values disclosed therein, and that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value or within 2% of the recited value.

For purposes of describing and defining the present teachings, it is noted that unless indicated otherwise, the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety. Any patent, publication, or information, in whole or in part, that is said to be incorporated by reference herein is only to the extent that the incorporated material does not conflict with existing definitions, statements, or other disclosure material set forth in this document. As such the disclosure as explicitly set forth herein supersedes any conflicting material incorporated herein by reference.

What is claimed is:

1. A method, comprising:
    inserting an outer sleeve of a surgical instrument at least partially into a first natural body lumen, the outer sleeve having a working channel extending therethrough;
    inserting at least one channel arm of the surgical instrument through the working channel of the outer sleeve and at least partially into a second natural body lumen that is in communication with the first natural body lumen, wherein the at least one channel arm has at least one first anchor member arranged at least partially on an outer surface of the at least one channel arm and at least one control actuator operatively coupled to the at least one first anchor member;
    expanding the at least one first anchor member from an unexpanded state to an expanded state to form an anchor point at a portion of the second natural body lumen; and
    controlling, by the control actuator, a motion of the at least one channel arm to selectively manipulate an organ associated with the first and second natural body lumens.

2. The method of claim 1, wherein the surgical instrument includes at least one second anchor member operatively coupled to the outer sleeve, the method further comprises expanding the at least one second anchor member from an unexpanded state to an expanded state to form an anchor point at a portion of the first natural body lumen.

3. The method of claim 2, wherein, the at least one second anchor member, when in the expanded state, at least partially contacts the internal surface of the first natural body lumen.

4. The method of claim 1, wherein, the at least one anchor member, when in the expanded state, at least partially contacts the internal surface of the second natural body lumen.

5. The method of claim 1, further comprising applying a force to the second natural body lumen through the at least one first anchor member to manipulate the second natural body lumen relative to the first natural body lumen.

6. The method of claim 1, further comprising coordinating, with a controller, a motion of the at least one channel arm within the second natural body lumen with a motion of at least one instrument arranged outside of the second natural body lumen to prevent tearing of the second natural body lumen.

7. The method of claim 1, further comprising moving, by the control actuator, the at least one first anchor member axially along a length of the at least one channel arm.

8. The method of claim 1, further comprising selectively locking, by a releasable locking mechanism, the at least one first anchor member at an axial position along a length of the at least one channel arm.

9. A method, comprising:
    inserting an instrument at least partially into a natural body lumen along an axis of axial movement, the instrument having an anchor assembly coupled to a tubular member having a first plurality of working channels, the anchor assembly having a first anchor member having a second plurality of working channels, a second anchor member that is distal to the first anchor member along the axis, and a plurality of actuators that pass through the first plurality of working channels of the tubular member and the second plurality of working channels of the first anchor member;
    expanding the first anchor member from an unexpanded state to an expanded state to anchor the first anchor member to a first anatomical location within the natural body lumen;
    expanding the second anchor member from an unexpanded state to an expanded state to anchor the second anchor member to a second anatomical location within the natural body lumen;
    rotating the plurality of actuators to axially displace the second anchor member relative to the first anchor member; and
    moving the second anchor member relative to the first anchor member to selectively reposition the second anatomical location relative to the first anatomical location.

10. The method of claim 9, further comprising positioning an endoscope within a central lumen of the tubular member.

11. The method of claim 9, wherein expanding the first anchor member comprises deforming a plurality of expandable anchoring elements of the first anchor member such that the first anchor member contacts an inner surface of the natural body lumen at the first anatomical location.

12. The method of claim 9, wherein expanding the second anchor member comprises deforming a plurality of expandable anchoring elements of the second anchor member such that the second anchor member contacts an inner surface of the natural body lumen at the second anatomical location.

13. The method of claim 9, wherein the plurality of actuators pass through a third plurality of working channels of the second anchor member, wherein expanding the second anchor member comprises:

rotating the plurality of actuators to expand a plurality of expandable anchoring elements of the second anchor member.

14. The method of claim 9, wherein the plurality of actuators that pass through the second plurality of working channels of the first anchor member and the first plurality of working channels of the tubular member terminate at a proximal surface of the second anchor member, and wherein expanding the first anchor member comprises:

rotating the plurality of actuators to expand a plurality of expandable anchoring elements of the first anchor member.

* * * * *